United States Patent
Casillas et al.

(10) Patent No.: US 10,781,205 B2
(45) Date of Patent: Sep. 22, 2020

(54) CONJUGATES COMPRISING RIPK2 INHIBITORS

(71) Applicant: GlaxoSmithKline Intellectual Property Development Limited, Brentford, Middlesex (GB)

(72) Inventors: Linda N. Casillas, Collegeville, PA (US); John David Harling, Stevenage (GB); Afjal Hussain Miah, Stevenage (GB); Mark David Rackham, Stevenage (GB); Ian Edward David Smith, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/094,564

(22) PCT Filed: Apr. 18, 2017

(86) PCT No.: PCT/EP2017/059090
§ 371 (c)(1),
(2) Date: Oct. 18, 2018

(87) PCT Pub. No.: WO2017/182418
PCT Pub. Date: Oct. 26, 2017

(65) Prior Publication Data
US 2019/0119271 A1    Apr. 25, 2019

Related U.S. Application Data

(60) Provisional application No. 62/324,944, filed on Apr. 20, 2016.

(51) Int. Cl.
| | | |
|---|---|---|
| *C07D 471/04* | (2006.01) | |
| *C07D 417/14* | (2006.01) | |
| *C07D 471/10* | (2006.01) | |
| *C07D 519/00* | (2006.01) | |
| *A61P 37/00* | (2006.01) | |
| *A61P 29/00* | (2006.01) | |

(52) U.S. Cl.
CPC ......... *C07D 471/04* (2013.01); *C07D 417/14* (2013.01); *C07D 471/10* (2013.01); *C07D 519/00* (2013.01); *C12Y 207/10002* (2013.01); *C12Y 207/11001* (2013.01); *A61P 29/00* (2018.01); *A61P 37/00* (2018.01)

(58) Field of Classification Search
CPC .. C07D 471/04; C07D 403/14; C07D 417/14; C07D 519/00; C07D 471/10
See application file for complete search history.

(56) References Cited

U.S. PATENT DOCUMENTS

| | | | | |
|---|---|---|---|---|
| 9,604,938 | B2 * | 3/2017 | Bury | C07D 417/12 |
| 9,604,963 | B2 * | 3/2017 | Bury | A61K 31/4709 |
| 9,650,364 | B2 * | 5/2017 | Casillas | C07D 403/12 |
| 9,988,376 | B2 * | 6/2018 | Campos | C07D 413/14 |
| 9,993,514 | B2 * | 6/2018 | Campos | A61K 38/06 |
| 10,220,030 | B2 * | 3/2019 | Bury | A61K 31/4709 |
| 10,336,744 | B2 * | 7/2019 | Harling | A61K 31/4725 |
| 10,435,391 | B2 * | 10/2019 | Casillas | C07D 487/04 |
| 2016/0368911 | A1 * | 12/2016 | Campos | C07D 413/14 |
| 2018/0134688 | A1 * | 5/2018 | Casillas | A61P 29/00 |

FOREIGN PATENT DOCUMENTS

| | | | |
|---|---|---|---|
| WO | WO 2009/140447 A1 | 11/2009 | |
| WO | WO-2009140447 A1 * | 11/2009 | ........... A61K 31/437 |
| WO | WO 2012/122011 A2 | 9/2012 | |
| WO | WO-2012122011 A2 * | 9/2012 | ......... A61K 31/4709 |
| WO | WO 2012/143726 A1 | 10/2012 | |
| WO | WO-2012143726 A1 * | 10/2012 | ........... C07D 401/06 |
| WO | WO 2013/025958 A1 | 2/2013 | |
| WO | WO-2013025958 A1 * | 2/2013 | ........... C07D 403/12 |

OTHER PUBLICATIONS

P. Wu et al., 36 Trends in Pharmacological Sciences, 422-439 (2015) (Year: 2015).*
Z. Wang et al., 19 Drug Discovery Today, 145-150 (2014) (Year: 2014).*
U.K. Marelli et al., 3 Frontiers in Oncology, 1-12 (2013) (Year: 2013).*
A. A Kooistra et al., Kinase-Centric Computational Drug Development, In 50 Annual Reports in Medicinal Chemistry, 197-236 (2017) Year: 2017).*
Jun et al., 94 Journal of Leukocyte Biology (2013) (Year: 2013).*
H. Jeong et al., Immunopharmacology and Immunotoxicology, 195-201 (2014) (Year: 2014).*
P.A. Haile et al., 59 Journal of Medicinal Chemistry, 4867-4880 (2014) (Year: 2014).*

* cited by examiner

*Primary Examiner* — Kahsay Habte
(74) *Attorney, Agent, or Firm* — Nora L. Stein; Fang Qian; Kathryn A. Lutomski

(57) ABSTRACT

The present invention relates to compounds, compositions, combinations and medicaments containing said compounds and processes for their preparation. The invention also relates to the use of said compounds, combinations, compositions and medicaments, for example as inhibitors of the activity of RIP2 kinase, including degrading RIP2 kinase, the treatment of diseases and conditions mediated by the RIP2 kinase, in particular for the treatment of inflammatory diseases or conditions.

9 Claims, No Drawings

CONJUGATES COMPRISING RIPK2 INHIBITORS

FIELD OF THE INVENTION

The present invention relates to compounds, compositions, combinations and medicaments containing said compounds and processes for their preparation. The invention also relates to the use of said compounds, combinations, compositions and medicaments, for example as inhibitors of the activity of RIP2 kinase, including degrading RIP2 kinase, the treatment of diseases and conditions mediated by RIP2 kinase, in particular for the treatment of inflammatory diseases or conditions

BACKGROUND OF THE INVENTION

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J Biol. Chem.* 273, 12296-12300; *Current Biology* 8, 885-889; and (1998) *J Biol Chem.* 273, 16968-16975). The CARD domain of RIP2 kinase mediates interaction with other CARD-containing proteins, such as NOD1 and NOD2 ((2000) *J Biol Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD 1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J Bioi. Chem.* 284, 19183-19188).

Dysregulation of RIP2-dependent signaling has been linked to auto inflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J Hum. Genet.* 70, 845-857; (2004) *European Journal of Human Genetics* 12, 206-212; (2008) *Mucosal Immunology* (2008) 1 (SuppII), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extra-intestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in auto inflammatory diseases characterized by increased and/or dysregulated RIP2 kinase activity.

It would be desirable to investigate other approaches to antagonise RIP2 kinase.

One approach would be to develop selective RIP2 kinases down regulators or degraders that reduce RIP2 expression at either the transcript or protein level.

Several methods are available for the manipulation of protein levels, including proteolysis targeting chimeric molecules (Protacs) which contain a ligand that recognizes the target protein linked to a ligand that binds to a specific E3 ubiquitin ligase. It would be desirable to have a small molecule which can simultaneously bind RIP2 kinase and an E3 ubiquitin ligase and which promotes ubiquitination of RIP2 Kinase and leads to its degradation by the proteasome. One suitable E3 ubiquitin ligase is the von Hippel-Lindau tumour suppressor (VHL), see for example WO2013/106643.

It would be desirable to identify further ubiquitin ligase binding molecules to incorporate into Protac molecules.

Inhibitors of Apoptosis (IAP) have been proposed with limited success, see for example Okuhira et al, *Cell Death and Disease*, 2014, 5, e1513. IAP inhibitors now known which can be of use in their own right as antitumour agents, see for example L. Bai et al./*Pharmacology & Therapeutics* 144 (2014) 82-95 Apoptosis is one form of programmed cell-death and is a normal cellular process used by multicellular organisms to eliminate damaged or unwanted cells. Apoptosis is a tightly regulated process and faulty regulation of apoptosis is implicated in many human diseases, including cancer, autoimmune diseases, inflammation, and neurogenesis (Lowe S. W and Lin 2000 Carcinogenesis 21(3), 485-495, Nicholson D. W. 2000, Nature 407 (6805) 810-816, Reed J. C. 2002 Nat Rev Drug Discovery 1(2) 111-121).

IAP inhibitors are disclosed for example, in. WO08016893, WO15092420, WO14060768 and WO14060767.

The present inventors have identified IAP compounds which when incorporated into Protacs targeting RIP2 kinase are capable of promoting target degradation.

SUMMARY OF THE INVENTION

The present invention provides Protac compounds which modulate RIP2 kinase activity including degradation thereof which comprise RIP2 kinase inhibitors having the following substructure:

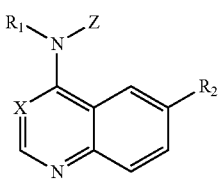

wherein X represents N or —CH.

RIP 2 inhibitors with this substructure are disclosed in WO2014/128622, WO20140/43437, WO 2013/025958, WO 2012/122011, WO 2012/021580 and WO 2011140442. These applications describe suitable substitutions on equivalent positions to Z, $R^1$ and $R^2$ in the RIP2 binding portion depicted.

In a first aspect the present invention provides a compound of formula (I):

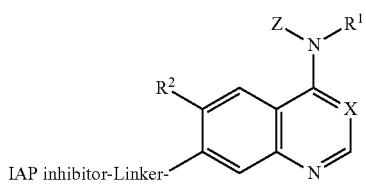

wherein
X represents N or CH;
L is a linking group comprising a length of 4-16 atoms in shortest length,
$R^1$ is H, —$SO_2(C_1-C_4)$alkyl, —$CO(C_1-C_4)$alkyl, or $(C_1-C_4)$alkyl;
$R^2$ is —$SR^a$, —$SOR^a$, —$SO_2R^a$, —$SO_2NH_2$, or —$SO_2NR^bR^c$,
wherein $R^a$ is $(C_1-C_6)$alkyl, halo$(C_1-C_6)$alkyl, $(C_3-C_7)$cycloalkyl, 4-7 membered heterocycloalkyl, aryl, or heteroaryl, wherein:
said $(C_1-C_6)$alkyl is optionally substituted by one or two groups each independently selected from the group consisting of cyano, hydroxyl, $(C_1-C_6)$alkoxy, $(C_1-C_6)$alkoxy$(C_2-C_6)$alkoxy, —$CO_2H$, —$CO_2(C_1-C_4)$alkyl, —$SO_2(C_1-C_4)$alkyl, $(C_3-C_7)$cycloalkyl, phenyl, 5-6 membered heteroaryl, 9-10 membered heteroaryl, 4-7 membered heterocycloalkyl and (phenyl)$(C_1-C_4$ alkyl)amino-, wherein said $(C_3-C_7)$cycloalkyl, phenyl, (phenyl)$(C_1-C_4$ alkyl)amino-, 5-6 membered heteroaryl, 9-10 membered heteroaryl or 4-7 membered heterocycloalkyl is optionally substituted by 1-3 groups each independently selected from the group consisting of halogen, —$CF_3$, hydroxyl, amino, $((C_1-C_4)$alkyl)amino-, $((C_1-C_4)$alkyl)$((C_1-C_4)$alkyl)amino-, $(C_1-C_4)$alkyl, phenyl$(C_1-C_4)$alkyl-, hydroxy$(C_1-C_4)$alkyl and $(C_1-C_4)$alkoxy,
said $(C_3-C_7)$cycloalkyl or 4-7 membered heterocycloalkyl is optionally substituted by 1-3 groups each independently selected from the group consisting of halogen, —$CF_3$, hydroxyl, amino, $((C_1-C_4)$alkyl)amino-, $((C_1-C_4)$alkyl)$((C_1-C_4)$alkyl)amino-, $(C_1-C_4)$alkyl, phenyl$(C_1-C_4)$alkyl-, hydroxy$(C_1-C_4)$alkyl-, oxo and $(C_1-C_4)$alkoxy, and
said aryl or heteroaryl is optionally substituted by 1-3 groups each independently selected from the group consisting of halogen, —$CF_3$, hydroxyl, amino, $((C_1-C_4)$alkyl)amino-, $((C_1-C_4)$alkyl)$((C_1-C_4)$alkyl)amino-, $(C_1-C_4)$alkyl, phenyl$(C_1-C_4)$alkyl-, hydroxy$(C_1-C_4)$alkyl- and $(C_1-C_4)$alkoxy;

$R^b$ is $(C_1-C_6)$alkyl or 4-7 membered heterocycloalkyl, wherein:
said $(C_1-C_6)$alkyl is optionally substituted by one or two groups each independently selected from the group consisting of hydroxyl, $(C_1-C_6)$alkoxy, $(C_1-C_6)$alkoxy$(C_2-C_6)$alkoxy, —$CO_2H$, —$CO_2(C_1-C_4)$alkyl, $(C_1-C_4$ alkyl)amino-, $(C_1-C_4$ alkyl)$(C_1-C_4$ alkyl)amino-, 5-6 membered heteroaryl, and 4-7 membered heterocycloalkyl, wherein said 5-6 membered heteroaryl or 4-7 membered heterocycloalkyl is optionally substituted by 1-3 groups each independently selected from the group consisting of halogen, $(C_1-C_4)$alkyl, hydroxy$(C_1-C_4)$alkyl and $(C_1-C_4)$alkoxy,
said 4-7 membered heterocycloalkyl is optionally substituted by 1-3 groups each independently selected from the group consisting of hydroxyl, amino, $(C_1-C_4)$alkyl, $(C_1-C_4)$alkoxycarbonyl-, hydroxy$(C_1-C_4)$alkyl-, oxo and $(C_1-C_4)$alkoxy, and
$R^c$ is H, $(C_1-C_4)$alkoxy or $(C_1-C_6)$alkyl;
or $R^b$ and $R^c$ taken together with the nitrogen atom to which they are attached form a 3-7 membered heterocycloalkyl group, optionally containing one or two additional ring heteroatoms each independently selected from nitrogen and oxygen, wherein said 3-7 membered heterocycloalkyl is optionally substituted by 1-3 groups each independently selected from the group consisting of $(C_1-C_4)$alkyl, hydroxy, —$CO_2H$ and —$CO(C_1-C_4)$alkyl;
Z is phenyl or aryl$(C_1-C_4)$alkyl-, wherein in the phenyl group or the aryl moiety of the aryl$(C_1-C_4)$alkyl- group is substituted by $R^4$, $R^5$, $R^6$ and $R^7$, wherein:
$R^4$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, wherein the phenyl moiety of said phenoxy or phenyl$(C_1-C_4)$alkoxy- is optionally substituted by 1-3 substituents each independently selected from the group consisting of halogen, —$CF_3$, $(C_1-C_4)$alkyl and $(C_1-C_4)$alkoxy; and
each of $R^5$, $R^6$ and $R^7$ is independently selected from the group consisting of H, hydroxyl, halogen, —$CF_3$, hydroxy$(C_1-C_4)$alkyl, $(C_1-C_4)$alkyl and $(C_1-C_4)$alkoxy; or
Z is phenyl or pyridyl, substituted by $R^8$, $R^9$ and $R^{10}$, wherein:
$R^8$ and $R^9$ are located on adjacent atoms and taken together with the atoms to which they are attached form a 5-membered ring containing 1, 2 or 3 heteroatoms each independently selected from N, O and S, which 5-membered ring is substituted by $R^{11}$;
wherein one of $R^{10}$ or $R^{11}$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy; and
the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy; or Z is pyrazolyl, having the formula:

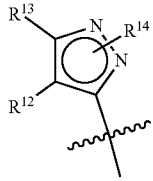

wherein:

R$^{12}$ is H, methyl or hydroxymethyl;

R$^{13}$ is methyl, trifluoromethyl or hydroxymethyl;

R$^{14}$ is H, OH, or (C$_1$-C$_3$)alkyl; or

R$^{12}$ and R$^{13}$, taken together with the atoms to which they are attached, form a 6-membered ring substituted by R$^{15}$ and R$^{16}$, wherein the 6-membered ring optionally contains 1 nitrogen atom;

wherein R$^{15}$ and R$^{16}$ are each independently selected from the group consisting of H, halogen, cyano, (C$_1$-C$_4$) alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, and aminocarbonyl, wherein the phenyl moiety of said phenoxy or phenyl(C$_2$-C$_4$)alkoxy is optionally substituted by 1-3 substituents each independently selected from the group consisting of halogen, —CF$_3$, (C$_1$-C$_4$) alkyl and (C$_1$-C$_4$)alkoxy;

and the IAP moiety is of formula II, IIA, III, IV, V or VA (L in the formulae below denotes the linker)

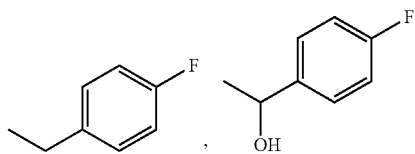

(II)

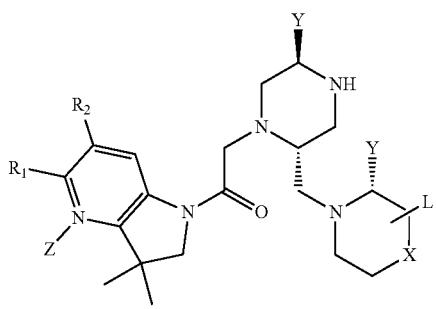

(IIA)

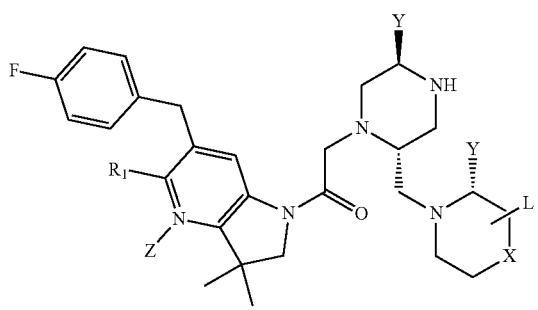

where each Y in Formula (II) and (IIA) is independently H or C$_{1-3}$ alkyl and X is CH, O or N (but cannot be O when attached to the linker). Z represents C$_{1-3}$ alkyl or is absent, R$^1$ is oxo or is absent, R$_2$ in Formula (II) is CH(F$_2$) CH$_2$CH$_2$CH$_3$, COCH$_2$CH$_2$CH$_3$, CH(OH)CH$_2$CH$_2$CH$_3$, (III)

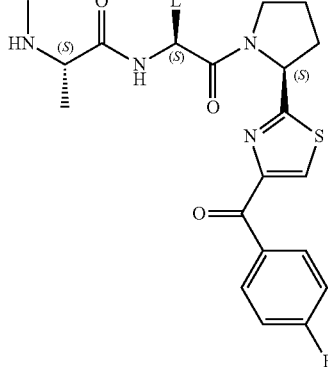

(IV)

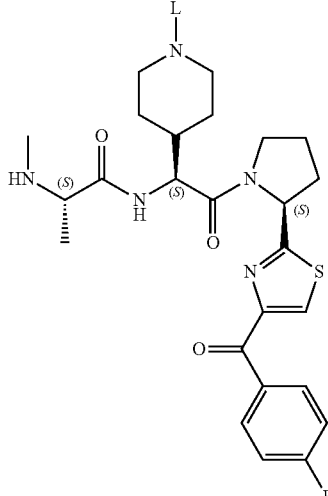

(V)

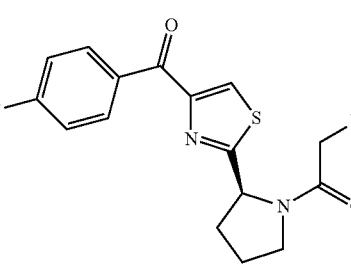

(VA)

Where each Y is independently H or $C_{1-3}$ alkyl and X is CH, O or N (but cannot be O when attached to the linker). or a pharmaceutically acceptable salt thereof.

In a further aspect of the present invention, there is provided a compound of formula (I) or a pharmaceutically acceptable salt thereof for use in therapy.

In a further aspect there is provided a compound of formula (I) or a pharmaceutically acceptable salt thereof for use in the treatment of diseases conditions mediated by RIP2 Kinase.

In a further aspect of the present invention, there is provided a pharmaceutical composition comprising a compound of formula (I) or a pharmaceutically acceptable salt thereof and one or more of pharmaceutically acceptable carriers, diluents and excipients.

In a further aspect of the present invention, there is provided a method of treating diseases and conditions mediated by the RIP2 Kinase in a subject comprising administering a therapeutically effective amount of a compound of formula (I) or a pharmaceutically acceptable salt thereof.

In a further aspect of the present invention, there is provided the use of a compound of formula (I), or a pharmaceutically acceptable salt thereof in the manufacture of a medicament for use in treating diseases and conditions mediated by the RIP2 Kinase.

In a further aspect there is provided a combination comprising a compound of formula (I), or a pharmaceutically acceptable salt thereof and at least one further therapeutic agent.

In a further aspect there is provided a combination comprising a compound of formula (I) or a pharmaceutically acceptable salt thereof and at least one further therapeutic agent for use in therapy.

In a further aspect of the present invention, there is provided a pharmaceutical composition comprising a combination comprising a compound of formula (I) or a pharmaceutically acceptable salt thereof and at least one further therapeutic agent and one or more of pharmaceutically acceptable carriers, diluents and excipients.

In a further aspect of the invention there is provided a combination comprising compound of formula (I) or a pharmaceutically acceptable salt thereof and at least one further therapeutic agent for use in treating diseases and conditions mediated by the RIP2 Kinase.

In a further aspect there is provided a method of treating diseases and conditions mediated by the RIP2 Kinase comprising administering to a human in need thereof a therapeutically effective amount of a combination comprising compound of formula (I) or a pharmaceutically acceptable salt thereof, and at least one further therapeutic agent.

In a further aspect there is provided the use of a combination comprising compound of formula (I) or a pharmaceutically acceptable salt thereof and at least one further therapeutic agent in the manufacture of a medicament for treating diseases and conditions mediated by RIP2 Kinase.

In a further aspect there is provided a method of degrading RIP2 kinase comprising administering to a human in need thereof a therapeutically effective amount of a compound of Formula (I) or a pharmaceutically acceptable salt thereof

DETAILED DESCRIPTION OF THE INVENTION

As used herein, "a compound of the invention" includes all solvates, complexes, polymorphs, radiolabelled derivatives, stereoisomers and optical isomers of the compounds of formula (I) and salts thereof.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of formula (I) may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

It is also noted that the compounds of formula (I) may form tautomers. It is understood that all tautomers and mixtures of tautomers of the compounds of the present invention are included within the scope of the compounds of the present invention.

The compound of Formula (I) is a Protac targeting RIP Kinase wherein the RIP2 kinase inhibitor is linked via a linker to a IAP binder.

In one aspect the RIP2 kinase inhibitor is

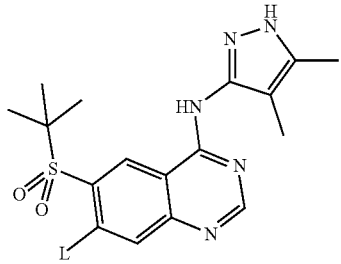

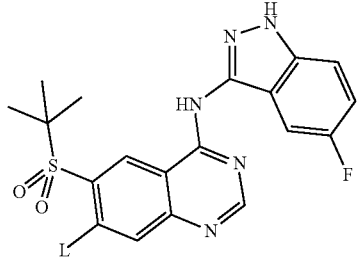

where L denotes the linker
and the IAP moiety is of formula II, IIA, III, IV V or VA (L in the formulae below denotes the linker)

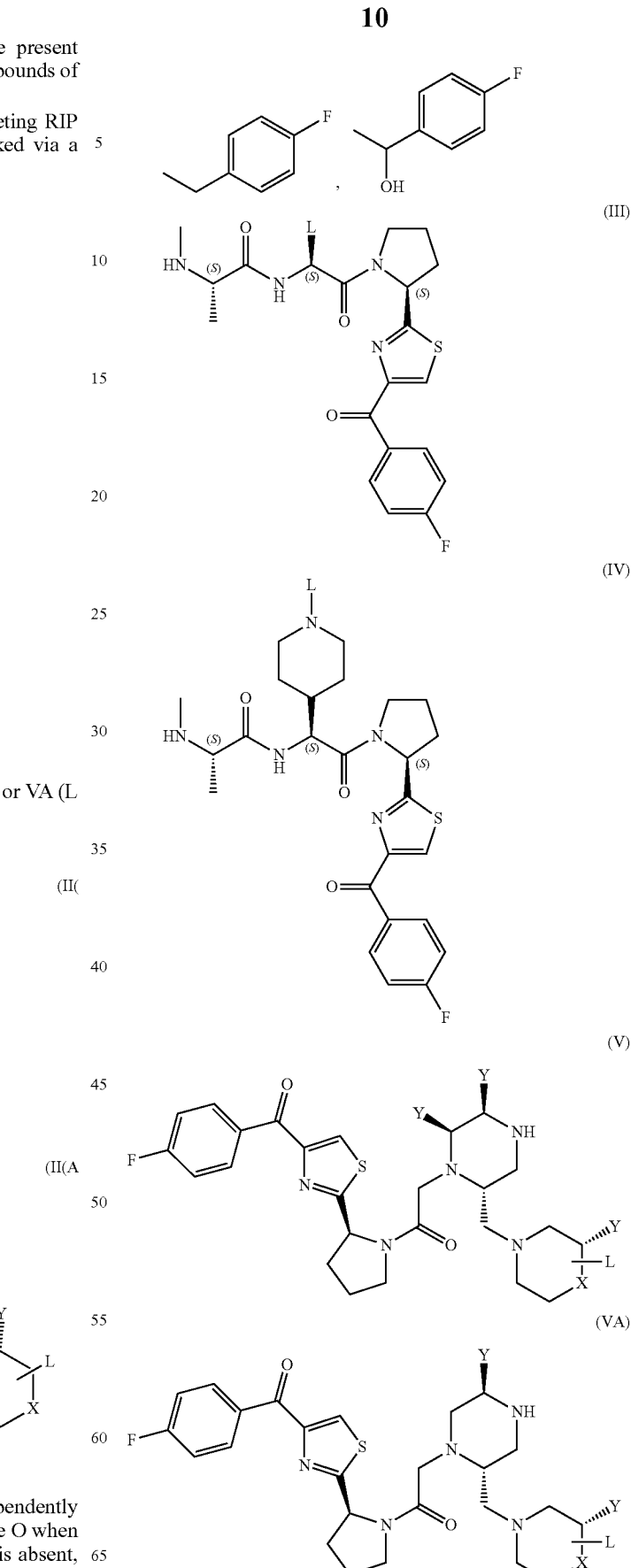

Where each Y in Formula (II) and (IIA) is independently H or $C_{1-3}$ alkyl and X is CH, O or N (but cannot be O when attached to the linker). Z represents $C_{1-3}$ alkyl or is absent, $R^1$ is oxo or is absent, $R_2$ in Formula (II) is $CH(F_2)$ $C_2CH_2CH_2C_3$, $COCH_2CH_2CH_3$, $CH(OH)CH_2CH_2CH_3$, Where each Y is independently H or $C_{1-3}$ alkyl and X is CH, O or N (but cannot be O when attached to the linker).

In one aspect the linker is 4-20 atoms in shortest length

In one aspect the linker is a straight chain alkylene group of 4-20 carbon atoms wherein one or more carbon atoms are replaced by a group each independently selected from —O—, —NH—, —N(CH$_3$)—, —CO—, piperidine, piperazine, pyrimidine, pyridine, phenyl.

In one aspect the linker is (in the direction RIP2 Kinase inhibitor-IAP inhibitor):

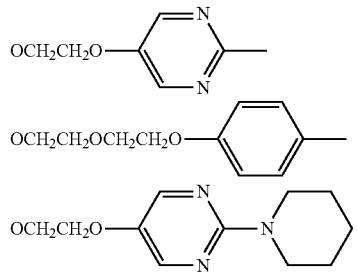

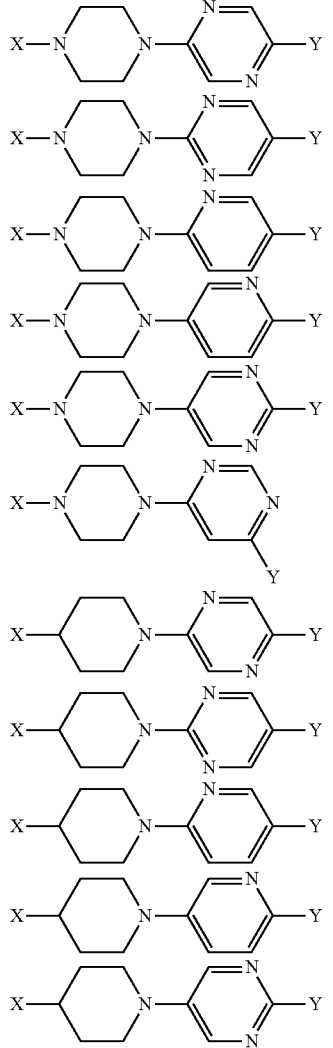

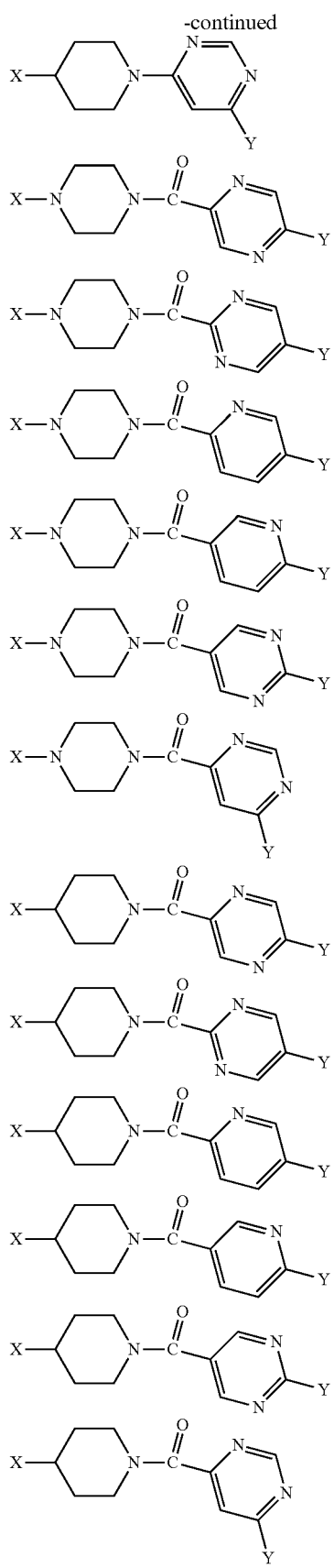

wherein x is —O(CH$_2$CH$_2$)$_{0-4}$, -
and Y is a bond, -, —O—, O(CH$_2$)$_{1-3}$ or —CO—.

In one embodiment X is CH$_2$.
In one embodiment X is OCH$_2$CH$_2$.
In one embodiment X is OCH$_2$CH$_2$CH$_2$.
In one embodiment Y is O.
In one embodiment Y is CO.
In one embodiment Y is OCH$_2$.
In one embodiment Y is an bond.
For the avoidance of doubt, each embodiment of Y and be combined with each embodiment of X.
In one embodiment, the IAP binding moiety is
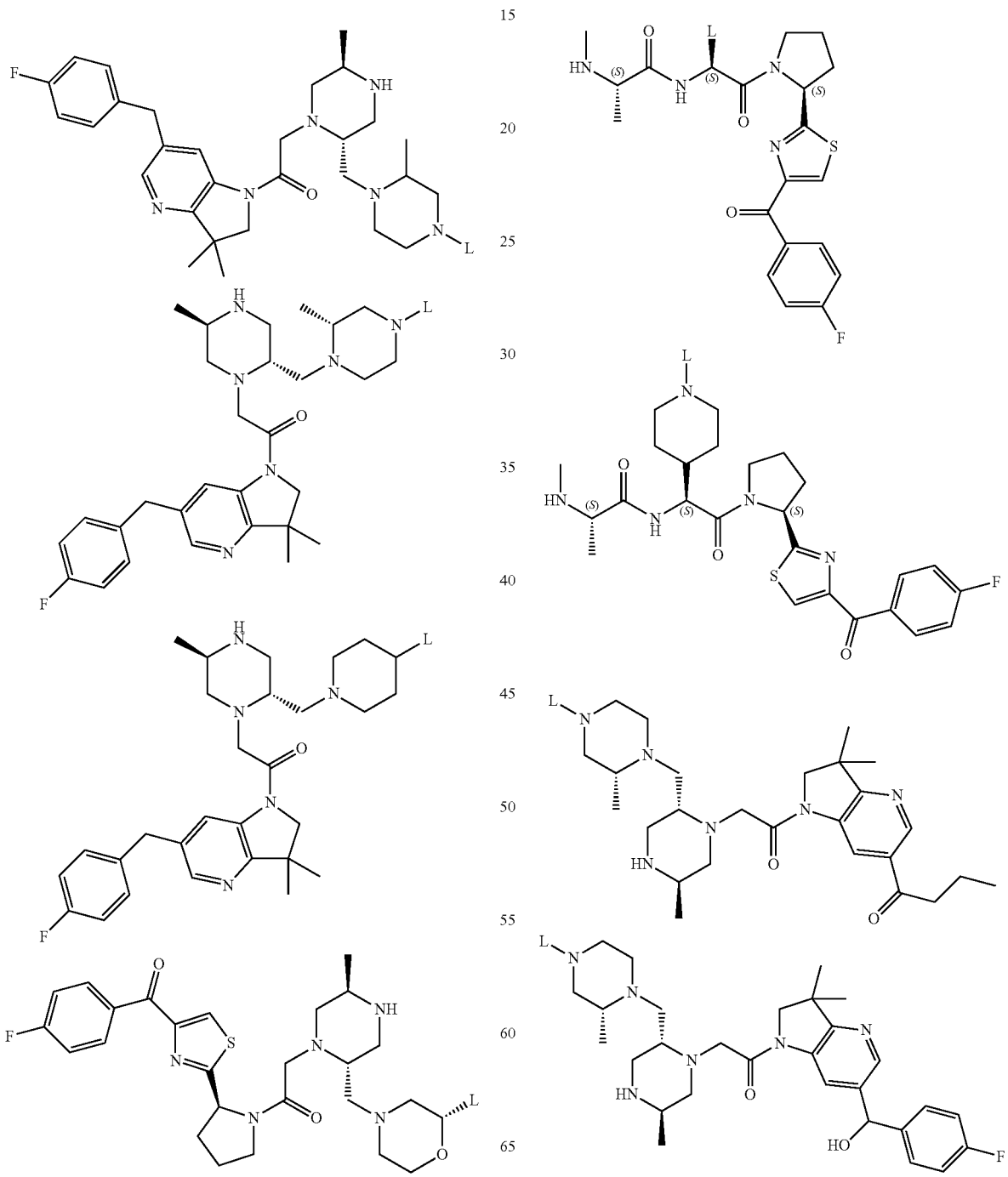

-continued

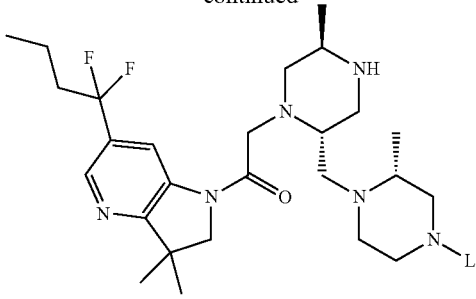

Wherein L denotes the linker.
Compounds of Formula (I) include:
14-((6-(Tert-butylsulfonyl)-4-((3,4-dimethyl-1H-pyrazol-5-yl)amino)quinazolin-7-yl)oxy)-1-(4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)-3,6,9,12-tetraoxatetradecan-1-one,
2-((2R,5R)-2-(((R)-4-(5-(2-((6-(Tert-butylsulfonyl)-4-((3,4-dimethyl-1H-pyrazol-5-yl)amino)quinazolin-7-yl)oxy)ethoxy)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(((6-(Tert-butylsulfonyl)-4-((3,4-dimethyl-1H-pyrazol-5-yl)amino)quinazolin-7-yl)oxy)methyl)piperidin-1-yl)pyrimidin-4-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((9-(5-(2-((6-(Tert-butylsulfonyl)-4-((3,4-dimethyl-1H-pyrazol-5-yl)amino)quinazolin-7-yl)oxy)ethoxy)pyrimidin-2-yl)-3,9-diazaspiro[5.5]undecan-3-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-((S)-2-(4-(4-fluorobenzoyl)thiazol-2-yl)pyrrolidin-1-yl)ethanone,
2-((2R,5R)-2-(((R)-4-(2-(2-(2-(2-((6-(tert-butylsulfonyl)-4-((5-fluoro-1H-indazol-3-yl)amino)quinolin-7-yl)oxy)ethoxy)ethoxy)ethoxy)ethyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(3-((6-(tert-butylsulfonyl)-4-((3,4-dimethyl-1H-pyrazol-5-yl)amino)quinazolin-7-yl)oxy)propyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(3-((6-(Tert-butylsulfonyl)-4-((3,4-dimethyl-1H-pyrazol-5-yl)amino)quinazolin-7-yl)oxy)propyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-yl)-2-(4-(4-fluorobenzoyl)thiazol-2-yl)pyrrolidin-1-yl)ethanone,
2-((2R,5R)-2-(((R)-2-(((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-2-(((2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((9-(5-(2-((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]undecan-3-yl)methyl)-5-methylpiperazin-1-yl)-1-yl)-2-(4-(4-fluorobenzoyl)thiazol-2-yl)pyrrolidin-1-yl)ethanone,
2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrazine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrimidine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(2-(4-(3-((6-(Tert-butylsulfonyl)-4-((3,4-dimethyl-1H-pyrazol-5-yl)amino)quinazolin-7-yl)oxy)propyl)piperidin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, (S)—N—((S)-3-(4-(2-(2-((6-(Tert-butylsulfonyl)-4-((4,5-dimethyl-1H-pyrazol-3-yl)amino)quinazolin-7-yl)oxy)ethoxy)ethoxy)phenyl)-1-((S)-2-(4-(4-fluorobenzoyl)thiazol-2-yl)pyrrolidin-1-yl)-1-oxopropan-2-yl)-2-(methylamino)propanamide, (S)—N—((S)-1-(1-(2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(6-(4-(2-((6-(tert-butylsulfonyl)-4-((4,5-dimethyl-1H-pyrazol-3-yl)amino)quinazolin-7-yl)oxy)ethyl)piperazin-1-yl)nicotinoyl)piperidin-4-yl)-2-((S)-2-(4-(4-fluorobenzoyl) thiazol-2-yl)pyrrolidin-1-yl)-2-oxoethyl)-2-(methylamino)propanamide (S)—N—((S)-1-(1-(6-(4-(2-((6-(tert-butylsulfonyl)-4-((4,5-dimethyl-1H-pyrazol-3-yl)amino)quinazolin-7-yl)oxy)ethyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(2-(4-(((6-(tert-butylsulfonyl)-4-((4,5-dimethyl-1H-pyrazol-3-yl)amino)quinazolin-7-yl)oxy)methyl)piperidin-1-yl)pyrimidine-5-carbonyl)piperidin-4-yl)-2-((S)-2-(4-(4-fluorobenzoyl)thiazol-2-yl))pyrrolidin-1-yl)-2-oxoethyl)-2-(methylamino)propanamide (S)—N—((S)-1-(1-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(5-(4-(3-((6-(Tert-butylsulfonyl)-4-((4,5-dimethyl-1H-pyrazol-3-yl)amino)quinazolin-7-yl)oxy)propyl)piperazin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(2-(4-(3-((6-(Tert-butylsulfonyl)-4-((4,5-dimethyl-1H-pyrazol-3-yl)amino)quinazolin-7-yl)oxy)propyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide (S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, (S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperazin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, 2-((2R,5R)-2-(((R)-4-(2-(4-(2-((6-(tert-butylsulfonyl)-4-((5-fluoro-1H-indazol-3-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyridin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 1-(1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-3,3-dimethyl-2,3-dihydro-1H-pyrrolo[3,2-b]pyridin-6-yl)butan-1-one, 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-((4-fluorophenyl)(hydroxy)methyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1-hydroxybutyl)-3,3-dimethyl-2,3-dihydro-1H-pyrrolo[3,2-b]pyridin-1-yl)ethanone, 1-(2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b]pyridin-5(4H)-one, 1-(2-((2R,5R)-2-((2R,5R)-2-(((2-(4-(3-((6-(Tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)acetyl)-6-(4-fluorobenzyl)-3,3-dimethyl-2,3-dihydro-1H-pyrrolo[3,2-b]pyridin-5(4H)-one.

1-(2-((2R,5R)-2-(((2R,5R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one.

2-((2R,5R)-2-(((2R,5R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5- methylpiperazin-1-yl)-1-(6-(4-fluorobenzyl)-3,3-dimethyl-2,3-dihydro-1H-pyrrolo[3,2-b]pyridin-1-yl)ethanone.

1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3-dimethyl-2,3-dihydro-1H-pyrrolo[3,2-b]pyridin-5(4H)-one.

1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one.

1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one.

1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one 2-(4-(3-((6-(Tert-butylsulfonyl)-4-((3,4-dimethyl-1H-pyrazol-5-yl)amino)quinazolin-7-yl)oxy)propyl)piperazin-1-yl)-1-((R)-4-((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)ethanone 1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-((S)-2-(4-(4-fluorobenzoyl)thiazol-2-yl)pyrrolidin-1-yl)ethanone 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1,1-difluorobutyl)-3,3-dimethyl-2,3-dihydro-1H-pyrrolo[3,2-b]pyridin-1-yl)ethanone 6-(4-(3-((6-(tert-butylsulfonyl)-4-((3,4-dimethyl-1H-pyrazol-5-yl)amino)quinazolin-7-yl)oxy)propyl)piperazine-1-carbonyl)-2-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)isoindolin-1-one, 1-(2-((2R,5R)-2-(((R)-4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-2-methyl-3-oxopiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, (R)-1-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-2-one, 1-(2-((2R, 5R)-2-(((R)-4-(2-(2-(4-(3-(6-(tert-butylsulfonyl)-4-(4, 5-dimethyl-1H-pyrazol-3-ylamino)quinazolin-7-yloxy)propyl)piperazin-1-yl)pyrimidin-5-yloxy)ethyl)-2-methyl-3-oxopiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R,5R)-2-(((R)-4-(5-(4-(3-(6-(tert-butylsulfonyl)-4-(4, 5-dimethyl-1H-pyrazol-3-ylamino)quinazolin-7-yloxy)propyl)piperazine-1-carbonyl)pyrazin-2-yl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R, 5R)-2-(((R)-4-(5-(4-(3-(6-(tert-butylsulfonyl)-4-(4,5-dimethyl-1H-pyrazol-3-ylamino)quinazolin-7-yloxy)propyl)piperazin-1-yl)pyrazine-2-carbonyl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R,5R)-2-(((R)-4-(2-(4-(3-(6-(tert-butylsulfonyl)-4-(4,5-dimethyl-1H-pyrazol-3-ylamino)quinazolin-7-yloxy)propyl)piperazin-1-yl)pyrimidine-5-carbonyl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, and pharmaceutically acceptable salts thereof The compounds of Formula (I) may be in the form of a salt.

Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

Suitable pharmaceutically acceptable salts can include acid addition salts.

A pharmaceutically acceptable acid addition salt can be formed by reaction of a compound of formula (I) with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, p-toluenesulfonate, benzenesulfonate, methanesulfonate, ethanesulfonate, naphthalenesulfonate (e.g. 2-naphthalenesulfonate) salt.

In one aspect the salt is a hydrochloride salt.

Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of formula (I).

While it is possible that, for use in therapy, the compound of the invention may be administered as the raw chemical, it is possible to present the compound of the invention as the active ingredient as a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavouring, preservative, dispersing and colouring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories, rectal foams, rectal gels or as enemas.

Dosage forms for nasal or inhaled administration may conveniently be formulated as aerosols, solutions, suspensions drops, gels or dry powders.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In one aspect the pharmaceutical composition is is suitable for oral or rectal administration for non systemic or local delivery to the GI tract, or is formulated for subcutaneous delivery.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions.

The amounts of the compound(s) of formula (I) or pharmaceutically acceptable salt(s) thereof and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

The compounds of the invention may be particularly useful for treatment of RIP2 kinase-mediated diseases or disorders, particularly inflammatory disorders.

In one aspect the disease or condition is inflammation.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The compound of formula (I) may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of formula (I) include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of formula (I) include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of formula (I) include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of formula (I) include arthrosclerosis, arthritis, phlebitis, vasculitis, and lymphangitis.

Examples of inflammatory conditions of the digestive system which may be treated with the compounds of formula (I) include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of formula (I) include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compound of formula (I) may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compound of formula (I) may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic obstructive pulmonary disease, and inflammation accompanying infectious conditions (e.g., sepsis).

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, with or include one or more other therapeutic agents, for example selected from NSAIDS, corticosteroids, COX-2 inhibitors, cytokine inhibitors, anti-TNF agents, inhibitors oncostatin M, anti-malarials, immunosuppressive and cytostatics.

This invention also provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein; more specifically, for use in the treatment of a disease mediated by inhibition of RIP2 kinase.

The invention also provides for the use of a compound of Formula (I), or a salt thereof, particularly a pharmaceutically acceptable salt thereof, in the manufacture of a medicament for use in the treatment of a RIP2 kinase-mediated disease or disorder, for example the diseases and disorders recited herein.

In a further aspect there is provided a combination comprising a compound of formula (I) or a pharmaceutically acceptable salt thereof and at least one further therapeutic agent useful in the treatment of a disease mediated by inhibition of RIP2 kinase In a further aspect there is provided a combination comprising a compound of formula (I) or a pharmaceutically acceptable salt thereof and at least one further therapeutic agent useful in the treatment of a disease mediated by inhibition of RIP2 kinase for use in therapy.

In a further aspect there is provided a combination comprising a compound of formula (I) or pharmaceutically acceptable salt thereof and at least one one further therapeutic agent useful in the treatment of allergic disease, inflammation or autoimmune disease, for use in the treatment a disease mediated by inhibition of RIP2 kinase.

In a further aspect there is provided the use of a combination comprising a compound of formula (I) or a pharmaceutically acceptable salt thereof and at least one one further therapeutic agent useful in the treatment of allergic disease, inflammation or autoimmune disease in the manufacture of a medicament for the treatment of a disease mediated by inhibition of RIP2 kinase In a further aspect there is provided a method of treating allergic disease, inflammation or autoimmune disease comprising administering to a human in need thereof a therapeutically effective amount of a combination comprising a compound of formula (I) or a pharmaceutically acceptable salt thereof and at least one further therapeutic agent useful in the treatment of a disease mediated by inhibition of RIP2 kinase.

In a further aspect there is provided a pharmaceutical composition comprising a combination comprising a compound of formula (I) or a pharmaceutically acceptable salt thereof and at least one further therapeutic agent useful in the treatment of a disease mediated by inhibition of RIP2 kinase and one or more of pharmaceutically acceptable excipients.

General Synthetic Methods

Compounds of general formula (I) may be prepared by methods known in the art of organic synthesis. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

In particular, methods for preparing IAP compounds included in the present invention can be found in WO 2014/047024, WO 2014/055461, WO 2014/031487 and WO 2008/128171

Methods for preparing RIP2 inhibitors included in the present invention can be found in WO 2014/128622, WO 2014/043437, WO 2013/025958, WO 2012/122011, WO 2012/021580 and WO 2011/140442.

EXPERIMENTAL

Novel Compounds

General Synthetic Methods

Compounds of general formula (I) may be prepared by methods known in the art of organic synthesis. In all of the methods, it is well understood that protecting groups for sensitive or reactive groups may be employed where necessary in accordance with general principles of chemistry. Protecting groups are manipulated according to standard methods of organic synthesis (T. W. Green and P. G. M.

Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

In particular, methods for preparing IAP compounds included in the present invention can be found in WO 2014/047024, WO 2014055461, WO 2014031487 and WO 2008128171

Methods for preparing RIP2 inhibitors included in the present invention can be found in WO 2014/128622, WO 2014/043437, WO 2013/025958, WO 2012/122011, WO 2012/021580 and WO 2011/140442.

EXPERIMENTAL

Abbreviations:
DCM: dichloromethane.
DIAD: diisopropyl azodicarboxylate
DIPEA: N,N-diisopropylethylamine
DMF: N,N-dimethylformamide
h: hour.
HATU: 1-[Bis(dimethylamino)methylene]-1H-1,2,3-triazolo[4,5-b]pyridinium 3-oxide hexafluoro phosphate
HPLC: high-performance liquid chromatography
LCMS: liquid chromatography-mass spectrometry
Min: minutes.
NMP: N-methylpyrrolidone
NMR: Nuclear magnetic resonance
RT: retention time
tBu: tert-butyl.
TFA: trifluoroacetic acid.
THF: tetrahydrofuran.

LCMS Method A:

Unless specified, Method A was used for analysis.

The analysis was conducted on an Acquity UPLC BEH C18 column (50 mm×2.1 mm internal diameter 1.7 μm packing diameter) at 40° C.

The solvents employed were:
A=0.1% v/v solution of formic acid in water.
B=0.1% v/v solution of formic acid in acetonitrile.

The gradient employed was as follows:

| Time (minutes) | Flow Rate (mL/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

LCMS Method B:

The analysis was conducted on an Acquity UPLC BEH C18 column (50 mm×2.1 mm internal diameter 1.71 μm packing diameter) at 40° C.

The solvents employed were:
A=10 mM ammonium bicarbonate in water adjusted to pH 10 with ammonia solution.
B=acetonitrile.

The gradient employed was as follows:

| Time (minutes) | Flow Rate (mL/min) | % A | % B |
| --- | --- | --- | --- |
| 0 | 1 | 99 | 1 |
| 1.5 | 1 | 3 | 97 |
| 1.9 | 1 | 3 | 97 |
| 2.0 | 1 | 99 | 1 |

The UV detection was an averaged signal from wavelength of 210 nm to 350 nm and mass spectra were recorded on a mass spectrometer using alternate-scan positive and negative mode electrospray ionization.

LCMS Method C:

The analysis was conducted on an Acquity UPLC CSH C18 column (50 mm×2.1 mm internal diameter 1.7 μm packing diameter) at 40° C.

The solvents employed were:
A=0.1% v/v solution of trifluoroacetic acid in water.
B=0.1% v/v solution of trifluoroacetic acid in acetonitrile.

The gradient employed was as follows:

| Time (minutes) | Flow Rate (mL/min) | % A | % B |
| --- | --- | --- | --- |
| 0 | 1 | 95 | 5 |
| 1.5 | 1 | 5 | 95 |
| 1.9 | 1 | 5 | 95 |
| 2.0 | 1 | 95 | 5 |

The UV detection was an averaged signal from wavelength of 210 nm to 350 nm and mass spectra were recorded on a mass spectrometer using alternate-scan positive and negative mode electrospray ionization.

The following illustrates the mobile phases and gradients used when compounds underwent purification by mass-directed autopreparative HPLC.

Mass-Directed Autooreparative HPLC (Formic Acid Modifier)

The HPLC analysis was conducted on a Sunfire C18 column (150 mm×30 mm internal diameter, 5 μm packing diameter) at ambient temperature.

The solvents employed were:
A=0.1% v/v solution of formic acid in water.
B=0.1% v/v solution of formic acid in acetonitrile.

Mass-Directed Autopreparative HPLC (Trifluoroacetic Acid Modifier)

The HPLC analysis was conducted on a Sunfire C18 column (150 mm×30 mm internal diameter, 5 μm packing diameter) at ambient temperature.

The solvents employed were:
A=0.1% v/v solution of trifluoroacetic acid in water.
B=0.1% v/v solution of trifluoroacetic acid in acetonitrile.

Mass-Directed Autopreparative HPLC (Ammonium Bicarbonate Modifier)

The HPLC analysis was conducted on an XBridge C18 column (150 mm×30 mm internal diameter, 5 μm packing diameter) at ambient temperature.

The solvents employed were:
A=10 mM ammonium bicarbonate in water adjusted to pH 10 with ammonia solution.
B=acetonitrile.

For each of the mass-directed autopreparative purifications, irrespective of the modifier used, the gradient employed was dependent upon the retention time of the particular compound undergoing purification as recorded in the analytical LCMS, and was as follows:

For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ChemBioDraw Ultra v12 from CambridgeSoft.

6-(Tert-butylsulfonyl)-N-(5-fluoro-1H-indazol-3-yl)-7-methoxyquinolin-4-amine

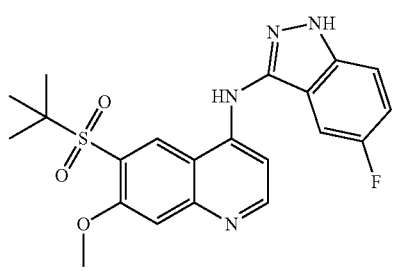 [SMILES: COc1cc2nccc(Nc3n[nH]c4ccc(F)cc34)c2cc1S(=O)(=O)C(C)(C)C]

A mixture of 6-(tert-butylsulfonyl)-4-chloro-7-methoxyquinoline (200 mg, 0.637 mmol) and 5-fluoro-1H-indazol-3-amine (106 mg, 0.701 mmol) were taken up in ethanol (3 mL) and 3 drops of conc HCl was added. The reaction was stirred at room temperature overnight, concentrated and the residue was purified by flash chromatography (0→10% MeOH with 1% $NH_4OH$ in DCM). Concentration of the desired fractions afforded the title compound (240 mg, 0.560 mmol, 88% yield). LCMS RT=0.60 min, ES+ve 429.

6-(Tert-butylsulfonyl)-4-((5-fluoro-1H-indazol-3-yl)amino)quinolin-7-ol

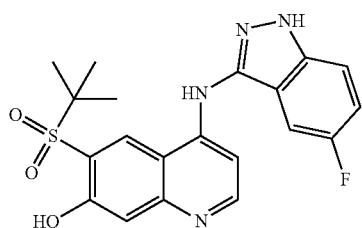 [SMILES: CC(C)(C)S(=O)(=O)c1cc2c(Nc3n[nH]c4ccc(F)cc34)ccnc2cc1O]

To a DMF (30 mL) solution of 6-(tert-butylsulfonyl)-N-(5-fluoro-1H-indazol-3-yl)-7-methoxyquinolin-4-amine (2 g, 4.67 mmol) was added sodium 2-methylpropane-2-thiolate (2.62 g, 23.34 mmol). The reaction was then heated to 150° C. for 1 hour. It was cooled to room temperature and concentrated under vacuum. The residue was purified by flash chromatography (0→15% MeOH with 1% $NH_4OH$ in DCM). Desired fractions were combined and concentrated to afford the title compound (1.22 g, 2.94 mmol, 63.1% yield). LCMS RT=0.61 min, ES+ve 415.

6-(Tert-butylsulfonyl)-7-(2-(2-(2-(2-chloroethoxy)ethoxy)ethoxy)-N-(5-fluoro-1H-indazol-3-yl)quinolin-4-amine

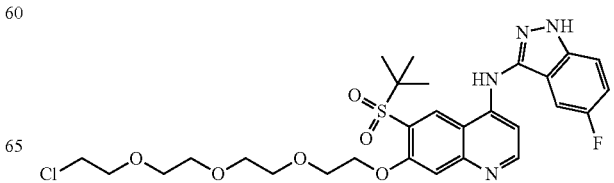

To a solution of 6-(tert-butylsulfonyl)-4-((5-fluoro-1H-indazol-3-yl)amino)quinolin-7-ol (100 mg, 0.241 mmol) in NMP (1.0 mL) was added 1-chloro-2-(2-(2-(2-chloroethoxy)ethoxy)ethoxy)ethane (167 mg, 0.724 mmol), sodium iodide (3.62 mg, 0.024 mmol) and potassium carbonate (100 mg, 0.724 mmol) and the reaction was stirred at 95° C. in the microwave for 1 hour. The residue was purified by flash chromatography (30 g pre-packed C-18 SNAP cartridge: 30% to 85% acetonitrile (0.1% ammonia) in water (10 mM ammonium bicarbonate)). The desired fractions were combined and concentrated to afford the title compound (90 mg, 0.148 mmol, 61.2% yield). LCMS Method B RT=1.08 min, ES+ve 609.

Tert-butyl 14-((6-(tert-butylsulfonyl)-4-((3,4-dimethyl-1H-pyrazol-5-yl)amino)quinazolin-7-yl)oxy)-3,6,9,12-tetraoxatetradecan-1-oate

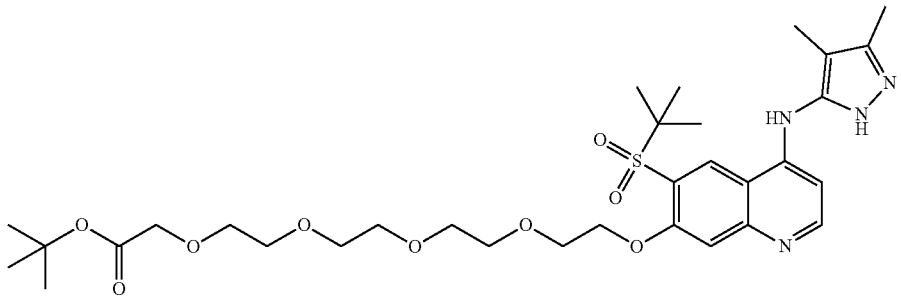 [SMILES: Cc1n[nH]c(Nc2ccnc3cc(OCCOCCOCCOCCOCC(=O)OC(C)(C)C)c(S(=O)(=O)C(C)(C)C)cc23)c1C]

To a solution of 6-(tert-butylsulfonyl)-4-((4,5-dimethyl-1H-pyrazol-3-yl)amino)quinazolin-7-ol (140 mg, 0.373 mmol, obtained as described in WO 2014/128622) in DMF (2 mL) was added tert-butyl 14-(tosyloxy)-3,6,9,12-tetraoxatetradecan-1-oate (259 mg, 0.559 mmol, prepared as described in Nature Chemical Biology, 2015, 11, 611), potassium carbonate (155 mg, 1.119 mmol) and sodium iodide (55.9 mg, 0.373 mmol) and the reaction was stirred at 80° C. for 2 hours. The product was subjected directly to purification by mass-directed automated preparative HPLC (formic acid modifier) to afford the title compound (35 mg, 0.046 mmol, 12% yield). LCMS RT=0.83 min, ES+ve 666.

Tert-butyl 4-(14-((6-(tert-butylsulfonyl)-4-((3,4-dimethyl-1H-pyrazol-5-yl)amino)quinazolin-7-yl)oxy)-3,6,9,12-tetraoxatetradecan-1-oyl)-2-methyl piperazine-1-carboxylate

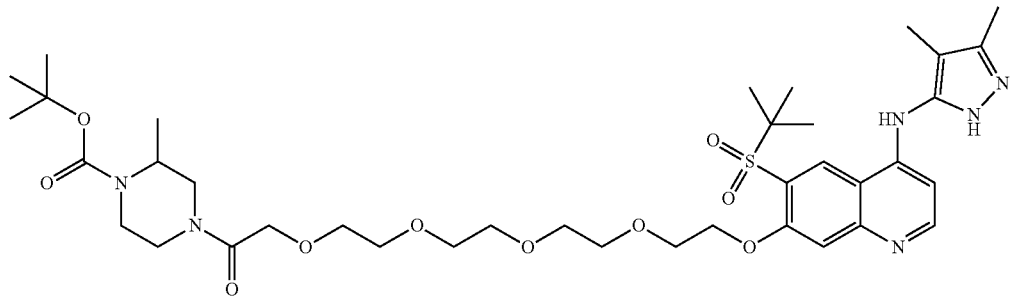 [SMILES: Cc1n[nH]c(Nc2ccnc3cc(OCCOCCOCCOCCOCC(=O)N4CCN(C(=O)OC(C)(C)C)C(C)C4)c(S(=O)(=O)C(C)(C)C)cc23)c1C]

To a solution of tert-butyl 14-((6-(tert-butylsulfonyl)-4-((4,5-dimethyl-1H-pyrazol-3-yl)amino)quinazolin-7-yl)oxy)-3,6,9,12-tetraoxatetradecan-1-oate (200 mg, 0.300 mmol) in DCM (2 mL) was added hydrochloric acid (2.253 mL, 9.01 mmol) 4M in dioxane and the reaction was stirred at 20° C. under an atmosphere of nitrogen for one hour. The volatiles were removed under vacuum, and to the resulting residue was added DCM (2 mL) and DMF (200 ul), DIPEA (0.210 mL, 1.202 mmol), tert-butyl 2-methylpiperazine-1-carboxylate (0.085 mL, 0.360 mmol) and 1-ethyl-3-(3-dimethylaminopropyl)carbodiimide (69.1 mg, 0.360 mmol). The reaction was stirred at room temperature under an atmosphere of nitrogen for 3 days. The reaction was diluted in 50 mL EtOAc, washed with 50 mL saturated sodium bicarbonate solution, 50 mL water, 50 mL 2 M HCl and 50 mL brine. The aqueous layer was neutralised with saturated sodium bicarbonate solution, and washed with 3×100 mL EtOAc. The organic layer was passed through a Biotage phase separator and concentrated under vacuum to afford the title compound (75 mg, 0.095 mmol, 32% yield). LCMS RT=0.83 min, ES+ve 792.

(2R,5S)-Tert-butyl 5-((4-(14-((6-(tert-butylsulfonyl)-4-((3,4-dimethyl-1H-pyrazol-5-yl)amino)quinazolin-7-yl)oxy)-3,6,9,12-tetraoxatetradecan-1-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

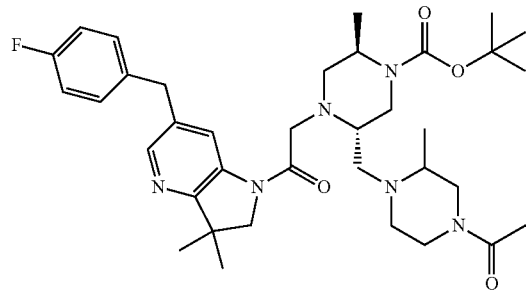

To a solution of tert-butyl 4-(14-((6-(tert-butylsulfonyl)-4-((4,5-dimethyl-1H-pyrazol-3-yl)amino)quinazolin-7-yl)oxy)-3,6,9,12-tetraoxatetradecan-1-oyl)-2-methylpiperazine-1-carboxylate (75 mg, 0.095 mmol) in chloroform (0.5 mL) was added HCl (0.713 mL, 2.85 mmol) 4M in dioxane and the reaction was stirred at room temperature for 1 hour. The solvents were removed in vacuo, and the compound was resuspended in 0.5 mL acetonitrile. To this solution was added (2R,5R)-tert-butyl 5-(chloromethyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (51.8 mg, 0.095 mmol, obtained as described in WO 2012/143726) in acetonitrile (0.5 mL), potassium carbonate (131 mg, 0.950 mmol) and sodium iodide (28.5 mg, 0.190 mmol) and the reaction was stirred at 50° C. for 18 h. The reaction was diluted in 10 mL DCM and washed with 10 mL saturated sodium bicarbonate solution. The aqueous layer was washed with an additional 3×10 mL DCM, and the combined organic layers were washed with 30 mL brine and passed through a Biotage phase separator. The volatiles were removed in vacuo, and the residue was subjected directly to purification by flash chromatography (12 g pre-packed C-18 SNAP cartridge: 50% to 95% acetonitrile (0.1% ammonia) in water (10 mM ammonium bicarbonate)). The desired fractions were combined and concentrated to afford the title compound (40 mg, 0.033 mmol, 35.1% yield). LCMS Method B RT=1.32 min, ES+ve 1200.

2-((6-(Tert-butylsulfonyl)-4-((3,4-dimethyl-1H-pyrazol-5-yl)amino)quinazolin-7-yl)oxy)ethanol

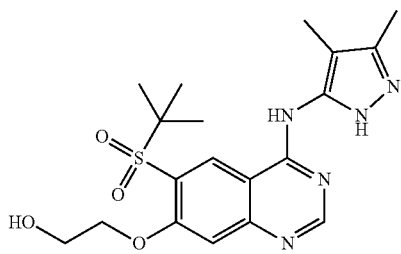 [SMILES: Cc1n[nH]c(Nc2ncnc3cc(OCCO)c(S(=O)(=O)C(C)(C)C)cc23)c1C]

To a solution of 6-(tert-butylsulfonyl)-N-(4,5-dimethyl-1H-pyrazol-3-yl)-7-fluoroquinazolin-4-amine (250 mg, 0.662 mmol, obtained as described in WO 2014/128622) in ethylene glycol (923 µl, 16.56 mmol) was added sodium hydride (79 mg, 3.31 mmol) and the reaction was stirred at 100° C. for 105 minutes in a Biotage microwave. It was cooled to room temperature and subjected directly to purification by flash chromatography (60 g pre-packed C-18 SNAP cartridge: 5% to 30% acetonitrile (0.1% formic acid) in water (0.1% formic acid)). The desired fractions were combined and concentrated to afford the title compound (200 mg, 0.48 mmol, 72% yield). LCMS RT=0.54 min, ES+ve 420.

6-(Tert-butylsulfonyl)-7-(2-((2-chloropyrimidin-5-yl)oxy)ethoxy)-N-(3,4-dimethyl-1H-pyrazol-5-yl)quinazolin-4-amine

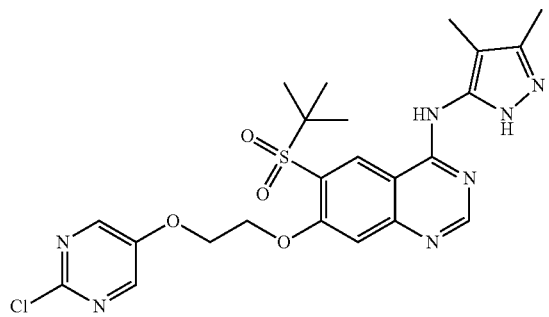 [SMILES: Cc1n[nH]c(Nc2ncnc3cc(OCCOc4cnc(Cl)nc4)c(S(=O)(=O)C(C)(C)C)cc23)c1C]

To a solution of 2-((6-(tert-butylsulfonyl)-4-((4,5-dimethyl-1H-pyrazol-3-yl)amino)quinazolin-7-yl)oxy)ethanol (247 mg, 0.589 mmol) in THF (5 mL) was added 2-chloropyrimidin-5-ol (85 mg, 0.648 mmol), triphenylphosphine (232 mg, 0.883 mmol) and DIAD (0.172 mL, 0.883 mmol) and the reaction was stirred at 20° C. under an atmosphere of nitrogen for 42 hours. The reaction was concentrated, and the residue was subjected directly to purification by flash chromatography (60 g pre-packed C-18 SNAP cartridge: 5% to 30% acetonitrile (0.1% formic acid) in water (0.1% formic acid)). The desired fractions were combined and concentrated to afford the title compound (167 mg, 0.31 mmol, 53.3% yield). LCMS RT=0.73 min, ES+ve 532.

Tert-butyl 9-(5-(2-((6-(tert-butylsulfonyl)-4-((3,4-dimethyl-1H-pyrazol-5-yl)amino)quinazolin-7-yl)oxy)ethoxy)pyrimidin-2-yl)-3,9-diazaspiro[5.5]undecane-3-carboxylate

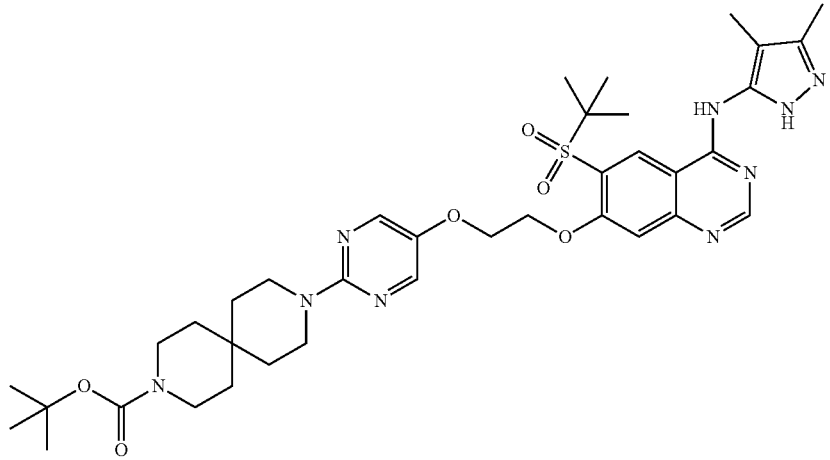 [SMILES: Cc1n[nH]c(Nc2ncnc3cc(OCCOc4cnc(N5CCC6(CCN(C(=O)OC(C)(C)C)CC6)CC5)nc4)c(S(=O)(=O)C(C)(C)C)cc23)c1C]

To 6-(tert-butylsulfonyl)-7-(2-((2-chloropyrimidin-5-yl)oxy)ethoxy)-N-(4,5-dimethyl-1H-pyrazol-3-yl)quinazolin-4-amine (81 mg, 0.152 mmol) in NMP (1 mL) was added tert-butyl 3,9-diazaspiro[5.5]undecane-3-carboxylate (58.1 mg, 0.228 mmol) and DIPEA (0.080 mL, 0.457 mmol). The reaction was stirred at 110° C. in a sealed tube for 18 h. Additional tert-butyl 3,9-diazaspiro[5.5]undecane-3-carboxylate (58.1 mg, 0.228 mmol) was added and the reaction was stirred at 110° C. in a sealed tube for a further 4 h.

The reaction was concentrated, and the residue was subjected directly to purification by flash chromatography (12 g pre-packed C-18 SNAP cartridge: 30% to 85% acetonitrile (0.1% formic acid) in water (0.1% formic acid)). The desired fractions were combined and concentrated to afford the title compound (64 mg, 0.085 mmol, 56.1% yield). LCMS RT=1.09 min, ES+ve 750.

7-(2-((2-(3,9-Diazaspiro[5.5]undecan-3-yl)pyrimidin-5-yl)oxy)ethoxy)-6-(tert-butylsulfonyl)-N-(3,4-dimethyl-1H-pyrazol-5-yl)quinazolin-4-amine

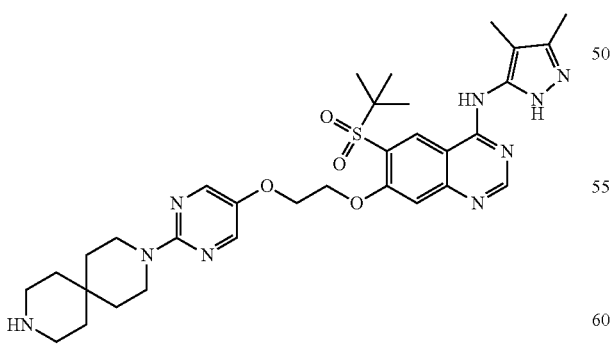

To tert-butyl 9-(5-(2-((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]undecane-3-carboxylate (64 mg, 0.085 mmol) in DCM (0.5 mL), was added TFA (0.329 mL, 4.27 mmol) and the reaction was stirred at room temperature under an atmosphere of nitrogen for 30 minutes. The volatiles were removed under vacuum to afford the title compound (82 mg, 0.083 mmol, 97% yield). LCMS RT=0.54 min, ES+ve 650.

6-(Tert-butylsulfonyl)-N-(3,4-dimethyl-1H-pyrazol-5-yl)-7-(piperidin-4-yloxy)quinazolin-4-amine Under nitrogen, a mixture of 6-(tert-butylsulfonyl)-N-(4,5-dimethyl-1H-pyrazol-3-yl)-7-fluoroquinazolin-4-amine (300 mg, 0.795 mmol, obtained as described in WO 2014/128622) and piperidin-4-ol (402 mg, 3.97 mmol) in dioxane (5 mL) and NMP (1.5 mL) was treated with sodium hydride (57.2 mg, 2.385 mmol) and stirred for 10 minutes. The mixture was then heated at 80° C. for 4 hours and cooled. The mixture was treated with acetic acid (0.5 mL) and evaporated down to ~1.5 mL. The product was subjected directly to purification by mass-directed automated preparative HPLC (ammonium bicarbonate modifier) to afford the title compound (270 mg, 0.59 mmol, 74.1% yield). LCMS RT=0.46 min, ES+ve 459.

6-(tert-butylsulfonyl)-N-(3,4-dimethyl-1H-pyrazol-5-yl)-7-(piperidin-4-ylmethoxy)quinazolin-4-amine

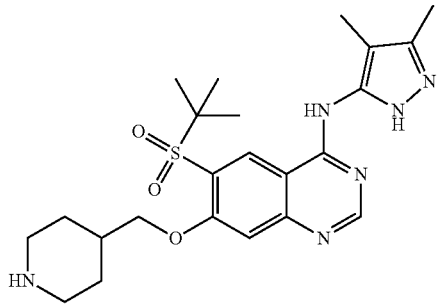 [SMILES: Cc1n[nH]c(Nc2ncnc3cc(OCC4CCNCC4)c(S(=O)(=O)C(C)(C)C)cc23)c1C]

Under nitrogen, a mixture of 6-(tert-butylsulfonyl)-N-(4,5-dimethyl-1H-pyrazol-3-yl)-7-fluoroquinazolin-4-amine (300 mg, 0.795 mmol, obtained as described in WO 2014/128622) and piperidin-4-ylmethanol (275 mg, 2.385 mmol) in 1,4-dioxane (5 mL) and NMP (1.5 mL) was treated with sodium hydride (60% w/w in mineral oil) (191 mg, 4.77 mmol) and stirred for 10 minutes. The mixture was then heated at 80° C. for 4 hours and cooled. The mixture was treated with acetic acid (0.5 mL) and evaporated down to ~1.5 mL. The product was subjected directly to purification by mass-directed automated preparative HPLC (ammonium bicarbonate modifier) to afford the title compound (298 mg, 0.631 mmol, 79% yield). LCMS RT=0.44 min, ES+ve 473.

Tert-butyl 4-(2-((6-(tert-butylsulfonyl)-4-((3,4-dimethyl-1H-pyrazol-5-yl)amino)quinazolin-7-yl)oxy)ethyl)piperazine-1-carboxylate

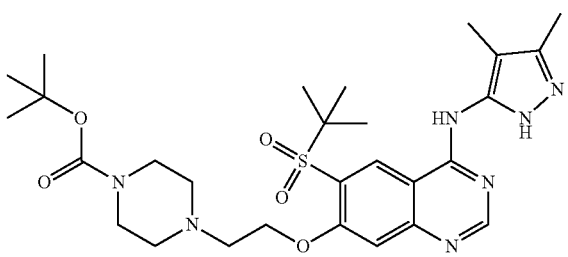 [SMILES: Cc1n[nH]c(Nc2ncnc3cc(OCCN4CCN(C(=O)OC(C)(C)C)CC4)c(S(=O)(=O)C(C)(C)C)cc23)c1C]

To a 100 mL round bottom flask was added sodium hydride (60% w/w in mineral oil) (1.590 g, 39.7 mmol) and 1,4-Dioxane (15 mL), the mixture was stirred under nitrogen to form a grey suspension. To the suspension was added tert-butyl 4-(2-hydroxyethyl)piperazine-1-carboxylate (9.15 g, 39.7 mmol) dropwise in 1,4-Dioxane (20 mL), the mixture was stirred for 20 mins to form a milky solution. Into the solution was added 6-(tert-butylsulfonyl)-N-(4,5-dimethyl-1H-pyrazol-3-yl)-7-fluoroquinazolin-4-amine (3 g, 7.95 mmol) via solid addition. The mixture immediately turned a deep red colour upon addition. The reaction mixture was stirred for 30 mins and then heated to 100° C. and stirred vigorously for a further hour The mixture was acidified to pH 7 with aqueous HCl (2M) and then partitioned between water and ethyl acetate. The aqueous layer was extracted and washed with ethyl acetate (2×40 mL). The combined organic layers were washed with water (40 mL) and saturated brine solution (40 mL). The organic layer was then dried over magnesium sulfate, filtered, concentrated, and the residue subjected directly to purification by flash chromatography (100 g pre-packed silica cartridge: 0% to 50% methanol in tert butyl methyl ether). Desired fractions were combined and concentrated to afford the title compound (1.31 g, 2.17 mmol, 27.4% yield). LCMS Method B RT=1.04 min, ES+ve 588.

(R)-tert-butyl 2-(((2-chloropyrimidin-5-yl)oxy)methyl)morpholine-4-carboxylate

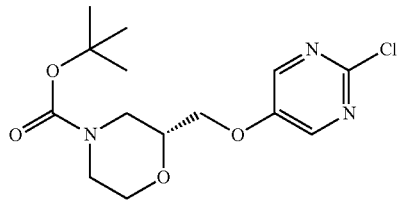 [SMILES: CC(C)(C)OC(=O)N1CCO[C@@H](COc2cnc(Cl)nc2)C1]

To a solution of (R)-tert-butyl 2-(hydroxymethyl)morpholine-4-carboxylate (605 mg, 2.79 mmol) in THF (5 mL) was added 2-chloropyrimidin-5-ol (200 mg, 1.532 mmol), triphenylphosphine (548 mg, 2.089 mmol) and DIAD (0.406 mL, 2.089 mmol) and the reaction was stirred at 20° C. under an atmosphere of nitrogen for 5 hours. The reaction was concentrated and resuspended in 1 mL DMSO, then was subjected directly to purification by flash chromatography (60 g pre-packed C-18 SNAP cartridge: 35% to 90% acetonitrile (0.1% formic acid) in water (0.1% formic acid)). The desired fractions were combined and concentrated to afford the title compound (410 mg, 1.24 mmol, 89% yield).

LCMS Method A RT=1.01 min, ES+ve 274 (M+H-tBu).

6-(Tert-butylsulfonyl)-N-(3,4-dimethyl-1H-pyrazol-5-yl)-7-(2-(piperazin-1-yl)ethoxy)quinazolin-4-amine

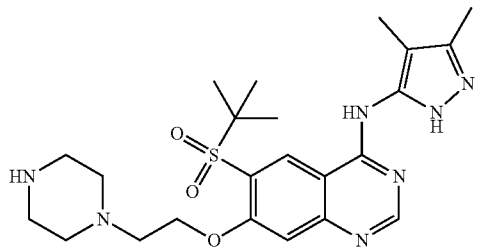 [SMILES: Cc1n[nH]c(Nc2ncnc3cc(OCCN4CCNCC4)c(S(=O)(=O)C(C)(C)C)cc23)c1C]

To a solution of tert-butyl 4-(2-((6-(tert-butylsulfonyl)-4-((4,5-dimethyl-1H-pyrazol-3-yl)amino)quinazolin-7-yl)

oxy)ethyl)piperazine-1-carboxylate (1.3 g, 2.212 mmol) in THF (5 mL) and methanol (10 mL) under nitrogen was added HCl (4M in dioxane) (5 ml, 20.00 mmol). The mixture was stirred at room temperature for 6 hours then filtered under vacuum to afford the title compound (1.25 g, 2.10 mmol, 95% yield). LCMS Method B RT=0.74 min, ES+ve 488.

Methyl 6-(4-(2-((6-(tert-butylsulfonyl)-4-((3,4-dimethyl-1H-pyrazol-5-yl)amino)quinazolin-7-yl)oxy)ethyl)piperazin-1-yl)nicotinate

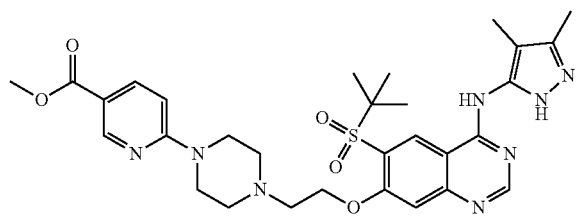

To a solution of 6-(tert-butylsulfonyl)-N-(4,5-dimethyl-1H-pyrazol-3-yl)-7-(2-(piperazin-1-yl)ethoxy)quinazolin-4-amine, 3Hydrochloride (400 mg, 0.670 mmol) in NMP (2 mL) was added DIPEA (0.585 mL, 3.35 mmol) and methyl 6-chloronicotinate (138 mg, 0.804 mmol), and the reaction was heated to 120° C. by microwave irradiation for 3 hours. The reaction was subjected directly to purification by flash chromatography (60 g pre-packed C-18 SNAP cartridge: 30% to 85% acetonitrile (0.1% ammonia) in water (10 mM ammonium formate)). The desired fractions were combined and concentrated to afford the title compound (261 mg, 0.42 mmol, 62.6% yield). LCMS Method B RT=1.00 min, ES+ve 623.

6-(4-(2-((6-(Tert-butylsulfonyl)-4-((3,4-dimethyl-1H-pyrazol-5-yl)amino)quinazolin-7-yl)oxy)ethyl)piperazin-1-yl)nicotinic acid

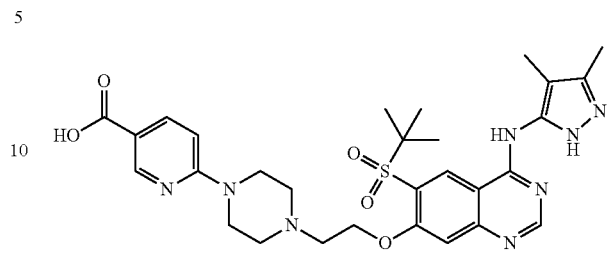

To a solution of methyl 6-(4-(2-((6-(tert-butylsulfonyl)-4-((4,5-dimethyl-1H-pyrazol-3-yl)amino)quinazolin-7-yl)oxy)ethyl)piperazin-1-yl)nicotinate (261 mg, 0.419 mmol) in methanol (2 mL) was added lithium hydroxide (2.24 mL) 1M solution in water, and the reaction was stirred at 40° C. for 25 hours. The reaction was neutralised with HCl (1.048 mL, 4.19 mmol) (4M solution in dioxane) and the volatiles were removed under vacuum to afford the title compound, which was used without further purification (291 mg, 0.41 mmol, 97% yield). LCMS RT=0.52 min, ES+ve 609.

6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinic acid

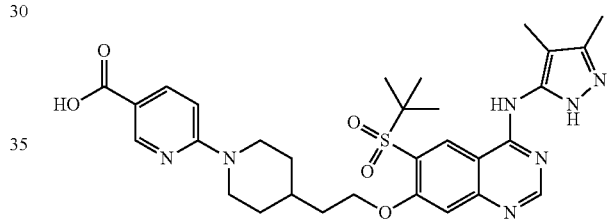

The title compound was prepared by a method analogous to those above.

| Compound Name | Structure | Yield | LCMS RT | ES +ve |
|---|---|---|---|---|
| tert-butyl 4-(2-((6-(tert-butylsulfonyl)-4-((3,4-dimethyl-1H-pyrazol-5-yl)amino)quinazolin-7-yl)oxy)ethyl)piperidine-1-carboxylate | 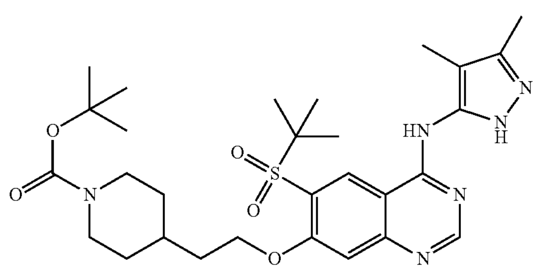 [SMILES: Cc1n[nH]c(Nc2ncnc3cc(OCCC4CCN(C(=O)OC(C)(C)C)CC4)c(S(=O)(=O)C(C)(C)C)cc23)c1C] | 52.1% | Method B 1.17 mins | 587 |
| 6-(tert-butylsulfonyl)-N-(3,4-dimethyl-1H-pyrazol-5-yl)-7-(2-(piperidin-4-yl)ethoxy)quinazolin-4-amine | 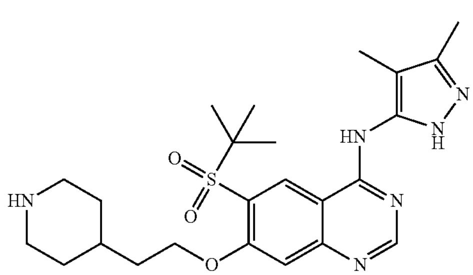 [SMILES: Cc1n[nH]c(Nc2ncnc3cc(OCCC4CCNCC4)c(S(=O)(=O)C(C)(C)C)cc23)c1C] | 85% | Method B 0.95 mins | 487 |

| Compound Name | Structure | Yield | LCMS RT | ES + ve |
|---|---|---|---|---|
| Methyl 6-(4-(2-((6-(tert-butylsulfonyl)-4-((3,4-dimethyl-1H-pyrazol-5-yl)amino)quinazolin-7-yl)oxy)ethyl)piperidin-1-yl)nicotinate | 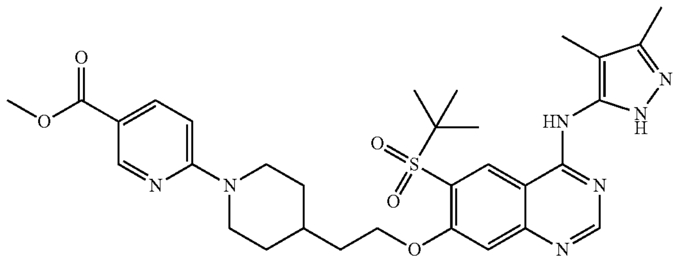 [SMILES: COC(=O)c1ccc(N2CCC(CCOc3cc4ncnc(Nc5[nH]nc(C)c5C)c4cc3S(=O)(=O)C(C)(C)C)CC2)nc1] | 35.5% | Method B 1.14 mins | 622 |
| 6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinic acid | 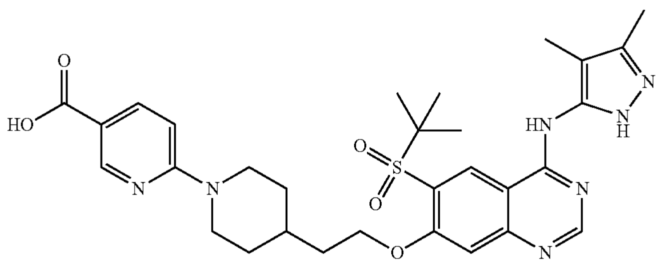 [SMILES: Cc1n[nH]c(Nc2ncnc3cc(OCCC4CCN(c5ccc(C(=O)O)cn5)CC4)c(S(=O)(=O)C(C)(C)C)cc23)c1C] | 99% | Method A 0.66 mins | 608 |

6-(4-(3-((6-tert-butylsulfonyl)-4-((3,4-dimethyl-1H-pyrazol-5-yl)amino)quinazolin-7-yl)oxy)propyl)piperazin-1-yl)nicotinic acid

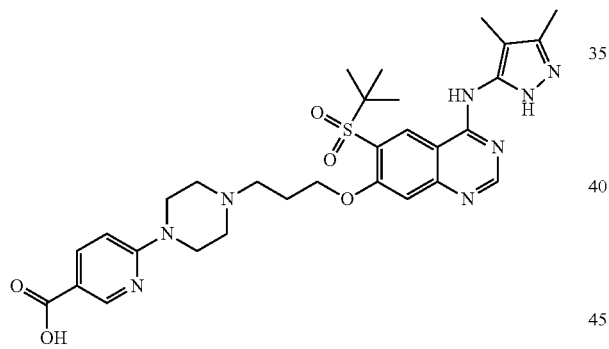

The title compound was prepared by a method analogous to those above.

| Compound Name | Structure | Yield | LCMS RT | ES + ve |
|---|---|---|---|---|
| Tert-butyl 4-(3-((6-(tert-butylsulfonyl)-4-((3,4-dimethyl-1H-pyrazol-5-yl)amino)quinazolin-7-yl)oxy)propyl)piperazine-1-carboxylate | 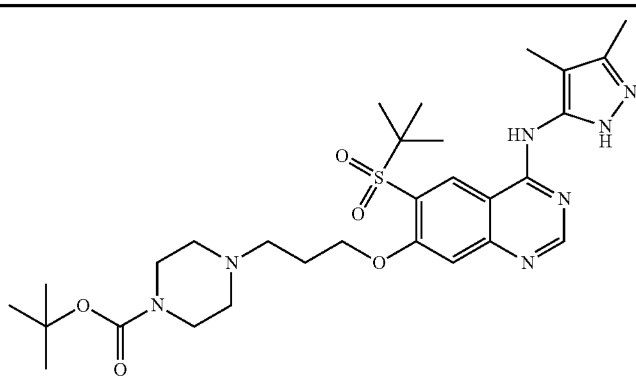 | 17.1% | Method B 1.06 mins | 602 |

| Compound Name | Structure | Yield | LCMS RT | ES + ve |
|---|---|---|---|---|
| 6-(tert-butylsulfonyl)-N-(3,4-dimethyl-1H-pyrazol-5-yl)-7-(3-(piperazin-1-yl)propoxy)quinazolin-4-amine | 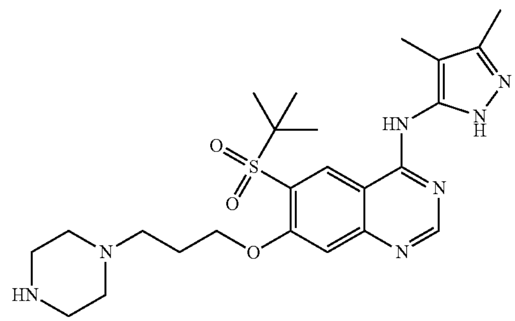 [SMILES: Cc1n[nH]c(Nc2ncnc3cc(OCCCN4CCNCC4)c(S(=O)(=O)C(C)(C)C)cc23)c1C] | 98% | Method B 0.84 mins | 502 |
| Methyl 6-(4-(3-((6-(tert-butylsulfonyl)-4-((3,4-dimethyl-1H-pyrazol-5-yl)amino)quinazolin-7-yl)oxy)propyl)piperazin-1-yl)nicotinate | 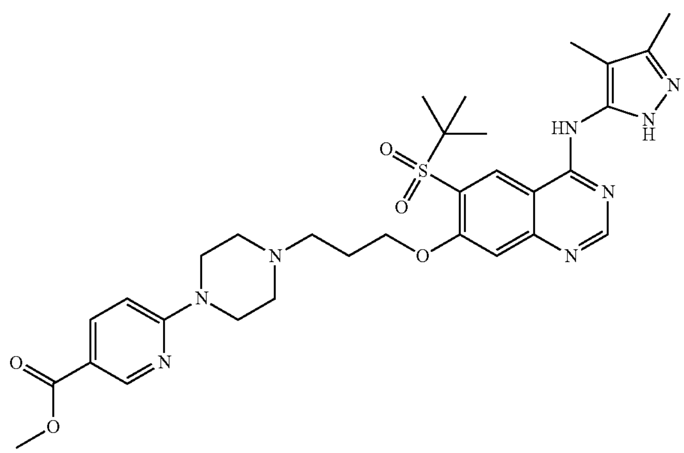 | 49.9% | Method B 1.02 mins | 637 |
| 6-(4-(3-((6-(Tert-butylsulfonyl)-4-((3,4-dimethyl-1H-pyrazol-5-yl)amino)quinazolin-7-yl)oxy)propyl)piperazin-1-yl)nicotinic acid | 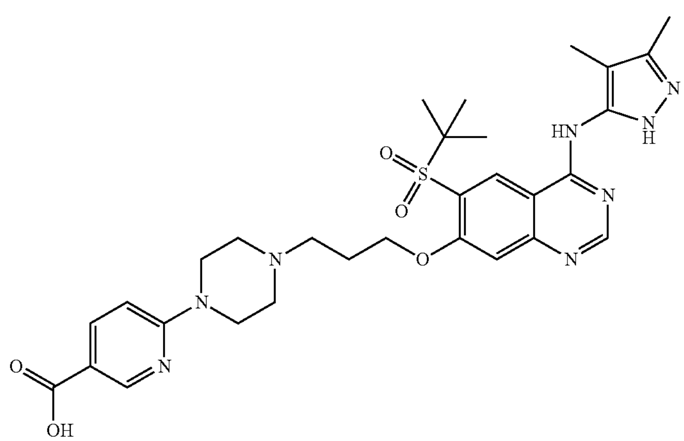 [SMILES: Cc1n[nH]c(Nc2ncnc3cc(OCCCN4CCN(c5ccc(C(=O)O)cn5)CC4)c(S(=O)(=O)C(C)(C)C)cc23)c1C] | 99% | Method A 0.49 mins | 623 |

6-(4-(3-((6-(tert-butylsulfonyl)-4-((3,4-dimethyl-1H-pyrazol-5-yl)amino)quinazolin-7-yl)oxy)propyl)piperidin-1-yl)nicotinic acid

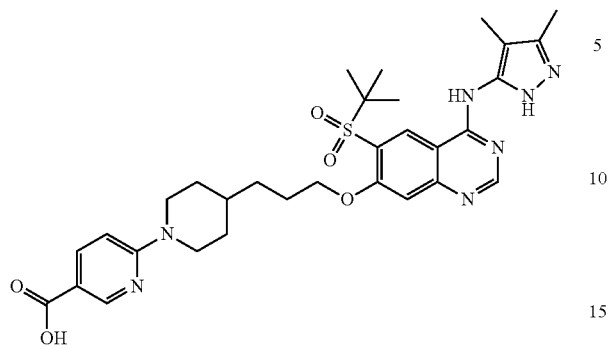

The title compound was prepared by a method analogous to those above.

| Compound Name | Structure | Yield | LCMS RT | ES + ve |
|---|---|---|---|---|
| tert-butyl 4-(3-((6-(tert-butylsulfonyl)-4-((3,4-dimethyl-1H-pyrazol-5-yl)amino)quinazolin-7-yl)oxy)propyl)piperidine-1-carboxylate | 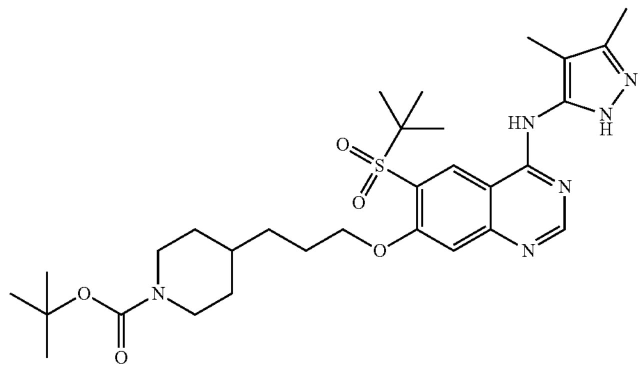 [SMILES: Cc1n[nH]c(Nc2ncnc3cc(OCCCC4CCN(C(=O)OC(C)(C)C)CC4)c(S(=O)(=O)C(C)(C)C)cc23)c1C] | 58.4% | Method A 1.03 mins | 601 |
| 6-(Tert-butylsulfonyl)-N-(3,4-dimethyl-1H-pyrazol-5-yl)-7-(3-(piperidin-4-yl)propoxy)quinazolin-4-amine | 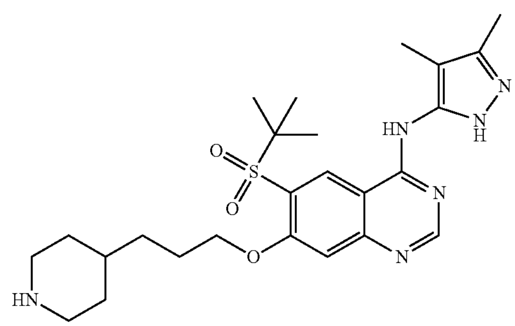 [SMILES: Cc1n[nH]c(Nc2ncnc3cc(OCCCC4CCNCC4)c(S(=O)(=O)C(C)(C)C)cc23)c1C] | 99% | Method A 0.47 mins | 501 |
| Methyl 6-(4-(3-((6-(tert-butylsulfonyl)-4-((3,4-dimethyl-1H-pyrazol-5-yl)amino)quinazolin-7-yl)oxy)propyl)piperidin-1-yl)nicotinate | 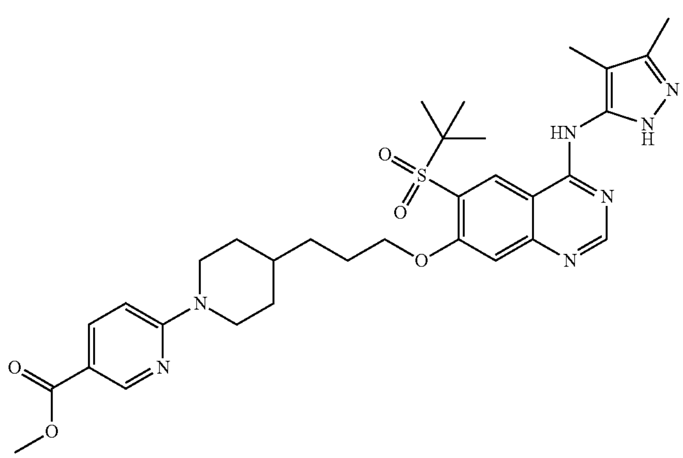 [SMILES: COC(=O)c1ccc(N2CCC(CCCOc3cc4ncnc(Nc5[nH]nc(C)c5C)c4cc3S(=O)(=O)C(C)(C)C)CC2)nc1] | 66.4% | Method B 1.19 mins | 636 |

| Compound Name | Structure | Yield | LCMS RT | ES +ve |
|---|---|---|---|---|
| 6-(4-(3-((6-(tert-butylsulfonyl)-4-((3,4-dimethyl-1H-pyrazol-5-yl)amino)quinazolin-7-yl)oxy)propyl)piperidin-1-yl)nicotinic acid | 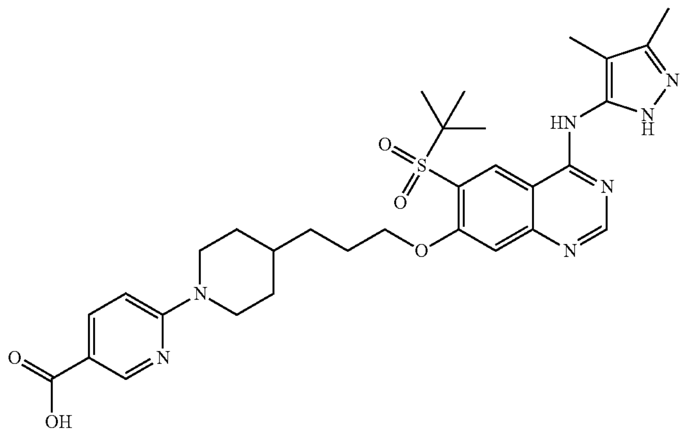 [SMILES: Cc1n[nH]c(Nc2ncnc3cc(OCCCC4CCN(c5ccc(C(=O)O)cn5)CC4)c(S(=O)(=O)C(C)(C)C)cc23)c1C] | 96% | Method A 0.70 mins | 622 |

2-(4-(2-((6-(Tert-butylsulfonyl)-4-((4,5-dimethyl-1H-pyrazol-3-yl)amino)quinazolin-7-yl)oxy)ethyl)piperazin-1-yl)pyrimidine-5-carboxylic acid, 3 Hydrochloride

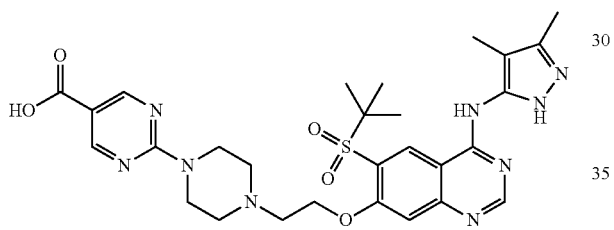

The title compound was prepared by a method analogous to those above.

| Compound Name | Structure | Yield | LCMS RT | ES +ve |
|---|---|---|---|---|
| Methyl 2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carboxylate | 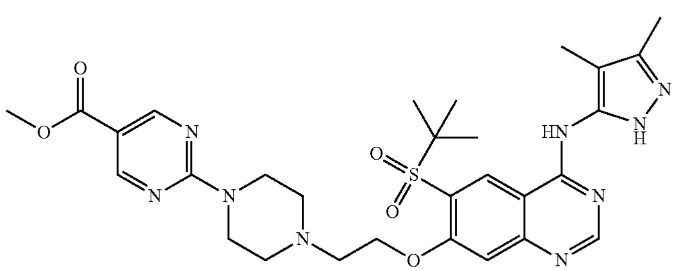 [SMILES: COC(=O)c1cnc(N2CCN(CCOc3cc4ncnc(Nc5[nH]nc(C)c5C)c4cc3S(=O)(=O)C(C)(C)C)CC2)nc1] | 71% | Method A 0.60 mins | 624 |
| 2-(4-(2-((6-(Tert-butylsulfonyl)-4-((4,5-dimethyl-1H-pyrazol-3-yl)amino)quinazolin-7-yl)oxy)ethyl)piperazin-1-yl)pyrimidine-5-carboxylic acid, 3 Hydrochloride | 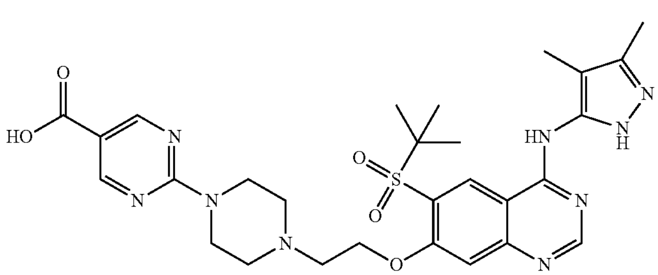 [SMILES: Cc1n[nH]c(Nc2ncnc3cc(OCCN4CCN(c5ncc(C(=O)O)cn5)CC4)c(S(=O)(=O)C(C)(C)C)cc23)c1C] | 98% | Method A 0.52 mins | 610.2 |

5-(4-(((6-(Tert-butylsulfonyl)-4-((3,4-dimethyl-1H-pyrazol-5-yl)amino)quinazolin-7-yl)oxy)methyl)piperidin-1-yl)pyrazine-2-carboxylic acid

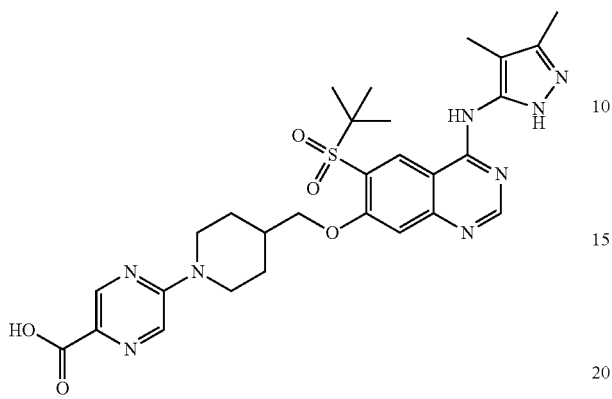

The title compound was prepared by a method analogous to those above.

| Compound Name | Structure | Yield | LCMS RT | ES + ve |
|---|---|---|---|---|
| Methyl 5-(4-(((6-(tert-butylsulfonyl)-4-((3,4-dimethyl-1H-pyrazol-5-yl)amino)quinazolin-7-yl)oxy)methyl)piperidin-1-yl)pyrazine-2-carboxylate | 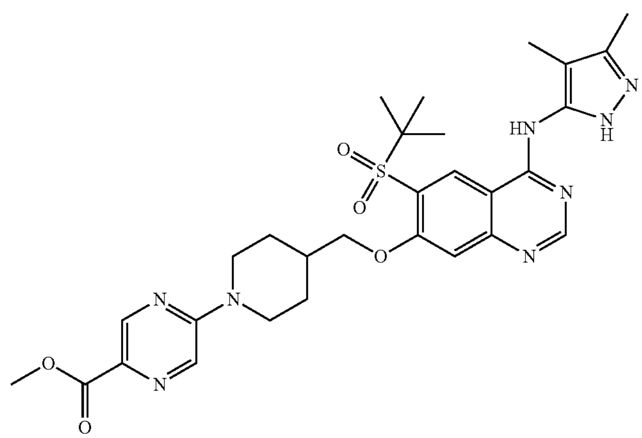 [SMILES: COC(=O)c1cnc(N2CCC(COc3cc4ncnc(Nc5[nH]nc(C)c5C)c4cc3S(=O)(=O)C(C)(C)C)CC2)cn1] | 23% | Method B 0.98 mins | 609.2 |
| 5-(4-(((6-(Tert-butylsulfonyl)-4-((3,4-dimethyl-1H-pyrazol-5-yl)amino)quinazolin-7-yl)oxy)methyl)piperidin-1-yl)pyrazine-2-carboxylic acid | 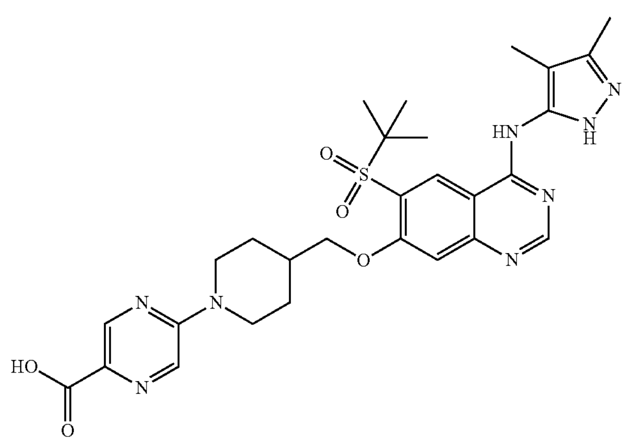 [SMILES: Cc1n[nH]c(Nc2ncnc3cc(OCC4CCN(c5cnc(C(=O)O)cn5)CC4)c(S(=O)(=O)C(C)(C)C)cc23)c1C] | 25% | Method B 0.69 mins | 595.1 |

2-(4-(((6-(Tert-butylsulfonyl)-4-((3,4-dimethyl-1H-pyrazol-5-yl)amino)quinazolin-7-yl)oxy)methyl)piperidin-1-yl)pyrimidine-5-carboxylic acid

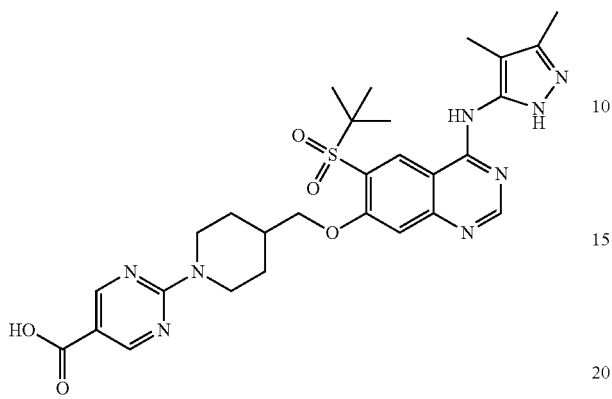

The title compound was prepared by a method analogous to those above.

| Compound Name | Structure | Yield | LCMS RT | ES + ve |
|---|---|---|---|---|
| Methyl 2-(4-(((6-(tert-butylsulfonyl)-4-((3,4-dimethyl-1H-pyrazol-5-yl)amino)quinazolin-7-yl)oxy)methyl)piperidin-1-yl)pyrimidine-5-carboxylate | 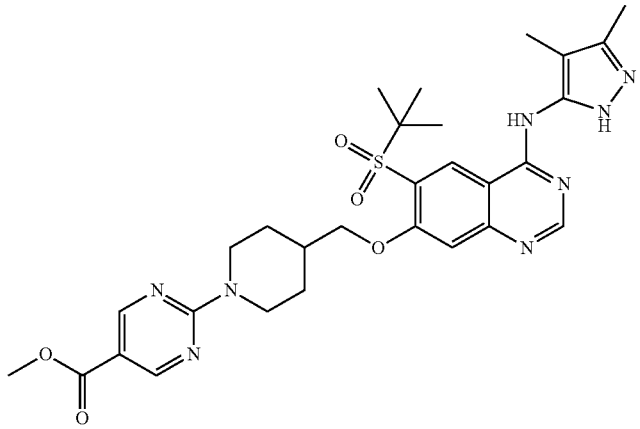 [SMILES: COC(=O)c1cnc(N2CCC(COc3cc4ncnc(Nc5[nH]nc(C)c5C)c4cc3S(=O)(=O)C(C)(C)C)CC2)nc1] | 50% | Method A 0.88 mins | 609.2 |
| 2-(4-(((6-(tert-butylsulfonyl)-4-((3,4-dimethyl-1H-pyrazol-5-yl)amino)quinazolin-7-yl)oxy)methyl)piperidin-1-yl)pyrimidine-5-carboxylic acid | 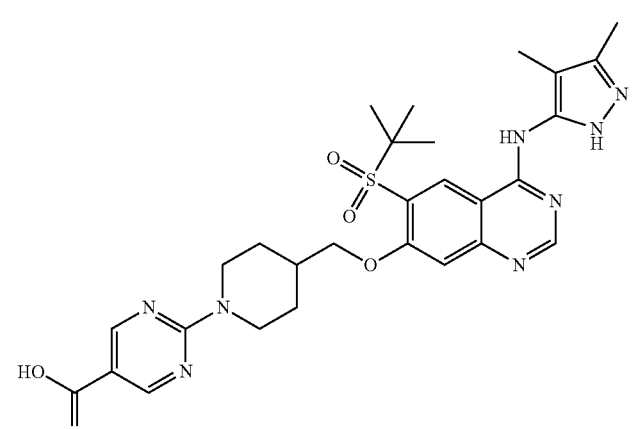 | 98% | Method A 0.78 mins | 595.1 |

2-(4-(3-((6-(Tert-butylsulfonyl)-4-((4,5-dimethyl-1H-pyrazol-3-yl)amino)quinazolin-7-yl)oxy)propyl)piperidin-1-yl)pyrimidine-5-carboxylic acid

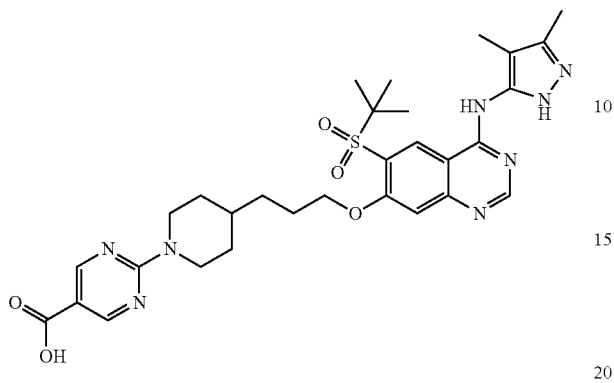

The title compound was prepared by a method analogous to those above.

| Compound Name | Structure | Yield | LCMS Method RT | ES +ve |
|---|---|---|---|---|
| methyl 2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carboxylate | 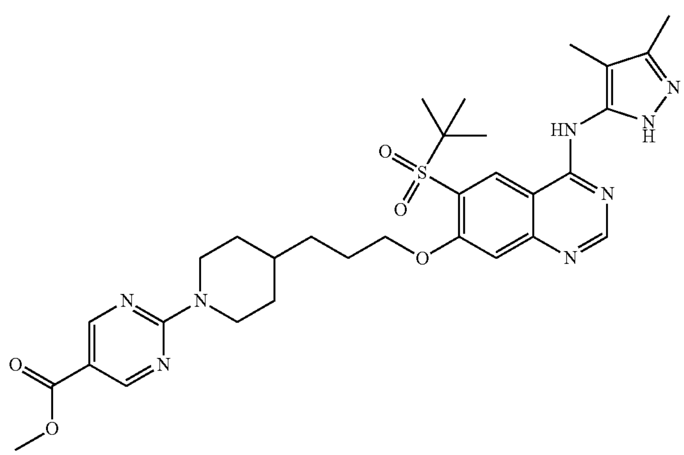 | 43% | Method A 0.97 mins | 637 |
| 2-(4-(3-((6-(Tert-butylsulfonyl)-4-((4,5-dimethyl-1H-pyrazol-3-yl)amino)quinazolin-7-yl)oxy)propyl)piperidin-1-yl)pyrimidine-5-carboxylic acid | 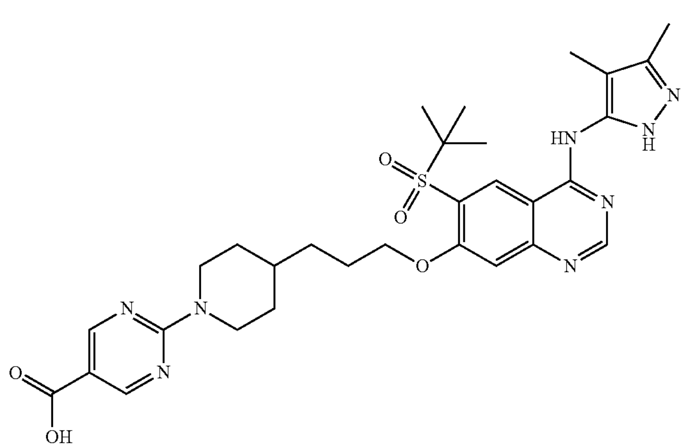 | 100% | Method A 0.85 mins | 623 |

5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylic acid

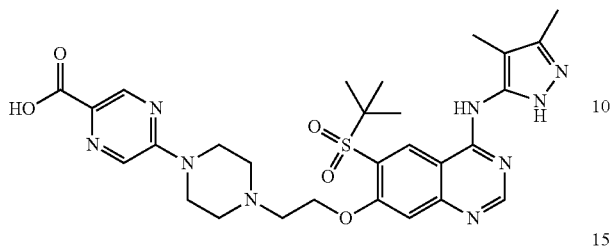

The title compound was prepared by a method analogous to those above.

| Compound Name | Structure | Yield | LCMS RT | ES + ve |
|---|---|---|---|---|
| methyl 5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylate | 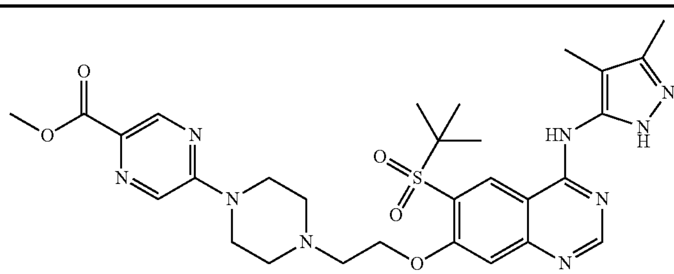 | 58% | Method B 0.92 mins | 624 |
| 5-(4-(2-((6-(tert-butylsulfonyl)-4-(4,5-dimethyl-1H-pyrazol-3-yl)amino)quinazolin-7-yl)oxy)ethyl)piperazin-1-yl)pyrazine-2-carboxylic acid | 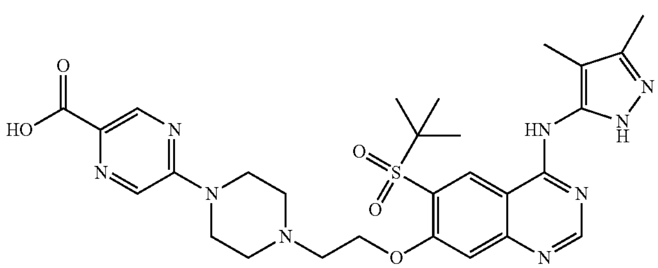 | 44% | Method B 0.67 mins | 610 |

5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylic acid

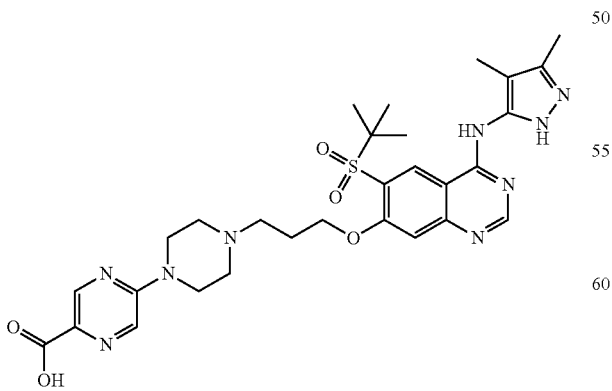

The title compound was prepared by a method analogous to those above.

| Compound Name | Structure | Yield | LCMS RT | ES + ve |
|---|---|---|---|---|
| methyl 5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylate | 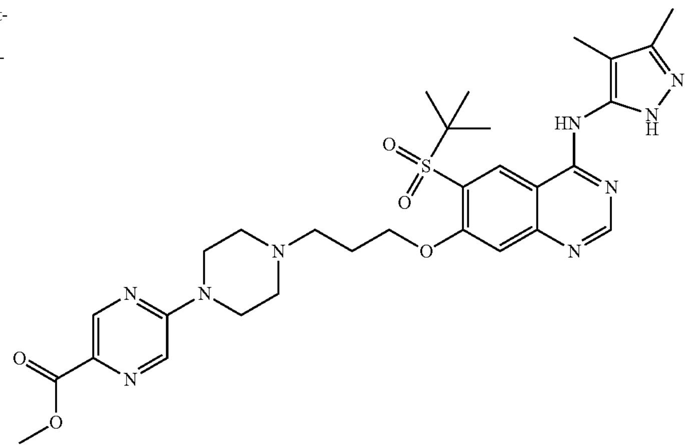 | 58% | Method A 0.52 mins | 638 |
| 5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylic acid | 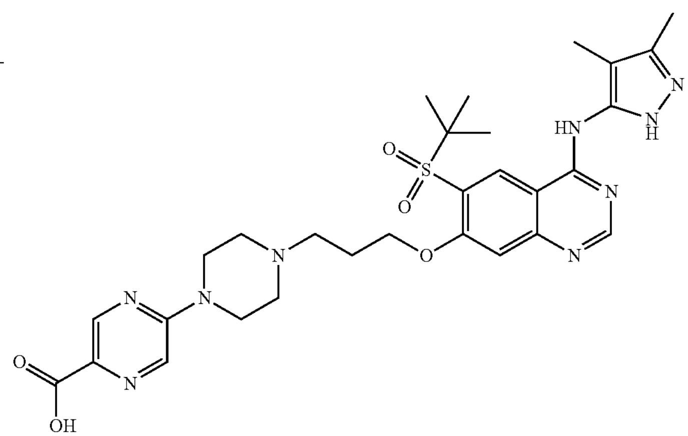 | 99% | Method A 0.47 mins | 624 |

5-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-2-carboxylic acid The title compound was prepared by a method analogous to those above.

| Compound Name | Structure | Yield | LCMS RT | ES + ve |
|---|---|---|---|---|
| 5-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-2-carboxylic acid | 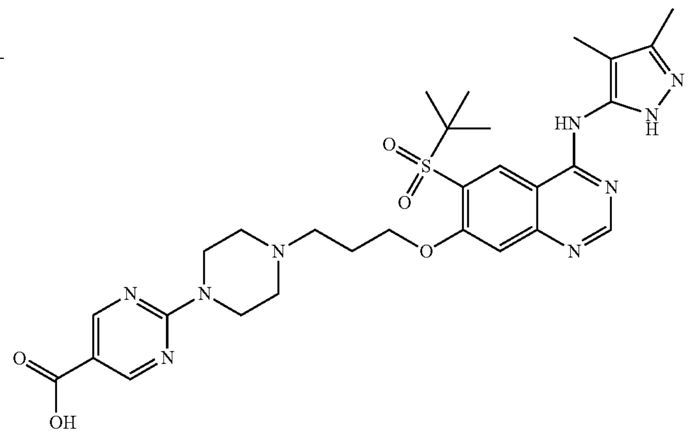 | 82% | Method B 0.67 mins | 624 |

2-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrimidine-5-carboxylic acid

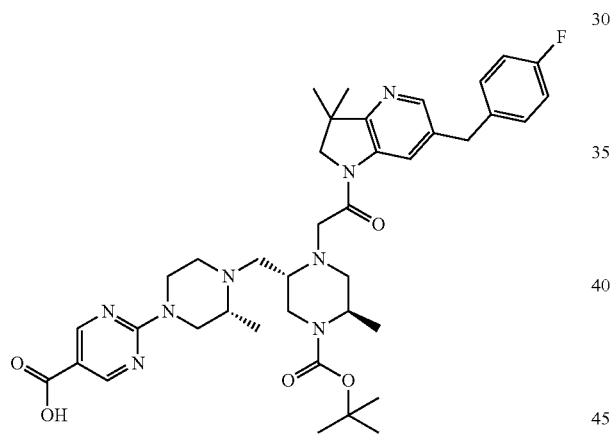

The title compound was prepared by a method analogous to those above.

| Compound Name | Structure | | Yield | LCMS RT | ES + ve |
|---|---|---|---|---|---|
| methyl 2-(((R)-4-(((2S,5R))-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrimidine-5-carboxylate | 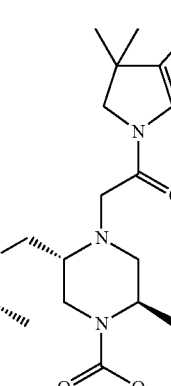 | F | 57% | Method A 1.01 mins | 745 |
| 2-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperaizn-1-yl)pyrimidine-5-carboxylic acid | 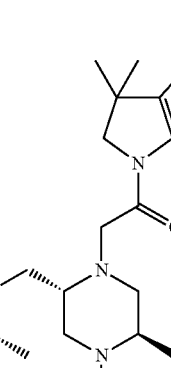 | F | 95% | Method B 1.03 mins | 731 |

Tert-butyl 4-((2-chloropyrimidin-5-yl)oxy)piperidine-1-carboxylate

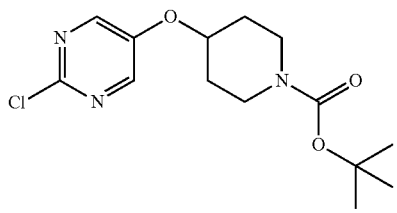 [SMILES: CC(C)(C)OC(=O)N1CCC(Oc2cnc(Cl)nc2)CC1]

To a solution of tert-butyl 4-hydroxypiperidine-1-carboxylate (561 mg, 2.79 mmol) in THF (5 mL) was added 2-chloropyrimidin-5-ol (200 mg, 1.532 mmol), triphenylphosphine (548 mg, 2.089 mmol) and DIAD (0.406 mL, 2.089 mmol) and the reaction was stirred at 20° C. under an atmosphere of nitrogen for 72 h. The reaction was concentrated, and the residue subjected directly to purification by flash chromatography (60 g pre-packed C-18 SNAP cartridge:35% to 90% acetonitrile (0.1% formic acid) in water (0.1% formic acid)). The desired fractions were combined and concentrated to afford the title compound (430 mg, 1.07 mmol, 77% yield). LCMS RT=1.12 min, ES+ve 258 (M+H-tBu).

Tert-butyl 4-((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidine-1-carboxylate

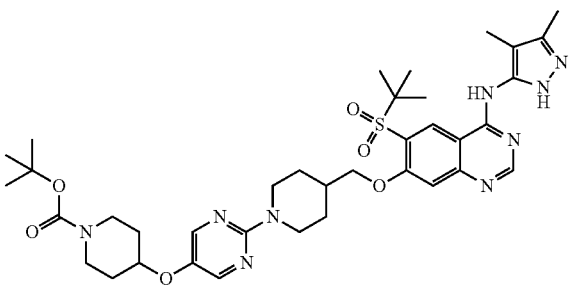 [SMILES: Cc1n[nH]c(Nc2ncnc3cc(OCC4CCN(c5ncc(OC6CCN(C(=O)OC(C)(C)C)CC6)cn5)CC4)c(S(=O)(=O)C(C)(C)C)cc23)c1C]

To a solution of tert-butyl 4-((2-chloropyrimidin-5-yl)oxy)piperidine-1-carboxylate (259 mg, 0.825 mmol) in NMP (2 mL) was added DIPEA (0.600 mL, 3.44 mmol) and 6-(tert-butylsulfonyl)-N-(4,5-dimethyl-1H-pyrazol-3-yl)-7-(piperidin-4-ylmethoxy)quinazolin-4-amine, 3 Hydrochloride (400 mg, 0.687 mmol) and the reaction was stirred at 140° C. under an atmosphere of nitrogen for 42 h. The residue was subjected directly to purification by flash chromatography (60 g pre-packed C-18 SNAP cartridge: 50% to 95% acetonitrile (0.1% ammonia) in water (10 mM ammonium bicarbonate)). The desired fractions were combined and concentrated to afford the title compound (240 mg, 0.32 mmol, 47% yield). LCMS RT=1.09 min, ES+ve 750.

To tert-butyl 4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)piperidine-1-carboxylate (240 mg, 0.320 mmol) in DCM (2.0 mL), was added TFA (1.233 mL, 16.00 mmol) and the reaction was stirred at room temperature under an atmosphere of nitrogen for 30 minutes. The volatiles were removed under vacuum to afford the title compound (350 mg, 0.32 mmol, 99% yield). LCMS RT=0.57 min, ES+ve 650.

6-(Tert-butylsulfonyl)-N-(3,4-dimethyl-1H-pyrazol-5-yl)-7-((1-(5-(piperidin-4-yloxy)pyrimidin-2-yl)piperidin-4-yl)methoxy)quinazolin-4-amine

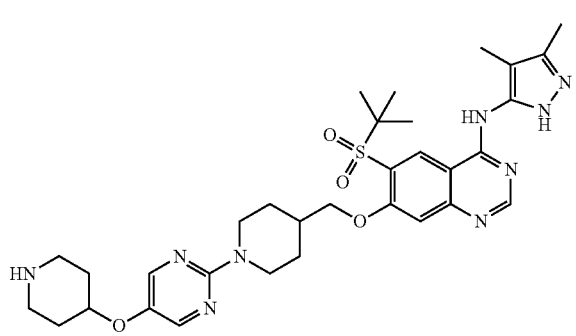 [SMILES: Cc1n[nH]c(Nc2ncnc3cc(OCC4CCN(c5ncc(OC6CCNCC6)cn5)CC4)c(S(=O)(=O)C(C)(C)C)cc23)c1C]

(R)-6-(Tert-butylsulfonyl)-N-(3,4-dimethyl-1H-pyrazol-5-yl)-7-((1-(5-(morpholin-2-ylmethoxy)pyrimidin-2-yl)piperidin-4-yl)methoxy)quinazolin-4-amine

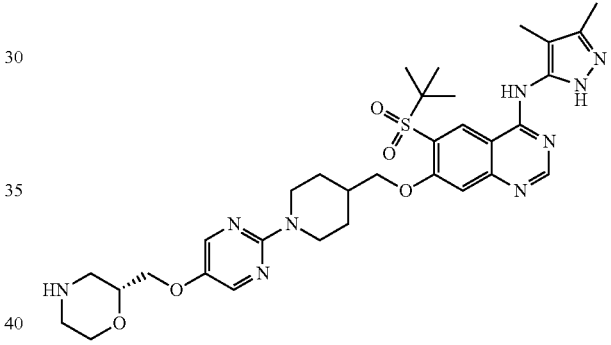

The title compound was prepared by a method analogous to those above.

| Compound Name | Structure | Yield | LCMS RT | ES+ve |
|---|---|---|---|---|
| (R)-Tert-butyl 2-(((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)methyl)morpholine-4-carboxylate | 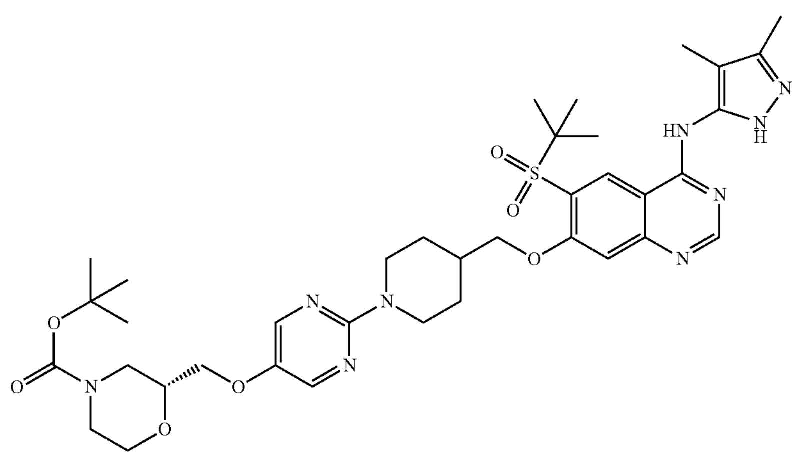 [SMILES: Cc1n[nH]c(Nc2ncnc3cc(OCC4CCN(c5ncc(OC[C@H]6CN(C(=O)OC(C)(C)C)CCO6)cn5)CC4)c(S(=O)(=O)C(C)(C)C)cc23)c1C] | 61% | Method B 1.24 mins | 766.3 |

| Compound Name | Structure | Yield | LCMS RT | ES + ve |
|---|---|---|---|---|
| (R)-6-(Tert-butylsulfonyl)-N-(3,4-dimethyl-1H-pyrazol-5-yl)-7-((1-(5-(morpholin-2-ylmethoxy)pyrimidin-2-yl)piperidin-4-yl)methoxy)quinazolin-4-amine | 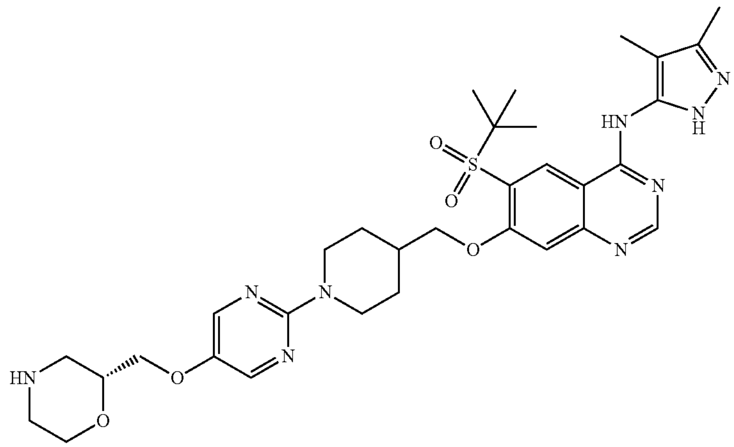 [SMILES: Cc1n[nH]c(Nc2ncnc3cc(OCC4CCN(c5ncc(OC[C@H]6CNCCO6)cn5)CC4)c(S(=O)(=O)C(C)(C)C)cc23)c1C] | 98% | Method B 0.93 mins | 666.2 |

(R)-6-(Tert-butylsulfonyl)-N-(3,4-dimethyl-1H-pyrazol-5-yl)-7-(2-(4-(S-(morpholin-2-ylmethoxy)pyrimidin-2-yl)piperazin-1-yl)ethoxy)quinazolin-4-amine

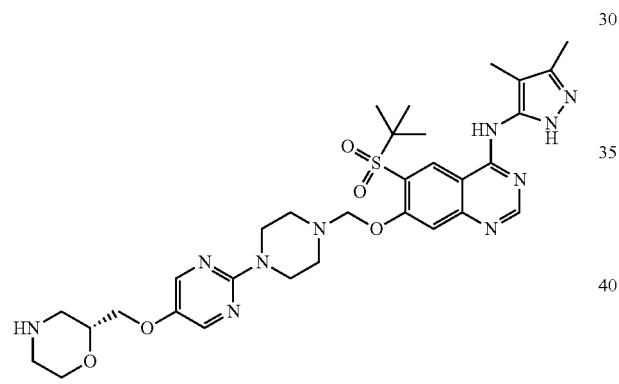

The title compound was prepared by a method analogous to those above.

| Compound Name | Structure | Yield | LCMS RT | ES + ve |
|---|---|---|---|---|
| (R)-Tert-butyl 2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholine-4-carboxylate | 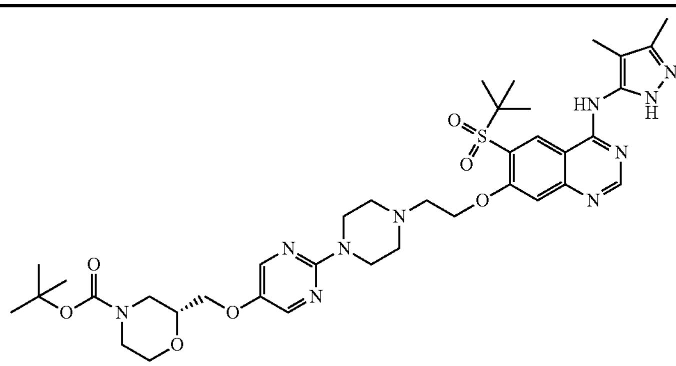 | 77% | Method B 1.15 mins | 781.3 |

| Compound Name | Structure | Yield | LCMS RT | ES +ve |
|---|---|---|---|---|
| (R)-6-(tert-butylsulfonyl)-N-(3,4-dimethyl-1H-pyrazol-5-yl)-7-(2-(4-(5-(morpholin-2-ylmethoxy)pyrimidin-2-yl)piperazin-1-yl)ethoxy)quinazolin-4-amine | 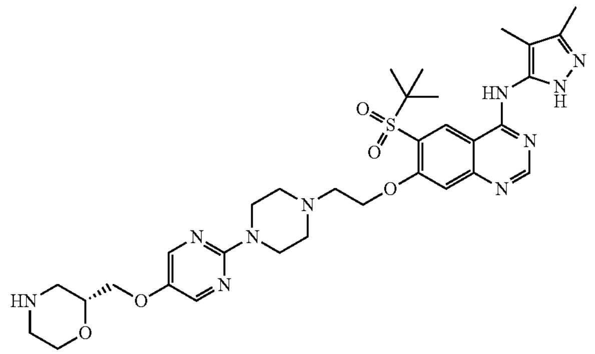 [SMILES: Cc1n[nH]c(Nc2ncnc3cc(OCCN4CCN(c5ncc(OC[C@H]6CNCCO6)cn5)CC4)c(S(=O)(=O)C(C)(C)C)cc23)c1C] | 99% | Method B 0.86 mins | 681.3 |

(R)-6-(Tert-butylsulfonyl)-N-(3,4-dimethyl-1H-pyrazol-5-yl)-7-(3-(4-(5-(morpholin-2-ylmethoxy)pyrimidin-2-yl)piperazin-1-yl)propoxy)quinazolin-4-amine

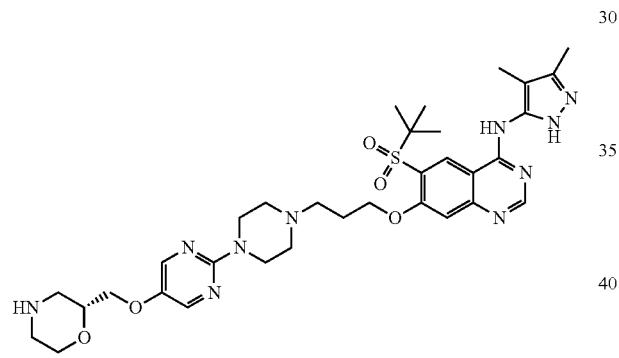

The title compound was prepared by a method analogous to those above.

| Compound Name | Structure | Yield | LCMS RT | ES +ve |
|---|---|---|---|---|
| (R)-Tert-butyl 2(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholine-4-carboxylate | 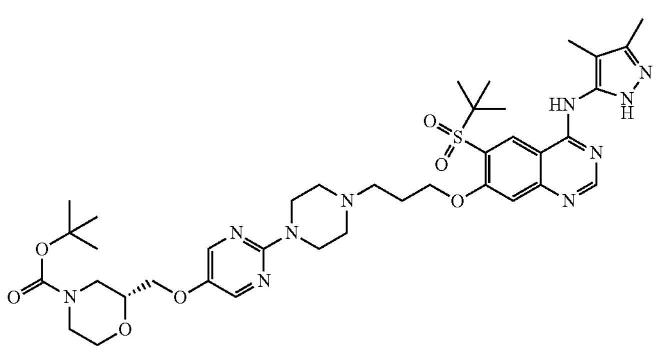 [SMILES: Cc1n[nH]c(Nc2ncnc3cc(OCCCN4CCN(c5ncc(OC[C@H]6CN(C(=O)OC(C)(C)C)CCO6)cn5)CC4)c(S(=O)(=O)C(C)(C)C)cc23)c1C] | 72% | Method B 1.17 mins | 795.3 |

| Compound Name | Structure | Yield | LCMS RT | ES +ve |
|---|---|---|---|---|
| (R)-6-(Tert-butylsulfonyl)-N-(3,4-dimethyl-1H-pyrazol-5-yl)-7-(3-(4-(5-(morpholin-2-ylmethoxy)pyrimidin-2-yl)piperazin-1-yl)propoxy)quinazolin-4-amine | 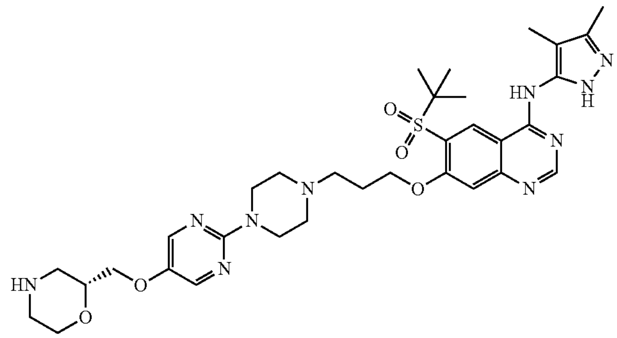 [SMILES: Cc1n[nH]c(Nc2ncnc3cc(OCCCN4CCN(c5ncc(OC[C@H]6CNCCO6)cn5)CC4)c(S(=O)(=O)C(C)(C)C)cc23)c1C] | 99% | Method B 0.88 mins | 695 |

(2R,5S)-Tert-butyl 5-(((R)-4-((benzyloxy)carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

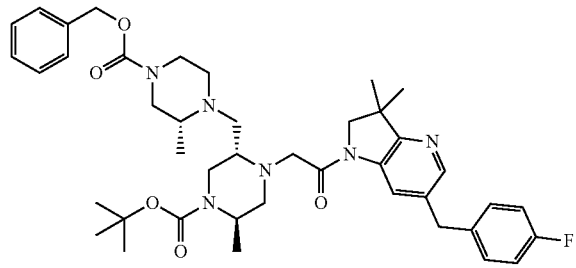 [SMILES: C[C@@H]1CN(C(=O)OCc2ccccc2)CCN1C[C@H]1CN(C(=O)OC(C)(C)C)[C@H](C)CN1CC(=O)N1CC(C)(C)c2ncc(Cc3ccc(F)cc3)cc21]

To a solution of (2R,5R)-tert-butyl 5-(chloromethyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (8.67 g, 15.91 mmol, obtained as described in WO 2012/143726) in acetonitrile (50.0 mL) and was added (R)-benzyl 3-methylpiperazine-1-carboxylate (4.10 g, 17.50 mmol, commercially available from, for example, Fluorochem), sodium iodide (0.238 g, 1.591 mmol) and potassium carbonate (6.59 g, 47.7 mmol) and the reaction was stirred at 80° C. for 18 hours. The volatiles were removed in vacuo, the reaction was diluted in 100 mL DCM and was washed with 100 mL saturated sodium bicarbonate solution and 100 mL water. The aqueous layer was washed with an additional 2×100 mL DCM, and the combined organic layers were washed with 100 mL brine and passed through a Biotage phase separator. The volatiles were removed in vacuo. The residue was dissolved in 25 mL DCM and loaded onto 340 g KP-Sil SNAP cartridge and purified by flash chromatography: 2% methanol in DCM for 1 column volume, 10 column volumes gradient 2% to 12% methanol in DCM and 2 column volumes 12% methanol in DCM. Compound eluted at 7 column volumes to afford the title compound (9.26 g, 12.5 mmol, 78% yield). LCMS RT=1.05 min, ES+ve 743.

(2R,5S)-Tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate

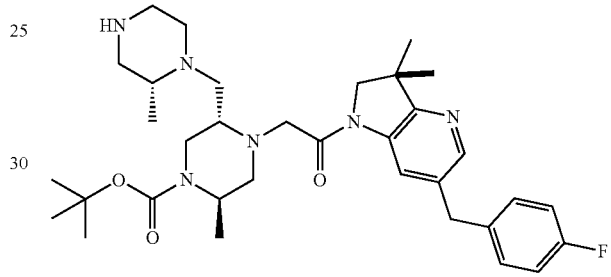

Palladium on carbon (1.326 g, 1.246 mmol) was added to a flask which was purged of air and filled with a nitrogen atmosphere. (2R,5S)-Tert-butyl 5-(((R)-4-((benzyloxy)carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (9.26 g, 12.46 mmol) was dissolved in ethanol (120 mL) and added via a dropping funnel. The reaction vessel was filled with hydrogen and the reaction was stirred at room temperature under an atmosphere of hydrogen for 2 hours. The reaction was filtered through a celite plug, then the plug was washed with 200 mL ethanol. The volatiles were removed under vacuum to afford the title compound (7.32 g, 12.0 mmol, 96% yield). LCMS RT=0.72 min, ES+ve 609.

(2R,5R)-Tert-butyl 4-(2-((S)-2-(4-(4-fluorobenzoyl)thiazol-2-yl)pyrrolidin-1-yl)-2-oxoethyl)-5-(hydroxymethyl)-2-methylpiperazine-1-carboxylate

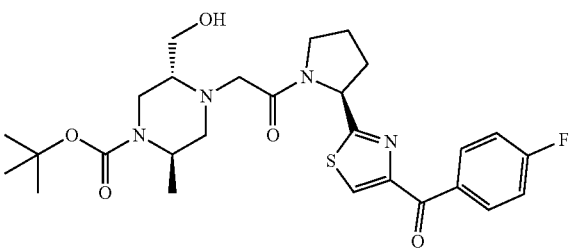 [SMILES: C[C@@H]1CN(CC(=O)N2CCC[C@H]2c2nc(C(=O)c3ccc(F)cc3)cs2)[C@@H](CO)CN1C(=O)OC(C)(C)C]

To a solution of (S)-(4-fluorophenyl)(2-(pyrrolidin-2-yl)thiazol-4-yl)methanone, Hydrochloride (94 mg, 0.301 mmol, obtained as described in WO 2011/018474 A1) in DCM (3 mL) was added triethylamine (0.209 mL, 1.503 mmol) and the reaction was stirred at room temperature under an atmosphere of nitrogen. Chloroacetyl chloride (0.048 mL, 0.601 mmol) was added and the reaction was stirred at room temperature for 15 minutes. (2R,5R)-tert-butyl 5-(hydroxymethyl)-2-methylpiperazine-1-carboxylate, Hydrochloride (320 mg, 1.202 mmol, obtained as described in WO 2012/143726) was added followed by 100 uL of triethylamine. The reaction was heated to 40° C. for 25 h, and the residue was subjected directly to purification by flash chromatography (60 g pre-packed C-18 SNAP cartridge: 15% to 55% acetonitrile (0.1% formic acid) in water (0.1% formic acid)). The desired fractions were combined and concentrated to afford the title compound (114 mg, 0.21 mmol, 69.4% yield). LCMS RT=0.82 min, ES+ve 547.

(2R,5R)-Tert-butyl 5-(chloromethyl)-4-(2-((S)-2-(4-(4-fluorobenzoyl)thiazol-2-yl)pyrrolidin-1-yl)-2-oxoethyl)-2-methylpiperazine-1-carboxylate

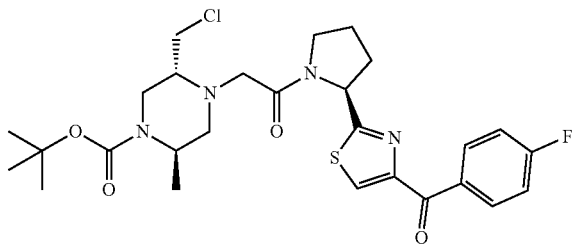 [SMILES: C[C@@H]1CN(CC(=O)N2CCC[C@H]2c2nc(C(=O)c3ccc(F)cc3)cs2)[C@@H](CCl)CN1C(=O)OC(C)(C)C]

To a solution of (2R,5R)-tert-butyl 4-(2-((S)-2-(4-(4-fluorobenzoyl)thiazol-2-yl)pyrrolidin-1-yl)-2-oxoethyl)-5-(hydroxymethyl)-2-methylpiperazine-1-carboxylate (114 mg, 0.209 mmol) in DCM (2 mL) and was added triethylamine (0.145 mL, 1.043 mmol) and the reaction was stirred at 20° C. under an atmosphere of nitrogen. Methanesulfonyl chloride (0.049 mL, 0.626 mmol) was added and the reaction was stirred at room temperature under an atmosphere of nitrogen for 18 h. The reaction was diluted in 25 mL DCM and washed with 25 mL saturated sodium bicarbonate solution. The aqueous layer was washed with additional 2×25 mL DCM, and the combined organic layers were washed with 50 mL brine and passed through a Biotage Phase Separator. The volatiles were removed in vacuo to afford the title compound (115 mg, 0.20 mmol, 98% yield). LCMS RT=1.32 min, ES+ve 565.

(2R,5S)-Tert-butyl 5-(((R)-4-(6-(4-(((6-(tert-butylsulfonyl)-4-((3,4-dimethyl-1H-pyrazol-5-yl)amino)quinazolin-7-yl)oxy)methyl)piperidin-1-yl)pyrimidin-4-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

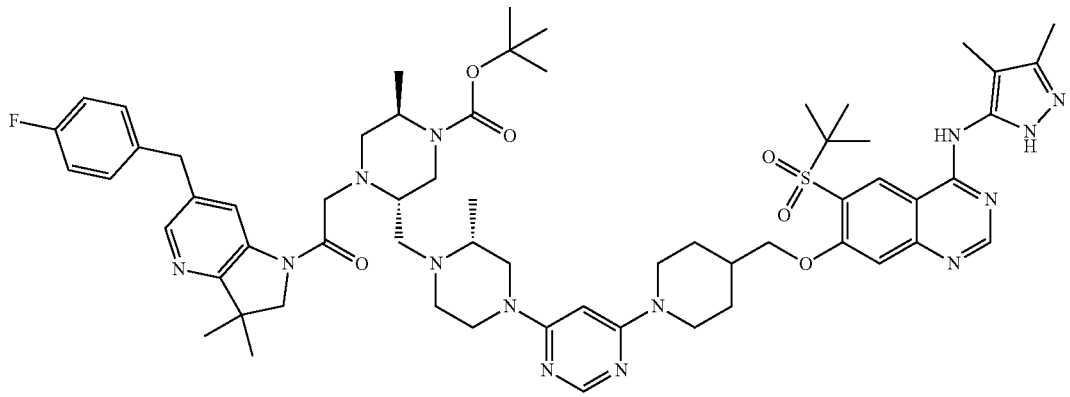 [SMILES: Cc1n[nH]c(Nc2ncnc3cc(OCC4CCN(c5cc(N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)ncn5)CC4)c(S(=O)(=O)C(C)(C)C)cc23)c1C]

To a solution of of 6-(tert-butylsulfonyl)-N-(4,5-dimethyl-1H-pyrazol-3-yl)-7-(piperidin-4-ylmethoxy)quinazolin-4-amine (22.0 mg, 0.047 mmol) in NMP (0.2 mL) was added 4,6-dichloropyrimidine (7.63 mg, 0.051 mmol) and DIPEA (0.024 mL, 0.140 mmol) and the reaction was stirred at room temperature under an atmosphere of nitrogen for 2 h. Additional DIPEA (0.024 mL, 0.140 mmol) was added, followed by (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (56.6 mg, 0.096 mmol) in NMP (0.2 mL). The reaction was warmed to 130° C. for 5 days.

The product was subjected directly to purification by mass-directed automated preparative HPLC (ammonium carbonate modifier) to afford the title compound (9 mg, 0.008 mmol, 16.7% yield). LCMS Method B RT=1.49 min, ES+ve 1157.

(2R,5S)-Tert-butyl 5-(((R)-4-(5-(2-((6-(tert-butylsulfonyl)-4-((3,4-dimethyl-1H-pyrazol-5-yl)amino)quinazolin-7-yl)oxy)ethoxy)pyrimidin-2-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

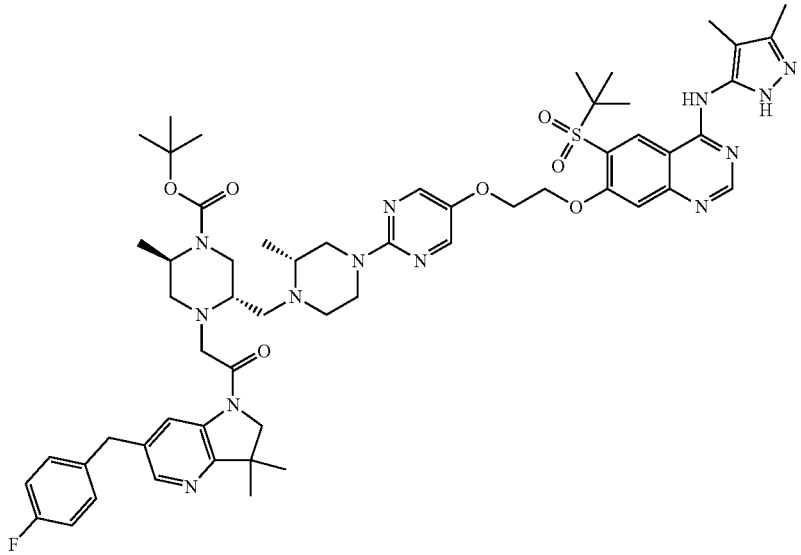 [SMILES: Cc1n[nH]c(Nc2ncnc3cc(OCCOc4cnc(N5CCN(C[C@H]6CN(C(=O)OC(C)(C)C)[C@H](C)CN6CC(=O)N6CC(C)(C)c7ncc(Cc8ccc(F)cc8)cc76)[C@H](C)C5)nc4)c(S(=O)(=O)C(C)(C)C)cc23)c1C]

To (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (32 mg, 0.053 mmol) in NMP (0.5 mL), was added 6-(tert-butylsulfonyl)-7-(2-((2-chloropyrimidin-5-yl)oxy)ethoxy)-N-(4,5-dimethyl-1H-pyrazol-3-yl)quinazolin-4-amine (41.9 mg, 0.079 mmol) and DIPEA (0.028 mL, 0.158 mmol). The reaction was stirred at 110° C. in a sealed tube for 18 h. The product was subjected directly to purification by mass-directed automated preparative HPLC (ammonium carbonate modifier) to afford the title compound (10 mg, 0.009 mmol, 17% yield). LCMS Method B RT=1.47 min, ES+ve 1104.

(2R,5S)-Tert-butyl 5-((9-(5-(2-((6-(tert-butylsulfonyl)-4-((3,4-dimethyl-1H-pyrazol-5-yl)amino)quinazolin-7-yl)oxy)ethoxy)pyrimidin-2-yl)-3,9-diazaspiro[5.5]undecan-3-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

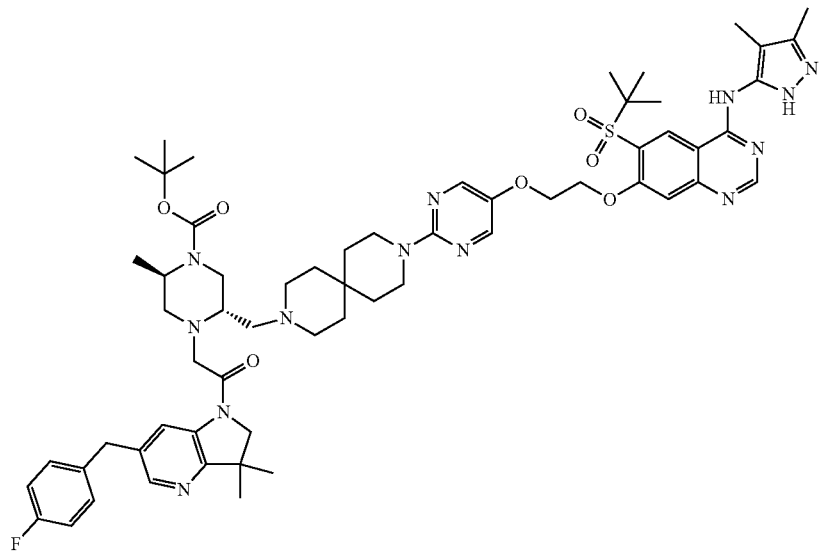 [SMILES: Cc1n[nH]c(Nc2ncnc3cc(OCCOc4cnc(N5CCC6(CCN(C[C@H]7CN(C(=O)OC(C)(C)C)[C@H](C)CN7CC(=O)N7CC(C)(C)c8ncc(Cc9ccc(F)cc9)cc87)CC6)CC5)nc4)c(S(=O)(=O)C(C)(C)C)cc23)c1C]

To a solution of (2R,5R)-tert-butyl 5-(chloromethyl)-4-(2-(6-(4-fluorobenzyl)-3,3-dimethyl-2,3-dihydro-1H-pyrrolo[3,2-b]pyridin-1-yl yl)-2-methylpiperazine-1-carboxylate (50 mg, 0.092 mmol) in NMP (1.0 mL) was added 7-(2-((2-(3,9-diazaspiro[5.5]undecan-3-yl)pyrimidin-5-yl)oxy)ethoxy)-6-(tert-butylsulfonyl)-N-(4,5-dimethyl-1H-pyrazol-3-yl)quinazolin-4-amine, 3Trifluoroacetic acid salt (91 mg, 0.092 mmol), sodium iodide (27.5 mg, 0.183 mmol) and potassium carbonate (127 mg, 0.917 mmol) and the reaction was stirred at 100° C. for 1 hour. The reaction mixture containing the crude product was subjected directly to purification by mass-directed automated preparative HPLC (ammonium carbonate modifier) to afford the title compound (32 mg, 0.03 mmol, 30.1% yield). LCMS Method B RT=1.59 min, ES+ve 1158.

(2R,5S)-Tert-butyl 5-((4-((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

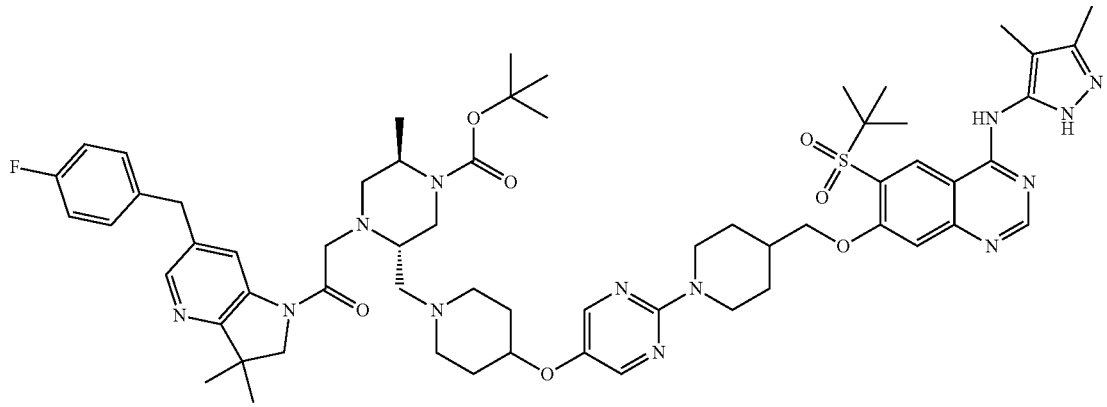 [SMILES: Cc1n[nH]c(Nc2ncnc3cc(OCC4CCN(c5ncc(OC6CCN(C[C@H]7CN(C(=O)OC(C)(C)C)[C@H](C)CN7CC(=O)N7CC(C)(C)c8ncc(Cc9ccc(F)cc9)cc87)CC6)cn5)CC4)c(S(=O)(=O)C(C)(C)C)cc23)c1C]

To a solution of (2R,5R)-tert-butyl 5-(chloromethyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (50 mg, 0.092 mmol) in NMP (1.0 mL) was added 6-(tert-butylsulfonyl)-N-(4,5-dimethyl-1H-pyrazol-3-yl)-7-((1-(5-(piperidin-4-yloxy)pyrimidin-2-yl)piperidin-4-yl)methoxy)quinazolin-4-amine, 3Trifluoroacetic acid salt (91 mg, 0.092 mmol), sodium iodide (27.5 mg, 0.183 mmol) and potassium carbonate (127 mg, 0.917 mmol) and the reaction was stirred at 80° C. overnight. The reaction mixture containing the crude product was subjected directly to purification by mass-directed automated preparative HPLC (TFA modifier) to afford the title compound (52 mg, 0.05 mmol, 48.9% yield). LCMS Method C RT=0.90 min, ES+ve 579 (M+2H/2).

(2R,5S)-Tert-butyl 5-((4-((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-4-(2-((S)-2-(4-(4-fluorobenzoyl)thiazol-2-yl)pyrrolidin-1-yl)-2-oxoethyl)-2-methylpiperazine-1-carboxylate

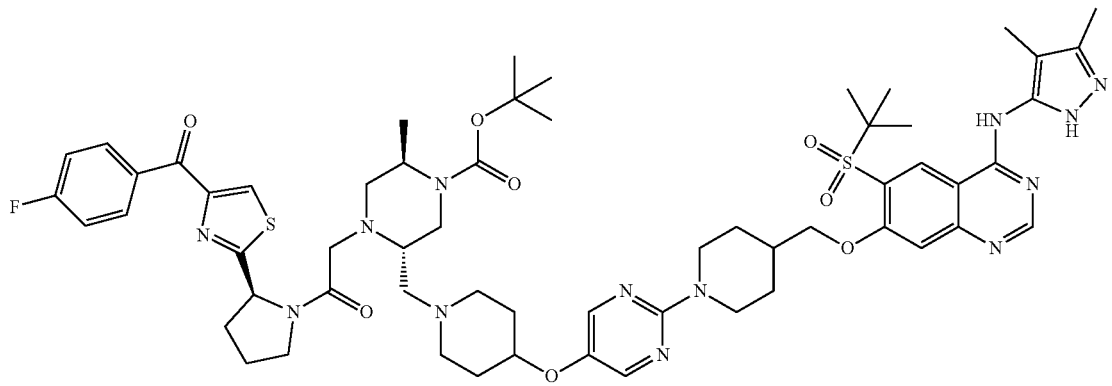 [SMILES: Cc1n[nH]c(Nc2ncnc3cc(OCC4CCN(c5ncc(OC6CCN(C[C@H]7CN(C(=O)OC(C)(C)C)[C@H](C)CN7CC(=O)N7CCC[C@H]7c7nc(C(=O)c8ccc(F)cc8)cs7)CC6)cn5)CC4)c(S(=O)(=O)C(C)(C)C)cc23)c1C]

To a solution of (2R,5R)-tert-butyl 5-(chloromethyl)-4-(2-((S)-2-(4-(4-fluorobenzoyl)thiazol-2-yl)pyrrolidin-1-yl)-2-oxoethyl)-2-methylpiperazine-1-carboxylate (60 mg, 0.106 mmol) in NMP (1.0 mL) was added 6-(tert-butylsulfonyl)-N-(4,5-dimethyl-1H-pyrazol-3-yl)-7-((1-(5-(piperidin-4-yloxy)pyrimidin-2-yl)piperidin-4-yl)methoxy)quinazolin-4-amine, 3Trifluoroacetic acid salt (105 mg, 0.106 mmol), sodium iodide (31.8 mg, 0.212 mmol) and potassium carbonate (147 mg, 1.062 mmol) and the reaction was stirred at 80° C. The reaction mixture containing the crude product was subjected directly to purification by mass-directed automated preparative HPLC (TFA modifier) to afford the title compound (59 mg, 0.05 mmol, 47.2% yield). LCMS Method C RT=0.92 min, ES+ve 590 (M+2H/2).

Using a method analogous to that for (2R,5S)-tert-butyl 5-((4-((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-4-(2-((S)-2-(4-(4-fluorobenzoyl)thiazol-2-yl)pyrrolidin-1-yl)-2-oxoethyl)-2-methylpiperazine-1-carboxylate the following compounds were prepared:

| Compound Name | Structure | Yield | LCMS RT | ES +ve |
|---|---|---|---|---|
| (2R,5S)-tert-butyl 5-(((R)-2-(((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)methyl)morpholino)methyl)-4-(2-((S)-2-(4-(4-fluorobenzoyl)thiazol-2-yl)pyrrolidin-1-yl)-2-oxoethyl-2-methylpiperazine-1-carboxylate | 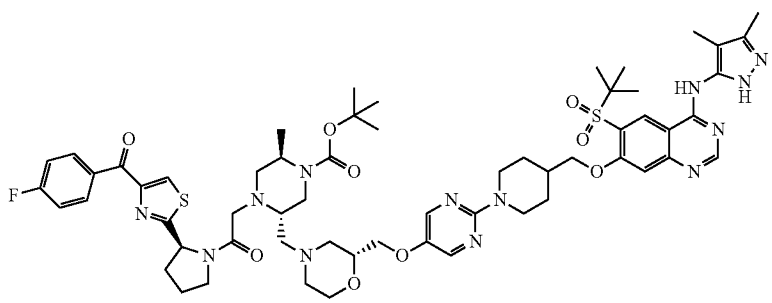 [SMILES: Cc1n[nH]c(Nc2ncnc3cc(OCC4CCN(c5ncc(OC[C@H]6CN(C[C@H]7CN(C(=O)OC(C)(C)C)[C@H](C)CN7CC(=O)N7CCC[C@H]7c7nc(C(=O)c8ccc(F)cc8)cs7)CCO6)cn5)CC4)c(S(=O)(=O)C(C)(C)C)cc23)c1C] | 18% | Method C 0.90 min | 597 |
| (2R,5S)-Tert-butyl-5-(((R)-2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-4-(2-((S)-2-(4-(4-fluorobenzoyl)thiazol-2-yl)pyrrolidin-1-yl)-2-oxoethyl)-2-methylpiperazine-1-carboxylate | 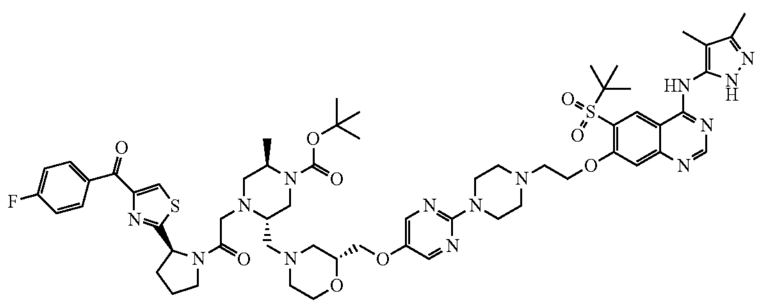 [SMILES: Cc1n[nH]c(Nc2ncnc3cc(OCCN4CCN(c5ncc(OC[C@H]6CN(C[C@H]7CN(C(=O)OC(C)(C)C)[C@H](C)CN7CC(=O)N7CCC[C@H]7c7nc(C(=O)c8ccc(F)cc8)cs7)CCO6)cn5)CC4)c(S(=O)(=O)C(C)(C)C)cc23)c1C] | 15% | Method B 1.36 min | 1209 |
| (2R,5S)-Tert-butyl 5-(((R)-2-(((2-(4-(((6-(tert-butylsulfonyl)-(4-((3,4-dimethyl-1H-pyrazol-5-yl)amino)quinazolin-7-yl)oxy)methyl)piperidin-1-yl)pyrimidin-5-yl)oxy)methyl)morpholino)methyl)-(4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 13% | Method B 1.51 min | 1174 |

| Compound Name | Structure | Yield | LCMS RT | ES +ve |
|---|---|---|---|---|
| (2R,5S)-Tert-butyl 5-(((R)-2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | 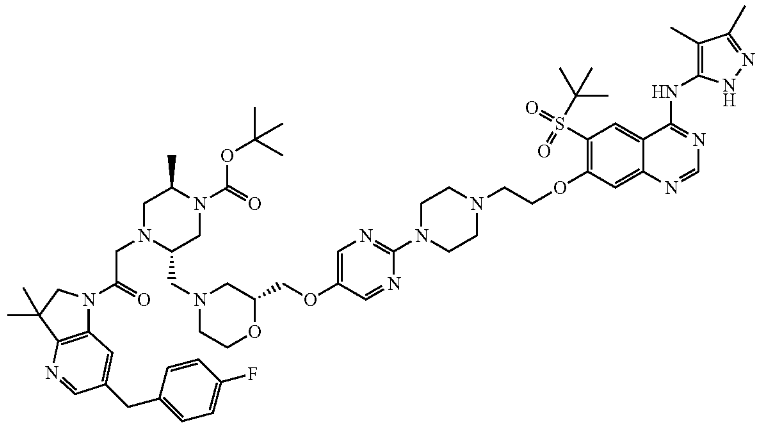 [SMILES: Cc1n[nH]c(Nc2ncnc3cc(OCCN4CCN(c5ncc(OC[C@H]6CN(C[C@H]7CN(C(=O)OC(C)(C)C)[C@H](C)CN7CC(=O)N7CC(C)(C)c8ncc(Cc9ccc(F)cc9)cc87)CCO6)cn5)CC4)c(S(=O)(=O)C(C)(C)C)cc23)c1C] | 14% | Method B 1.44 min | 1189 |
| (2R,5S)-Tert-butyl 5-((9-(5-(2-((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]undecan-3-yl)methyl)-4-(2-((S)-2-(4-(4-fluorobenzoyl)thiazol-2-yl)pyrrolidin-1-yl)-2-oxoethyl)-2-methylpiperazine-1-carboxylate | 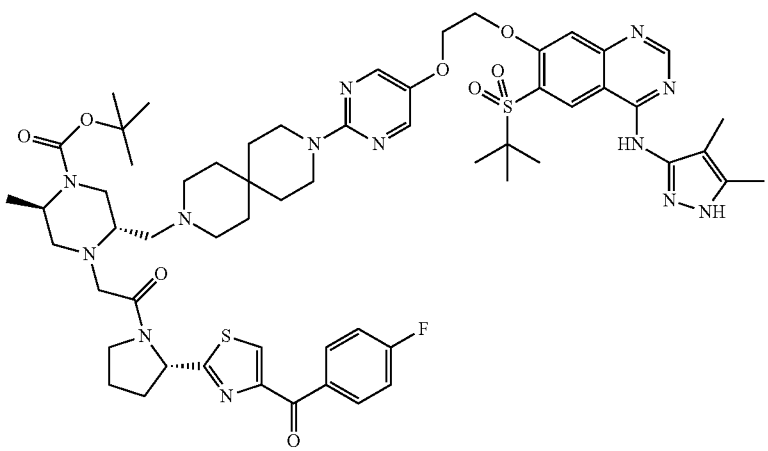 | 16% | Method B 1.48 min | 1178 |
| (2R,5S)-Tert-butyl 5-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 44% | Method C 0.75 min | 602 |

(2R,5S)-Tert-butyl 5-(((R)-4-(6-(4-(3-((6-(tert-butyl-sulfonyl)-4-((3,4-dimethyl-1H-pyrazol-5-yl)amino)quinazolin-7-yl)oxy)propyl)piperidin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

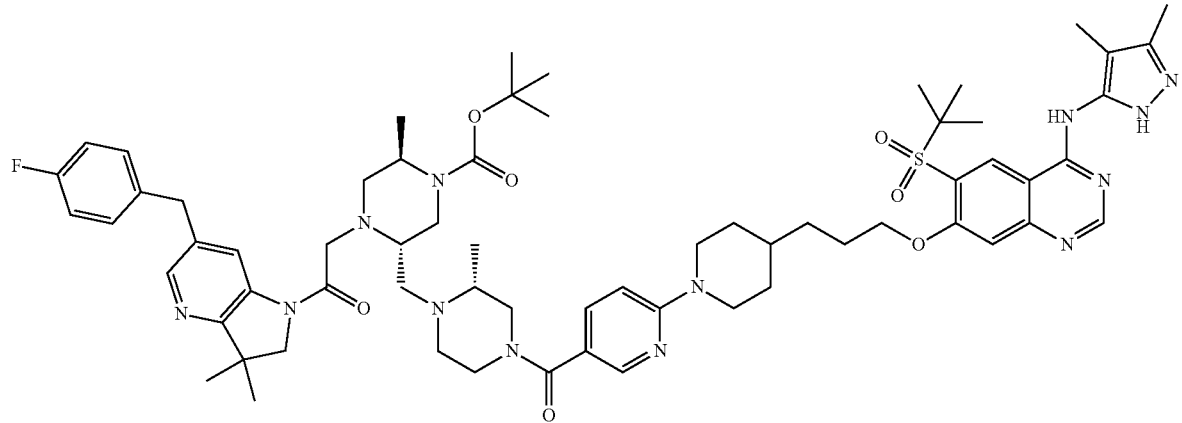 [SMILES: Cc1n[nH]c(Nc2ncnc3cc(OCCCC4CCN(c5ccc(C(=O)N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (50 mg, 0.082 mmol) in NMP (0.5 mL) was added 6-(4-(3-((6-(tert-butylsulfonyl)-4-((4,5-dimethyl-1H-pyrazol-3-yl)amino)quinazolin-7-yl)oxy)propyl)piperidin-1-yl)nicotinic acid, 3Hydrochloride (90 mg, 0.123 mmol), DIPEA (0.072 mL, 0.411 mmol) and HATU (46.8 mg, 0.123 mmol) and the reaction was stirred at room temperature for 15 minutes. The reaction was subjected directly to purification by flash chromatography (12 g pre-packed C-18 SNAP cartridge: 60% to 95% acetonitrile (0.1% ammonia) in water (10 mM ammonium bicarbonate)). The desired fractions were combined and concentrated to afford the title compound (42 mg, 0.04 mmol, 42.2% yield). LCMS Method B RT=1.50 min, ES+ve 1212.

(2R,5S)-Tert-butyl 5-(((R)-4-(6-(4-(3-((6-(tert-butyl-sulfonyl)-4-((3,4-dimethyl-1H-pyrazol-5-yl)amino)quinazolin-7-yl)oxy)propyl)piperazin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

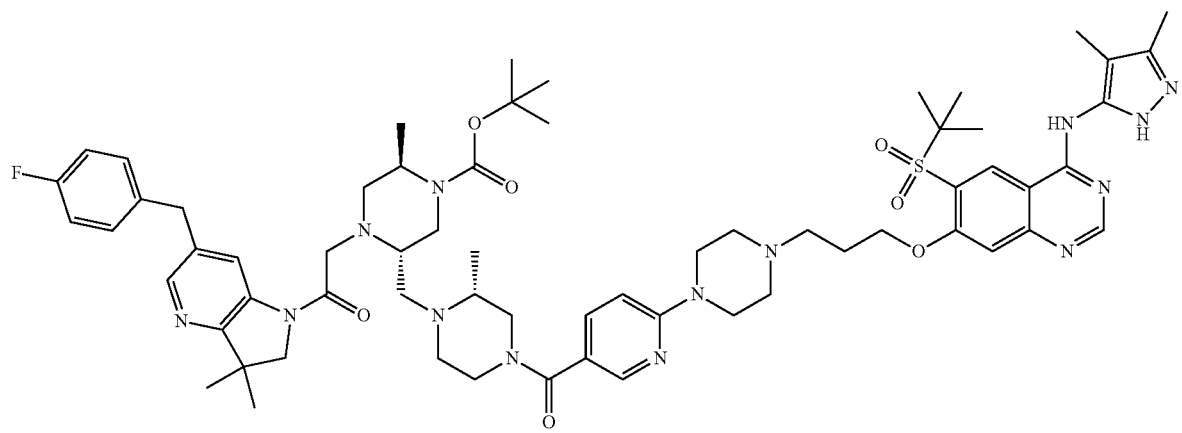 [SMILES: Cc1n[nH]c(Nc2ncnc3cc(OCCCN4CCN(c5ccc(C(=O)N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (50 mg, 0.082 mmol) in NMP (0.5 mL) was added 6-(4-(3-((6-(tert-butylsulfonyl)-4-((4,5-dimethyl-1H-pyrazol-3-yl)amino)quinazolin-7-yl)oxy)propyl)piperazin-1-yl)nicotinic acid, 3Hydrochloride (90 mg, 0.123 mmol), DIPEA (0.072 mL, 0.411 mmol) and HATU (46.8 mg, 0.123 mmol) and the reaction was stirred at room temperature. The reaction was subjected directly to purification by flash chromatography (30 g pre-packed C-18 SNAP cartridge: 50% to 95% acetonitrile (0.1% ammonia) in water (10 mM ammonium bicarbonate)). The desired fractions were combined and concentrated to afford the title compound (18 mg, 0.02 mmol, 18.1% yield). LCMS Method B RT=1.39 min, ES+ve 1213.

(2R,5S)-Tert-butyl 5-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

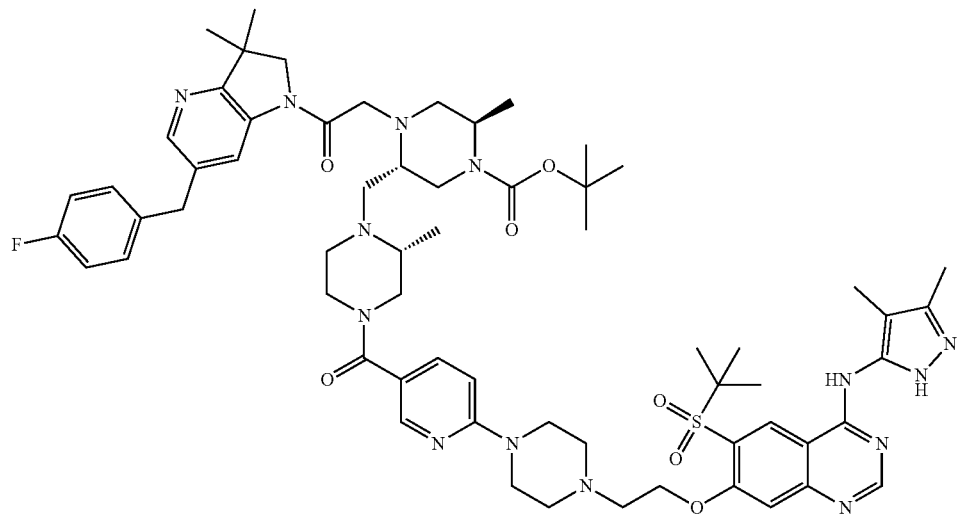 [SMILES: Cc1n[nH]c(Nc2ncnc3cc(OCCN4CCN(c5ccc(C(=O)N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (50 mg, 0.082 mmol) in NMP (0.5 mL) was added 6-(4-(2-((6-(tert-butylsulfonyl)-4-((4,5-dimethyl-1H-pyrazol-3-yl)amino)quinazolin-7-yl)oxy)ethyl)piperazin-1-yl)nicotinic acid, 3Hydrochloride (88 mg, 0.123 mmol), DIPEA (0.072 mL, 0.411 mmol) and HATU (46.8 mg, 0.123 mmol) and the reaction was stirred at room temperature for 15 minutes. The reaction was subjected directly to purification by flash chromatography (12 g pre-packed C-18 SNAP cartridge: 60% to 95% acetonitrile (0.1% ammonia) in water (10 mM ammonium bicarbonate)). The desired fractions were combined and concentrated to afford the title compound (50 mg, 0.04 mmol, 50.8% yield). LCMS Method B RT=1.38 min, ES+ve 1119.

Using a method analogous to that for (2R,5S)-tert-butyl 5-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate the following compounds were prepared:

| Compound Name | Structure | Yield | LCMS RT | ES +ve |
|---|---|---|---|---|
| (2R,5S)-Tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrazine-2-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | 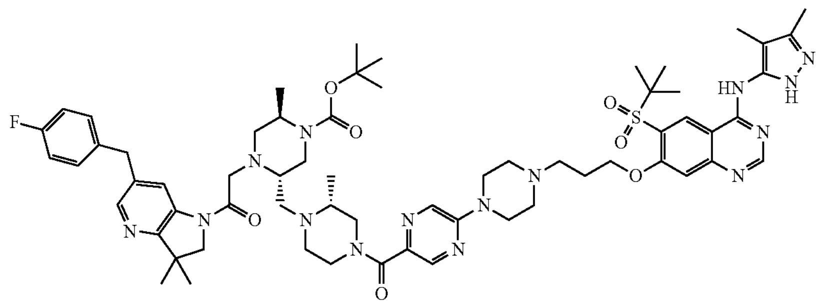 [SMILES: Cc1n[nH]c(Nc2ncnc3cc(OCCCN4CCN(c5cnc(C(=O)N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C] | 36% | Method C 0.75 min | 607 |
| (2R,5S)-Tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrimidine-2-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | 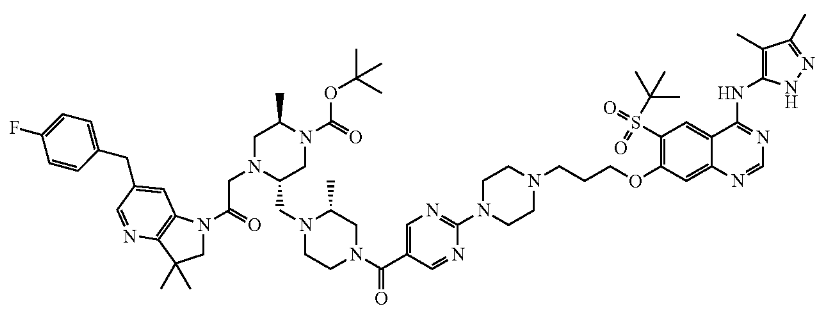 [SMILES: Cc1n[nH]c(Nc2ncnc3cc(OCCCN4CCN(c5ncc(C(=O)N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C] | 91% | Method C 0.76 min | 607 |
| (2R,5S)-tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | 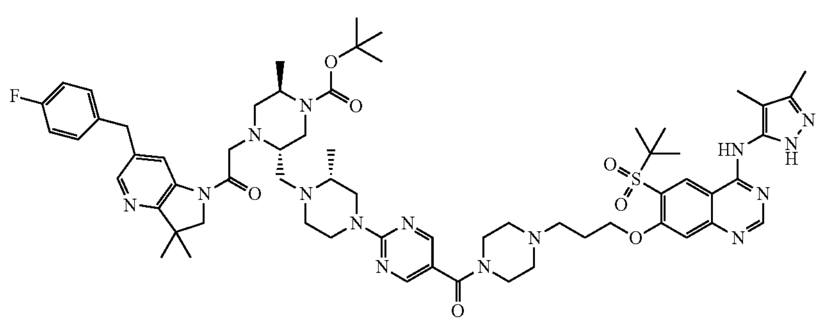 [SMILES: Cc1n[nH]c(Nc2ncnc3cc(OCCCN4CCN(C(=O)c5cnc(N6CCN(C[C@H]7CN(C(=O)OC(C)(C)C)[C@H](C)CN7CC(=O)N7CC(C)(C)c8ncc(Cc9ccc(F)cc9)cc87)[C@H](C)C6)nc5)CC4)c(S(=O)(=O)C(C)(C)C)cc23)c1C] | 62% | Method C 0.76 min | 608 |

89

6-(Tert-butylsulfonyl)-7-(2-(2-chloroethoxy)ethoxy)-N-(4,5-dimethyl-1H-pyrazol-3-yl)quinazolin-4-amine

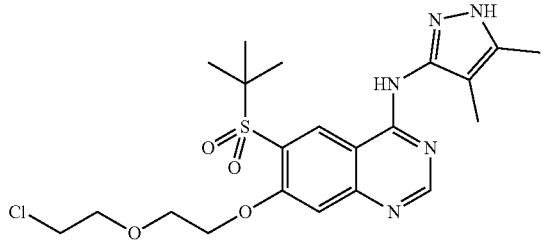 [SMILES: Cc1[nH]nc(Nc2ncnc3cc(OCCOCCCl)c(S(=O)(=O)C(C)(C)C)cc23)c1C]

To a solution of 6-(tert-butylsulfonyl)-4-((4,5-dimethyl-1H-pyrazol-3-yl)amino)quinazolin-7-ol (50 mg, 0.13 mmol, obtained as described in WO 2014/128622) in DMSO (0.8 mL) was added 1-chloro-2-(2-chloroethoxy)ethane (38.1 mg, 0.266 mmol), sodium iodide (2.0 mg, 0.013 mmol) and potassium carbonate (55 mg, 0.40 mmol) and the reaction was stirred at 80° C. in a microwave for 3 h. The reaction mixture containing the crude product was subjected directly to purification by mass-directed automated preparative HPLC (formic acid modifier) to afford the title compound (27 mg, 0.06 mmol, 42% yield). LCMS Method A RT=0.72 min, ES+ve 482.

(S)-Methyl 2-((S)-2-((tert-butoxycarbonyl)(methyl)amino)propanamido)-3-(4-hydroxyphenyl)propanoate

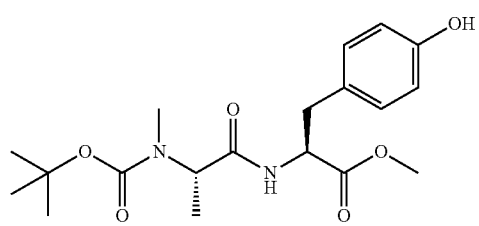 [SMILES: COC(=O)[C@H](Cc1ccc(O)cc1)NC(=O)[C@H](C)N(C)C(=O)OC(C)(C)C]

HATU (1.02 g, 2.68 mmol) was added to a mixture of (S)-2-((tert-butoxycarbonyl)(methyl)amino)propanoic acid (500 mg, 2.46 mmol) (commercially available from, for example, Matrix Scientific), (S)-methyl 2-amino-3-(4-hydroxyphenyl)propanoate, Hydrochloride (518 mg, 2.24 mmol) (commercially available from, for example, Fluka) and DIPEA (1.17 mL, 6.71 mmol) in DMF (2 mL). The reaction was stirred at ambient temperature for 30 min. The reaction mixture containing the crude product was subjected directly to purification by reverse phase flash chromatography (60 g column) using a gradient elution from 5% to 80% acetonitrile in water (formic acid modifier) to afford the title compound (775 mg, 2.04 mmol, 91% yield). LCMS Method A RT=0.91 min, ES+ve 381.

90

(S)-2-((S)-2-((Tert-butoxycarbonyl)(methyl)amino)propanamido)-3-(4-hydroxyphenyl)propanoic acid

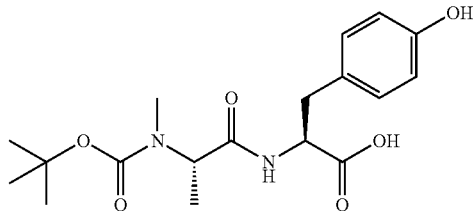 [SMILES: C[C@@H](C(=O)N[C@@H](Cc1ccc(O)cc1)C(=O)O)N(C)C(=O)OC(C)(C)C]

LiOH (238 mg, 9.94 mmol) in water (2 mL) was added to a solution of (S)-methyl 2-((S)-2-((tert-butoxycarbonyl)(methyl)amino)propanamido)-3-(4-hydroxyphenyl)propanoate (630 mg, 1.66 mmol) in THF (2 mL) and methanol (1 mL) at 0° C. After stirring for 1 h, the reaction mixture was concentrated to remove the organic solvent, acidified with 1 M HCl to pH around 2-3, and the product was extracted with ethyl acetate (2×50 mL). The combined organic extracts were washed with brine (40 mL), dried using a hydrophobic frit and evaporated under reduced pressure to afford the title compound (602 mg, 1.64 mmol, 99% yield). LCMS Method A RT=0.80 min, ES+ve 367.

Tert-butyl ((S)-1-(((S)-1-((S)-2-(4-(4-fluorobenzoyl)thiazol-2-yl)pyrrolidin-1-yl)-3-(4-hydroxyphenyl)-1-oxopropan-2-yl)amino)-1-oxopropan-2-yl)(methyl)carbamate

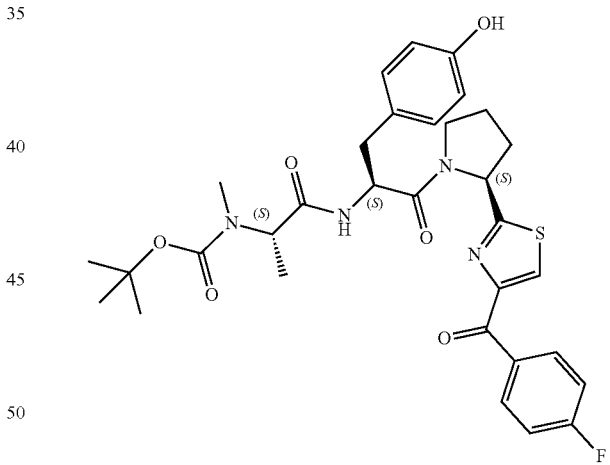

HATU (292 mg, 0.767 mmol) was added to a mixture of (S)-2-((S)-2-((tert-butoxycarbonyl)(methyl)amino)propanamido)-3-(4-hydroxyphenyl)propanoic acid (234 mg, 0.639 mmol), (S)-(4-fluorophenyl)(2-(pyrrolidin-2-yl)thiazol-4-yl)methanone, Hydrochloride (200 mg, 0.639 mmol, (obtained as described in WO 2011/018474 A1) and DIPEA (0.34 mL, 1.92 mmol) in DMF (2 mL), and the reaction was stirred at ambient temperature for 30 min. The reaction mixture containing the crude product was subjected directly to purification by reverse phase flash chromatography (30 g column) using a gradient elution from 5% to 90% acetonitrile in water (formic acid modifier) to afford the title compound (256 mg, 0.41 mmol, 64% yield). LCMS Method A RT=1.15 min, ES+ve 625.

Tert-butyl ((S)-1-(((S)-3-(4-(2-(2-((6-(tert-butylsulfonyl)-4-((4,5-dimethyl-1H-pyrazol-3-yl)amino)quinazolin-7-yl)oxy)ethoxy)ethoxy)phenyl)-1-((S)-2-(4-(4-fluorobenzoyl)thiazol-2-yl)pyrrolidin-1-yl)-1-oxopropan-2-yl)amino)-1-oxopropan-2-yl)(methyl)carbamate

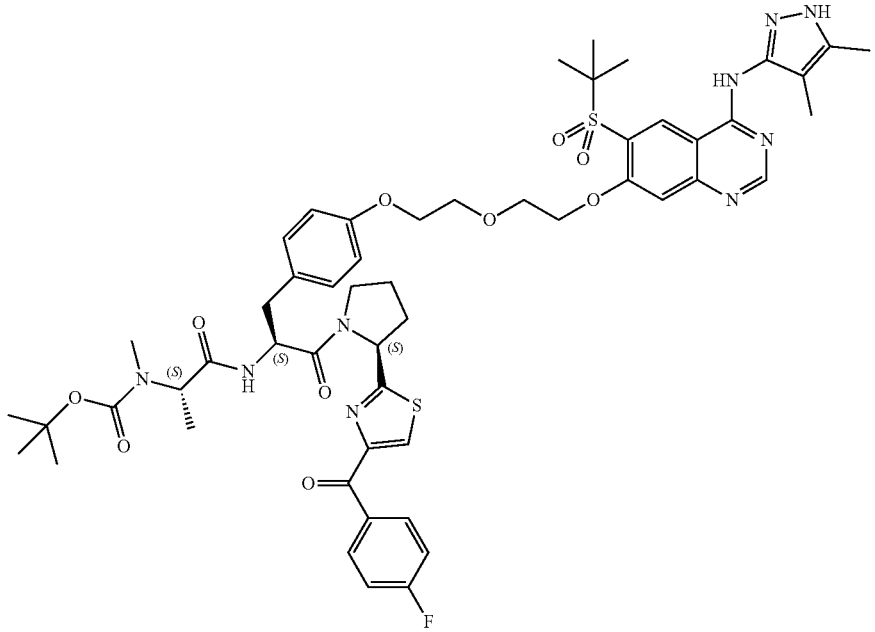

6-(Tert-butylsulfonyl)-7-(2-(2-chloroethoxy)ethoxy)-N-(4,5-dimethyl-1H-pyrazol-3-yl)quinazolin-4-amine (13 mg, 0.027 mmol) dissolved in NMP (0.5 mL) was added to a vial containing tert-butyl ((S)-1-(((S)-1-((S)-2-(4-(4-fluorobenzoyl)thiazol-2-yl)pyrrolidin-1-yl)-3-(4-hydroxyphenyl)-1-oxopropan-2-yl)amino)-1-oxopropan-2-yl)(methyl)carbamate (25.3 mg, 0.040 mmol), potassium carbonate (15 mg, 0.11 mmol) and sodium iodide (4.0 mg, 0.03 mmol). The vial was sealed and the reaction was heated at 110° C. for 18 h. The sample was filtered and subjected directly to purification by mass-directed automated preparative HPLC (formic acid modifier) to afford the title compound (2 mg, 1.87 μmol, 6.9% yield). LCMS Method B RT=1.27 min, ES+ve 1069.

(S)-2-((((9H-Fluoren-9-yl)methoxy)carbonyl)amino)-2-(1-(tert-butoxycarbonyl)piperidin-4-yl)acetic acid

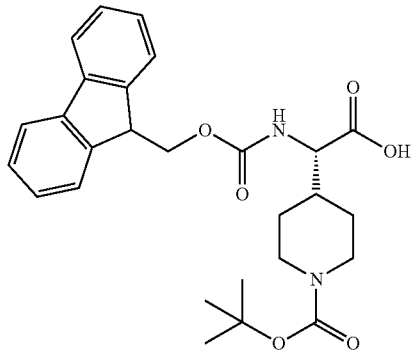 [SMILES: CC(C)(C)OC(=O)N1CCC([C@H](NC(=O)OCC2c3ccccc3-c3ccccc32)C(=O)O)CC1]

To a suspension of (S)-2-amino-2-(1-(tert-butoxycarbonyl)piperidin-4-yl)acetic acid (0.51 g, 1.97 mmol) (commercially available from, for example, Fluorochem) in THF (7.5 mL) and water (7.5 mL) at 0° C., was added (9H-fluoren-9-yl)methyl carbonochloridate (0.51 g, 1.97 mmol) and sodium carbonate (0.21 g, 1.98 mmol). The resulting mixture was stirred at 0° C. for 30 min, and then stirred at ambient temperature overnight. The reaction mixture was diluted with EtOAc (40 mL) and the pH was adjusted to around 2-3 with 1N HCl. The organic layer was separated, and the aqueous layer was extracted with additional EtOAc (2×40 mL). The combined organic layers were washed with brine (50 mL), dried using a hydrophobic frit and concentrated under reduced pressure to afford the title compound (930 mg, 1.94 mmol, 98% yield). No further purification was carried out. LCMS Method A RT=1.27 min, ES+ve 503 [M+Na]+, 479 [M−H]⁻.

Tert-butyl 4-((S)-1-amino-2-((S)-2-(4-(4-fluorobenzoyl)thiazol-2-yl)pyrrolidin-1-yl)-2-oxoethyl)piperidine-1-carboxylate, Formic Acid Salt

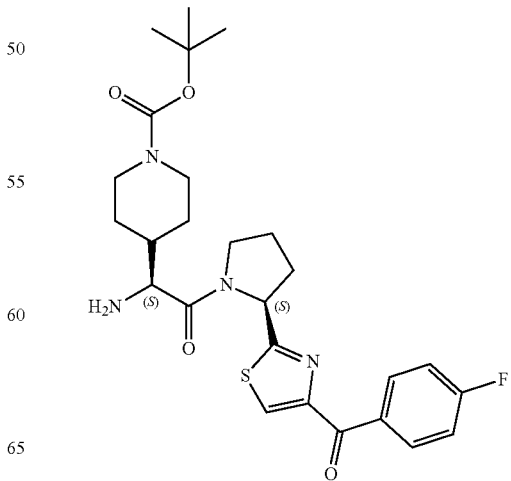

HATU (511 mg, 1.34 mmol) was added to a mixture of (S)-2-((((9H-fluoren-9-yl)methoxy)carbonyl)amino)-2-(1-(tert-butoxycarbonyl)piperidin-4-yl)acetic acid (565 mg, 1.18 mmol), (S)-(4-fluorophenyl)(2-(pyrrolidin-2-yl)thiazol-4-yl)methanone, Hydrochloride (350 mg, 1.119 mmol, obtained as described in WO 2011/018474 A1) and DIPEA (0.59 mL, 3.36 mmol) in DMF (3 mL). The reaction was stirred at ambient temperature for 18 h. Piperidine (0.33 mL, 3.36 mmol) was then added, and the mixture was stirred for an additional 30 min. The reaction mixture containing the crude product was subjected directly to purification by reverse phase flash chromatography (60 g column) using a gradient elution from 5% to 60% acetonitrile in water (formic acid modifier) to afford the title compound (335 mg, 0.60 mmol, 53% yield). LCMS Method A RT=0.76 min, ES+ve 517.

(9H-fluoren-9-yl)methyl ((S)-1-(((S)-2-((S)-2-(4-(4-fluorobenzoyl)thiazol-2-yl)pyrrolidin-1-yl)-2-oxo-1-(piperidin-4-yl)ethyl)amino)-1-oxopropan-2-yl)(methyl)carbamate, Hydrochloride

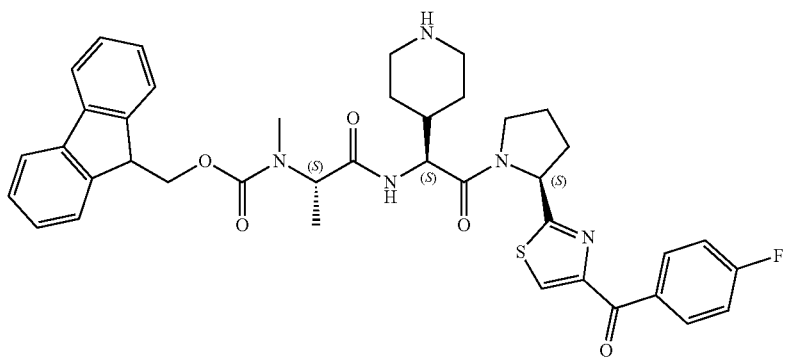

HATU (272 mg, 0.714 mmol) was added to a mixture of (S)-2-((((9H-fluoren-9-yl)methoxy)carbonyl)(methyl)amino)propanoic acid (232 mg, 0.714 mmol) (commercially available from, for example, Novabiochem), tert-butyl 4-((S)-1-amino-2-((S)-2-(4-(4-fluorobenzoyl)thiazol-2-yl)pyrrolidin-1-yl)-2-oxoethyl)piperidine-1-carboxylate, Formic acid salt (335 mg, 0.595 mmol) and DIPEA (0.312 mL, 1.79 mmol) in DMF (3 mL). After stirring at ambient temperature for 30 min, the reaction mixture was partitioned between EtOAc (80 mL) and water (50 mL). The organic layer was separated, washed with water (50 mL), brine (50 mL), dried using a hydrophobic frit, and concentrated under reduced pressure. The crude material was loaded in DCM and purified on a 50 g silica (Si) column, using a gradient of 0-100% EtOAc in cyclohexane, followed by 0-10% methanol in DCM. The appropriate fractions were combined and evaporated under reduced pressure. The purified material was taken up in DCM (5 mL), treated with 4M HCl in dioxane (0.74 mL, 2.98 mmol), and stirred at ambient temperature for 1 h. The solvent was removed under reduced pressure, and the residual acid was removed by addition and evaporation of toluene (2×20 mL) to afford the title compound (275 mg, 0.36 mmol, 61% yield). LCMS Method A RT=0.90 min, ES+ve 724.

Tert-butyl ((S)-1-(((S)-2-((2S,4S)-4-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate

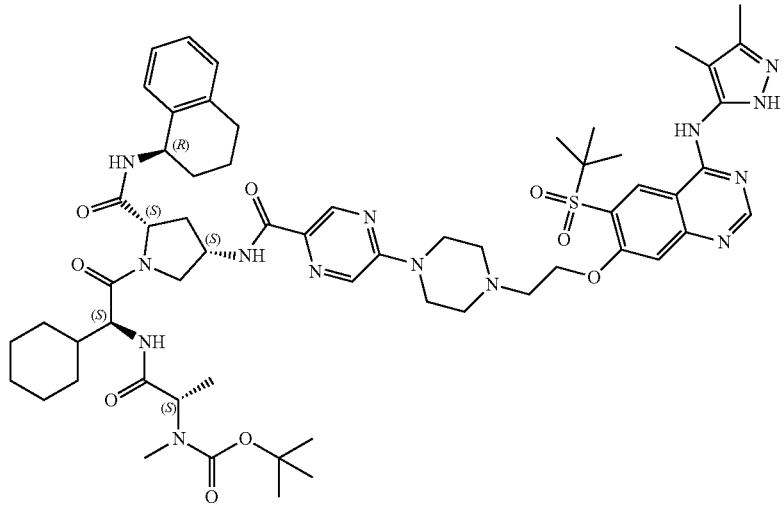

HATU (92 mg, 0.241 mmol) was added to a mixture of DIPEA (0.1 mL, 0.57 mmol), 5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylic acid (70 mg, 0.115 mmol) and tert-butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (78 mg, 0.13 mmol, obtained as described in WO 2014090709 A1) dissolved in DMF (0.55 mL). The reaction was stirred at ambient temperature for 1.5 h. The reaction mixture containing the crude product was subjected directly to purification by mass-directed automated preparative HPLC (formic acid modifier) to afford the title compound (74 mg, 0.06 mmol, 55% yield). LCMS Method B RT=1.32 min, ES+ve 1175.

Tert-butyl 4-(2-((6-(tert-butylsulfonyl)-4-((5-fluoro-1H-indazol-3-yl)amino)quinolin-7-yl)oxy)ethyl)piperazine-1-carboxylate

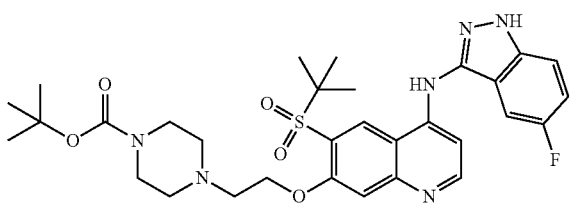 [SMILES: CC(C)(C)OC(=O)N1CCN(CCOc2cc3nccc(Nc4n[nH]c5ccc(F)cc45)c3cc2S(=O)(=O)C(C)(C)C)CC1]

To a solution of 6-(tert-butylsulfonyl)-4-((5-fluoro-1H-indazol-3-yl)amino)quinolin-7-ol (100 mg, 0.24 mmol) and tert-butyl 4-(2-chloroethyl)piperazine-1-carboxylate (72 mg, 0.20 mmol) in N,N-Dimethylformamide (DMF) (0.8 mL) was added potassium carbonate (50.0 mg, 0.36 mmol) and sodium iodide (7.2 mg, 0.05 mmol). The reaction was warmed to 50° C. and stirred under an atmosphere of nitrogen. It was cooled to room temperature and concentrated under vacuum. The residue was subjected directly to purification by flash chromatography (60 g pre-packed C-18 SNAP cartridge: 40% to 90% acetonitrile (0.1% ammonia) in water (10 mM ammonium bicarbonate)). The desired fractions were combined and concentrated to afford the title compound (100 mg, 0.16 mmol, 66% yield). LCMS Method B RT=1.18 min, ES+ve 627.

6-(Tert-butylsulfonyl)-N-(5-fluoro-1H-indazol-3-yl)-7-(2-(piperazin-1-yl)ethoxy)quinolin-4-amine, 3 Trifluoroacetic Acid Salt

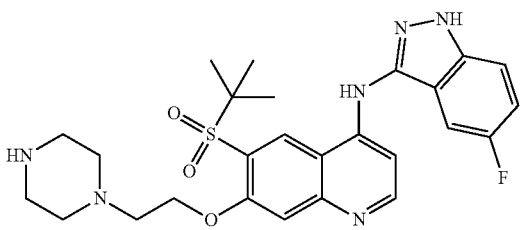 [SMILES: CC(C)(C)S(=O)(=O)c1cc2c(Nc3n[nH]c4ccc(F)cc34)ccnc2cc1OCCN1CCNCC1]

To a solution of tert-butyl 4-(2-((6-(tert-butylsulfonyl)-4-((5-fluoro-1H-indazol-3-yl)amino)quinolin-7-yl)oxy)ethyl)piperazine-1-carboxylate (100 mg, 0.16 mmol) in Dichloromethane (DCM) (1 mL) was added trifluoroacetic acid (1.23 mL, 16.0 mmol) and the reaction was stirred under an atmosphere of nitrogen. The reaction was concentrated under vacuum. to afford the title compound (138 mg, 0.16 mmol, 100% yield). LCMS Method B RT=0.89 min, ES+ve 527.

(R)-Tert-butyl 2-(((2-chloropyrimidin-5-yl)oxy)methyl)morpholine-4-carboxylate

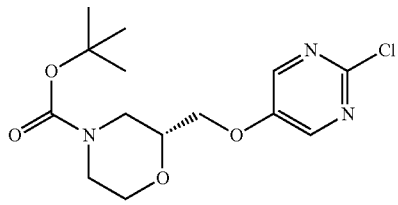 [SMILES: CC(C)(C)OC(=O)N1CCO[C@@H](COc2cnc(Cl)nc2)C1]

To a solution of (R)-tert-butyl 2-(hydroxymethyl)morpholine-4-carboxylate (605 mg, 2.8 mmol) in THF (5 mL) was added 2-chloropyrimidin-5-ol (200 mg, 1.53 mmol), triphenylphosphine (548 mg, 2.089 mmol) and DIAD (0.41 mL, 2.09 mmol) and the reaction was stirred at 20° C. under an atmosphere of nitrogen for 5 hours. The reaction was concentrated and resuspended in 1 mL DMSO, then was subjected directly to purification by flash chromatography (60 g pre-packed C-18 SNAP cartridge: 35% to 90% acetonitrile (0.1% formic acid) in water (0.1% formic acid)). The desired fractions were combined and concentrated to afford the title compound (410 mg, 1.24 mmol, 89% yield). LCMS Method A RT=1.01 min, ES+ve 274 (M+H-tBu).

(R)-Tert-butyl 2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholine-4-carboxylate

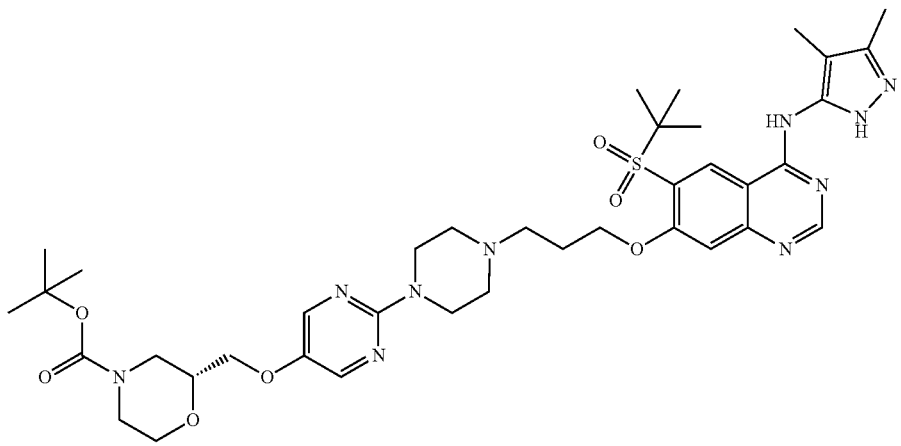 [SMILES: Cc1n[nH]c(Nc2ncnc3cc(OCCCN4CCN(c5ncc(OC[C@H]6CN(C(=O)OC(C)(C)C)CCO6)cn5)CC4)c(S(=O)(=O)C(C)(C)C)cc23)c1C]

To a solution of 6-(tert-butylsulfonyl)-N-(3,4-dimethyl-1H-pyrazol-5-yl)-7-(3-(piperazin-1-yl)propoxy)quinazolin-4-amine (0.60 g, 1.20 mmol) and (R)-tert-butyl 2-((2-chloropyrimidin-5-yloxy)methyl)morpholine-4-carboxylate (0.28 g, 0.83 mmol) in NMP (10 mL) was added NaHCO$_3$ (0.34 g, 4.4 mmol) and then stirred at 110° C. for 18 hours. To the solution was added 3 mL of MeOH, the filtrate was collected and was purified by preperative HPLC (Method A, Gradient: 15-50% organic) to afford the title compound (0.28 g, 0.35 mmol, 42% yield). LCMS Method D RT=1.34 min, ES+ve 794.

(R)-6-(Tert-butylsulfonyl)(34-dimeth(3,4-dimethyl-pyrazol-5-yl)-7-(3-(4-(5-(morpholin-2-ylmethoxy)pyrimidin-2-yl)piperazin-1-yl)propoxy)quinazolin-4-amine

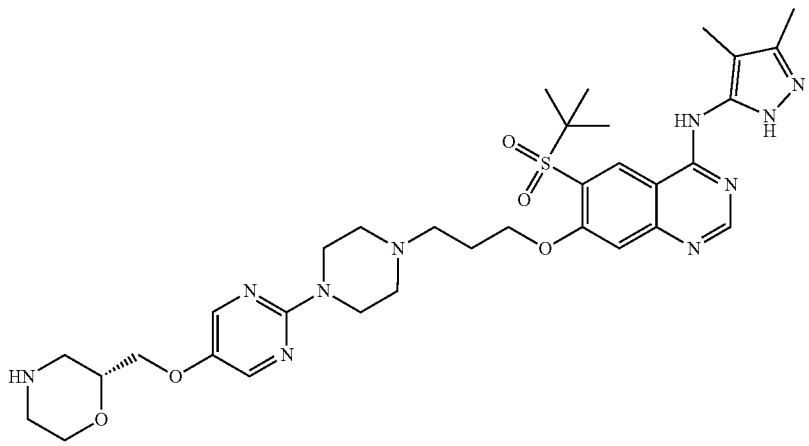 [SMILES: Cc1n[nH]c(Nc2ncnc3cc(OCCCN4CCN(c5ncc(OC[C@H]6CNCCO6)cn5)CC4)c(S(=O)(=O)C(C)(C)C)cc23)c1C]

To a solution of (R)-tert-butyl 2-((2-(4-(3-(6-(tert-butylsulfonyl)-4-(3,4-dimethyl-1H-pyrazol-5-ylamino)quinazolin-7-yloxy)propyl)piperazin-1-yl)pyrimidin-5-yloxy)methyl)morpholine-4-carboxylate (0.28 g, 0.35 mmol) in DCM (10 mL) was added TFA (1 ml) and then the reaction was stirred at room temperature for 3 hours. Then the solvent was evaporated to dryness to afford the title compound (0.25 g, 0.31 mmol, 89% yield). LCMS Method D RT=1.14 min, ES+ve 694.

(R)-2-(Benzylamino)propan-1-ol

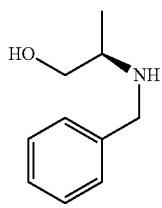

To a solution of (R)-2-aminopropan-1-ol (20 g, 267 mmol) and benzaldehyde (28.3 g, 267 mmol) in dichloroethane (300 mL) was added acetic acid (16 g, 267 mmol) at 0° C. and the reaction was stirred for 10 mins. To the mixture was added sodium triacetoxyborohyride (28.2 g, 133 mmol) and the reaction was stirred at room temperature overnight. To the reaction mixture was added 20 g of $K_2CO_3$ and 300 ml of water, the organic layer was washed with saturated brine and was evaporated to dryness. The residue was purified by flash chromatography, eluting with methanol:dichloromethane=1:10 and concentrating under vacuum to afford the title compound (13.2 g, 80.1 mmol, 30% yield). LCMS Method D RT=0.87 min, ES+ve 166 (M+H).

((2R,5R)-4-Benzyl-5-methylmorpholin-2-yl)methanol

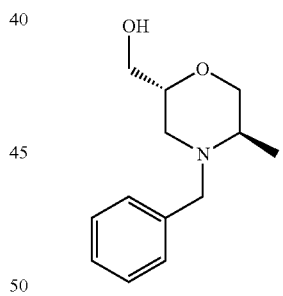

To a solution of (R)-2-(benzylamino)propan-1-ol (4.5 g, 2.7 mmol) in toluene was added (S)-2-(chloromethyl)oxirane (3.7 g, 4.1 mmol) and lithium perchlorate (4.5 g, 41 mmol) at room temperature under $N_2$ atmosphere, the reaction was stirred at room temperature for 18 hours. To the solution was added 3.2 g of NaOH and 50 ml of methanol dropwise, then the reaction was stirred at room temperature for 18 hours. To the solution was added to 100 ml of water and 100 ml of ethyl acetate, the organic layer was washed with saturated brine and was evaporated to dryness. The residue was purified by flash chromatography, eluting with 0-5% methanol to afford the title compound (2.7 g, 1.27 mmol, 47% yield). LCMS Method D RT=0.96 min, ES+ve 222 (M+H).

(2R,5R)-Tert-butyl 2-(hydroxymethyl)-5-methyl-morpholine-4-carboxylate

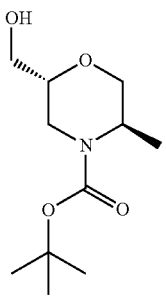 [SMILES: C[C@@H]1CO[C@@H](CO)CN1C(=O)OC(C)(C)C]

To a solution of ((2R,5R)-4-benzyl-5-methylmorpholin-2-yl)methanol (2.7 g, 12.2 mmol), palladium hydroxide (170 mg, 1.2 mmol) in methanol (50 mL) was added di-tert-butyl dicarbonate (5.2 g, 2.4 mmol) and the reaction was stirred under 1 atm of $H_2$ atmosphere at room temperature overnight. The solution was filtered, the filtrate was evaporated to dryness and the residue was purified by flash column chromatography, eluting with ethyl acetate:petroleum ether=2:1 to afford the title compound (1.2 g, 5.2 mmol, 43% yield). LCMS Method D RT=1.34 min, ES+ve 176 (M-tBu+H).

(2R,5R)-Tert-butyl 2-(((2-chloropyrimidin-5-yl)oxy)methyl)-5-methylmorpholine-4-carboxylate

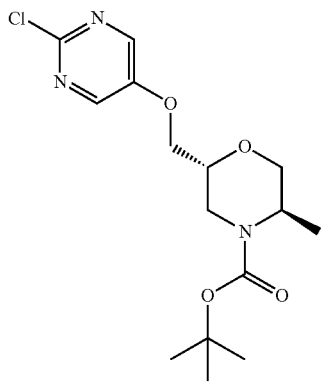 [SMILES: C[C@@H]1CO[C@@H](COc2cnc(Cl)nc2)CN1C(=O)OC(C)(C)C]

To a solution of (2R,5R)-tert-butyl 2-(hydroxymethyl)-5-methylmorpholine-4-carboxylate (1.2 g, 5.2 mmol) and 2-chloropyrimidin-5-ol (1 g, 7.5 mmol), DIAD (1.5 g 7.5 mmol) in THF (30 mL) was added triphenylphosphine (2 g, 7.5 mmol) at 0° C., then the reaction was stirred at room temperature for 12 hours. The reaction solution was evaporated to dryness and the residue was purified by flash column chromatography, eluting with ethyl acetate:petroleum ether=1:3 to afford the title compound (0.52 g, 1.52 mmol, 29% yield). LCMS Method D RT=1.54 min, ES+ve 287.9 (M-tBu+H).

(2R,5R)-Tert-butyl 2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholine-4-carboxylate

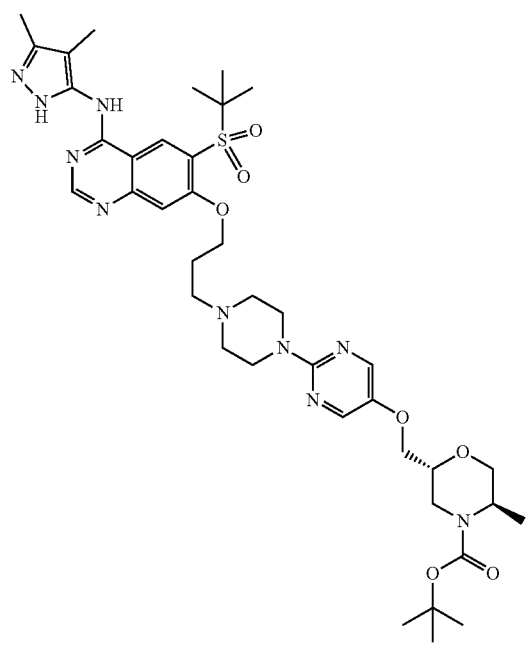 [SMILES: Cc1n[nH]c(Nc2ncnc3cc(OCCCN4CCN(c5ncc(OC[C@H]6CN(C(=O)OC(C)(C)C)[C@H](C)CO6)cn5)CC4)c(S(=O)(=O)C(C)(C)C)cc23)c1C]

To a solution of 6-(tert-butylsulfonyl)-N-(3,4-dimethyl-1H-pyrazol-5-yl)-7-(3-(piperazin-1-yl)propoxy)quinazolin-4-amine (1.1 g, 2.2 mmol) and (2R,5R)-tert-butyl 2-((2-chloropyrimidin-5-yloxy)methyl)-5-methylmorpholine-4-carboxylate (0.76 g, 2.2 mmol) in N-methyl-2-pyrrolidone (10 mL) was added $NaHCO_3$ (0.9 g, 11 mmol) and the reaction was stirred at 110° C. for 18 hours. To the reaction mixture was added 5 ml of MeOH and the resulting precipitate was filtered. The filtrate was concentrated to dryness, and the residue was purified by preparative HPLC (Method A, Gradient: 10-60%) to afford the title compound (0.52 g, 0.64 mmol, 29% yield). LCMS Method D RT=1.34 min, ES+ve 809 (M+H).

6-(Tert-butylsulfonyl)-N-(3,4-dimethyl-1H-pyrazol-5-yl)-7-(3-(4-(5-((2R,5R)-5-methylmorpholin-2-yl)methoxy)pyrimidin-2-yl)piperazin-1-yl)propoxy)quinazolin-4-amine

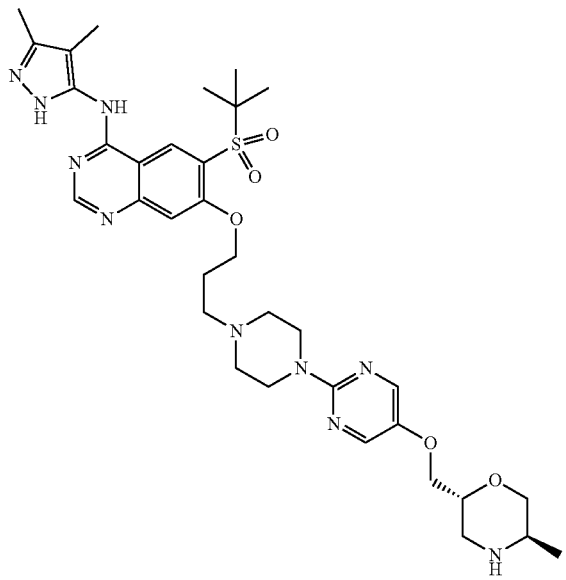 [SMILES: Cc1n[nH]c(Nc2ncnc3cc(OCCCN4CCN(c5ncc(OC[C@H]6CN[C@H](C)CO6)cn5)CC4)c(S(=O)(=O)C(C)(C)C)cc23)c1C]

To a solution of (2R,5R)-tert-butyl 2-((2-(4-(3-(6-(tert-butylsulfonyl)-4-(3,4-dimethyl-1H-pyrazol-5-ylamino)quinazolin-7-yloxy)propyl)piperazin-1-yl)pyrimidin-5-yloxy)methyl)-5-methylmorpholine-4-carboxylate (0.53 g, 0.66 mmol) in DCM (10 mL) was added TFA (1 ml) and the reaction was stirred at room temperature for 3 hours. The reaction solution was evaporated to dryness to afford the title compound (0.44 g, 0.62 mmol, 94% yield). LCMS Method D RT=1.12 min, ES+ve 708.9 (M+H). The compound was carried through without further purification.

5-(2-Bromoethoxy)-2-chloropyrimidine

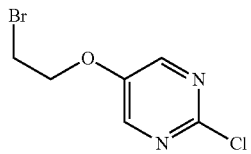 [SMILES: Clc1ncc(OCCBr)cn1]

To a mixture solution of 2-chloropyrimidin-5-ol (4.0 g, 30.8 mmol) and potassium carbonate (12.7 g, 92.0 mmol) in DMF (50 mL) was added 1,2-dibromoethane (23.0 g, 122 mmol), and the reaction was stirred for 16 hours at 70° C. The reaction mixture was poured into water, extracted with ethyl acetate (80 mL×3), the combined organic layers were washed with brine and dried over anhydrous sodium sulfate. The organic layers were concentrated to dryness and the residue was purified by silica gel column chromatography, eluting with petroleum ether/ethyl acetate (5:1) to afford the title compound (4.0 g, 17.0 mmol, 55% yield). LCMS Method D RT=1.47 min, ES+ve 236 (M+H).

(R)-Tert-butyl 2-methyl-3-oxopiperazine-1-carboxylate

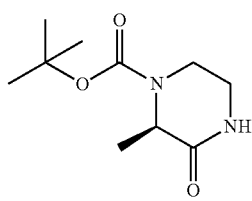

To a stirred solution of (R)-3-methylpiperazin-2-one (2.0 g, 17.5 mmol) and triethylamine (2.7 g, 26.3 mmol) in DCM (20 mL) was added (Boc)$_2$O (5.0 g, 22.8 mmol). The resulting mixture was stirred for 16 hours at ambient temperature. The solvent was removed under reduced pressure and the residue was purified by silica gel column chromatography, eluting with CH$_2$Cl$_2$/MeOH (50:1) to afford the title compound (2.1 g, 9.81 mmol, 56% yield). LCMS Method D RT=1.47 min, ES+ve 236 (M+H). $^1$H NMR (400 MHz, CDCl$_3$) δ 7.02 (s, 1H), 4.59 (s, 1H), 4.14 (s, 1H), 3.46 (td, J=11.6, 4.1 Hz, 1H), 3.32-3.22 (m, 1H), 3.17 (d, J=11.0 Hz, 1H), 1.48 (s, 9H), 1.44 (d, J=7.1 Hz, 3H).

(R)-Tert-butyl 4-(2-((2-chloropyrimidin-5-yl)oxy)ethyl)-2-methyl-3-oxopiperazine-1-carboxylate

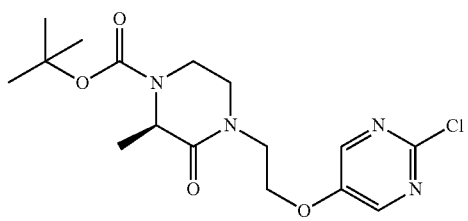 [SMILES: C[C@@H]1C(=O)N(CCOc2cnc(Cl)nc2)CCN1C(=O)OC(C)(C)C]

To a stirred solution of (R)-tert-butyl 2-methyl-3-oxopiperazine-1-carboxylate (950 mg, 4.44 mmol) in dry DMF (10 mL) was added sodium hydride (60%, 355 mg, 8.87 mmol) by portions at 0° C., then the reaction was stirred for 20 mins at 0° C., then 5-(2-bromoethoxy)-2-chloropyrimidine (1.26 g, 5.34 mmol) was added and the resulting mixture was stirred for 16 hours at room temperature. The reaction mixture was poured into water, extracted with ethyl acetate (30 mL×3), the combined organic layers were washed with brine and dried over anhydrous sodium sulfate. The organic layer was evaporated to dryness, the residue was purified by silica gel column chromatography, eluting with CH$_2$Cl$_2$/MeOH (50:1) to afford the title compound (0.9 g, 2.43 mmol, 55% yield). LCMS Method D RT=1.49 min, ES+ve 315 (M-tBu+H).

(R)-Tert-butyl 4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-2-methyl-3-oxopiperazine-1-carboxylate

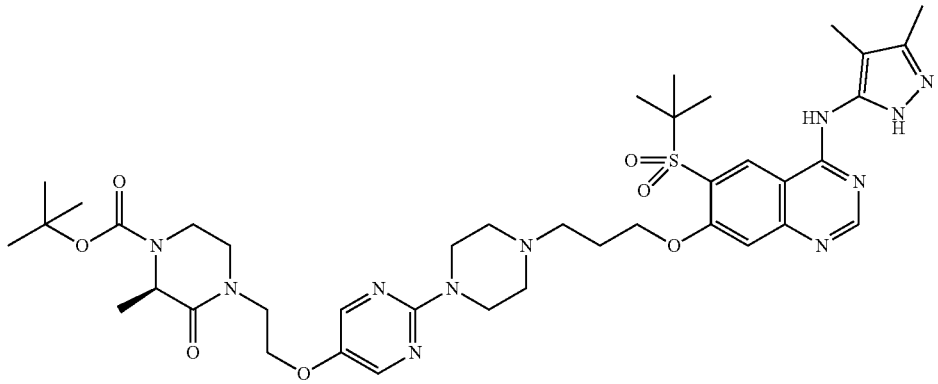 [SMILES: Cc1n[nH]c(Nc2ncnc3cc(OCCCN4CCN(c5ncc(OCCN6CCN(C(=O)OC(C)(C)C)[C@H](C)C6=O)cn5)CC4)c(S(=O)(=O)C(C)(C)C)cc23)c1C]

A mixture solution of (R)-tert-butyl 4-(2-(2-chloropyrimidin-5-yloxy)ethyl)-2-methyl-3-oxopiperazine-1-carboxylate (207 mg, 0.56 mmol), 6-(tert-butylsulfonyl)-N-(3,4-dimethyl-1H-pyrazol-5-yl)-7-(3-(piperazin-1-yl)propoxy)quinazolin-4-amine hydrochloride (360 mg, 0.67 mmol) and sodium bicarbonate (140 mg, 1.67 mmol) in NMP (6 mL) was stirred for 16 h at 110° C. under an argon atmosphere. The reaction mixture was cooled down to room temperature, then poured into water, extracted with ethyl acetate (50 mL×3), the combined organic layers were washed with brine and dried over anhydrous sodium sulfate. The solids were removed by filtration, the filtrate was concentrated to dryness and the residue was purified by silica gel column chromatography, eluting with $CH_2Cl_2$/MeOH/$NH_4OH$ (400:8:1) to afford the title compound (210 mg, 0.25 mmol, 45% yield). LCMS Method D RT=1.26 min, ES+ve 835.9 (M+H).

(R)-1-(2-((2-(4-(3-((6-(Tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-3-methylpiperazin-2-one hydrochloride

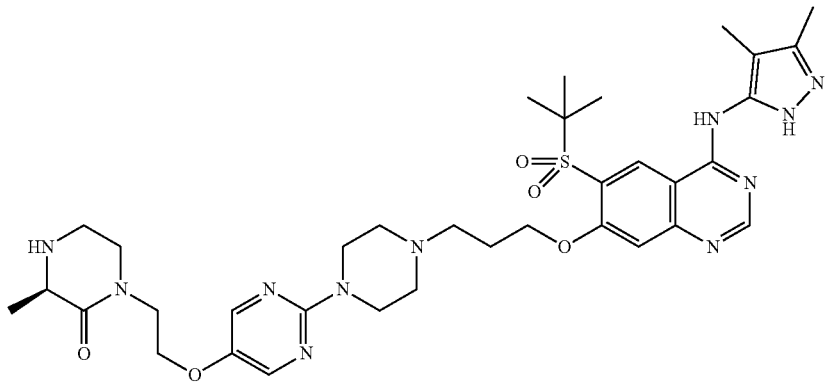 [SMILES: Cc1n[nH]c(Nc2ncnc3cc(OCCCN4CCN(c5ncc(OCCN6CCN[C@H](C)C6=O)cn5)CC4)c(S(=O)(=O)C(C)(C)C)cc23)c1C]

To a stirred solution of (R)-tert-butyl 4-(2-(2-(4-(3-(6-(tert-butylsulfonyl)-4-(3,4-dimethyl-1H-pyrazol-5-ylamino)quinazolin-7-yloxy)propyl)piperazin-1-yl)pyrimidin-5-yloxy)ethyl)-2-methyl-3-oxopiperazine-1-carboxylate (210 mg, 0.25 mmol) in EtOH (16 mL) at 0° C. was added HCl (gas) in EtOH (33% weight, 8 mL) slowly. The reaction mixture was stirred for 3 hours and the temperature was allowed to warm to room temperature. The solvent was removed under vacuum to afford the title compound (180 mg, 0.23 mmol, 93% yield). LCMS Method D RT=1.17 min, ES+ve 736 (M+H).

Methyl 2-(4-(2-((6-(tert-butylsulfonyl)-4-((5-fluoro-1H-indazol-3-yl)amino)quinolin-7-yl)oxy)ethyl)piperazin-1-yl)pyrimidine-5-carboxylate

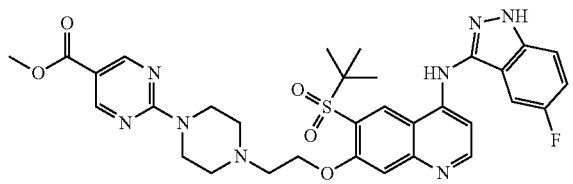 [SMILES: COC(=O)c1cnc(N2CCN(CCOc3cc4nccc(Nc5n[nH]c6ccc(F)cc56)c4cc3S(=O)(=O)C(C)(C)C)CC2)nc1]

To a solution of 6-(tert-butylsulfonyl)-N-(5-fluoro-1H-indazol-3-yl)-7-(2-(piperazin-1-yl)ethoxy)quinolin-4-amine (120 mg, 0.23 mmol) in NMP (2 mL) was added methyl 2-chloropyrimidine-5-carboxylate (47 mg, 0.27 mmol), and sodium bicarbonate (57 mg, 0.68 mmol) and the reaction was stirred at 110° C. for 1 h. The residue was subjected directly to purification by flash chromatography (30 g pre-packed C-18 SNAP cartridge: 30% to 85% acetonitrile (0.1% ammonia) in water (10 mM ammonium bicarbonate)). The desired fractions were combined and concentrated to afford the title compound (106 mg, 0.16 mmol, 70% yield). LCMS RT=1.15 min, ES+ve 663.

2-(4-(2-((6-(Tert-butylsulfonyl)-4-((5-fluoro-1H-indazol-3-yl)amino)quinolin-7-yl)oxy)ethyl)piperazin-1-yl)pyrimidine-5-carboxylic acid

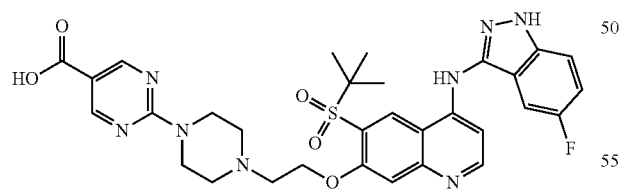

To a solution of methyl 2-(4-(2-((6-(tert-butylsulfonyl)-4-((5-fluoro-1H-indazol-3-yl)amino)quinolin-7-yl)oxy)ethyl)piperazin-1-yl)pyrimidine-5-carboxylate (106 mg, 0.16 mmol) in Methanol (1 mL) was added sodium hydroxide (0.24 mL, 0.48 mmol) 2M solution in water and reaction stirred at 20° C. The reaction was neutralised with HCl (0.80 mL, 1.59 mmol) 2M solution and the volatiles were removed under vacuum. The residue was subjected directly to purification by flash chromatography (12 g pre-packed C-18 SNAP cartridge: 15% to 55% acetonitrile (0.1% formic) in water (0.1% formic acid)). The desired fractions were combined and concentrated to afford the title compound (52 mg, 0.08 mmol, 50% yield). LCMS RT=0.78 min, ES+ve 649.

(R)-Ethyl 2-(4-(tert-butoxycarbonyl)-3-methylpiperazin-1-yl)pyrimidine-5-carboxylate

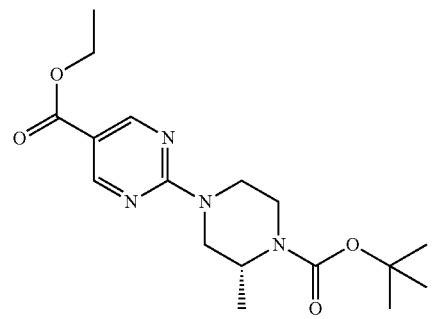 [SMILES: CCOC(=O)c1cnc(N2CCN(C(=O)OC(C)(C)C)[C@H](C)C2)nc1]

To a solution of (R)-tert-butyl 2-methylpiperazine-1-carboxylate (631 mg, 3.15 mmol) in acetonitrile (10 mL) was added ethyl 2-chloropyrimidine-5-carboxylate (560 mg, 3.00 mmol), and sodium bicarbonate (756 mg, 9.00 mmol) and reaction stirred at 82° C. for 2 hours. The reaction was diluted with 100 mL ethyl acetate and washed with 3×40 mL water and 40 mL brine. The organic phase was dried by passing through a Biotage Phase Separator and concentrated under vacuum to afford the title compound (1.85 g, 5.28 mmol, 99% yield). LCMS Method B RT=1.32 min, ES+ve 351.

(6(R)-Ethyl 2-(3-methylpiperazin-1-yl)pyrimidine-5-carboxylate.Hydrochloride

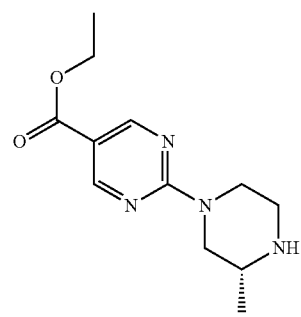 [SMILES: CCOC(=O)c1cnc(N2CCN[C@H](C)C2)nc1]

To a solution of (R)-ethyl 2-(4-(tert-butoxycarbonyl)-3-methylpiperazin-1-yl)pyrimidine-5-carboxylate (1850 mg, 5.28 mmol) in Methanol (25 mL) was added HCl (26.4 mL, 106 mmol, 4.0M in dioxane) and the reaction was stirred at room temperature for 3 h.

The reaction was concentrated under vacuum to afford the title compound (1.70 g, 5.26 mmol, 100% yield). LCMS Method B RT=0.85 min, ES+ve 251.

109
(R)-Methyl 5-(4-(tert-butoxycarbonyl)-3-methylpiperazin-1-yl)pyrazine-2-carboxylate

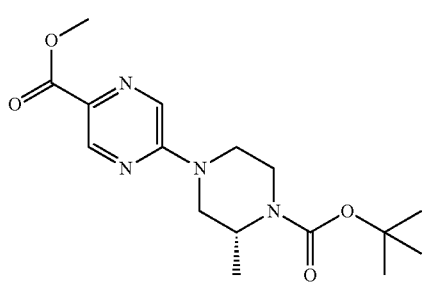 [SMILES: COC(=O)c1cnc(N2CCN(C(=O)OC(C)(C)C)[C@H](C)C2)cn1]

The mixture solution of (R)-tert-butyl 2-methylpiperazine-1-carboxylate (0.58 g, 2.9 mmol), methyl 5-chloropyrazine-2-carboxylate (0.6 g, 3.49 mmol), $Cs_2CO_3$ (1.9 g, 5.8 mmol) in 1,4-dioxane (50 mL) was stirred at 80° C. for 16 hours. The mixture was diluted with dichloromethane (20 mL), the precipitate was removed by filtration and the filtrate was concentrated to dryness. The residue was purified by flash column chromatography, eluting with ethyl acetate:petroleum ether, gradient of 1:100 to 1:20 to afford the title compound (400 mg, 1.19 mmol, 41% yield). LCMS Method D RT=1.55 min, ES+ve 337.

110
(R)-5-(4-(Tert-butoxycarbonyl)-3-methylpiperazin-1-yl)pyrazine-2-carboxylic acid

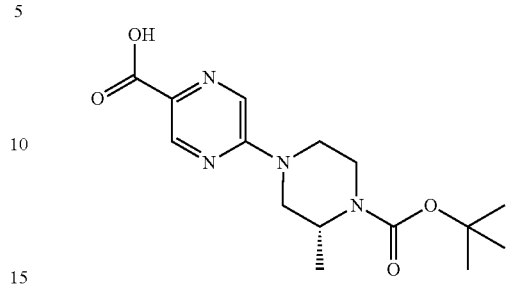

To a solution of (R)-methyl 5-(4-(tert-butoxycarbonyl)-3-methylpiperazin-1-yl)pyrazine-2-carboxylate (0.3 g, 0.89 mmol) in methanol (3 mL) and water (1 mL) was added lithium hydroxide (0.1 g, 4.5 mmol) and the reaction was stirred at room temperature for 3 hours. The reaction mixture was acidified to pH 3 with 1 N aqueous HCl solution, then the solvent was evaporated to dryness and the residue was purified by prep-HPLC (Method A Gradient: 15-65%) to afford the title compound (250 mg, 0.78 mmol, 87% yield). LCMS Method D RT=1.41 min, ES+ve 323.

(R)-Tert-butyl 4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazine-1-carboxylate

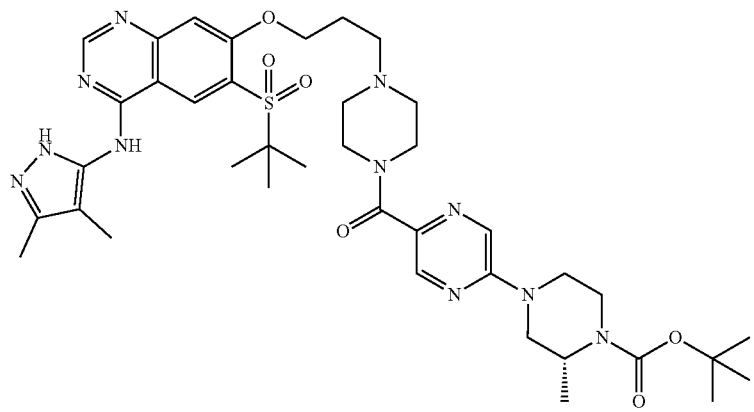 [SMILES: Cc1n[nH]c(Nc2ncnc3cc(OCCCN4CCN(C(=O)c5cnc(N6CCN(C(=O)OC(C)(C)C)[C@H](C)C6)cn5)CC4)c(S(=O)(=O)C(C)(C)C)cc23)c1C]

To a solution of 6-(tert-butylsulfonyl)-N-(3,4-dimethyl-1H-pyrazol-5-yl)-7-(3-(piperazin-1-yl)propoxy)quinazolin-4-amine (0.38 g, 0.76 mmol) and (R)-5-(4-(tert-butoxycarbonyl)-3-methylpiperazin-1-yl)pyrazine-2-carboxylic acid (0.25 g, 0.77 mmol) in DCM (10 mL) was added O-(Benzotriazol-1-yl)-N,N,N',N'-tetramethyluronium tetrafluoroborate (0.29 g, 0.9 mmol), N,N-diisopropylethylamine (0.34 g, 2.6 mmol) and then stirred at room temperature overnight. To the solution was added 10 mL of water, the organic layer was separated and concentrated to dryness, and the residue was purified by prep-HPLC (column: Gemini-C18 150×21.2 mm, 5 μm. Mobile phase:acetonitrile to $H_2O$ (0.1% TFA). Gradient: 30-35) to afford the title compound (150 mg, 0.19 mmol, 25% yield). LCMS Method D RT=1.30 min, ES+ve 805.9.

111

(R)-(4-(3-((6-(Tert-butylsulfonyl)-4-((3,4-dimethyl-1H-pyrazol-5-yl)amino)quinazolin-7-yl)oxy)propyl)piperazin-1-yl)(5-(3-methylpiperazin-1-yl)pyrazin-2-yl)methanone. Trifluoroacetete

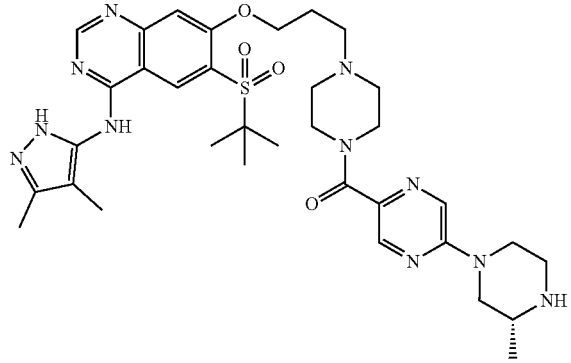 [SMILES: Cc1n[nH]c(Nc2ncnc3cc(OCCCN4CCN(C(=O)c5cnc(N6CCN[C@H](C)C6)cn5)CC4)c(S(=O)(=O)C(C)(C)C)cc23)c1C]

To a solution of (R)-tert-butyl 4-(5-(4-(3-(6-(tert-butyl-sulfonyl)-4-(4,5-dimethyl-1H-pyrazol-3-ylamino)quinazo-lin-7-yloxy)propyl)piperazine-1-carbonyl)pyrazin-2-yl)-2-methylpiperazine-1-carboxylate (0.15 g, 0.19 mmol) in dichloromethane (10 mL) was added TFA (2 mL) and the reaction was stirred at room temperature for 3 hours. The solvent was evaporated to dryness to afford the title compound (140 mg, 0.171 mmol, 90% yield). LCMS Method D RT=1.10 min, ES+ve 705.9.

(R)-Tert-butyl 4-(5-chloropyrazine-2-carbonyl)-2-methylpiperazine-1-carboxylate

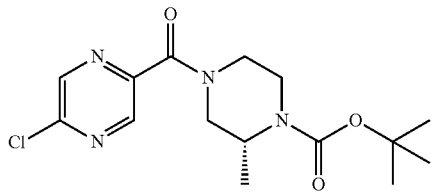 [SMILES: C[C@@H]1CN(C(=O)c2cnc(Cl)cn2)CCN1C(=O)OC(C)(C)C]

A solution of (R)-tert-butyl 2-methylpiperazine-1-car-boxylate (0.5 g, 2.5 mmol), 5-chloropyrazine-2-carboxylic acid (0.4 g, 2.5 mmol), HATU (1.14 g, 3 mmol) and triethylamine (0.64 g, 6.4 mmol) in dichloromethane (5 ml) was stirred at room temperature for 2 hours. To the mixture was added water (30 mL) and the organics were extracted with dichloromethane (20 mL). The organic layer was dried over Na$_2$SO$_4$ and concentrated to dryness, and the residue was purified by silica gel flash column chromatography, eluting with ethyl acetate:petroleum ether=1:5 to afford the title compound (780 mg, 2.29 mmol, 92% yield). LCMS Method D RT=1.54 min, ES+ve 241 [M-Boc+H]$^+$.

112

(R)-Tert-butyl 4-(5-(4-(3-(((6-(tert-butylsulfonyl)-4-((3,4-dimethyl-1H-pyrazol-5-yl)amino)quinazolin-7-yl)oxy)propyl)piperazin-1-yl) pyrazine-2-carbonyl)-2-methylpiperazine-1-carboxylate

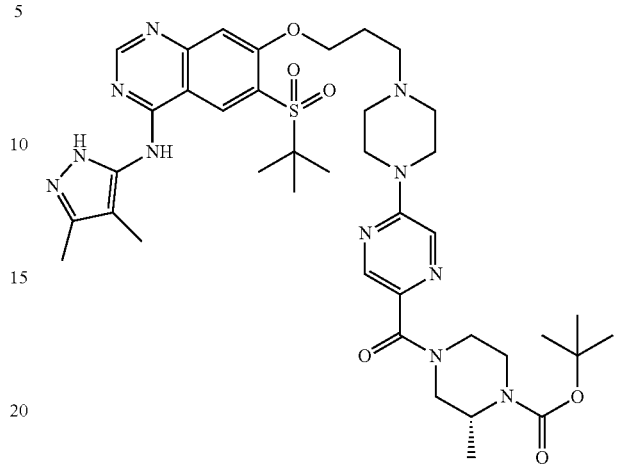

To a solution of 6-(tert-butylsulfonyl)-N-(3,4-dimethyl-1H-pyrazol-5-yl)-7-(3-(piperazin-1-yl)propoxy)quinazolin-4-amine (1 g, 2 mmol) and (R)-tert-butyl 4-(5-chloropyra-zine-2-carbonyl)-2-methylpiperazine-1-carboxylate (0.68 g, 2 mmol) in NMP (10 mL) was added NaHCO$_3$ (0.68 g, 8 mmol) and then stirred at 110° C. for 18 hours. The reaction was diluted with 5 mL of MeOH, the precipitate was removed by filtration and the filtrate was purified by pre-parative HPLC (Method A Gradient: 10-50%) to afford the title compound (320 mg, 0.40 mmol, 20% yield). LCMS Method D RT=1.27 min, ES+ve 807.0 [M+H]$^+$.

(R)-(5-(4-(3-((6-(Tert-butylsulfonyl)-4-((3,4-dim-ethyl-1H-pyrazol-5-yl)amino)quinazolin-7-yl)oxy) propyl)piperazin-1-yl)pyrazin-2-yl)(3-methylpiper-azin-1-yl)methanone

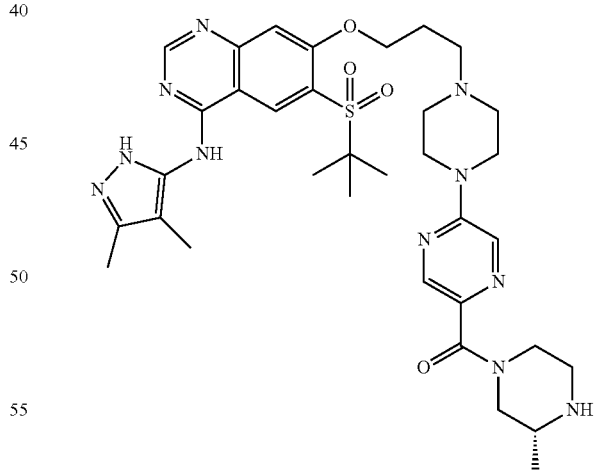

To a solution of (R)-tert-butyl 4-(5-(4-(3-(6-(tert-butyl-sulfonyl)-4-(4,5-dimethyl-1H-pyrazol-3-ylamino)quinazo-lin-7-yloxy)propyl)piperazin-1-yl)pyrazine-2-carbonyl)-2-methylpiperazine-1-carboxylate (0.32 g, 0.4 mmol) in DCM (10 mL) was added CF$_3$CO$_2$H (1 ml) and the reaction was stirred at room temperature for 6 hours. The solvent was evaporated to dryness to afford the title compound (240 mg, 0.34 mmol, 85% yield). LCMS Method D RT=1.11 min, ES+ve 705.9 [M+H]$^+$.

(R)-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yl)(3-methylpiperazin-1-yl)methanone

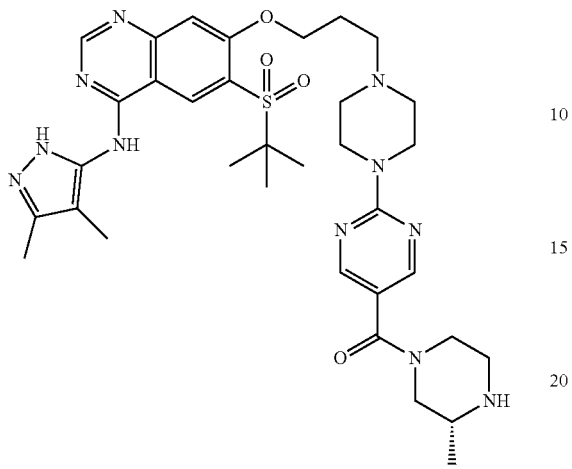

The title compound was prepared by a method analogous to those above, starting from 2-chloropyrimidine-5-carboxylic acid. In synthesis of (R)-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yl)(3-methylpiperazin-1-yl)methanone, the Boc group was removed in purification.

| Compound Name | Structure | Yield | LCMS RT | ES +ve |
|---|---|---|---|---|
| (R)-tert-butyl 4-(2-chloropyrimidine-5-carbonyl)-2-methylpiperazine-1-carboxylate | 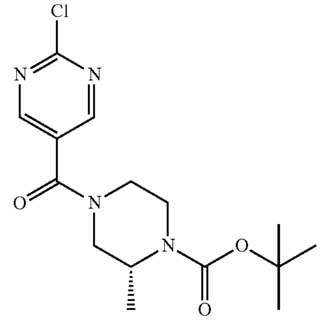 [SMILES: C[C@@H]1CN(C(=O)c2cnc(Cl)nc2)CCN1C(=O)OC(C)(C)C] | 47% | Method D 1.49 mins | 241 (M − Boc) |
| (R)-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yl)(3-methylpiperazin-1-yl)methanone | 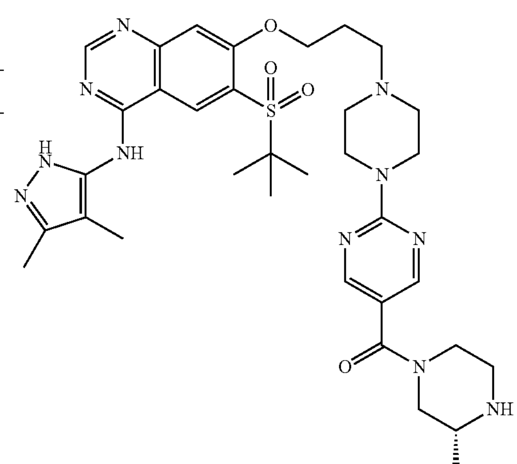 | 27% | Method D 1.15 mins | 706 |

Tert-butyl 6-(4-fluorobenzyl)-3,3,4-trimethyl-5-oxo-2,3,4,5-tetrahydro-1H-pyrrolo[3,2-b]pyridine-1-carboxylate

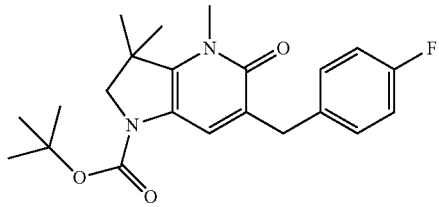 [SMILES: Cn1c2c(cc(Cc3ccc(F)cc3)c1=O)N(C(=O)OC(C)(C)C)CC2(C)C]

To a solution of tert-butyl 6-(4-fluorobenzyl)-3,3-dimethyl-5-oxo-2,3,4,5-tetrahydro-1H-pyrrolo[3,2-b]pyridine-1-carboxylate (100 mg, 0.27 mmol, obtained as described in WO 2012/143726) in Tetrahydrofuran (THF) (2 mL) was added lithium 2-methylpropan-2-olate (43.0 mg, 0.54 mmol) and iodomethane (0.03 mL, 0.54 mmol) and reaction stirred at 110° C. in a microwave reactor for 4 h. The crude reaction was subjected to purification by mass-directed automated preparative HPLC (formic acid modifier). The desired fractions were combined and concentrated to afford the title compound (71 mg, 0.18 mmol, 68% yield). LCMS Method A RT=1.23 min, ES+ve 387.

6-(4-Fluorobenzyl)-3,3,4-trimethyl-2,3-dihydro-1H-pyrrolo[3,2-b]pyridin-5(4H)-one

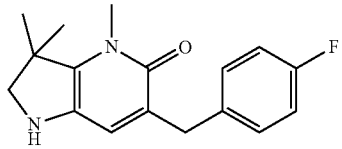 [SMILES: Cn1c2c(cc(Cc3ccc(F)cc3)c1=O)NCC2(C)C]

To a solution of tert-butyl 6-(4-fluorobenzyl)-3,3,4-trimethyl-5-oxo-2,3,4,5-tetrahydro-1H-pyrrolo[3,2-b]pyridine-1-carboxylate (71 mg, 0.18 mmol) in chloroform (1.0 mL) was added hydrochloric acid (0.92 mL, 3.67 mmol) 4.0M in dioxane and reaction stirred at room temperature for 2 h. The reaction was concentrated under vacuum to afford the title compound (59 mg, 0.18 mmol, 99% yield). LCMS Method A RT=0.51 min, ES+ve 287.

(2R,5R)-Tert-butyl 4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-5-(hydroxymethyl)-2-methylpiperazine-1-carboxylate

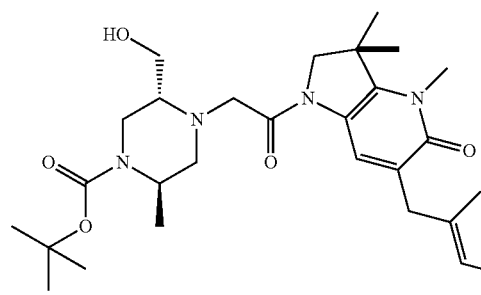

To a solution of 6-(4-fluorobenzyl)-3,3,4-trimethyl-2,3-dihydro-1H-pyrrolo[3,2-b]pyridin-5(4H)-one (190 mg, 0.66 mmol) in DCM (3.00 mL) and was added triethylamine (0.277 mL, 1.99 mmol) and the reaction was stirred at room temperature under an atmosphere of nitrogen. Chloroacetyl chloride (0.058 mL, 0.730 mmol) was added and the reaction was stirred at room temperature for 30 minutes. The reaction was diluted in 25 mL DCM and washed with 10 mL saturated sodium bicarbonate solution, 10 mL water and 10 mL brine. The organic layer was passed through a biotage phase separator and concentrated under vacuum. The residue was dissolved in 3 mL THF and triethylamine (0.28 mL, 1.99 mmol) and (2R,5R)-tert-butyl 5-(hydroxymethyl)-2-methylpiperazine-1-carboxylate (199 mg, 0.86 mmol, obtained as described in WO 2012/143726) was added. The reaction was stirred at 60° C. for 18 h, then was diluted in 25 mL EtOAc and washed with 2×10 mL water and 10 mL brine. The organic layer was passed a through biotage phase separator and concentrated under vacuum to afford the title compound (170 mg, 0.31 mmol, 46% yield). LCMS Method A RT=0.84 min, ES+ve 557.

(2R,5R)-Tert-butyl 5-(chloromethyl)-4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-2-methyl piperazine-1-carboxylate

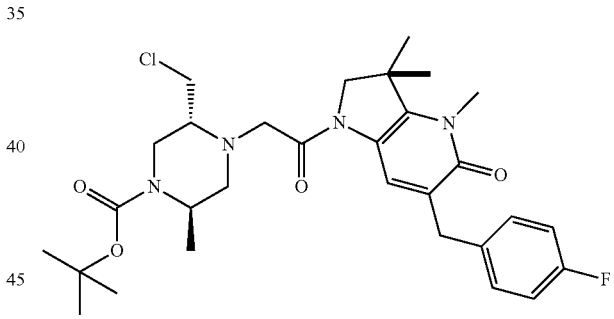

To a solution of (2R,5R)-tert-butyl 4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-5-(hydroxymethyl)-2-methylpiperazine-1-carboxylate (170 mg, 0.31 mmol) in DCM (3 mL) was added triethylamine (0.128 mL, 0.92 mmol) and the reaction was stirred at 20° C. under an atmosphere of nitrogen. Methanesulfonyl chloride (0.059 mL, 0.763 mmol) was added and reaction stirred at room temperature under an atmosphere of nitrogen for 18 h. The reaction was diluted in 25 mL EtOAc and washed with 2×10 mL saturated sodium bicarbonate solution, 2×10 mL water, 2×10 mL saturated ammonium chloride solution and 10 mL brine. The organic layer was passed through a Biotage Phase Separator and was concentrated under vacuum to afford the title compound (170 mg, 0.30 mmol, 97% yield). LCMS Method A RT=1.28 min, ES+ve 575.

Tert-butyl 5-(benzyloxy)-6-(4-fluorobenzyl)-3, 3-dimethyl-2, 3-dihydropyrrolo [3, 2-b] pyridine-1-carboxylate

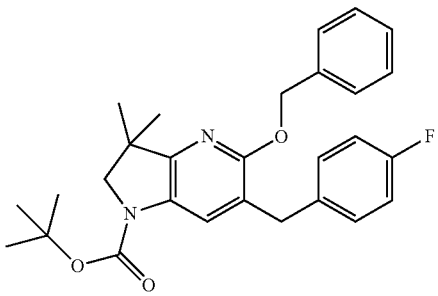 [SMILES: CC(C)(C)OC(=O)N1CC(C)(C)c2nc(OCc3ccccc3)c(Cc3ccc(F)cc3)cc21]

To a solution of tert-butyl 6-(4-fluorobenzyl)-3,3-dimethyl-5-oxo-2,3,4,5-tetrahydro-1H-pyrrolo[3,2-b]pyridine-1-carboxylate (1.5 g, 4.0 mmol, obtained as described in WO 2012/143726) and benzyl bromide (1.4 g, 8.2 mmol) in acetonitrile (20 mL) was added potassium carbonate (1.7 g, 12.3 mmol) and the reaction stirred at 80° C. for 16 h. The volatiles were removed under vacuum, and the residue was purified by flash column chromatography, eluting with ethyl acetate:petroleum ether 1:2 to afford the title compound as a colourless oil (1.3 g, 2.81 mmol, 70% yield). LCMS Method D RT=2.26 min, ES+ve 463.

(2R, 5R)-tert-butyl 4-(2-(5-(benzyloxy)-6-(4-fluorobenzyl)-3,3-dimethyl-2,3-dihydropyrrolo [3,2-b] pyridin-1-yl)-2-oxoethyl)-5-(chloromethyl)-2-methylpiperazine-1-carboxylate

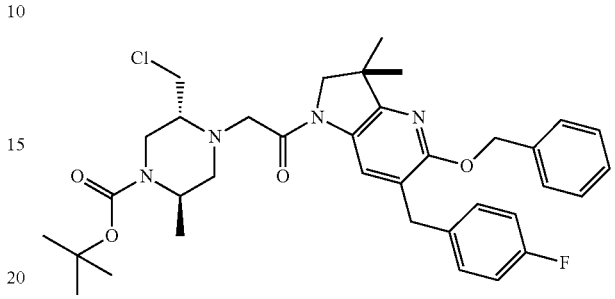

The title compound was prepared by a method analogous to those above, starting from tert-butyl 5-(benzyloxy)-6-(4-fluorobenzyl)-3, 3-dimethyl-2, 3-dihydropyrrolo [3, 2-b] pyridine-1-carboxylate.

| Compound Name | Structure | Yield | LCMS RT | ES +ve |
|---|---|---|---|---|
| 5-(Benzyloxy)-6-(4-fluorobenzyl)-3,3-dimethyl-2,3-dihydro-1H-pyrrolo [3,2-b] pyridine | 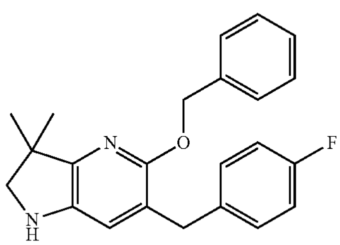 [SMILES: CC1(C)CNc2cc(Cc3ccc(F)cc3)c(OCc3ccccc3)nc21] | 80% | Method D 1.45 mins | 363 |
| 1-(5-(Benzyloxy)-6-(4-fluorobenzyl)-3,3-dimethyl-2,3-dihydropyrrolo [3,2-b] pyridin-1-yl)-2-chloroethanone | 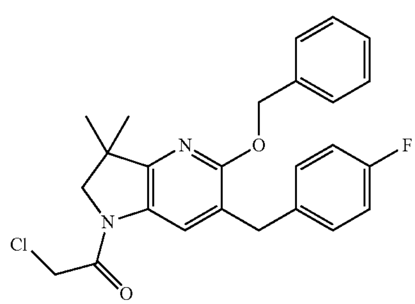 [SMILES: CC1(C)CN(C(=O)CCl)c2cc(Cc3ccc(F)cc3)c(OCc3ccccc3)nc21] | 80% | Method D 1.85 mins | 439 |
| (2R,5R)-Tert-butyl 4-(2-(5-(benzyloxy)-6-(4-fluorobenzyl)-3,3-dimethyl-2,3-dihydropyrrolo[3,2-b]pyridin-1-yl)-2-oxoethyl)-5-(hydroxymethyl)-2-methylpiperazine-1-carboxylate | 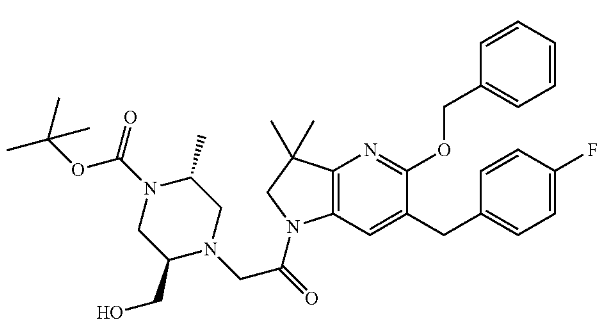 [SMILES: C[C@@H]1CN(CC(=O)N2CC(C)(C)c3nc(OCc4ccccc4)c(Cc4ccc(F)cc4)cc32)[C@@H](CCl)CN1C(=O)OC(C)(C)C] | 55% | Method D 1.58 mins | 633 |

| Compound Name | Structure | Yield | LCMS RT | ES + ve |
|---|---|---|---|---|
| (2R,5R)-tert-butyl 4-(2-(5-(benzyloxy)-6-(4-fluorobenzyl)-3,3-dimethyl-2,3-dihydropyrrolo [3,2-b] pyridin-1-yl)-2-oxoethyl)-5-(chloromethyl)-2-methylpiperazine-1-carboxylate | 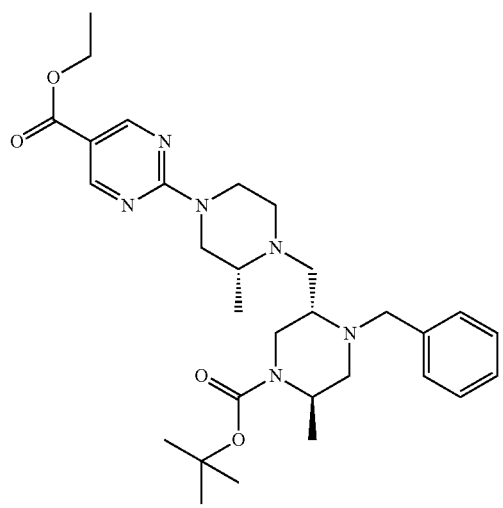 [SMILES: CCOC(=O)c1cnc(N2CCN(C[C@H]3CN(C(=O)OC(C)(C)C)[C@H](C)CN3Cc3ccccc3)[C@H](C)C2)nc1] | 65% | Method D 1.94 mins | 651 |

Ethyl 2-((R)-4-(((2S,5R)-1-benzyl-4-(tert-butoxycarbonyl)-5-methylpiperazin-2-yl)methyl)-3-methylpiperazin-1-yl)pyrimidine-5-carboxylate 2-((R)-4-(((2S,5R)-1-Benzyl-4-(tert-butoxycarbonyl)-5-methylpiperazin-2-yl)methyl)-3-methylpiperazin-1-yl)pyrimidine-5-carboxylic acid

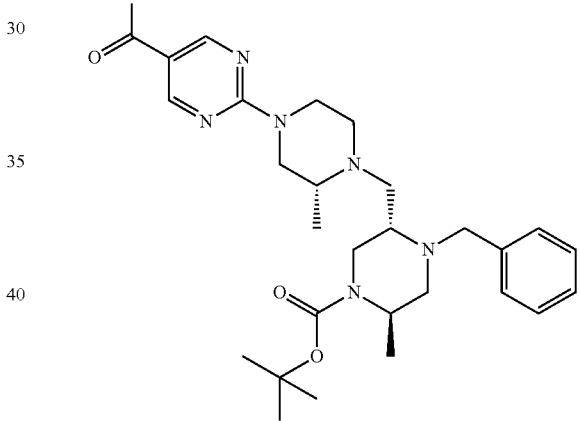

To a solution of sodium iodide (27.2 mg, 0.18 mmol) in acetonitrile (10 mL) and was added potassium carbonate (1254 mg, 9.07 mmol), (2R,5R)-tert-butyl 4-benzyl-5-(chloromethyl)-2-methylpiperazine-1-carboxylate (615 mg, 1.82 mmol, obtained as described in WO 2012/143726) and (R)-ethyl 2-(3-methylpiperazin-1-yl)pyrimidine-5-carboxylate, 2Hydrochloride (616 mg, 1.91 mmol) and reaction stirred at 70° C. for 23 h. The volatiles were removed under vacuum, and the residue was dissolved in 100 mL EtOAc and washed with 3×20 mL water. The organic layer was washed with brine (25 mL) and passed through a Biotage Phase Separator, and the volatiles were removed under vacuum to afford the title compound (995 mg, 1.80 mmol, 99% yield). LCMS Method A RT=0.98 min, ES+ve 553.

To a solution of ethyl 2-((R)-4-(((2S,5R)-1-benzyl-4-(tert-butoxycarbonyl)-5-methylpiperazin-2-yl)methyl)-3-methylpiperazin-1-yl)pyrimidine-5-carboxylate (1000 mg, 1.81 mmol) in methanol (3 mL) was added sodium hydroxide (2.71 mL, 5.43 mmol) 2M solution in water and reaction stirred at 40° C. for 3 h. The volatiles were removed under vacuum, and the crude was dissolved in 10 mL EtOAc and was washed with 2×10 mL water. The aqueous layers were back-extracted with 2×50 mL EtOAc and the combined organic layers were washed with brine (10 mL) and passed through a Biotage Phase Separator. The volatiles were removed under vacuum to afford the title compound (850 mg, 1.62 mmol, 90% yield). LCMS Method A RT=0.82 min, ES+ve 525.

121

(2R,5S)-Tert-butyl 4-benzyl-5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-2-methylpiperazine-1-carboxylate

122

(2R,5S)-Tert-butyl 4-benzyl-5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)-2-methylpiperazine-1-carboxylate

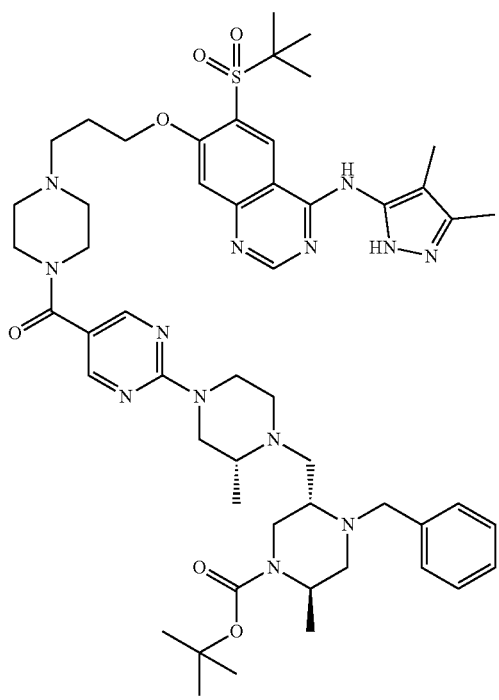 [SMILES: Cc1n[nH]c(Nc2ncnc3cc(OCCCN4CCN(C(=O)c5cnc(N6CCN(C[C@H]7CN(C(=O)OC(C)(C)C)[C@H](C)CN7Cc7ccccc7)[C@H](C)C6)nc5)CC4)c(S(=O)(=O)C(C)(C)C)cc23)c1C]

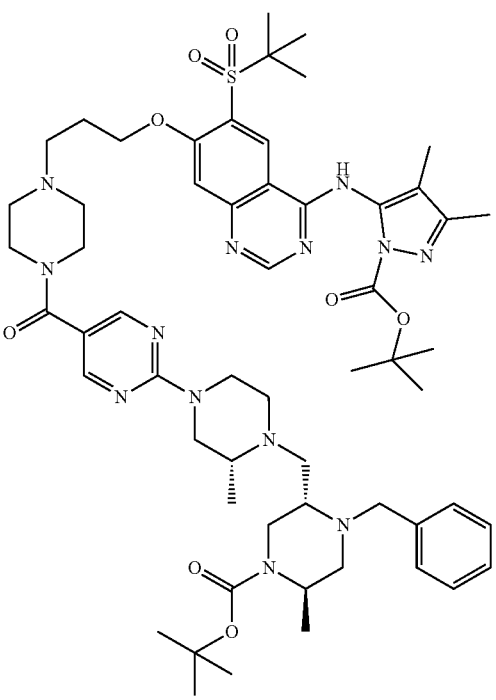 [SMILES: Cc1nn(C(=O)OC(C)(C)C)c(Nc2ncnc3cc(OCCCN4CCN(C(=O)c5cnc(N6CCN(C[C@H]7CN(C(=O)OC(C)(C)C)[C@H](C)CN7Cc7ccccc7)[C@H](C)C6)nc5)CC4)c(S(=O)(=O)C(C)(C)C)cc23)c1C]

To a solution of 2-((R)-4-(((2S,5R)-1-benzyl-4-(tert-butoxycarbonyl)-5-methylpiperazin-2-yl)methyl)-3-methylpiperazin-1-yl)pyrimidine-5-carboxylic acid (850 mg, 1.62 mmol) in DCM (10 mL) was added (1-Cyano-2-ethoxy-2-oxoethylidenaminooxy)dimethylamino-morpholino-carbenium hexafluorophosphate (833 mg, 1.94 mmol) and the reaction was stirred at 20° C. for 1 h. 6-(Tert-butylsulfonyl)-N-(3,4-dimethyl-1H-pyrazol-5-yl)-7-(3-(piperazin-1-yl)propoxy)quinazolin-4-amine (894 mg, 1.78 mmol) in 2 mL DCM was added and the reaction was stirred at 20° C. for 3 h. The reaction was diluted with 100 mL DCM and was washed with 100 mL saturated sodium bicarbonate solution and 2×100 mL water. The organic layer was washed with 50 mL brine, was passed through a Biotage Phase Separator and the volatiles were removed under vacuum to afford the title compound (1.58 g, 1.57 mmol, 97% yield). LCMS Method B RT=1.49 min, ES+ve 1008.

To a solution of tert-butyl (2R,5S)-4-benzyl-5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-2-methylpiperazine-1-carboxylate (300 mg, 0.30 mmol) in THF (2 mL) was added Boc-anhydride (0.10 mL, 0.45 mmol) and DMAP (18 mg, 0.15 mmol) and the reaction was stirred at 20° C. for 18 h. The reaction was diluted with 100 mL EtOAc and was washed with 100 mL saturated sodium bicarbonate solution, 100 mL water and 50 mL brine, was passed through a Biotage Phase Separator and the volatiles were removed under vacuum to afford the title compound (275 mg, 0.25 mmol, 83% yield). LCMS Method B RT=1.76 min, ES+ve 1108.

123

(2R,5S)-tert-butyl 5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)methyl)-2-methylpiperazine-1-carboxylate

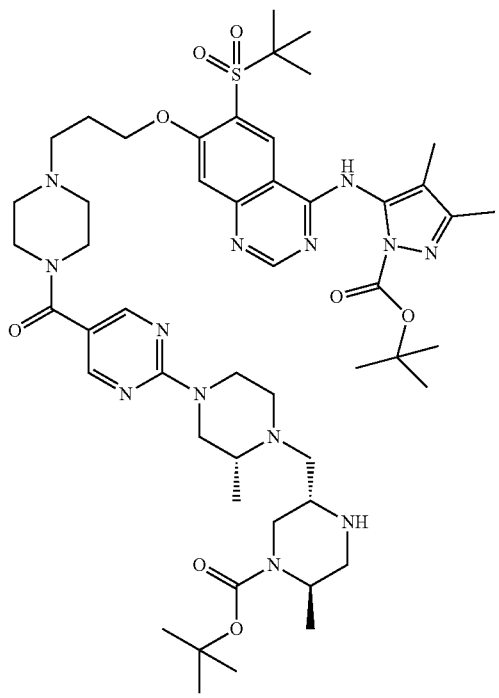 [SMILES: Cc1nn(C(=O)OC(C)(C)C)c(Nc2ncnc3cc(OCCCN4CCN(C(=O)c5cnc(N6CCN(C[C@H]7CN(C(=O)OC(C)(C)C)[C@H](C)CN7)[C@H](C)C6)nc5)CC4)c(S(=O)(=O)C(C)(C)C)cc23)c1C]

To a flask containing palladium hydroxide on carbon (38 mg, 0.05 mmol) was added tert-butyl (2R,5S)-4-benzyl-5-(((R)-4-(5-(4-(3-((4-((1-(tert-butoxycarbonyl)-4,5-dimethyl-1H-pyrazol-3-yl)amino)-6-(tert-butylsulfonyl)quinazolin-7-yl)oxy)propyl)piperazine-1-carbonyl)pyrimidin-2-yl)-2-methylpiperazin-1-yl)methyl)-2-methylpiperazine-1-carboxylate (300 mg, 0.27 mmol) in ethanol (3.0 mL) and acetic acid (0.40 mL) and the reaction was flushed with hydrogen and stirred at 20° C. under an atmosphere of hydrogen for 7 days. The reaction was purged of hydrogen, flushed with nitrogen and filtered through a celite plug under vacuum. The cake was washed with 50 mL EtOAc, the organics were collected and the volatiles were removed under vacuum to afford the title compound (240 mg, 0.24 mmol, 87% yield). LCMS Method B RT=1.38 min, ES+ve 1018.

124

5-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrazine-2-carboxylic acid

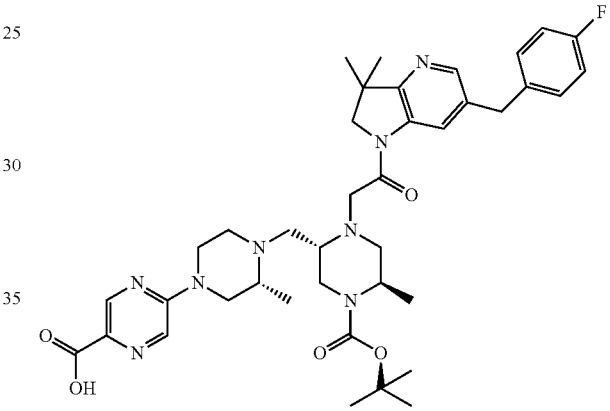

The title compound was prepared by a method analogous to those above.

| Compound Name | Structure | Yield | LCMS RT | ES+ve |
|---|---|---|---|---|
| methyl 2-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrazine-5-carboxylate | 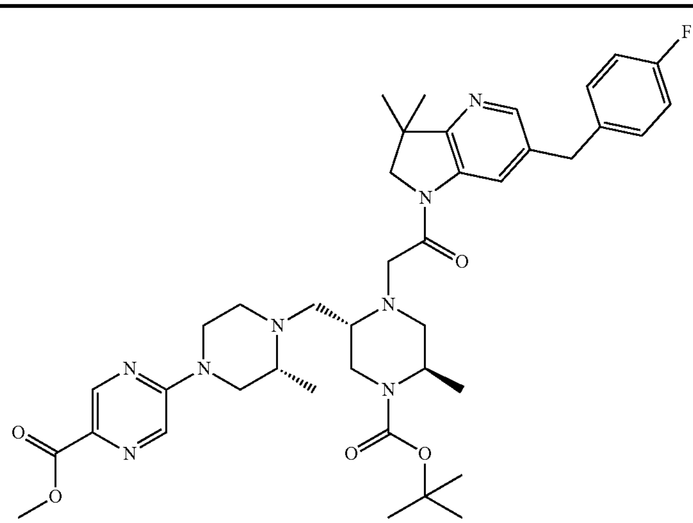 | 70% | Method A 0.93 mins | 745 |

| Compound Name | Structure | Yield | LCMS RT | ES + ve |
|---|---|---|---|---|
| 5-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrazine-2-carboxylic acid | 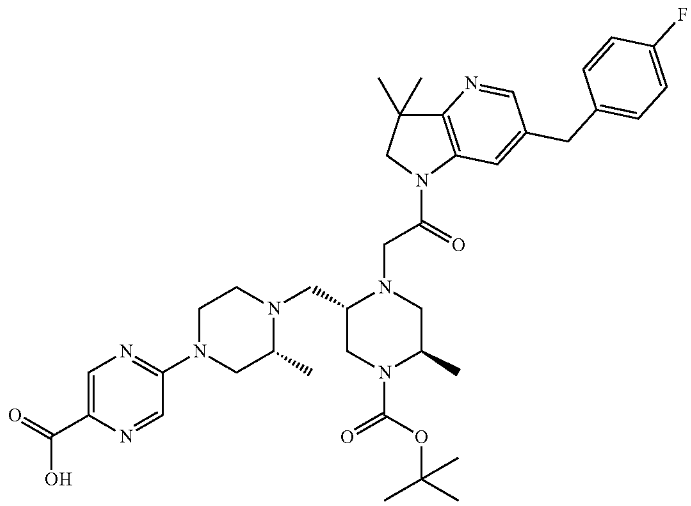 [SMILES: C[C@@H]1CN(c2cnc(C(=O)O)cn2)CCN1C[C@H]1CN(C(=O)OC(C)(C)C)[C@H](C)CN1CC(=O)N1CC(C)(C)c2ncc(Cc3ccc(F)cc3)cc21] | 59% | Method B 1.05 mins | 731 |

6-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methyl piperazin-2-yl)methyl)-3-methylpiperazin-1-yl)nicotinic acid

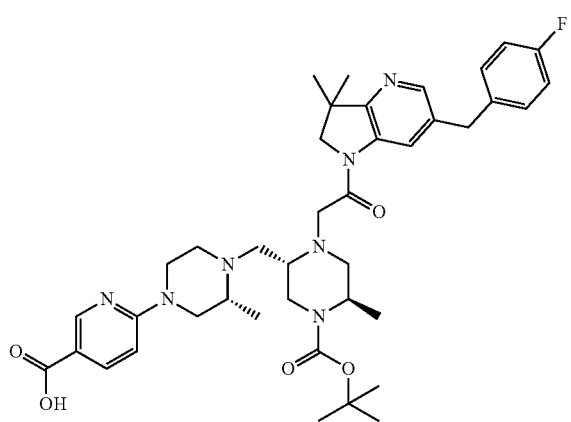 [SMILES: C[C@@H]1CN(c2ccc(C(=O)O)cn2)CCN1C[C@H]1CN(C(=O)OC(C)(C)C)[C@H](C)CN1CC(=O)N1CC(C)(C)c2ncc(Cc3ccc(F)cc3)cc21]

The title compound was prepared by a method analogous to those above.

| Compound Name | Structure | Yield | LCMS RT | ES + ve |
|---|---|---|---|---|
| (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-5-(((R)-4-(5-(methoxycarbonyl)pyridin-2-yl)-2-methylpiperazin-1-yl)methyl)-2-methylpiperazine-1-carboxylate | 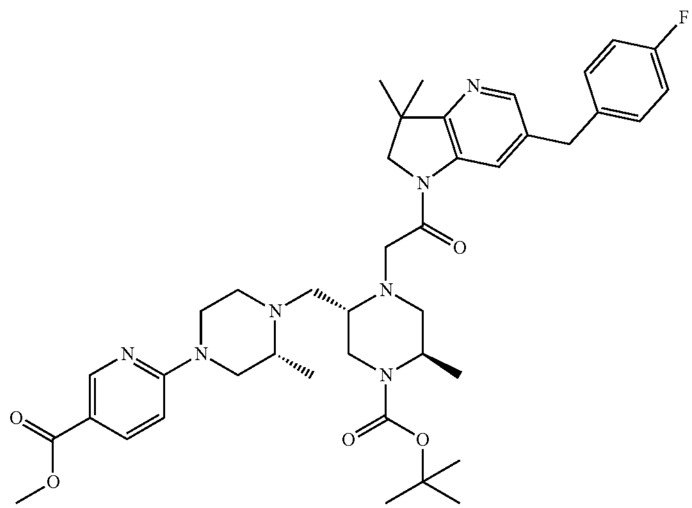 [SMILES: COC(=O)c1ccc(N2CCN(C[C@H]3CN(C(=O)OC(C)(C)C)[C@H](C)CN3CC(=O)N3CC(C)(C)c4ncc(Cc5ccc(F)cc5)cc43)[C@H](C)C2)nc1] | 25% | Method A 1.00 mins | 744 |
| 6-((R)-4-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)nicotinic acid | 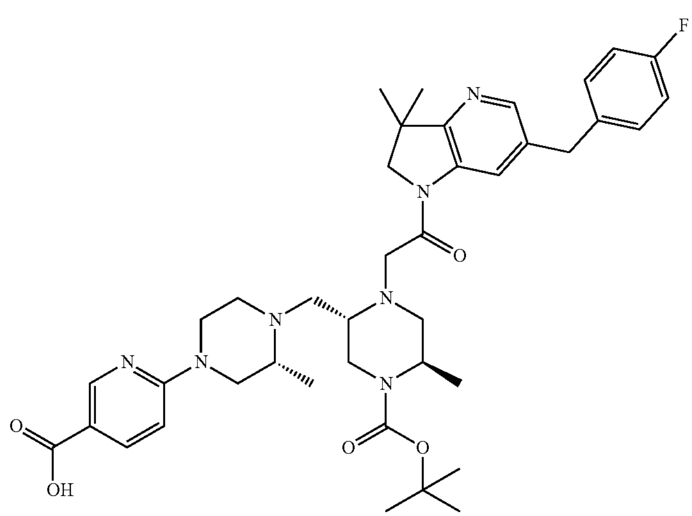 [SMILES: C[C@@H]1CN(c2ccc(C(=O)O)cn2)CCN1C[C@H]1CN(C(=O)OC(C)(C)C)[C@H](C)CN1CC(=O)N1CC(C)(C)c2ncc(Cc3ccc(F)cc3)cc21] | 61% | Method B 1.06 mins | 730 |

2-((R)-4-(((2S,5R)-4-(Tert-butoxycarbonyl)-1-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-5-methylpiperazin-2-yl)methyl)-3-methylpiperazin-1-yl)pyrimidine-5-carboxylic acid

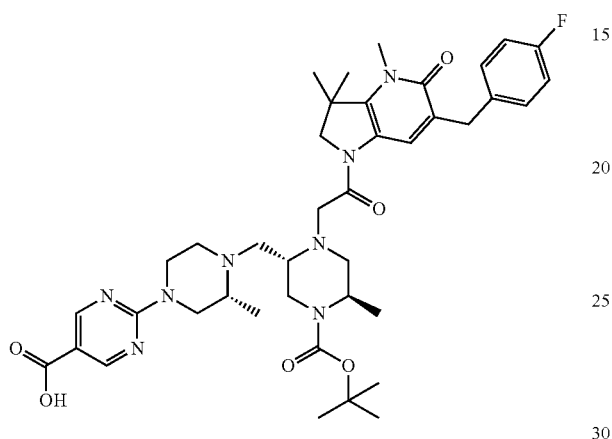

The title compound was prepared by a method analogous to those above.

| Compound Name | Structure | Yield | LCMS RT | ES + ve |
|---|---|---|---|---|
| Ethyl 2-((R)-4-(((2S,5R)-4-(tert-butoxycarbonyl)-1-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-5-methylpiperazin-2-yl)methyl)-3-methylpiperazin-1-yl)pyrimidine-5-carboxylate | 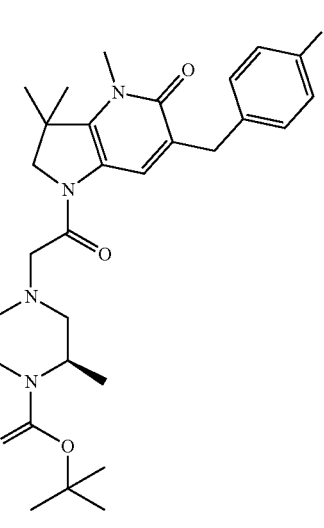 | 96% | Method B 1.52 mins | 789 |

| Compound Name | Structure | Yield | LCMS RT | ES + ve |
|---|---|---|---|---|
| 2-((R)-4-(((2S,5R)-4-(Tert-butoxycarbonyl)-1-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-5-methylpiperazin-2-yl)methyl)-3-methylpiperazin-1-yl)pyrimidine-5-carboxylic acid | 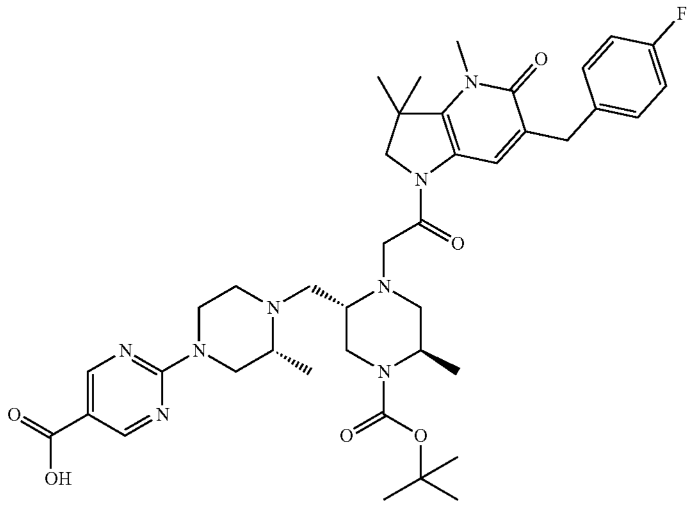 [SMILES: C[C@@H]1CN(c2ncc(C(=O)O)cn2)CCN1C[C@H]1CN(C(=O)OC(C)(C)C)[C@H](C)CN1CC(=O)N1CC(C)(C)c2c1cc(Cc1ccc(F)cc1)c(=O)n2C] | 97% | Method A 0.87 mins | 761 |

2-((R)-4-(((2S,5R)-4-(Tert-butoxycarbonyl)-1-(2-(6-(1,1-difluorobutyl)-3,3-dimethyl-2,3-dihydro-1H-pyrrolo[3,2-b]pyridin-1-yl)-2-oxoethyl)-5-methyl-piperazin-2-yl)methyl)-3-methylpiperazin-1-yl)pyrimidine-5-carboxylic acid

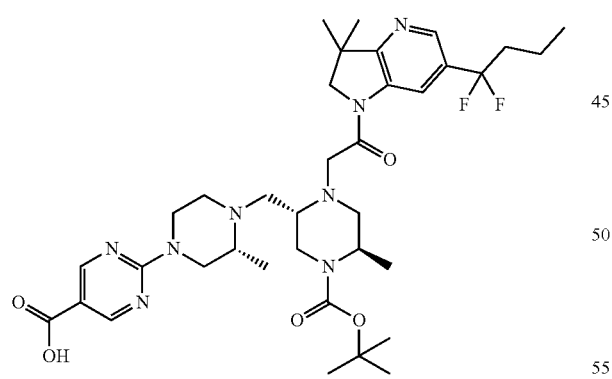

The title compound was prepared by a method analogous to those above, starting from (2R,5R)-tert-butyl 5-(chloromethyl)-4-(2-(6-(1,1-difluorobutyl)-3,3-dimethyl-2,3-dihydro-1H-pyrrolo[3,2-b]pyridin-1-yl)-2-oxoethyl)-2-methylpiperazine-1-carboxylate (obtained as described in WO 2012/143726).

| Compound Name | Structure | Yield | LCMS RT | ES + ve |
|---|---|---|---|---|
| Ethyl 2-((R)-4-(((2S,5R)-4-(tert-butoxycarbonyl)-1-(2-(6-(1,1-difluorobutyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrimidine-5-carboxylate | 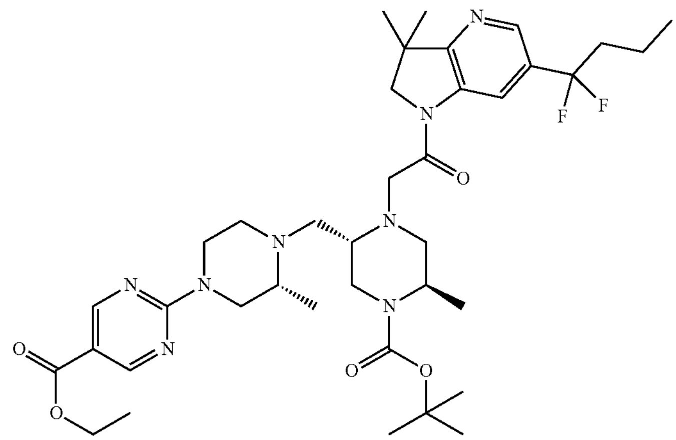 [SMILES: CCCC(F)(F)c1cnc2c(c1)N(C(=O)CN1C[C@@H](C)N(C(=O)OC(C)(C)C)C[C@@H]1CN1CCN(c3ncc(C(=O)OCC)cn3)C[C@H]1C)CC2(C)C] | 92% | Method A 1.07 mins | 743 |
| 2-((R)-4-(((2S,5R)-4-(Tert-butoxycarbonyl)-1-(2-(6-(1,1-difluorobutyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)pyrimidine-5-carboxylic acid | 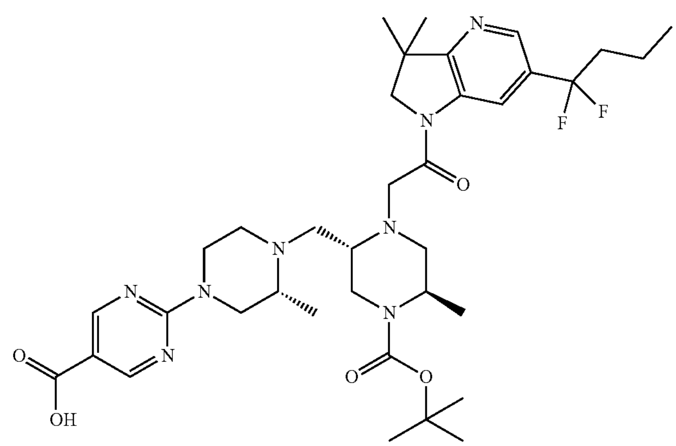 [SMILES: CCCC(F)(F)c1cnc2c(c1)N(C(=O)CN1C[C@@H](C)N(C(=O)OC(C)(C)C)C[C@@H]1CN1CCN(c3ncc(C(=O)O)cn3)C[C@H]1C)CC2(C)C] | 94% | Method B 1.07 mins | 715 |

(2R,5S)-Tert-butyl 5-(((R)-4-((benzyloxy)carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

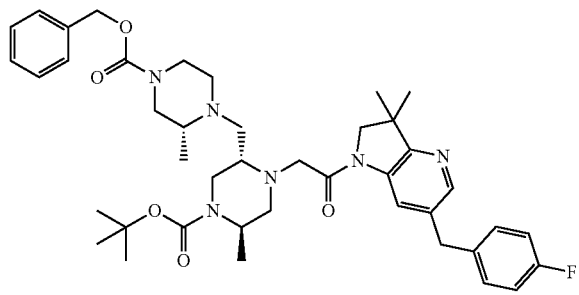 [SMILES: C[C@@H]1CN(C(=O)OCc2ccccc2)CCN1C[C@H]1CN(C(=O)OC(C)(C)C)[C@H](C)CN1CC(=O)N1CC(C)(C)c2ncc(Cc3ccc(F)cc3)cc21]

To a solution of (2R,5R)-tert-butyl 5-(chloromethyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (8.67 g, 15.91 mmol, obtained as described in WO 2012/143726) in acetonitrile (50.0 mL) and was added (R)-benzyl 3-methylpiperazine-1-carboxylate (4.10 g, 17.50 mmol, commercially available from, for example, Fluorochem), sodium iodide (0.238 g, 1.591 mmol) and potassium carbonate (6.59 g, 47.7 mmol) and the reaction was stirred at 80° C. for 18 hours. The volatiles were removed in vacuo, the reaction was diluted in 100 mL DCM and was washed with 100 mL saturated sodium bicarbonate solution and 100 mL water. The aqueous layer was washed with an additional 2×100 mL DCM, and the combined organic layers were washed with 100 mL brine and passed through a Biotage Phase Separator. The volatiles were removed in vacuo. The residue was dissolved in 25 mL DCM and loaded onto 340 g KP-Sil SNAP cartridge and purified by flash chromatography: 2% methanol in DCM for 1 column volume, 10 column volumes gradient 2% to 12% methanol in DCM and 2 column volumes 12% methanol in DCM. Compound eluted at 7 column volumes to afford the title compound (9.26 g, 12.5 mmol, 78% yield). LCMS RT=1.05 min, ES+ve 743.

(2R,5S)-Tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate

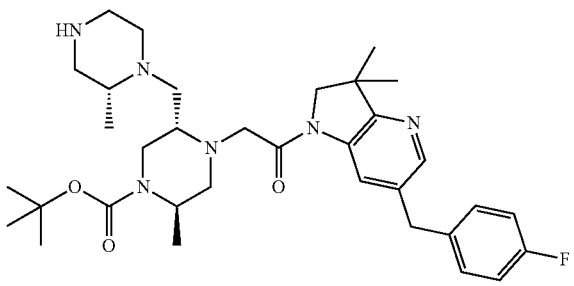 [SMILES: C[C@@H]1CNCCN1C[C@H]1CN(C(=O)OC(C)(C)C)[C@H](C)CN1CC(=O)N1CC(C)(C)c2ncc(Cc3ccc(F)cc3)cc21]

Palladium on carbon (1.326 g, 1.246 mmol) was added to a flask which was purged of air and filled with a nitrogen atmosphere. (2R,5S)-Tert-butyl 5-(((R)-4-((benzyloxy)carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (9.26 g, 12.46 mmol) was dissolved in ethanol (120.0 mL) and added via a dropping funnel. The reaction vessel was filled with hydrogen and the reaction was stirred at room temperature under an atmosphere of hydrogen for 2 hours. The reaction was filtered through a celite plug, then the plug was washed with 200 mL ethanol. The volatiles were removed under vacuum to afford the title compound (7.32 g, 12.0 mmol, 96% yield). LCMS RT=0.72 min, ES+ve 609.

(2R,5R)-Tert-butyl 4-(2-((S)-2-(4-(4-fluorobenzoyl)thiazol-2-yl)pyrrolidin-1-yl)-2-oxoethyl)-5-(hydroxymethyl)-2-methylpiperazine-1-carboxylate

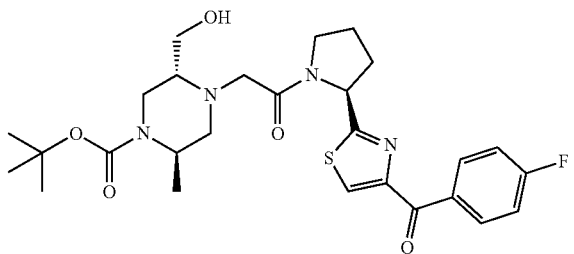 [SMILES: C[C@@H]1CN(CC(=O)N2CCC[C@H]2c2nc(C(=O)c3ccc(F)cc3)cs2)[C@@H](CO)CN1C(=O)OC(C)(C)C]

To a solution of (S)-(4-fluorophenyl)(2-(pyrrolidin-2-yl)thiazol-4-yl)methanone, Hydrochloride (94 mg, 0.301 mmol, obtained as described in WO 2011/018474 A1) in DCM (3 mL) was added triethylamine (0.209 mL, 1.503 mmol) and the reaction was stirred at room temperature under an atmosphere of nitrogen. Chloroacetyl chloride (0.048 mL, 0.601 mmol) was added and the reaction was stirred at room temperature for 15 minutes. (2R,5R)-tert-butyl 5-(hydroxymethyl)-2-methylpiperazine-1-carboxylate, Hydrochloride (320 mg, 1.202 mmol, obtained as described in WO 2012/143726) was added followed by 100 uL of triethylamine. The reaction was heated to 40° C. for 25 h, and the residue was subjected directly to purification by flash chromatography (60 g pre-packed C-18 SNAP cartridge: 15% to 55% acetonitrile (0.1% formic acid) in water (0.1% formic acid). The desired fractions were combined and concentrated to afford the title compound (114 mg, 0.21 mmol, 69.4% yield). LCMS RT=0.82 min, ES+ve 547.

(2R,5R)-Tert-butyl 5-(chloromethyl)-4-(2-((S)-2-(4-(4-fluorobenzoyl)thiazol-2-yl)pyrrolidin-1-yl)-2-oxoethyl)-2-methylpiperazine-1-carboxylate

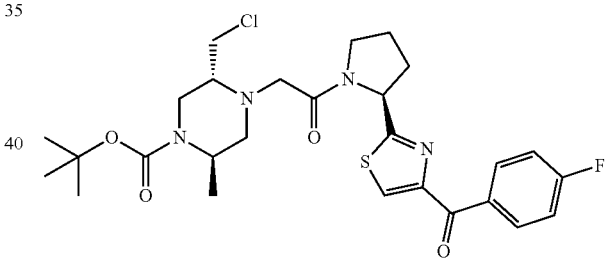

To a solution of (2R,5R)-tert-butyl 4-(2-((S)-2-(4-(4-fluorobenzoyl)thiazol-2-yl)pyrrolidin-1-yl)-2-oxoethyl)-5-(hydroxymethyl)-2-methylpiperazine-1-carboxylate (114 mg, 0.209 mmol) in DCM (2 mL) and was added triethylamine (0.145 mL, 1.043 mmol) and the reaction was stirred at 20° C. under an atmosphere of nitrogen. Methanesulfonyl chloride (0.049 mL, 0.626 mmol) was added and the reaction was stirred at room temperature under an atmosphere of nitrogen for 18 h. The reaction was diluted in 25 mL DCM and washed with 25 mL saturated sodium bicarbonate solution. The aqueous layer was washed with additional 2×25 mL DCM, and the combined organic layers were washed with 50 mL brine and passed through a Biotage Phase Separator. The volatiles were removed in vacuo to afford the title compound (115 mg, 0.20 mmol, 98% yield). LCMS RT=1.32 min, ES+ve 565.

Ethyl 2-((R)-4-(((2S,5R)-4-(tert-butoxycarbonyl)-1-(2-((S)-2-(4-(4-fluorobenzoyl)thiazol-2-yl)pyrrolidin-1-yl)-2-oxoethyl)-5-methylpiperazin-2-yl)methyl)-3-methylpiperazin-1-yl)pyrimidine-5-carboxylate

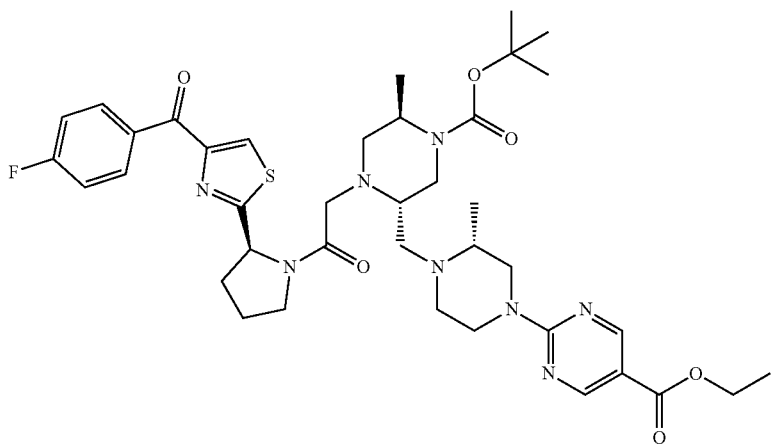 [SMILES: CCOC(=O)c1cnc(N2CCN(C[C@H]3CN(C(=O)OC(C)(C)C)[C@H](C)CN3CC(=O)N3CCC[C@H]3c3nc(C(=O)c4ccc(F)cc4)cs3)[C@H](C)C2)nc1]

To a solution of (R)-ethyl 2-(3-methylpiperazin-1-yl)pyrimidine-5-carboxylate, 2Hydrochloride (196 mg, 0.61 mmol) in acetonitrile (4 mL) and was added (2R,5R)-tert-butyl 5-(chloromethyl)-4-(2-((S)-2-(4-(4-fluorobenzoyl)thiazol-2-yl)pyrrolidin-1-yl)-2-oxoethyl)-2-methylpiperazine-1-carboxylate (285 mg, 0.50 mmol), sodium iodide (7.56 mg, 0.05 mmol) and potassium carbonate (349 mg, 2.5 mmol) and reaction stirred at 70° C. for 18 h. The reaction was diluted with 25 mL ethyl acetate and washed with 2×10 mL water. The organic phase was dried by passing through a Biotage Phase Separator and concentrated under vacuum to afford the title compound (375 mg, 0.48 mmol, 95% yield). LCMS Method C RT=1.56 min, ES+ve 779).

2-((R)-4-(((2S,5R)-4-(Tert-butoxycarbonyl)-1-(2-((S)-2-(4-(4-fluorobenzoyl)thiazol-2-yl)pyrrolidin-1-yl)-2-oxoethyl)-5-methylpiperazin-2-yl)methyl)-3-methylpiperazin-1-yl)pyrimidine-5-carboxylic acid

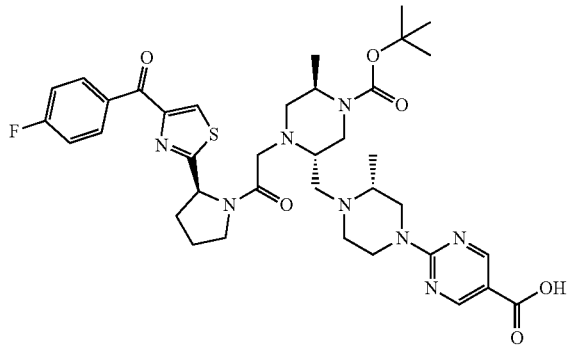 [SMILES: C[C@@H]1CN(c2ncc(C(=O)O)cn2)CCN1C[C@H]1CN(C(=O)OC(C)(C)C)[C@H](C)CN1CC(=O)N1CCC[C@H]1c1nc(C(=O)c2ccc(F)cc2)cs1]

To a solution of ethyl 2-((R)-4-(((2S,5R)-4-(tert-butoxycarbonyl)-1-(2-((S)-2-(4-(4-fluorobenzoyl)thiazol-2-yl)pyrrolidin-1-yl)-2-oxoethyl)-5-methylpiperazin-2-yl)methyl)-3-methylpiperazin-1-yl)pyrimidine-5-carboxylate (375 mg, 0.48 mmol) in methanol (3 mL) was added sodium hydroxide (0.72 mL, 1.44 mmol) 2M solution in water and reaction stirred at 40° C. for 1 h. The reaction was diluted with 50 mL ethyl acetate and washed with 10 mL water followed by 10 mL brine. The organic phase was dried by passing through a Biotage Phase Separator and concentrated under vacuum to afford the title compound (285 mg, 0.38 mmol, 79% yield). LCMS Method B RT=0.96 min, ES+ve 751).

Methyl 2-(((2S,5R)-1-benzyl-4-(tert-butoxycarbonyl)-5-methylpiperazin-2-yl)methyl)-3-oxoisoindoline-5-carboxylate

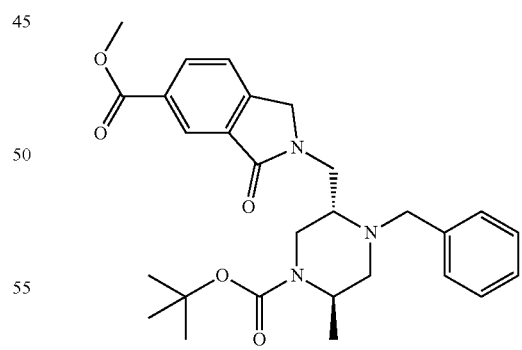

To a solution of methyl 3-oxoisoindoline-5-carboxylate (212 mg, 1.11 mmol) in DMF (5.0 mL) was added sodium hydride (44 mg, 1.84 mmol), and the reaction was stirred at room temperature for 30 minutes. (2R,5R)-tert-butyl 4-benzyl-5-(chloromethyl)-2-methylpiperazine-1-carboxylate (250 mg, 0.74 mmol, obtained as described in WO 2012/143726) was added and the reaction heated to 80° C. for 3 hours. The reaction was directly subjected to purification by flash chromatography (30 g pre-packed C-18 SNAP cartridge: 30% to 85% acetonitrile (0.1% formic acid) in water (0.1% formic acid)). The desired fractions were combined and concentrated to afford the title compound (144 mg, 0.29 mmol, 40% yield). LCMS Method B RT=1.40 min, ES+ve 494.

Methyl 2-(((2S,5R)-4-(tert-butoxycarbonyl)-5-methylpiperazin-2-yl)methyl)-3-oxoisoindoline-5-carboxylate

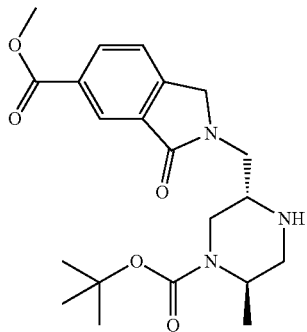 [SMILES: COC(=O)c1ccc2c(c1)C(=O)N(C[C@H]1CN(C(=O)OC(C)(C)C)[C@H](C)CN1)C2]

Palladium on carbon (31.0 mg, 0.03 mmol) was added to a flask which was purged of air and filled with a nitrogen atmosphere. Methyl 2-(((2S,5R)-1-benzyl-4-(tert-butoxycarbonyl)-5-methylpiperazin-2-yl)methyl)-3-oxoisoindoline-5-carboxylate (144 mg, 0.29 mmol) was dissolved in ethanol (2.0 mL) and acetic acid (0.67 mL, 11.7 mmol) and added via a dropping funnel. The reaction vessel was filled with hydrogen and the reaction was stirred at room temperature under an atmosphere of hydrogen for 3 hours. The hydrogen was purged, and the reaction was filtered through a celite plug and washed with 25 mL EtOAc. The organic layer was washed with 3×25 mL saturated sodium bicarbonate solution and 25 mL brine, and passed through a Biotage phase separator. The volatiles were removed under vacuum to afford the title compound (66 m g, 0.16 mmol, 56% yield). LCMS Method B RT=0.95 min, ES+ve 404.

Methyl 2-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-oxoisoindoline-5-carboxylate

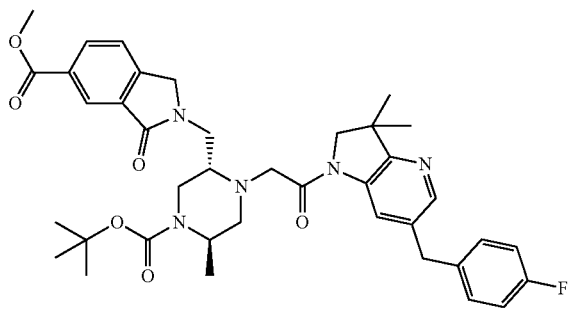 [SMILES: COC(=O)c1ccc2c(c1)C(=O)N(C[C@H]1CN(C(=O)OC(C)(C)C)[C@H](C)CN1CC(=O)N1CC(C)(C)c3ncc(Cc4ccc(F)cc4)cc31)C2]

To a solution of 6-(4-fluorobenzyl)-3,3-dimethyl-2,3-dihydro-1H-pyrrolo[3,2-b]pyridine (45 mg, 0.18 mmol, obtained as described in WO 2012/143726) in DCM (1 mL) and was added triethylamine (0.07 mL, 0.53 mmol) and the reaction was stirred at room temperature under an atmosphere of nitrogen. Chloroacetyl chloride (0.02 mL, 0.19 mmol) was added and the reaction was stirred at room temperature for 30 minutes. The reaction was diluted in 25 mL DCM and washed with 10 mL saturated sodium bicarbonate solution, 10 mL water and 10 mL brine. The organic layer was passed through a biotage phase separator and concentrated under vacuum. The crude was dissolved in 3 mL THF and triethylamine (0.07 mL, 0.53 mmol) and methyl 2-(((2S,5R)-4-(tert-butoxycarbonyl)-5-methylpiperazin-2-yl)methyl)-3-oxoisoindoline-5-carboxylate (70 mg, 0.18 mmol) were added. The reaction was stirred at 100° C. for 8 hours in a microwave reactor. The crude reaction was subjected to purification by mass-directed automated preparative HPLC (formic acid modifier). The desired fractions were combined and concentrated to afford the title compound (35 mg, 0.09 mmol, 29% yield). LCMS Method A RT=1.26 min, ES+ve 700.

2-(((2S,5R)-4-(Tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methyl piperazin-2-yl) methyl)-3-oxoisoindoline-5-carboxylic acid

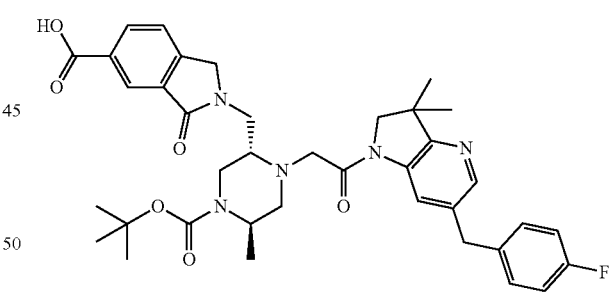

To a solution of methyl 2-(((2S,5R)-4-(tert-butoxycarbonyl)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-oxoisoindoline-5-carboxylate (35 mg, 0.05 mmol) in methanol (1 mL) was added sodium hydroxide (0.08 mL, 0.15 mmol) 2M solution in water and reaction stirred at 50° C. for 3 hours. The reaction was diluted with 25 mL ethyl acetate and washed with 10 mL water followed by 10 mL brine. The organic phase was dried by passing through a Biotage Phase Separator and concentrated under vacuum to afford the title compound (33 mg, 0.05 mmol, 96% yield). LCMS Method B RT=0.95 min, ES+ve 686.

(2R,5S)-Tert-butyl 5-(((R)-4-(2-(4-(3-((6-(tert-butyl-sulfonyl)-4-((3,4-dimethyl-1H-pyrazol-5-yl)amino)quinazolin-7-yl)oxy)propyl)piperazin-1-yl)acetyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

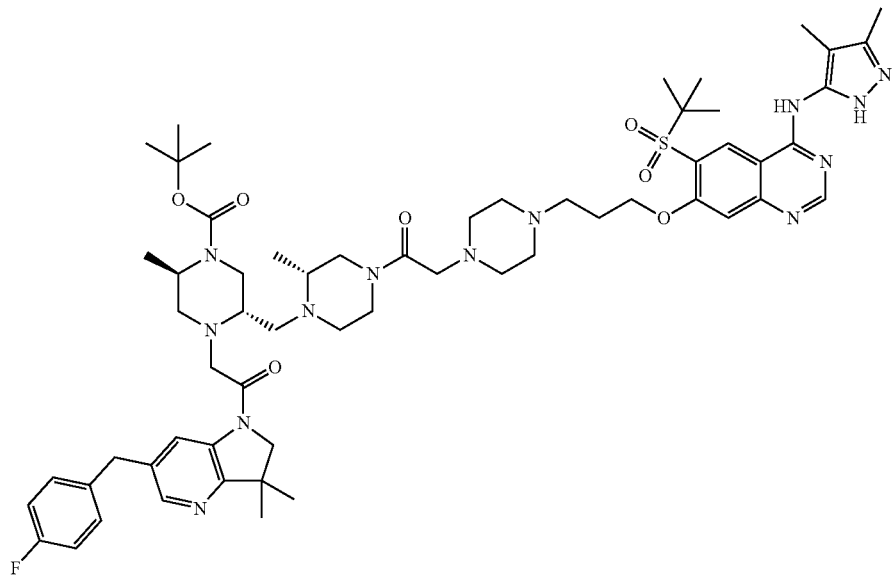 [SMILES: Cc1n[nH]c(Nc2ncnc3cc(OCCCN4CCN(CC(=O)N5CCN(C[C@H]6CN(C(=O)OC(C)(C)C)[C@H](C)CN6CC(=O)N6CC(C)(C)c7ncc(Cc8ccc(F)cc8)cc76)[C@H](C)C5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (100 mg, 0.16 mmol) in Tetrahydrofuran (THF) (1 mL) and was added triethylamine (0.114 mL, 0.82 mmol) and reaction stirred at room temperature under an atmosphere of nitrogen. Chloroacetyl chloride (0.016 mL, 0.20 mmol) was added and the reaction was stirred at room temperature for 15 minutes. 6-(Tert-butylsulfonyl)-N-(3,4-dimethyl-1H-pyrazol-5-yl)-7-(3-(piperazin-1-yl)propoxy)quinazolin-4-amine (132 mg, 0.26 mmol) and triethylamine (0.114 mL, 0.82 mmol) were added, and the reaction was stirred at 60° C. for 3 days. The crude reaction was subjected to purification by mass-directed automated preparative HPLC (TFA modifier). The desired fractions were combined and concentrated to afford the title compound (117 mg, 0.10 mmol, 62% yield). LCMS Method C RT=0.75 min, ES+ve 576 (M+2/2).

(2R,5S)-Tert-butyl 5-(((R)-4-(2-(4-(2-((6-(tert-butyl-sulfonyl)-4-((5-fluoro-1H-indazol-3-yl)amino)quinazolin-7-yl)oxy)ethyl)piperazin-1-yl)pyrimidine-5-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate

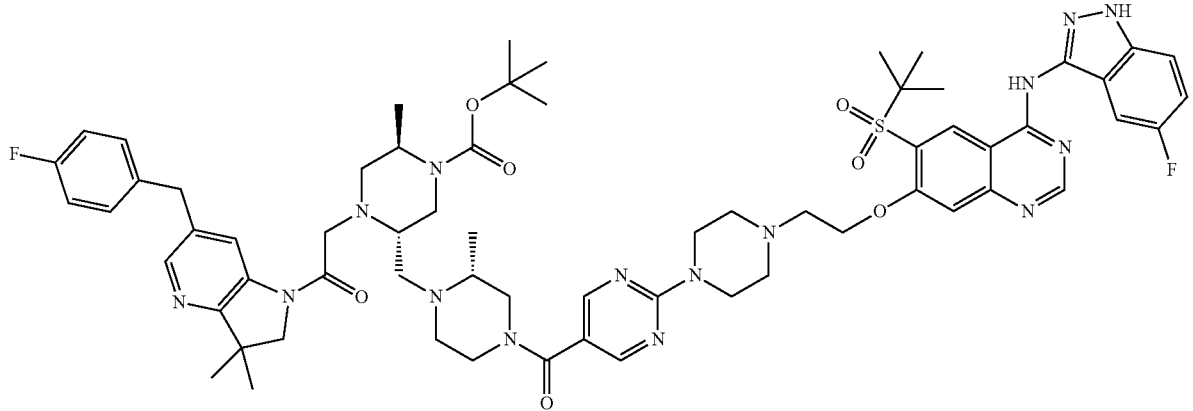 [SMILES: C[C@@H]1CN(C(=O)c2cnc(N3CCN(CCOc4cc5ncnc(Nc6n[nH]c7ccc(F)cc67)c5cc4S(=O)(=O)C(C)(C)C)CC3)nc2)CCN1C[C@H]1CN(C(=O)OC(C)(C)C)[C@H](C)CN1CC(=O)N1CC(C)(C)c2ncc(Cc3ccc(F)cc3)cc21]

To a solution of 2-(4-(2-((6-(tert-butylsulfonyl)-4-((5-fluoro-1H-indazol-3-yl)amino)quinolin-7-yl)oxy)ethyl)piperazin-1-yl)pyrimidine-5-carboxylic acid (52 mg, 0.08 mmol) in NMP (0.8 mL) was added (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (58.6 mg, 0.10 mmol), HATU (45.7 mg, 0.12 mmol) and DIPEA (0.042 mL, 0.24 mmol) and reaction stirred at 20° C. for 18 h. The crude reaction was subjected to purification by mass-directed automated preparative HPLC (TFA modifier). The desired fractions were combined and concentrated to afford the title compound (117 mg, 0.07 mmol, 92% yield). LCMS Method B RT=1.46 min, ES+ve 1239.

Using a method analogous to that for (2R,5S)-tert-butyl 5-(((R)-4-(2-(4-(2-((6-(tert-butylsulfonyl)-4-((5-fluoro-1H-indazol-3-yl)amino)quinazolin-7-yl)oxy)ethyl)piperazin-1-yl)pyrimidine-5-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate the following compounds were prepared:

| Compound Name | Structure | Yield | LCMS RT | ES +ve |
|---|---|---|---|---|
| (2R,5S)-Tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyridin-2-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 77% | Method B 1.39 min | 1214 |
| (2R,5S)-Tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 60% | Method B 1.40 min | 1215 |

| Compound Name | Structure | Yield | LCMS RT | ES +ve |
|---|---|---|---|---|
| (2R,5S)-Tert-butyl 5-(((6-(4-(3-((6-(tert-butylsulfonyl)-4-((3,4-dimethyl-1H-pyrazol-5-yl)amino)quinazolin-7-yl)oxy)propyl)piperazine-1-carbonyl)-1-oxoisoindolin-2-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 16% | Method C 0.77 min | 585 (M+2/2) |
| (2R,5S)-Tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)methyl)-4-(2-(6-(4-fluorobenzyl)-5-oxo-2,3,4,5-tetrahydro-1H-pyrrolo[3,2-b]pyridin-1-yl)-2-oxoethyl)-2-methylpiperazine-1-carboxylate | | 13% | Method C 0.76 min | 623 (M+2/2) |

-continued

| Compound Name | Structure | Yield | LCMS RT | ES +ve |
|---|---|---|---|---|
| (2R,5S)-tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-4-(2-((S)-2-(4-(4-fluorobenzoyl)thiazol-2-yl)pyrrolidin-1-yl)-2-oxoethyl)-2-methylpiperazine-1-carboxylate | 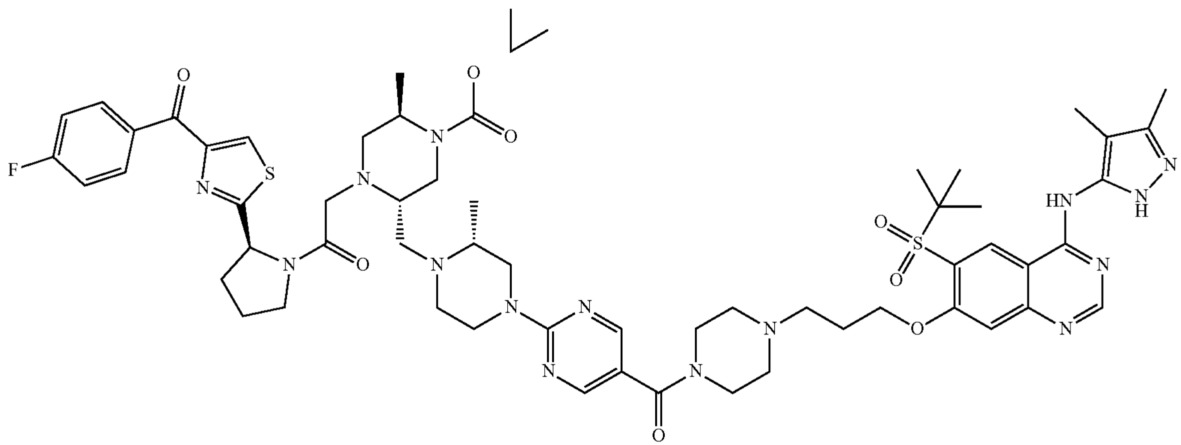 | 35% | Method C 0.81 min | 618 |
| (2R,5S)-tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-4-(2-(6-(1,1-difluorobutyl)-3,3-dimethyl-2,3-dihydro-1H-pyrrolo[3,2-b]pyridin-1-yl)-2-oxoethyl)-2-methylpiperazine-1-carboxylate | 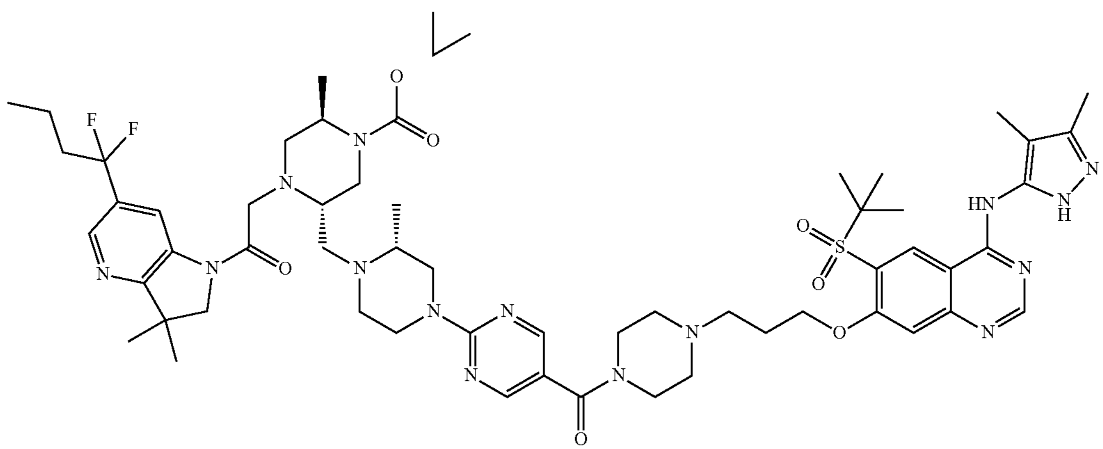 | 45% | Method B 1.44 min | 1198 |

1-(1-(2-Chloroacetyl)-3,3-dimethyl-2,3-dihydro-1H-pyrrolo[3,2-b]pyridin-6-yl)butan-1-one

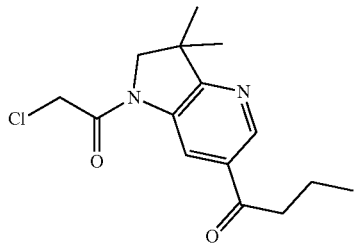 [SMILES: CCCC(=O)c1cnc2c(c1)N(C(=O)CCl)CC2(C)C]

To a solution of tert-butyl 6-butyryl-3,3-dimethyl-2,3-dihydro-1H-pyrrolo[3,2-b]pyridine-1-carboxylate (380 mg, 1.19 mmol, obtained as described in WO 2014/060770) in DCM (3.50 mL) was added HCl (2.98 mL, 11.9 mmol) 4M in dioxane and the reaction was stirred at 20° C. for 18 h. The reaction was concentrated under vacuum, and the crude was dissolved in DCM (3.50 mL) and triethylamine (0.5 mL, 3.6 mmol) was added and the reaction was stirred at room temperature under an atmosphere of nitrogen. Chloroacetyl chloride (0.105 mL, 1.313 mmol) was added and the reaction was stirred at room temperature for 20 h. The reaction was diluted in 50 mL DCM and washed with 20 mL saturated sodium bicarbonate solution, 20 mL water, 20 mL saturated ammonium chloride solution and 20 mL brine. The organic layer was passed through a Biotage phase separator and concentrated under vacuum to afford the title compound (360 mg, 1.11 mmol, 93% yield). LCMS Method A RT=1.03 min, ES+ve 295.

2-Chloro-1-(6-(1-hydroxybutyl)-3,3-dimethyl-2,3-dihydro-1H-pyrrolo[3,2-b]pyridin-1-yl)ethanone

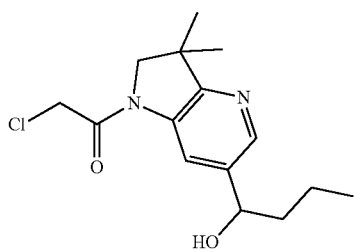 [SMILES: CCCC(O)c1cnc2c(c1)N(C(=O)CCl)CC2(C)C]

To a solution of 1-(1-(2-chloroacetyl)-3,3-dimethyl-2,3-dihydro-1H-pyrrolo[3,2-b]pyridin-6-yl)butan-1-one (100 mg, 0.34 mmol) in THF (1.00 mL) was added sodium borohydride (26 mg, 0.68 mmol) followed by methanol (1.0 mL) and the reaction was stirred at room temperature for 1 hour. The reaction was diluted in 50 mL DCM and washed with 20 mL saturated sodium bicarbonate solution, 20 mL water and 20 mL brine. The organic layer was passed through a biotage phase separator and concentrated under vacuum. The crude was resuspended in DCM (1.00 mL), and triethylamine (0.14 mL, 1.02 mmol) and 2-chloroacetyl chloride (0.03 mL, 0.41 mmol) were added. The reaction was stirred at room temperature under nitrogen for 3 h. The reaction was diluted in 30 mL DCM and washed with 10 mL saturated sodium bicarbonate solution, 10 mL water, 10 mL saturated ammonium chloride solution and 10 mL brine. The organic layer was passed through a Biotage phase separator and concentrated under vacuum to afford the title compound (80 mg, 0.27 mmol, 79% yield). LCMS Method A RT=0.84 min, ES+ve 279.

(2R,5S)-Tert-butyl 5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)methyl)-4-(2-(6-butyryl-3,3-dimethyl-2,3-dihydro-1H-pyrrolo-[3,2-b]pyridin-1-yl)-2-oxoethyl)-2-methylpiperazine-1-carboxylate

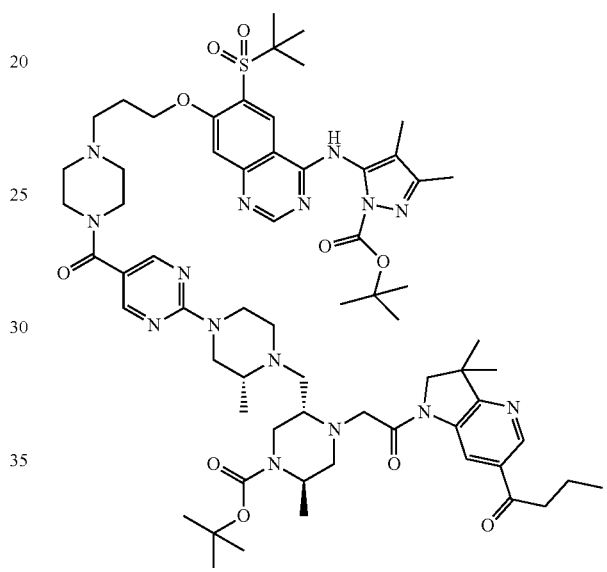

1-(1-(2-Chloroacetyl)-3,3-dimethyl-2,3-dihydro-1H-pyrrolo[3,2-b]pyridin-6-yl)butan-1-one (17 mg, 1.6 mmol) and (2R,5S)-tert-butyl 5-(((R)-4-(5-(4-(3-((4-((1-(tert-butoxycarbonyl)-4,5-dimethyl-1H-pyrazol-3-yl)amino)-6-(tert-butylsulfonyl)quinazolin-7-yl)oxy)propyl)piperazine-1-carbonyl)pyrimidin-2-yl)-2-methylpiperazin-1-yl)methyl)-2-methylpiperazine-1-carboxylate (40 mg, 0.04 mmol) were dissolved in acetonitrile (0.5 mL) and potassium carbonate (21 mg, 0.16 mmol) and potassium iodide (13 mg, 0.08 mmol) were added. The reaction was stirred at room temperature under an atmosphere of nitrogen for 2 h. The reaction was filtered and diluted with 1.5 mL 50:50 acetonitrile/DMSO, and the crude reaction was subjected to purification by mass-directed automated preparative HPLC (ammonium carbonate modifier). The desired fractions were combined and concentrated to afford the title compound (12 mg, 0.01 mmol, 24% yield). LCMS Method B RT=1.64 min, ES+ve 639 (M+2/2).

Using a method analogous to that above, the following compounds were prepared. 1-(2-Chloroacetyl)-6-(4-fluorobenzyl)-3,3-dimethyl-2,3-dihydro-1H-pyrrolo[3,2-b]pyridin-5(4H)-one was obtained from tert-butyl 6-(4-fluorobenzyl)-3,3-dimethyl-5-oxo-2,3,4,5-tetrahydro-1H-pyrrolo[3,2-b]pyridine-1-carboxylate, which was obtained as described in WO 2014/092420:

| Compound Name | Structure | Yield | LCMS RT | ES +ve |
|---|---|---|---|---|
| (2R,5S)-Tert-butyl 5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)methyl)-4-(2-(6-(1-hydroxybutyl)-3,3-dimethyl-2,3-dihydro-1H-pyrrolo[3,2-b]pyridin-1-yl)-2-oxoethyl)-2-methylpiperazine-1-carboxylate | 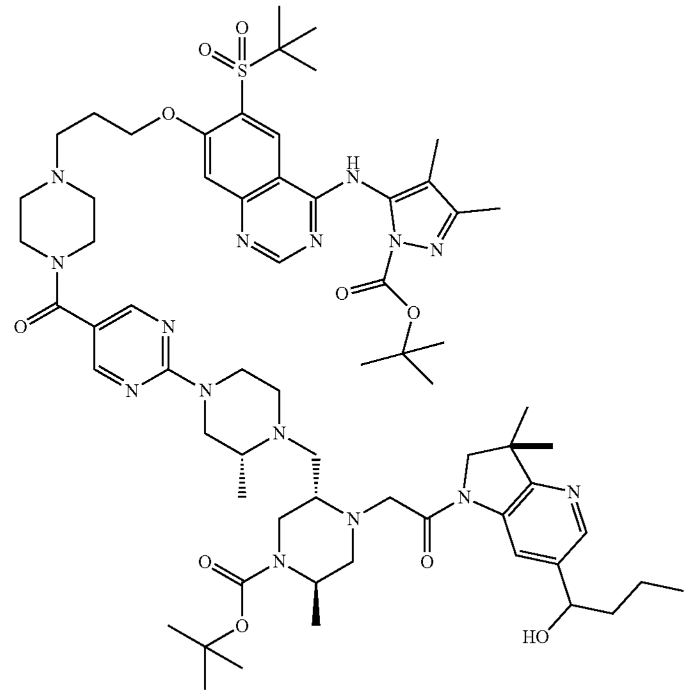 | 99% | Method B 1.53 min | 640 (M + 2/2 |
| 2-Chloro-1-(6-((4-fluorophenyl)(hydroxy)methyl)-3,3-dimethyl-2,3-dihydro-1H-pyrrolo[3,2-b]pyridin-1-yl)ethanone | 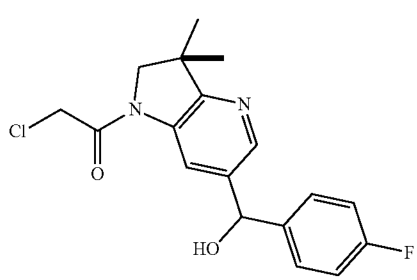 | 59% | Method A 0.93 min | 349 |

| Compound Name | Structure | Yield | LCMS RT | ES + ve |
|---|---|---|---|---|
| (2R,5S)-Tert-butyl 5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)methyl)-4-(2-(6-((4-fluorophenyl)(hydroxy)methyl)-3,3-dimethyl-2,3-dihydro-1H-pyrrolo[3,2-b]pyridin-1-yl)-2-oxoethyl)-2-methylpiperazine-1-carboxylate | | 96% | Method B 1.53 min | 666 (M + 2/ 2) |
| 1-(2-chloroacetyl)-6-(4-fluorobenzyl)-3,3-dimethyl-2,3-dihydro-1H-pyrrolo[3,2-b]pyridin-5(4H)-one | 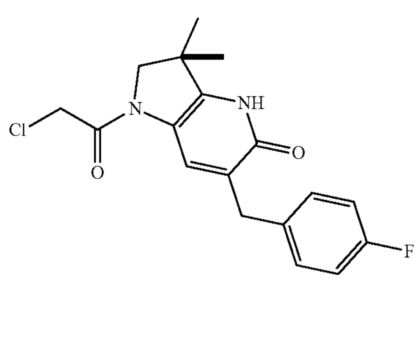 | 96% | Method A 0.93 min | 349 |

| Compound Name | Structure | Yield | LCMS RT | ES + ve |
|---|---|---|---|---|
| (2R,5S)-Tert-butyl 5-(((R)-4-(5-(4-(3-((4-((1-(tert-butoxycarbonyl)-3,4-dimethyl-1H-pyrazol-5-yl)amino)-6-(tert-butylsulfonyl)quinazolin-7-yl)oxy)propyl)piperazine-1-carbonyl)pyrimidin-2-yl)-2-methylpiperazin-1-yl)methyl)-4-(2-(6-(4-fluorobenzyl)-3,3-dimethyl-5-oxo-2,3,4,5-tetrahydro-1H-pyrrolo[3,2-b]pyridin-1-yl)-2-oxoethyl)-2-methylpiperazine-1-carboxylate | 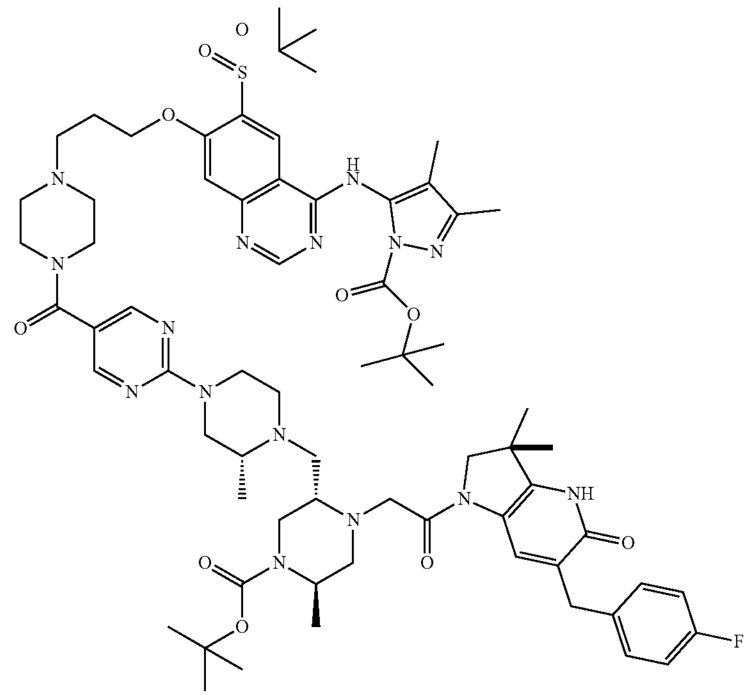 | 27% | Method B 1.52 min | 666 (M + 2/2) |

(2R,5R)-Tert-butyl 4-(2-(6-(4-fluorobenzyl)-3,3-dimethyl-5-oxo-2,3,4,5-tetrahydro-1H-pyrrolo[3,2-b]pyridin-1-yl)-2-oxoethyl)-5-(hydroxymethyl)-2-methylpiperazine-1-carboxylate

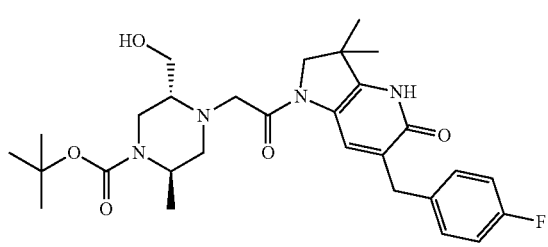 [SMILES: C[C@@H]1CN(CC(=O)N2CC(C)(C)c3[nH]c(=O)c(Cc4ccc(F)cc4)cc32)[C@@H](CO)CN1C(=O)OC(C)(C)C]

To a solution of 1-(2-chloroacetyl)-6-(4-fluorobenzyl)-3,3-dimethyl-2,3-dihydro-1H-pyrrolo[3,2-b]pyridin-5(4H)-one (0.5 g, 1.44 mmol) and triethylamine (0.44 g, 4.5 mmol) in THF (10 mL) was added (2R,5R)-tert-butyl 5-(hydroxymethyl)-2-methylpiperazine-1-carboxylate (0.3 g, 1.30 mmol) and the reaction was stirred at 80° C. overnight. To the reaction mixture was added 20 ml of water and 20 ml of ethyl acetate, the organic layer was separated and evaporated to dryness. The residue was purified by flash chromatography on silica gel, eluting with methanol:dichloromethane=1:20 to afford the title compound (450 mg, 0.83 mmol, 64% yield). LCMS Method D RT=1.35 min, ES+ve 543.

(2R,5R)-Tert-butyl 5-(chloromethyl)-4-(2-(6-(4-fluorobenzyl)-3,3-dimethyl-5-oxo-2,3,4,5-tetrahydro-1H-pyrrolo[3,2-b]pyridin-1-yl)-2-oxoethyl)-2-methylpiperazine-1-carboxylate

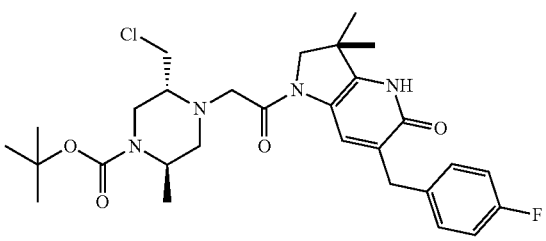

To a solution of (2R,5R)-tert-butyl 4-(2-(6-(4-fluorobenzyl)-3,3-dimethyl-5-oxo-2,3,4,5-tetra hydropyrrolo[3,2-b]pyridin-1-yl)-2-oxoethyl)-5-(hydroxymethyl)-2-methylpiperazine-1-carboxylate (0.4 g, 0.74 mmol) and triphenylphosphine (0.4 g, 1.4 mmol) in DCM (10 mL) was added carbon tetrachloride (0.42 g, 1.4 mmol) and the reaction was stirred at room temperature overnight. 20 ml water was added and the organic layer was separated and evaporated to dryness. The residue was purified by flash column chromatography, eluting with ethyl acetate:petroleum ether=1:1 to afford the title compound (140 mg, 0.25 mmol, 34% yield). LCMS Method D RT=1.58 min, ES+ve 560.9.

(2R,5S)-Tert-butyl 5-(((2R,5R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-4-(2-(6-(4-fluorobenzyl)-3,3-dimethyl-5-oxo-2,3,4,5-tetrahydro-1H-pyrrolo[3,2-b]pyridin-1-yl)-2-oxoethyl)-2-methylpiperazine-1-carboxylate

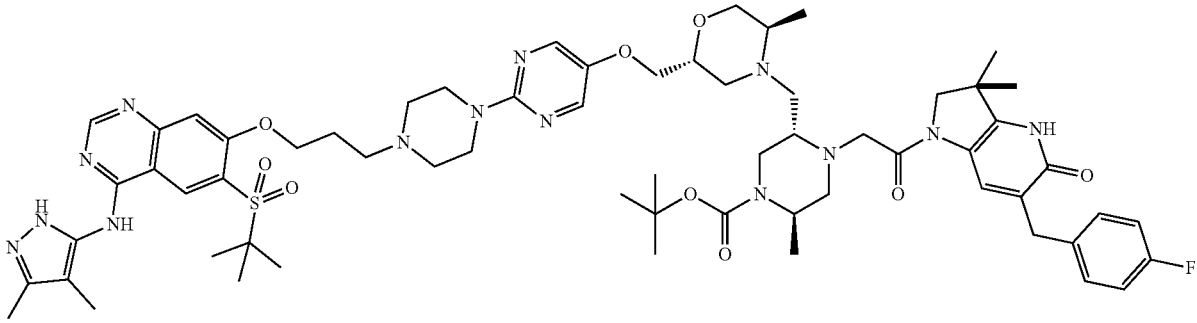

To a solution of (2R,5R)-tert-butyl 5-(chloromethyl)-4-(2-(6-(4-fluorobenzyl)-3,3-dimethyl-5-oxo-2,3,4,5-tetrahydropyrrolo[3,2-b]pyridin-1-yl)-2-oxoethyl)-2-methylpiperazine-1-carboxylate (70 mg, 0.13 mmol), 6-(tert-butylsulfonyl)-N-(3,4-dimethyl-1H-pyrazol-5-yl)-7-(3-(4-(5-(((2R,5R)-5-methylmorpholin-2-yl)methoxy)pyrimidin-2-yl)piperazin-1-yl)propoxy)quinazolin-4-amine (100 mg, 0.14 mmol) and sodium iodide (106 mg, 0.7 mmol) in acetonitrile (10 mL) was added Na₂CO₃ (74 mg, 1.7 mmol) and the reaction was stirred at 80° C. overnight. The reaction mixture was evaporated to dryness, the residue was diluted with 10 ml of methanol and the resulting precipitate was removed by filtration. The filtrate was concentrated to dryness to afford the title compound (100 mg, 0.081 mmol, 65% yield). LCMS Method D RT=1.38 min, ES+ve 1232.8.

Using a method analogous to that above, the following compounds were prepared.

| Compound Name | Structure | Yield | LCMS RT | ES+ ve |
|---|---|---|---|---|
| (2R,5S)-tert-butyl 5-(((2R,5R)-2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-2-methylpiperazine-1-carboxylate | | 57% | Method D 1.56 min | 1247 |
| (2R,5S)-tert-butyl 5-(((2R,5R)-2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | | 57% | Method D 1.38 min | 1217 |

| Compound Name | Structure | Yield | LCMS RT | ES +ve |
|---|---|---|---|---|
| (2R,5S)-tert-butyl 5-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-4-(2-(6-(4-fluorobenzyl)-3,3-dimethyl-5-oxo-2,3,4,5-tetrahydro-1H-pyrrolo[3,2-b]pyridin-1-yl)-2-oxoethyl)-2-methylpiperazine-1-carboxylate | | 57% | Method D 1.32 min | 1219 |
| (2R,5S)-tert-butyl 5-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-4-(2-(6-(4-fluorobenzyl)-5-oxo-2,3,4,5-tetrahydro-1H-pyrrolo[3,2-b]pyridin-1-yl)-2-oxoethyl)-3,3,4-trimethylpiperazine-1-carboxylate | | 54% | Method D 1.35 min | 1233 |

-continued

| Compound Name | Structure | Yield | LCMS RT | ES +ve |
|---|---|---|---|---|
| (2R,5S)-tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrazine-2-carbonyl)-2-methylpiperazin-1-yl)methyl)-4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-2-methylpiperazine-1-carboxylate | | 65% | Method D 1.34 min | 1244 |
| (2R,5S)-tert-butyl 5-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-2-methylpiperazine-1-carboxylate | | 60% | Method D 1.28 min | 1244 |

| Compound Name | Structure | Yield | LCMS RT | ES+ve |
|---|---|---|---|---|
| (2R,5S)-tert-butyl 5-(((R)-4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-3-oxopiperazin-1-yl)methyl)-4-(2-(6-(4-fluorobenzyl)-3,3,4-trimethyl-5-oxo-2,3,4,5-tetrahydro-1H-pyrrolo[3,2-b]pyridin-1-yl)-2-oxoethyl)-2-methylpiperazine-1-carboxylate | 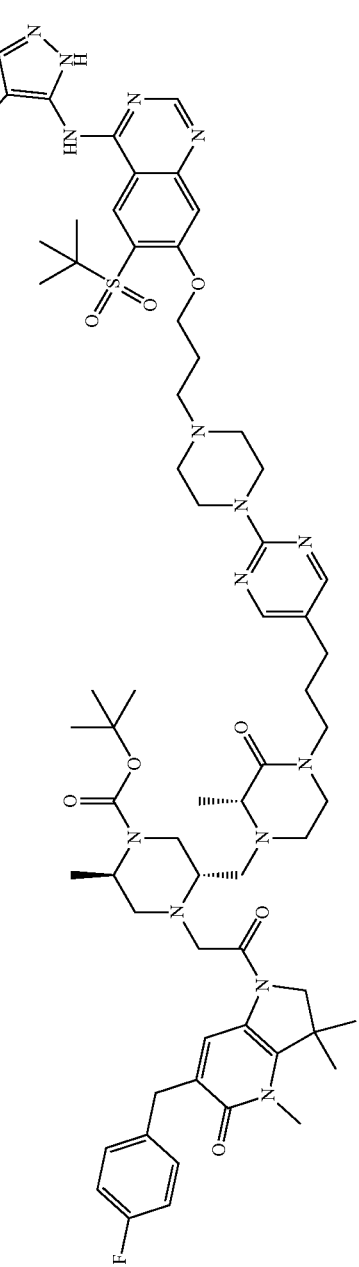 | 18% | Method D 1.30 min | 1274 |
| (2R,5S)-tert-butyl 5-(((R)-4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-3-oxopiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate | 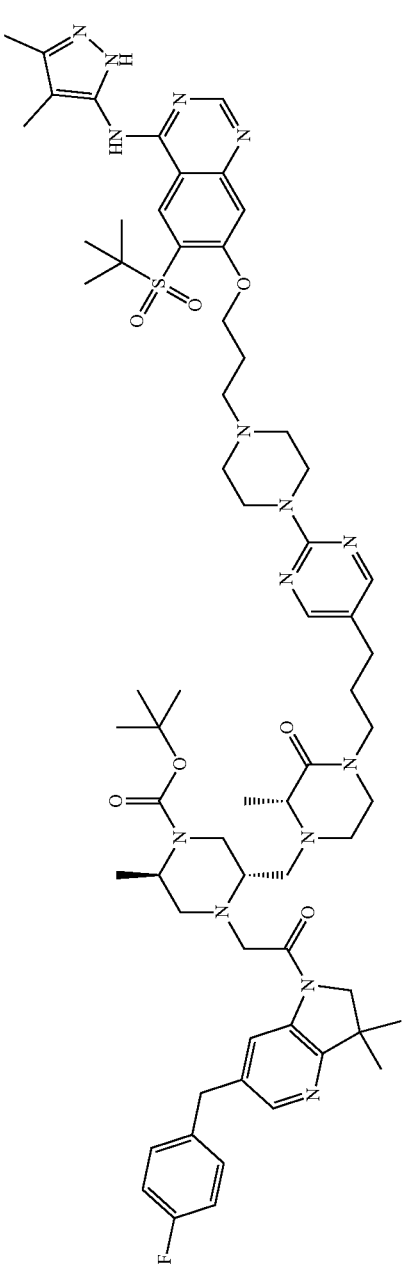 | 49% | Method D 1.34 min | 1244 |

| Compound Name | Structure | Yield | LCMS RT | ES +ve |
|---|---|---|---|---|
| (2R,5S)-tert-butyl 4-(2-(5-(benzyloxy)-6-(4-fluorobenzyl)-3,3-dimethyl-2,3-dihydropyrrolo[3,2-b]pyridin-1-yl)-2-oxoethyl)-5-(((R)-4-(2-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yloxy)ethyl)-2-methyl-3-oxopiperazin-1-yl)methyl)piperazine-1-carboxylate | | 24% | Method E 1.56 min | 1351 |
| (2R,5S)-tert-butyl 4-(2-(5-(benzyloxy)-6-(4-fluorobenzyl)-3,3-dimethyl-2,3-dihydropyrrolo[3,2-b]pyridin-1-yl)-2-oxoethyl)-5-(((R)-4-(3-(6-(tert-butylsulfonyl)-4-(4,5-dimethyl-1H-pyrazol-3-ylamino)quinazolin-7-yloxy)propyl)piperazin-1-yl)pyrimidin-5-yl)pyrimidine-2-carbonyl)-2-methyl-3-oxopiperazin-1-yl)methyl)piperazine-1-carboxylate | | 57% | Method D 1.47 min | 1320 |

| Compound Name | Structure | Yield | LCMS RT | ES +ve |
|---|---|---|---|---|
| (2R,5S)-tert-butyl 4-(2-(5-(benzyloxy)-6-(4-fluorobenzyl)-3,3-dimethyl-2,3-dihydropyrrolo[3,2-b]pyridin-1-yl)-2-oxoethyl)-5-(((R)-4-(5-(4-(3-(6-(tert-butylsulfonyl)-4-((4,5-dimethyl-1H-pyrazol-3-yl)amino)quinazolin-7-yloxy)propyl)piperazin-1-yl)pyrazine-2-carbonyl)-2-methylpiperazin-1-yl)methyl)-2-methylpiperazine-1-carboxylate | | 64% | Method D 1.49 min | 1320 |
| (2R,5S)-tert-butyl 5-(((R)-4-(2-(4-(3-(6-(tert-butylsulfonyl)-4-((4,5-dimethyl-1H-pyrazol-3-yl)amino)quinazolin-7-yloxy)propyl)piperazin-1-yl)pyrimidine-5-carbonyl)-2-methylpiperazin-1-yl)methyl)-4-(2-(6-(4-fluorobenzyl)-3,3,4-trimethyl-5-oxo-2,3,4,5-tetrahydropyrrolo[3,2-b]pyridin-1-yl)-2-oxoethyl)-2-methylpiperazine-1-carboxylate | | 70% | Method D 1.30 min | 1244 |

Example 1

14-((6-(Tert-butylsulfonyl)-4-((3,4-dimethyl-1H-pyrazol-5-yl)amino)quinazolin-7-yl)oxy))-1-(4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)-3,6,9,12-tetraoxatetradecan-1-one

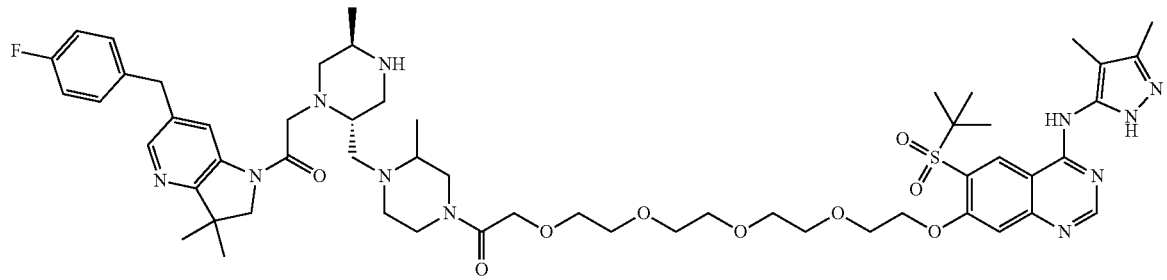 [SMILES: Cc1n[nH]c(Nc2ncnc3cc(OCCOCCOCCOCCOCC(=O)N4CCN(C[C@H]5CN[C@H](C)CN5CC(=O)N5CC(C)(C)c6ncc(Cc7ccc(F)cc7)cc65)C(C)C4)c(S(=O)(=O)C(C)(C)C)cc23)c1C]

To a solution of (2R,5S)-tert-butyl 5-((4-(14-((6-(tert-butylsulfonyl)-4-((4,5-dimethyl-1H-pyrazol-3-yl)amino)quinazolin-7-yl)oxy)-3,6,9,12-tetraoxatetradecan-1-oyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (41 mg, 0.034 mmol) in DCM (0.500 mL) was added hydrochloric acid (0.384 mL, 1.537 mmol) 4M in dioxane and the reaction was stirred at 20° C. under an atmosphere of nitrogen for 1 hour. The volatiles were removed under vacuum, the residue was redissolved in MeOH and subjected to purification by mass-directed automated preparative HPLC (ammonium bicarbonate modifier). The desired fractions were combined and concentrated to afford the title compound (24 mg, 0.02 mmol, 56.4% yield). LCMS Method B RT=1.09 min, ES+ve 1100.

Example 2

2-((2R,5R)-2-(((R)-4-(5-(2-((6-(Tert-butylsulfonyl)-4-((3,4-dimethyl-11H-pyrazol-5-yl)amino)quinazolin-7-yl)oxy)ethoxy)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 Trifluoroacetic Acid

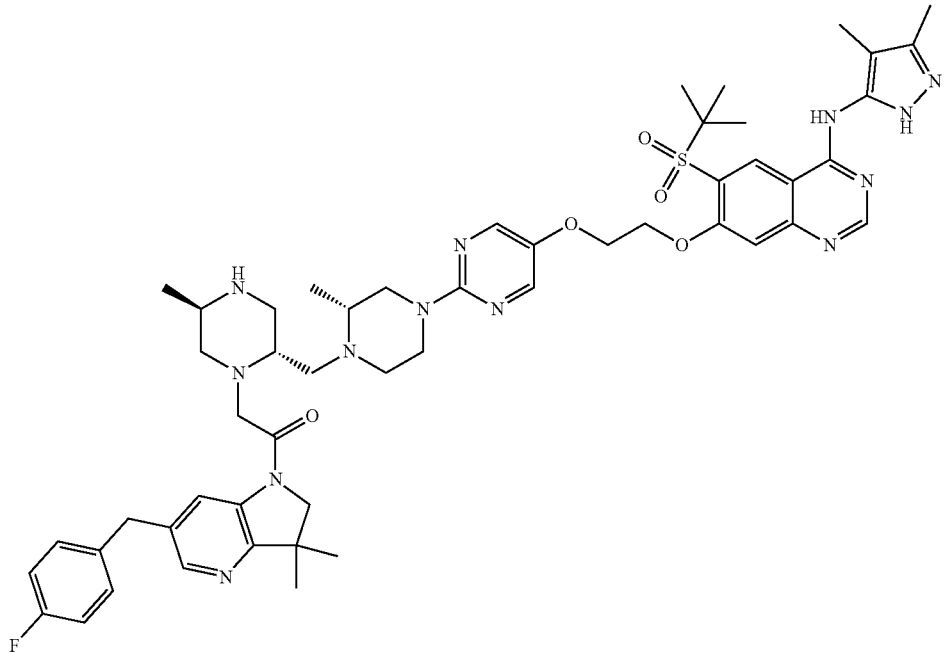 [SMILES: Cc1n[nH]c(Nc2ncnc3cc(OCCOc4cnc(N5CCN(C[C@H]6CN[C@H](C)CN6CC(=O)N6CC(C)(C)c7ncc(Cc8ccc(F)cc8)cc76)[C@H](C)C5)nc4)c(S(=O)(=O)C(C)(C)C)cc23)c1C]

To (2R,5S)-tert-butyl 5-(((R)-4-(5-(2-(((6-(tert-butylsulfonyl)-4-((4,5-dimethyl-1H-pyrazol-3-yl)amino)quinazolin-7-yl)oxy)ethoxy)pyrimidin-2-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (9 mg, 8.15 μmol) was added hydrochloric acid (0.407 mL, 1.630 mmol) 4M in dioxane. The reaction was stirred at 20° C. for 3 hours. The volatiles were removed under vacuum, and the residue was redissolved in MeOH and subjected to purification by mass-directed automated preparative HPLC (TFA modifier). The desired fractions were combined and concentrated to afford the title compound (5.7 mg, 0.004 mmol, 47.9% yield). LCMS Method B RT=1.25 min, ES+ve 1004.

Example 3

2-((2R,5R)-2-(((R)-4-(6-(4-(((6-(Tert-butylsulfonyl)-4-((3,4-dimethyl-1H-pyrazol-5-yl)amino)quinazolin-7-yl)oxy)methyl)piperidin-1-yl)pyrimidin-4-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 Trifluoroacetic Acid To (2R,5S)-tert-butyl 5-(((R)-4-(6-(4-(((6-(tert-butylsulfonyl)-4-((4,5-dimethyl-1H-pyrazol-3-yl)amino)quinazolin-7-yl)oxy)methyl)piperidin-1-yl)pyrimidin-4-yl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (9 mg, 7.78 μmol) in THF (0.4 mL) was added hydrochloric acid (0.097 mL, 0.389 mmol) in 4M dioxane diluted in THF (0.4 mL). The reaction was stirred at 20° C. for 4 hours. The reaction mixture containing the crude product was subjected directly to purification by mass-directed automated preparative HPLC (TFA modifier) to afford the title compound (6 mg, 0.004 mmol, 48.4% yield). LCMS Method B RT=1.28 min, ES+ve 1057.

Example 4

2-((2R,5R)-2-((9-(5-(2-(((6-(Tert-butylsulfonyl)-4-((3,4-dimethyl-1H-pyrazol-5-yl)amino)quinazolin-7-yl)oxy)ethoxy)pyrimidin-2-yl)-3,9-diazaspiro[5.5]undecan-3-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 Trifluoroacetic Acid

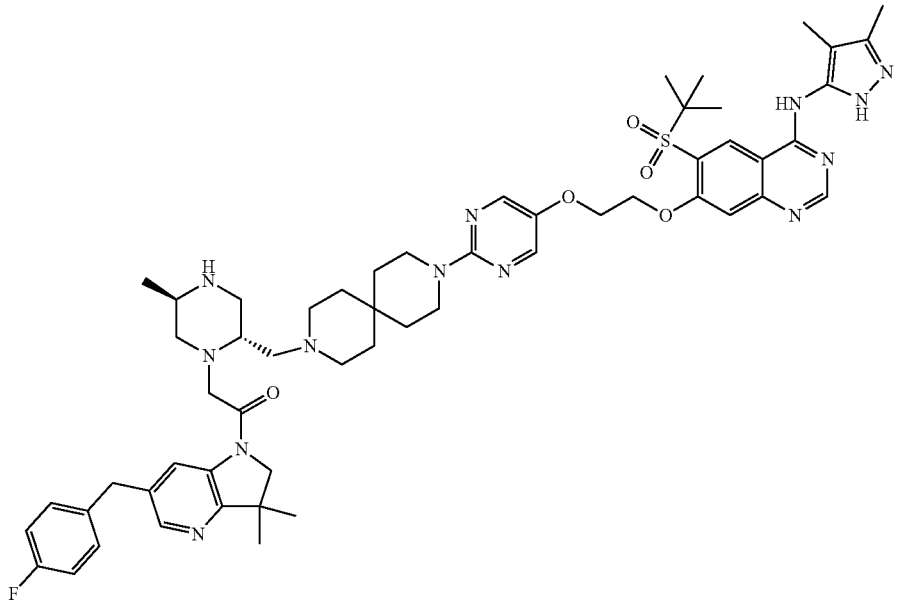 [SMILES: Cc1n[nH]c(Nc2ncnc3cc(OCCOc4cnc(N5CCC6(CCN(C[C@H]7CN[C@H](C)CN7CC(=O)N7CC(C)(C)c8ncc(Cc9ccc(F)cc9)cc87)CC6)CC5)nc4)c(S(=O)(=O)C(C)(C)C)cc23)c1C]

To (2R,5S)-tert-butyl 5-((9-(5-(2-(((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]undecan-3-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (32 mg, 0.028 mmol) in DCM (0.5 mL) was added TFA (0.532 mL, 6.91 mmol) and the reaction was stirred at room temperature under an atmosphere of nitrogen for 90 minutes. The volatiles were removed under vacuum, and the residue was redissolved in MeOH and subjected to purification by mass-directed automated preparative HPLC (TFA modifier). The desired fractions were combined and concentrated to afford the title compound (10 mg, 0.007 mmol, 23.9% yield). LCMS Method B RT=1.37 min, ES+ve 1058.

Example 5 2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2 Trifluoroacetic Acid

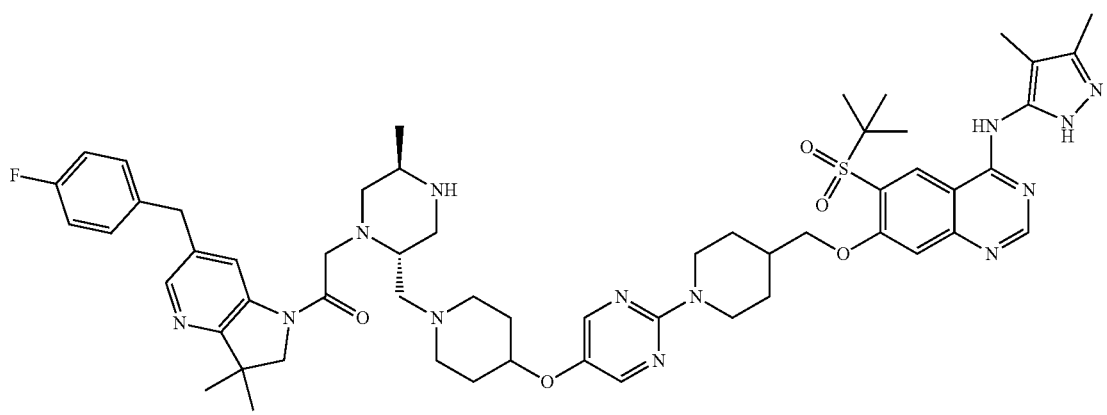 [SMILES: Cc1n[nH]c(Nc2ncnc3cc(OCC4CCN(c5ncc(OC6CCN(C[C@H]7CN[C@H](C)CN7CC(=O)N7CC(C)(C)c8ncc(Cc9ccc(F)cc9)cc87)CC6)cn5)CC4)c(S(=O)(=O)C(C)(C)C)cc23)c1C]

To (2R,5S)-tert-butyl 5-((4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)piperidin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (52 mg, 0.045 mmol) in DCM (0.5 mL) was added TFA (0.865 mL, 11.22 mmol) and the reaction was stirred at room temperature under an atmosphere of nitrogen for 2 hours. The reaction mixture containing the crude product was subjected directly to purification by mass-directed automated preparative HPLC (TFA modifier) to afford the title compound (30 mg, 0.03 mmol, 55.5% yield). LCMS Method B RT=1.38 min, ES+ve 1058.

Example 6 2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-((S)-2-(4-(4-fluorobenzoyl)thiazol-2-yl)pyrrolidin-1-yl)ethanone, 2 Trifluoroacetic Acid

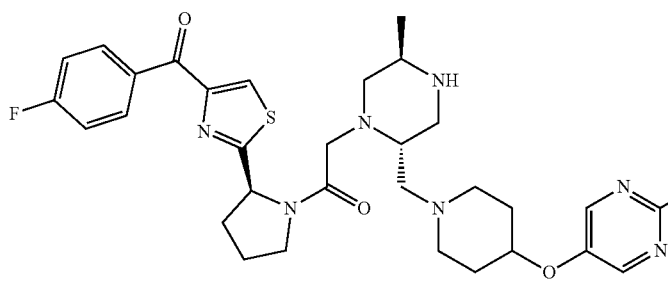
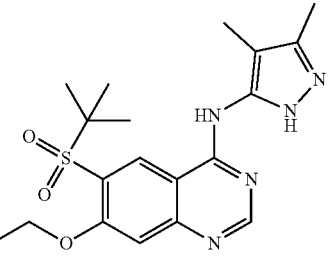

To (2R,5S)-tert-butyl 5-((4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)piperidin-1-yl)methyl)-4-(2-((S)-2-(4-(4-fluorobenzoyl)thiazol-2-yl)pyrrolidin-1-yl)-2-oxoethyl)-2-methylpiperazine-1-carboxylate (59 mg, 0.050 mmol) in DCM (0.5 mL) was added TFA (0.964 mL, 12.52 mmol) and the reaction was stirred at room temperature under an atmosphere of nitrogen for 2 hours. The reaction mixture containing the crude product was subjected directly to purification by mass-directed automated preparative HPLC (TFA modifier) to afford the title compound (35 mg, 0.03 mmol, 57.1% yield). LCMS Method B RT=1.33 min, ES+ve 1078.

Example 7 2-((2R,5R)-2-(((R)-4-(2-(2-(2-(2-((6-(tert-butylsulfonyl)-4-((5-fluoro-1H-indazol-3-yl)amino)quinolin-7-yl)oxy)ethoxy)ethoxy)ethoxy)ethyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 5 Trifluoroacetate

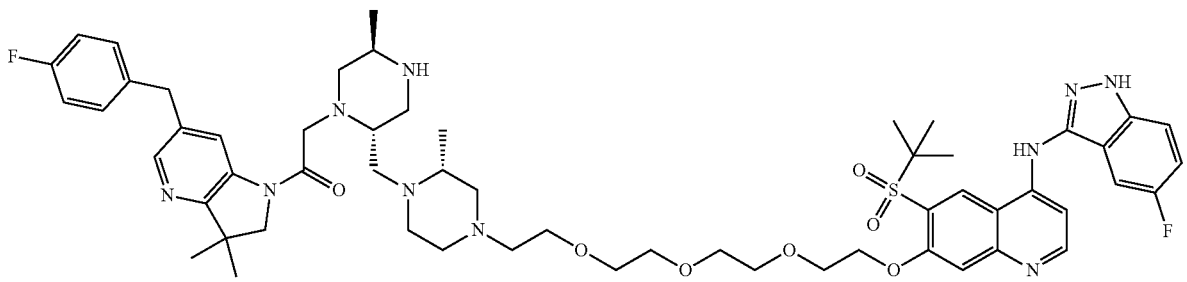 [SMILES: C[C@@H]1CN(CC(=O)N2CC(C)(C)c3ncc(Cc4ccc(F)cc4)cc32)[C@@H](CN2CCN(CCOCCOCCOCCOc3cc4nccc(Nc5n[nH]c6ccc(F)cc56)c4cc3S(=O)(=O)C(C)(C)C)C[C@H]2C)CN1]

To a solution of 6-(tert-butylsulfonyl)-7-(2-(2-(2-(2-chloroethoxy)ethoxy)ethoxy)-N-(5-fluoro-1H-indazol-3-yl)quinolin-4-amine (90 mg, 0.148 mmol) in NMP (1.0 mL) was added (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (180 mg, 0.296 mmol), sodium iodide (2.215 mg, 0.015 mmol) and potassium carbonate (61.3 mg, 0.443 mmol) and the reaction was stirred at 100° C. in the microwave for 4 hours. The reaction mixture containing the crude product was subjected directly to purification by flash chromatography (30 g pre-packed C-18 SNAP cartridge: 50% to 95% acetonitrile (0.1% ammonia) in water (10 mM ammonium bicarbonate)) and subsequently by mass-directed automated preparative HPLC (TFA modifier). The desired fractions were collected and concentrated under vacuum at 50° C., to afford the title compound (53 mg, 0.03 mmol, 21.7% yield). LCMS Method B RT=1.21 min, ES+ve 1081.

Example 8 2-((2R,5R)-2-(((R)-4-(6-(4-(3-((6-(tert-butylsulfonyl)-4-(3,4-dimethyl-1H-pyrazol-5-yl)amino)quinazolin-7-yl)oxy)propyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 5 Hydrochloride

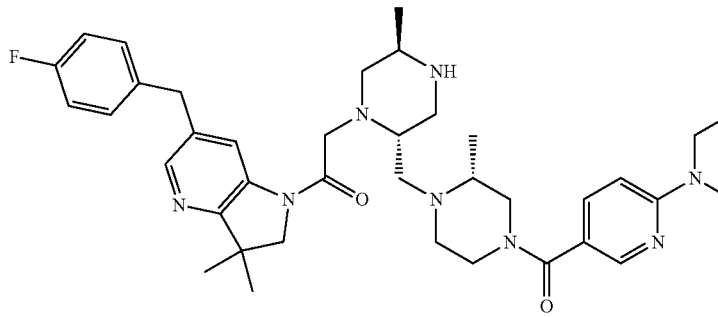
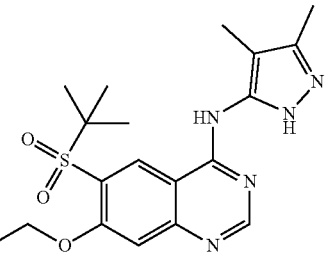

To a solution of (2R,5S)-tert-butyl 5-(((R)-4-(6-(4-(3-((6-(tert-butylsulfonyl)-4-((3,4-dimethyl-1H-pyrazol-5-yl)amino)quinazolin-7-yl)oxy)propyl)piperidin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (42 mg, 0.035 mmol) in DCM (0.500 mL) was added HCl (0.433 mL, 1.732 mmol) 4M solution in dioxane, and the reaction was stirred at room temperature for 2 hours. The reaction was concentrated under vacuum to afford the title compound (37 mg, 0.03 mmol, 85% yield). LCMS Method B RT=1.24 min, ES+ve 1112.

Example 9 2-((2R,5R)-2-(((R)-4-(6-(4-(3-((6-(Tert-butylsulfonyl)-4-((3,4-dimethyl-1H-pyrazol-5-yl)amino)quinazolin-7-yl)oxy)propyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 5 Hydrochloride

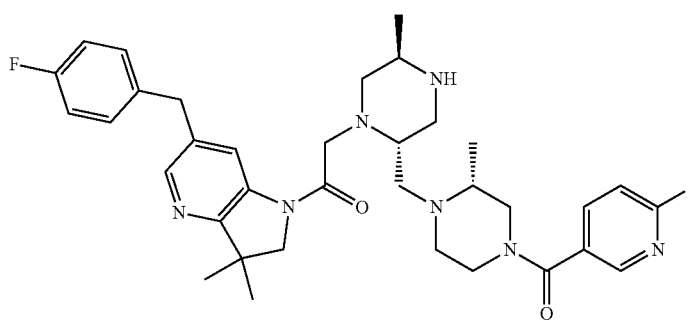
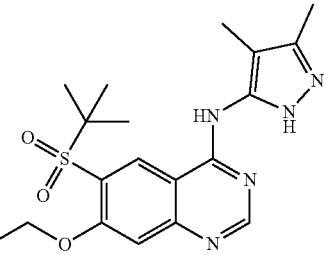

To a solution of (2R,5S)-tert-butyl 5-(((R)-4-(6-(4-(3-((6-(tert-butylsulfonyl)-4-((3,4-dimethyl-1H-pyrazol-5-yl)amino)quinazolin-7-yl)oxy)propyl)piperazin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (18 mg, 0.015 mmol) in DCM (0.200 mL) was added HCl (0.185 mL, 0.742 mmol) 4M solution in dioxane, and the reaction was stirred at room temperature for 2 hours. The reaction mixture containing the crude product was subjected directly to purification by mass-directed automated preparative HPLC (TFA modifier). The product was then taken up in THF (1 ml) and treated with 4M HCl in dioxane (7.5 ul) and the precipitate collected by filtration and dried under a stream of nitrogen to afford the title compound (12.5 mg, 0.01 mmol, 65% yield). LCMS Method B RT=1.11 min, ES+ve 1113.

Example 10

2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 Trifluoroacetic Acid

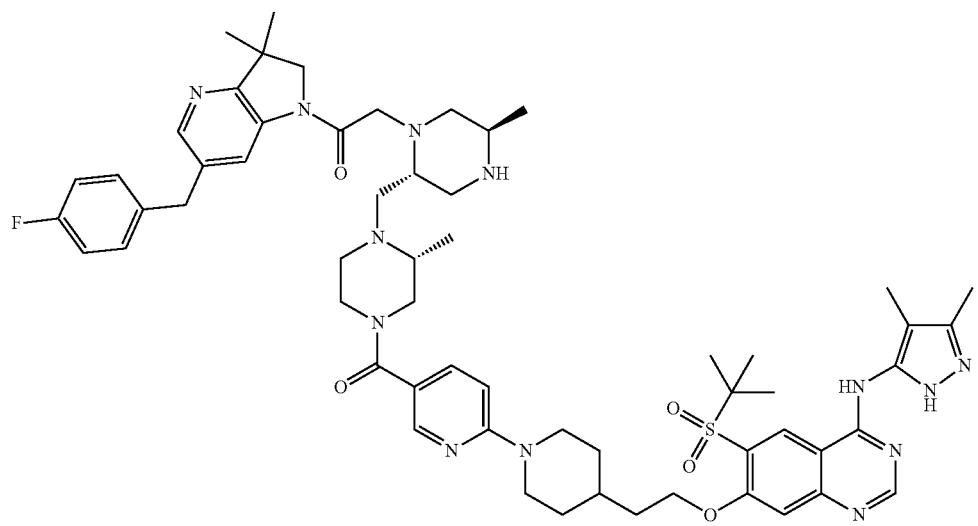 [SMILES: Cc1n[nH]c(Nc2ncnc3cc(OCCC4CCN(c5ccc(C(=O)N6CCN(C[C@H]7CN[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (50 mg, 0.082 mmol) in NMP (0.5 mL) was added 6-(4-(2-((6-(tert-butylsulfonyl)-4-((4,5-dimethyl-1H-pyrazol-3-yl)amino)quinazolin-7-yl)oxy)ethyl)piperidin-1-yl)nicotinic acid, 3Hydrochloride (88 mg, 0.123 mmol), DIPEA (0.072 mL, 0.411 mmol) and HATU (46.8 mg, 0.123 mmol) and the reaction was stirred at room temperature for 1 hour. The reaction mixture containing the crude product was subjected directly to purification by mass-directed automated preparative HPLC (TFA modifier), and the desired fractions were collected and concentrated under vacuum to afford a mixture of (2R,5S)-tert-butyl 5-(((R)-4-(6-(4-(2-((6-(tert-butylsulfonyl)-4-((3,4-dimethyl-1H-pyrazol-5-yl)amino)quinazolin-7-yl)oxy)ethyl)piperidin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate and the title compound. The mixture was taken up in DCM (0.200 mL) and HCl (0.980 mL, 3.92 mmol) 4M solution in dioxane was added, and the reaction was stirred at room temperature. The product was subjected directly to purification by mass-directed automated preparative HPLC (TFA modifier), and the desired fractions were collected and concentrated under vacuum to afford the title compound (37.5 mg, 0.03 mmol, 37.3% yield). LCMS Method B RT=1.20 min, ES+ve 1098.

Example 11

2-((2R,5R)-2-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 Trifluoroacetic Acid

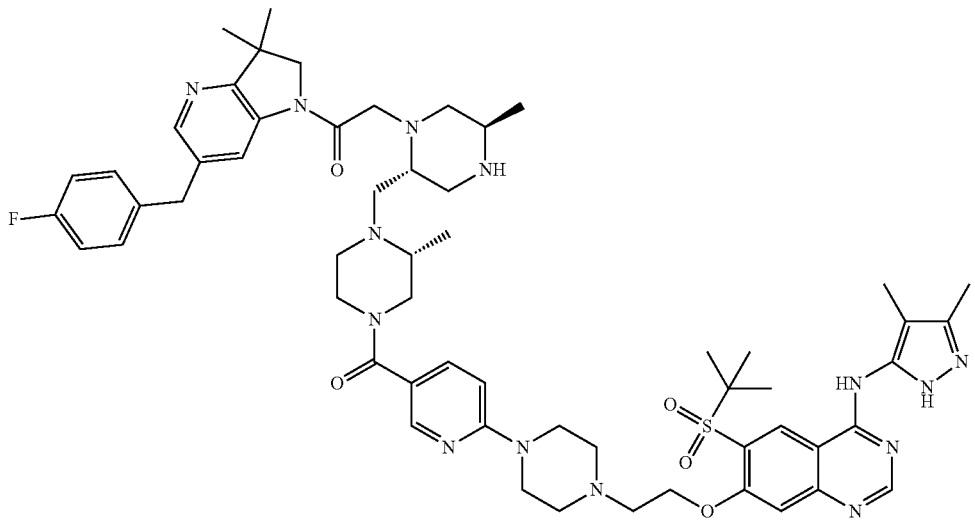 [SMILES: Cc1n[nH]c(Nc2ncnc3cc(OCCN4CCN(c5ccc(C(=O)N6CCN(C[C@H]7CN[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 5-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (52 mg, 0.043 mmol) in DCM (0.200 mL) was added HCl (0.542 mL, 2.168 mmol) 4M solution in dioxane, and the reaction was stirred at room temperature for 1 hour. The reaction mixture containing the crude product was subjected directly to purification by mass-directed automated preparative HPLC (TFA modifier), and the desired fractions were collected and concentrated under vacuum to afford the title compound (38 mg, 0.03 mmol, 68.4% yield). LCMS Method B RT=1.12 min, ES+ve 1099.

Using a method analogous to that for 2-((2R,5R)-2-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 4 trifluoroacetic acid the following compounds were prepared:

| Compound Name | Structure | Yield | LCMS RT | ES+ve |
|---|---|---|---|---|
| Example 12 2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2 trifluoroacetic acid | 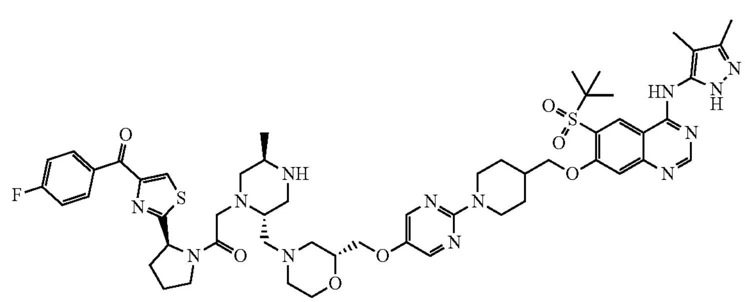 | 95% | Method B 1.19 min | 1094 |

| Compound Name | Structure | Yield | LCMS RT | ES +ve |
|---|---|---|---|---|
| Example 13 2-((2R,5R)-2-(((R)-2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-((S)-2-(4-(4-fluorobenzoyl)thiazol-2-yl)pyrrolidin-1-yl)ethanone, 3 trifluoroacetic acid | 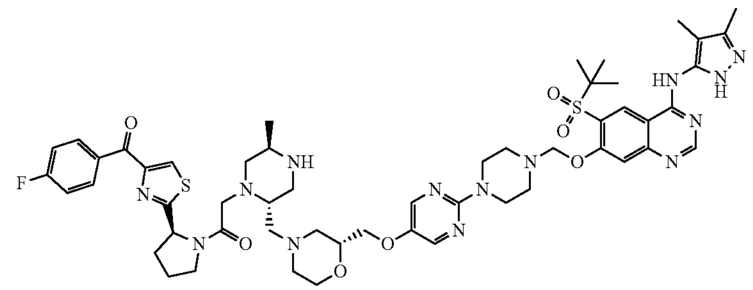 [SMILES: Cc1n[nH]c(Nc2ncnc3cc(OCC4CCN(c5ncc(OC[C@H]6CN(C[C@H]7CN[C@H](C)CN7CC(=O)N7CCC[C@H]7c7nc(C(=O)c8ccc(F)cc8)cs7)CCO6)cn5)CC4)c(S(=O)(=O)C(C)(C)C)cc23)c1C] | 88% | Method B 1.11 min | 1109 |
| Example 14 2-((2R,5R)-2-(((R)-2-(((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2 trifluoroacetic acid | 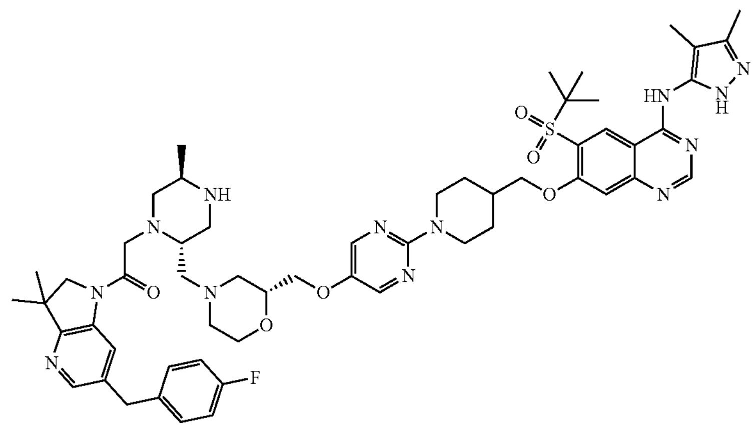 [SMILES: Cc1n[nH]c(Nc2ncnc3cc(OCC4CCN(c5ncc(OC[C@H]6CN(C[C@H]7CN[C@H](C)CN7CC(=O)N7CC(C)(C)c8ncc(Cc9ccc(F)cc9)cc87)CCO6)cn5)CC4)c(S(=O)(=O)C(C)(C)C)cc23)c1C] | 90% | Method B 1.24 min | 1074 |
| Example 15 2-((2R,5R)-2-(((R)-2-(((2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 trifluoroacetic acid | 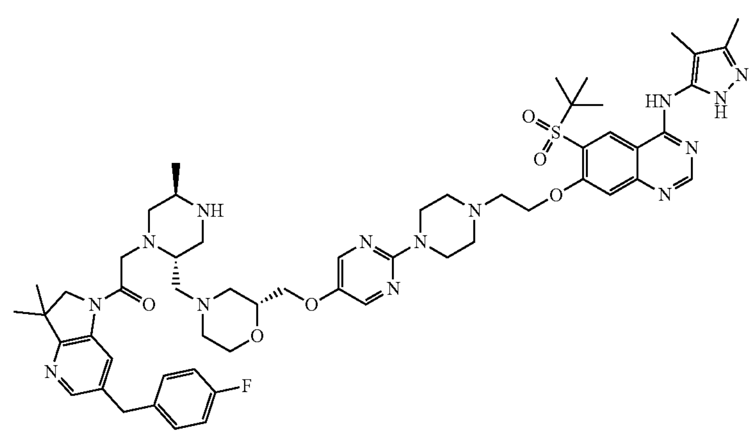 [SMILES: Cc1n[nH]c(Nc2ncnc3cc(OCCN4CCN(c5ncc(OC[C@H]6CN(C[C@H]7CN[C@H](C)CN7CC(=O)N7CC(C)(C)c8ncc(Cc9ccc(F)cc9)cc87)CCO6)cn5)CC4)c(S(=O)(=O)C(C)(C)C)cc23)c1C] | 87% | Method B 1.15 min | 1089 |

| Compound Name | Structure | Yield | LCMS RT | ES +ve |
|---|---|---|---|---|
| Example 16 2-((2R,5R)-2-((9-(5-(2-((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]un-decan-3-yl)methyl)-5-methylpiperazin-1-yl)-1-((S)-2-(4-(4-fluorobenzoyl)thiazol-2-yl)pyrrolidin-1-yl)ethanone, 2 trifluoroacetic acid | | 96% | Method B 1.23 min | 1078 |
| Example 17 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)pipera-zin-1-yl)pyrazine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 Hydrochloride | | 18% | Method B 1.15 min | 1114 |
| Example 18 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)pipera-zin-1-yl)pyrimidine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 Hydrochloride | | 39% | Method B 1.16 min | 1114 |

| Compound Name | Structure | Yield | LCMS RT | ES +ve |
|---|---|---|---|---|
| Example 19 2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 Hydrochloride | 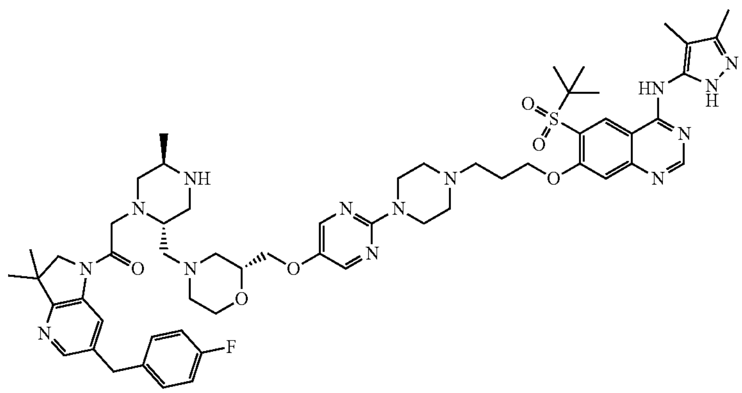 [SMILES: Cc1n[nH]c(Nc2ncnc3cc(OCCCN4CCN(c5ncc(OC[C@H]6CN(C[C@H]7CN[C@H](C)CN7CC(=O)N7CC(C)(C)c8ncc(Cc9ccc(F)cc9)cc87)CCO6)cn5)CC4)c(S(=O)(=O)C(C)(C)C)cc23)c1C] | 47.1% | Method B 1.20 min | 1103 |
| Example 20 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 Hydrochloride | 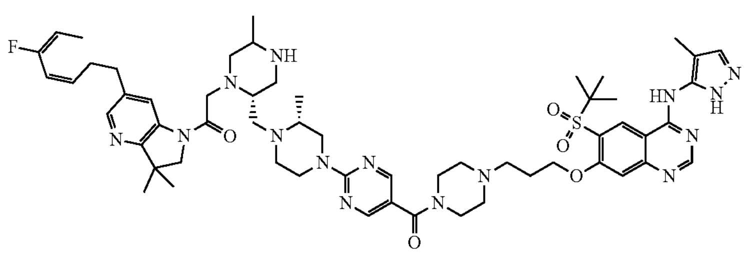 [SMILES: C/C=C(F)\C=C/CCc1cnc2c(c1)N(C(=O)CN1CC(C)NC[C@@H]1CN1CCN(c3ncc(C(=O)N4CCN(CCCOc5cc6ncnc(Nc7[nH]ncc7C)c6cc5S(=O)(=O)C(C)(C)C)CC4)cn3)C[C@H]1C)CC2(C)C] | 50.3% | Method B 1.16 min | 1114 |

Example 21

2-((2R,5R)-2-(((R)-4-(2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 5 Hydrochloride

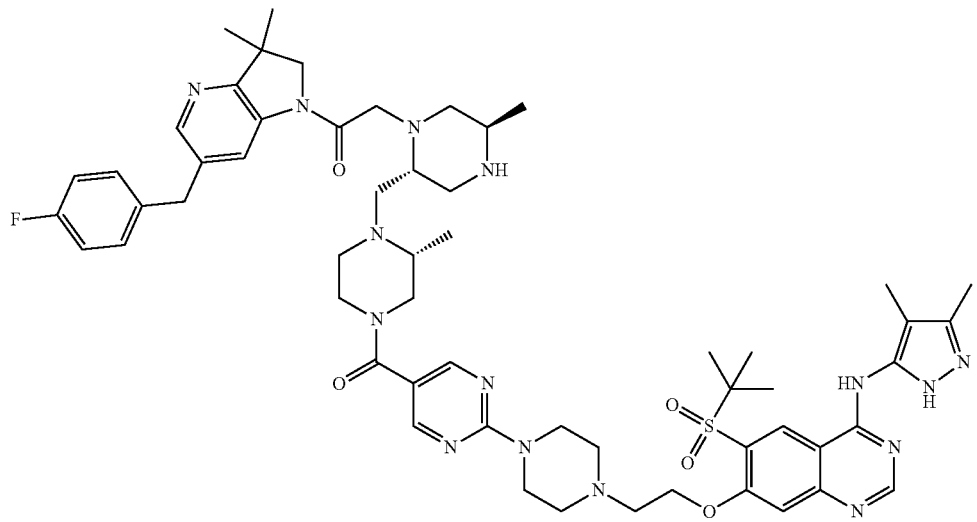 [SMILES: Cc1n[nH]c(Nc2ncnc3cc(OCCN4CCN(c5ncc(C(=O)N6CCN(C[C@H]7CN[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (50 mg, 0.082 mmol) in NMP (0.5 mL) was added 2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carboxylic acid, 3Hydrochloride (89 mg, 0.123 mmol), DIPEA (0.072 mL, 0.411 mmol) and HATU (46.8 mg, 0.123 mmol) and the reaction was stirred at room temperature for 1 hour. The reaction mixture containing the crude product was subjected directly to purification by mass-directed automated preparative HPLC (TFA modifier), and the desired fractions were collected and concentrated under vacuum to afford a mixture of (2R,5S)-tert-butyl 5-(((R)-4-(2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidine-5-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate and the title compound. The mixture was dissolved in DCM (0.200 mL) and HCl (0.823 mL, 3.29 mmol) 4M solution in dioxane was added, and the reaction was stirred at room temperature for 2 hours. The reaction mixture containing the crude product was subjected directly to purification by mass-directed automated preparative HPLC (TFA modifier), and the desired fractions were collected, diluted with 1 mL of 4M HCl in dioxane and concentrated under vacuum to afford the title compound (16 mg, 0.01 mmol, 19% yield). LCMS Method B RT=1.10 min, ES+ve 1100.

Example 22

2-((2R,5R)-2-(((R)-4-(2-(4-(3-((6-(Tert-butylsulfonyl)-4-((3,4-dimethyl-1H-pyrazol-5-yl)amino)quinazolin-7-yl)oxy)propyl)piperidin-1-yl)pyrimidine-5-carbonyl)-2-methylpiperazin-1-yl)methyl)-5-methylpiperazin-1-yl)-1-(6-(4-fluoro benzyl)-3,3-dimethyl-2,3-dihydro-1H-pyrrolo[3,2-b]pyridin-1-yl)ethanone, 4 Trifluoroacetic Acid

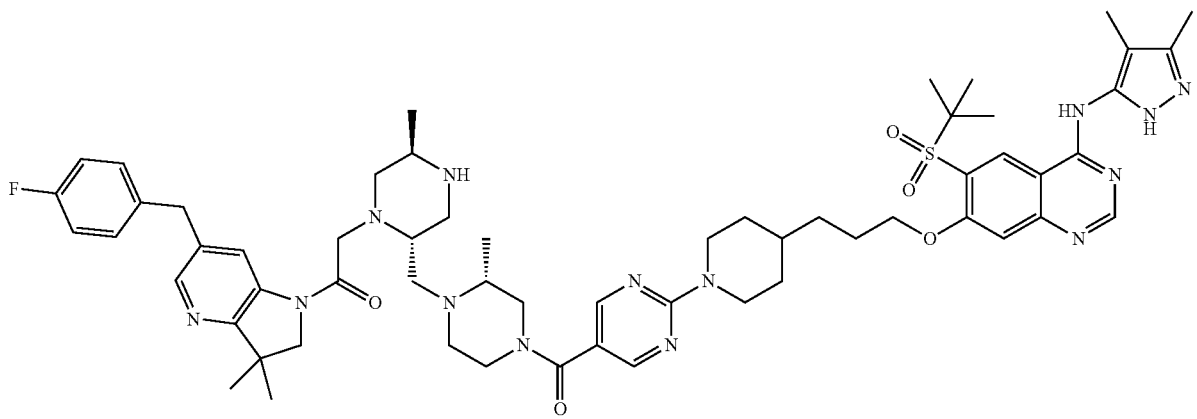 [SMILES: Cc1n[nH]c(Nc2ncnc3cc(OCCCC4CCN(c5ncc(C(=O)N6CCN(C[C@H]7CN[C@H](C)CN7CC(=O)N7CC(C)(C)c8ncc(Cc9ccc(F)cc9)cc87)[C@H](C)C6)cn5)CC4)c(S(=O)(=O)C(C)(C)C)cc23)c1C]

To a solution of (2R,5S)-tert-butyl 4-(2-(6-(4-fluorobenzyl)-3,3-dimethyl-2,3-dihydro-1H-pyrrolo[3,2-b]pyridin-1-yl)-2-oxoethyl)-2-methyl-5-(((R)-2-methylpiperazin-1-yl)methyl)piperazine-1-carboxylate (30 mg, 0.049 mmol) in NMP (0.5 mL) was added 2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carboxylic acid, 3Hydrochloride (54.1 mg, 0.074 mmol), DIPEA (0.043 mL, 0.246 mmol) and HATU (28.1 mg, 0.074 mmol) and the reaction was stirred at room temperature for 1 hour. The reaction mixture containing the crude product was subjected directly to purification by mass-directed automated preparative HPLC (TFA modifier), and the desired fractions were collected and concentrated under vacuum to afford a mixture of (2R,5S)-tert-butyl 5-(((R)-4-(2-(4-(3-((6-(tert-butylsulfonyl)-4-((3,4-dimethyl-1H-pyrazol-5-yl)amino)quinazolin-7-yl)oxy)propyl)piperidin-1-yl)pyrimidine-5-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate and the title compound. The mixture was dissolved in DCM (0.200 mL), HCl (0.433 mL, 1.731 mmol) 4M solution in dioxane was added, and the reaction was stirred at room temperature for 2 hours. The product was subjected directly to purification by mass-directed automated preparative HPLC (TFA modifier), and the desired fractions were collected and concentrated under vacuum to afford the title compound (23 mg, 0.02 mmol, 51.3% yield). LCMS Method B RT=1.25 min, ES+ve 1113.

Example 23

(S)—N—((S)-3-(4-(2-(2-((6-(Tert-butylsulfonyl)-4-((4,5-dimethyl-1H-pyrazol-3-yl)amino)quinazolin-7-yl)oxy)ethoxy)ethoxy)phenyl)-1-((S)-2-(4-(4-fluorobenzoyl)thiazol-2-yl)pyrrolidyl-1-yl)-1-oxopropan-2-yl)-2-(methylamino)propanamide, 2 Hydrochloride

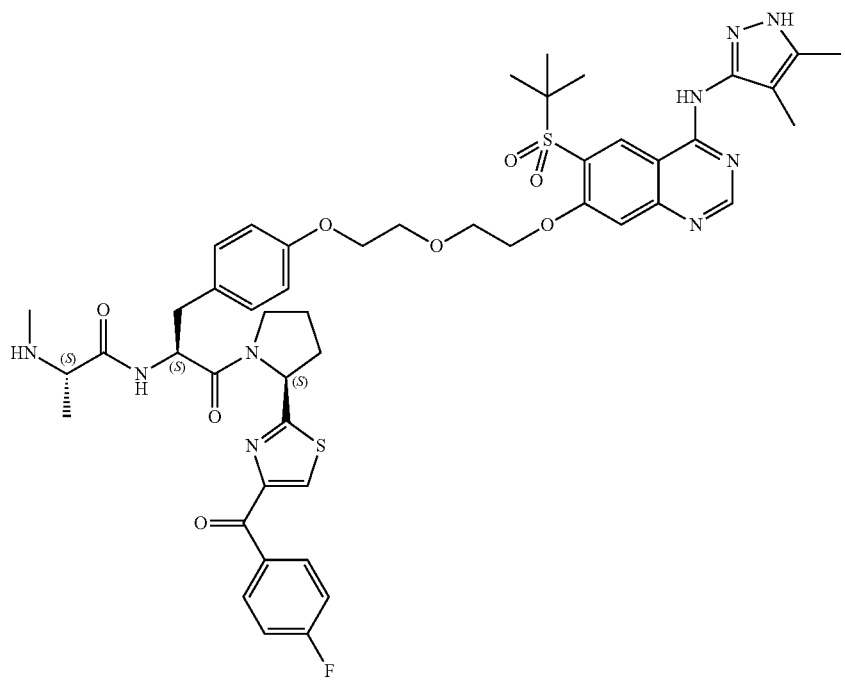

Trifluoroacetic acid (0.2 mL) was added to a solution of tert-butyl ((S)-1-(((S)-3-(4-(2-(2-((6-(tert-butylsulfonyl)-4-((4,5-dimethyl-1H-pyrazol-3-yl)amino)quinazolin-7-yl)oxy)ethoxy)ethoxy)phenyl)-1-((S)-2-(4-(4-fluorobenzoyl)thiazol-2-yl)pyrrolidin-1-yl)-1-oxopropan-2-yl)amino)-1-oxopropan-2-yl)(methyl)carbamate (2 mg, 1.87 µmol) in THF (0.1 mL), and the mixture was stirred at ambient temperature for 30 min. The reaction mixture was diluted with toluene (2×10 mL) to remove any excess TFA. The concentrated reaction product was taken up in DCM (5 mL), 4 M HCl in dioxane (0.2 mL, 6.58 mmol) was added, and the mixture was concentrated under reduced pressure, before being dissolved in toluene (10 mL) and concentrated once again to afford the title compound (1.8 mg, 1.73 µmol, 93% yield). LCMS Method A RT=0.74 min, ES+ve 970.

Example 24

(S)—N—((S)-1-(1-(2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carbonyl)piperidin-4-yl)-2-((S)-2-(4-(4-fluorobenzoyl)thiazol-2-yl) pyrrolidin-1-yl)-2-oxoethyl)-2-(methylamino)propanamide HATU (25 mg, 0.07 mmol) was added to a mixture of (9H-fluoren-9-yl)methyl ((S)-1-(((S)-2-((S)-2-(4-(4-fluorobenzoyl)thiazol-2-yl)pyrrolidin-1-yl)-2-oxo-1-(piperidin-4-yl)ethyl)amino)-1-oxopropan-2-yl)(methyl)carbamate (40 mg, 0.06 mmol), 2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carboxylic acid, 3Hydrochloride (57 mg, 0.08 mmol) and DIPEA (0.06 mL, 0.332 mmol) in DMF (0.8 mL). The reaction was stirred at ambient temperature for 30 min. Piperidine (0.11 mL, 1.11 mmol) was then added, and the mixture was stirred for 1 h. The product was subjected directly to purification by mass-directed automated preparative HPLC (ammonium bicarbonate modifier) to afford the title compound (12 mg, 10.85 µmol, 20% yield). LCMS Method B RT=1.14 min, ES+ve 1106.

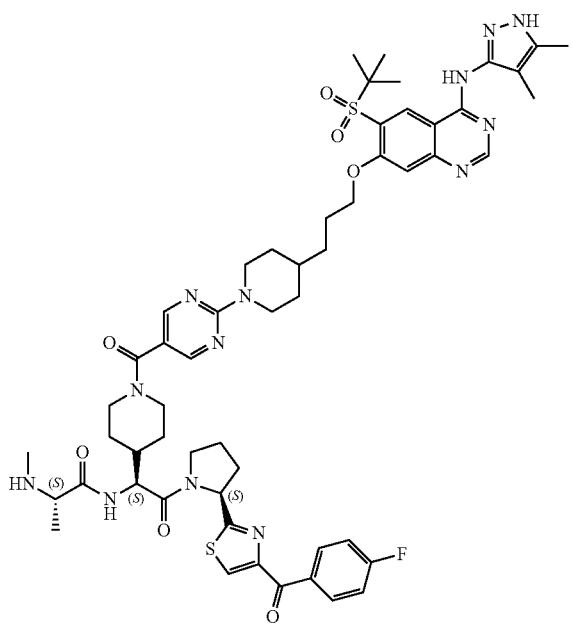

Using a method analogous to that for (S)—N—((S)-1-(1-(2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide the following compounds were prepared:

| Compound Name | Structure | Yield | LCMS RT | ES+ve |
|---|---|---|---|---|
| Example 25 (S)-N-((S)-1-(1-(2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide | 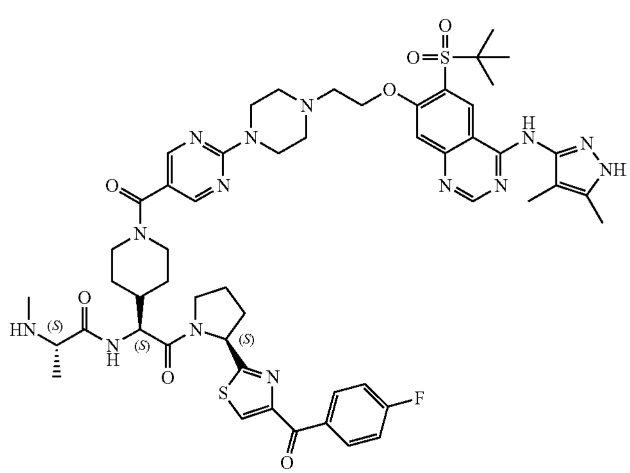 | 43% | Method B 1.02 min | 1093 |

| Compound Name | Structure | Yield | LCMS RT | ES + ve |
|---|---|---|---|---|
| Example 26 (S)-N-((S)-1-(1-(6-(4-(2-((6-(tert-butylsulfonyl)-4-((4,5-dimethyl-1H-pyrazol-3-yl)amino)quinazolin-7-yl)oxy)ethyl)piperazin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide | 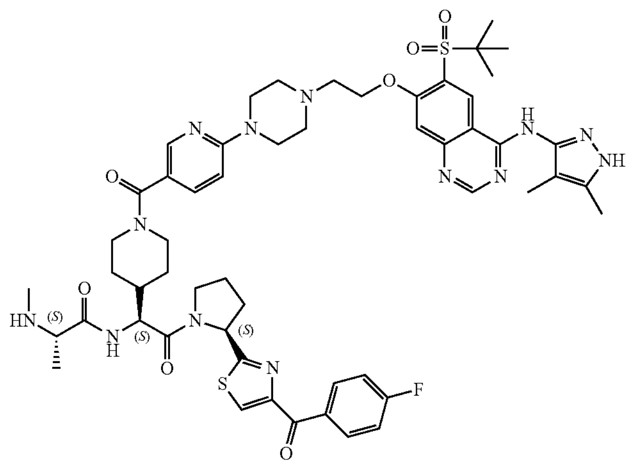 | 48% | Method B 1.02 min | 1092 |
| Example 27 (S)-N-((S)-1-(1-(6-(4-(2-((6-(tert-butylsulfonyl)-4-((4,5-dimethyl-1H-pyrazol-3-yl)amino)quinazolin-7-yl)oxy)ethyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide | | 32% | Method B 1.11 min | 1091 |
| Example 28 (S)-N-((S)-1-(1-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propanamide | 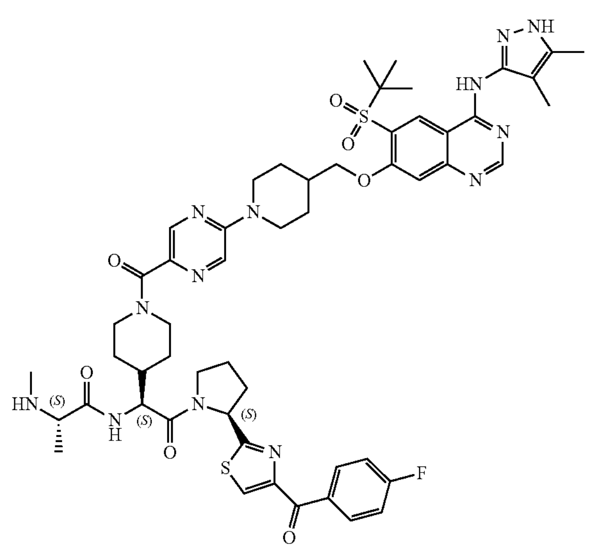 | 22% | Method B 1.07 min | 1078 |

| Compound Name | Structure | Yield | LCMS RT | ES +ve |
|---|---|---|---|---|
| Example 29 (S)-N-((S)-1-(1-(2-(4-(((6-(tert-butylsulfonyl)-4-((4,5-dimethyl-1H-pyrazol-3-yl)amino)quinazolin-7-yl)oxy)methyl)piperidin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide | 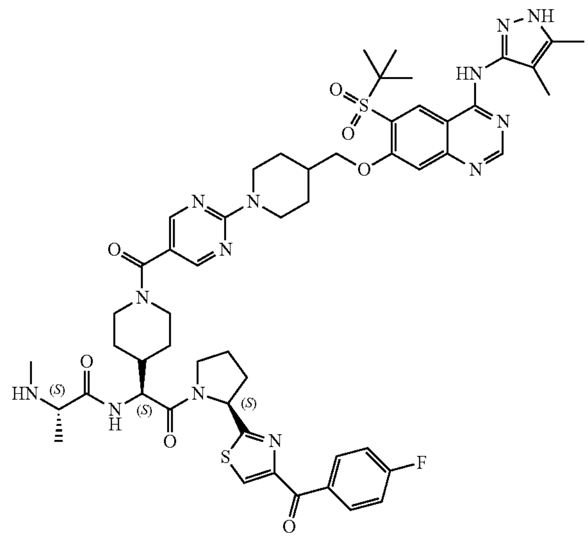 | 66% | Method B 1.08 min | 1078 |
| Example 30 (S)-N-((S)-1-(1-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carbonyl)piperridin-4-yl)-2-((S)-2-(4-(4-fluorobenzoyl)thiazol-2-yl)pyrrolidin-1-yl)-2-oxoethyl)-2-(methylamino)propanamide | 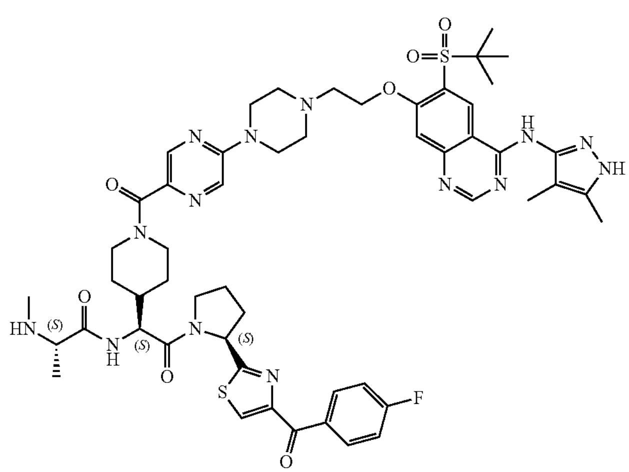 | 67% | Method B 1.01 min | 1093 |

| Compound Name | Structure | Yield | LCMS RT | ES +ve |
|---|---|---|---|---|
| Example 31 (S)-N-((S)-1-(1-(5-(4-(3-((6-(Tert-butylsulfonyl)-4-((4,5-dimethyl-1H-pyrazol-3-yl)amino)quinazolin-7-yl)oxy)propyl)piperazin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propanamide | 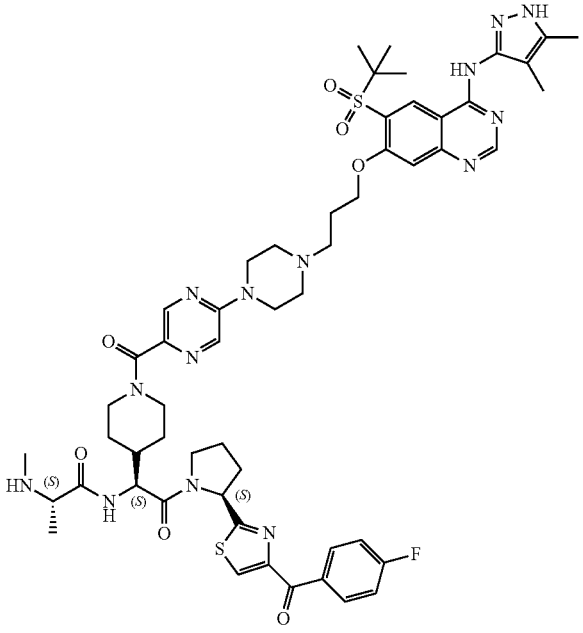 | 55% | Method B 1.03 min | 1107 |
| Example 32 (S)-N-((S)-1-(1-(2-(4-(3-((6-(Tert-butylsulfonyl)-4-((4,5-dimethyl-1H-pyrazol-3-yl)amino)quinazolin-7-yl)oxy)propyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propanamide | 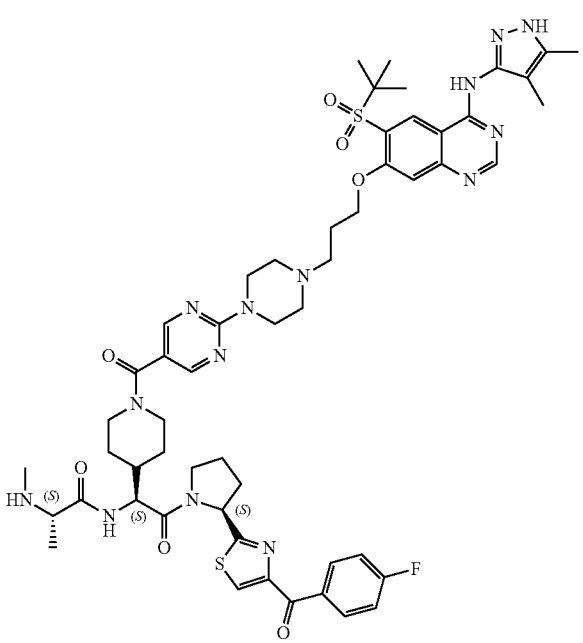 | 60% | Method B 1.04 min | 1107 |

Example 33

(S)—N—((S)-1-(1-(6-(4-(3-((6-(tert-butylsulfonyl)-4-((4,5-dimethyl-1H-pyrazol-3-yl)amino)quinazolin-7-yl)oxy)propy)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, 3 Hydrochloride

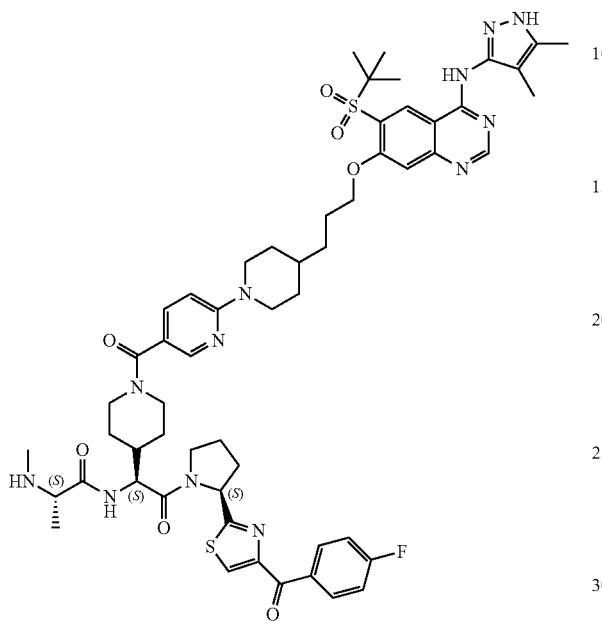

HATU (25 mg, 0.07 mmol) was added to a mixture of (9H-fluoren-9-yl)methyl ((S)-1-(((S)-2-((S)-2-(4-(4-fluorobenzoyl)thiazol-2-yl)pyrrolidin-1-yl)-2-oxo-1-(piperidin-4-Yl)ethyl)amino)-1-oxopropan-2-yl)(methyl)carbamate (40 mg, 0.06 mmol), 6-(4-(3-((6-(tert-butylsulfonyl)-4-((4,5-dimethyl-1H-pyrazol-3-yl)amino)quinazolin-7-yl)oxy)propyl)piperidin-1-yl)nicotinic acid, 3Hydrochloride (57 mg, 0.078 mmol) and DIPEA (0.06 mL, 0.33 mmol) in DMF (0.8 mL). The reaction was stirred at ambient temperature for 30 min. Piperidine (0.2 mL, 2.02 mmol) was then added, and the mixture was stirred for 1 h. The product was subjected directly to purification by mass-directed automated preparative HPLC (ammonium bicarbonate modifier) to give the free base of the desired product. The product was dissolved in THF (0.5 mL), and 4 M HCl in dioxane (0.11 mL, 0.44 mmol) was added. After stirring at ambient temperature for 10 min, excess acid and solvent was removed under reduced pressure to afford the title compound (27 mg, 0.02 mmol, 40% yield). LCMS Method B RT=1.14 min, ES+ve 1105.

Example 34

(S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperazin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, 3 Hydrochloride

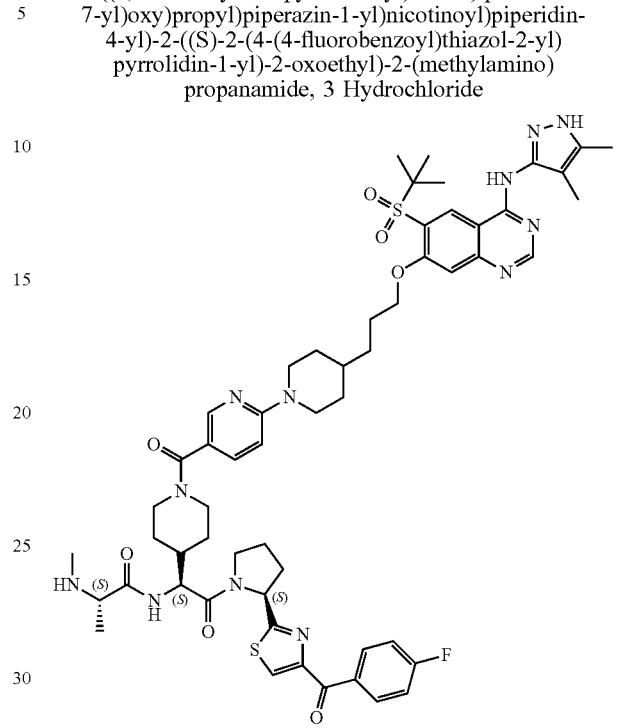

Using a method analogous to that for (S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, 3 Hydrochloride, the title compound (28 mg, 0.02 mmol, 42% yield) was prepared. LCMS Method B RT=1.03 min, ES+ve 1106.

Example 35

2-((2R,5R)-2-(((R)-4-(2-(4-(2-((6-(tert-butylsulfonyl)-4-((5-fluoro-1H-indazol-3-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 Trifluoroacetic Acid

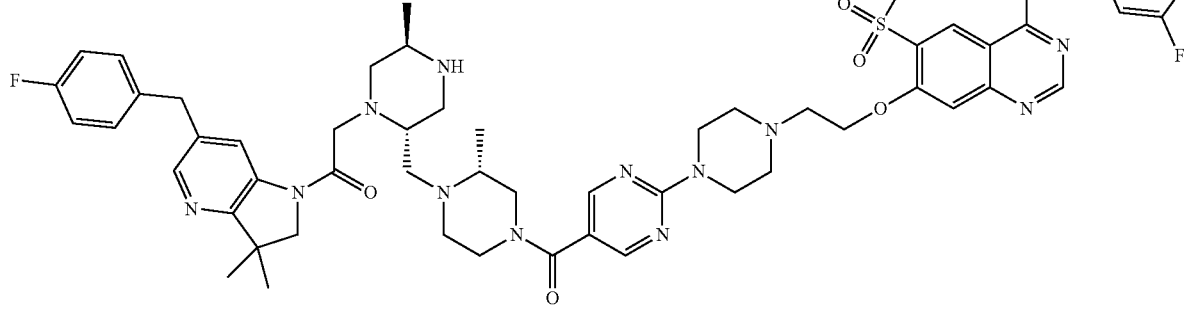

To a solution of (2R,5S)-tert-butyl 5-(((R)-4-(2-(4-(2-((6-(tert-butylsulfonyl)-4-((5-fluoro-1H-indazol-3-yl)amino)quinolin-7-yl)oxy)ethyl)piperazin-1-yl)pyrimidine-5-carbonyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate, 3Trifluoroacetic acid salt (120 mg, 0.08 mmol) in Dichloromethane (DCM) (0.5 mL) was added trifluoroacetic acid (0.585 mL, 7.6 mmol) and the reaction was stirred under an atmosphere of nitrogen. The volatiles were removed under vacuum, the residue was redissolved in DMSO and and the crude reaction was subjected to purification by mass-directed automated preparative HPLC (trifluoroacetic acid modifier). The desired fractions were combined and concentrated to afford the title compound (32 mg, 0.03 mmol, 37% yield). LCMS Method B RT=1.23 min, ES+ve 1140.

Using a method analogous to that above, the following compounds were prepared:

| Compound Name | Structure | Yield | LCMS Method | RT | ES +ve |
|---|---|---|---|---|---|
| Example 36 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 3 trifluoroacetic acid | 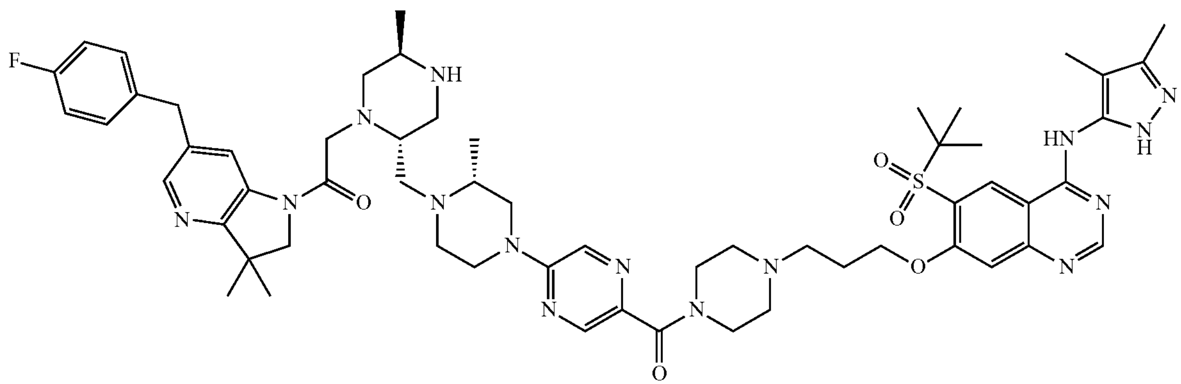 | 57% | Method B | 1.13 min | 1114 |
| Example 37 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyridin-2-yl)-2-methylpiperazin-1-yl)methyl)-5-methylpiperazin-1-yl)-1-(6-(4- | 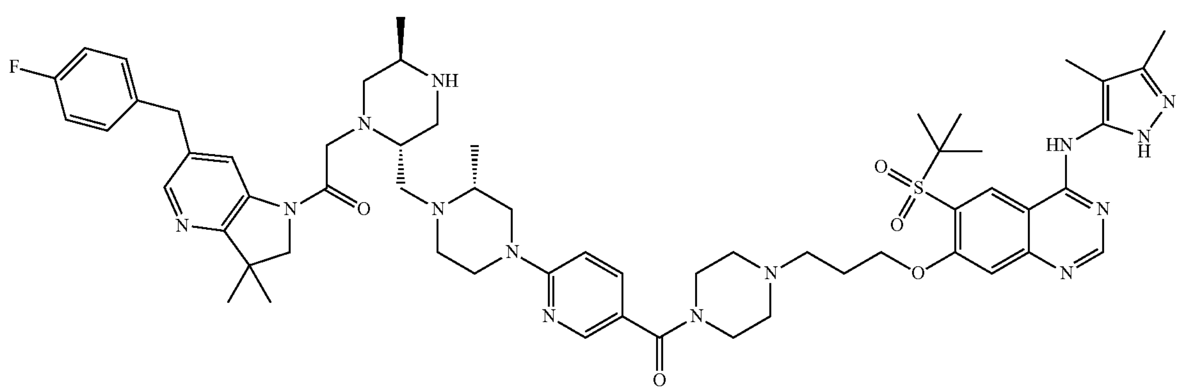 [SMILES: Cc1n[nH]c(Nc2ncnc3cc(OCCCN4CCN(C(=O)c5ccc(N6CCN(C[C@H]7CN[C@H](C)CN7CC(=O)N7CC(C)(C)c8ncc(Cc9ccc(F)cc9)cc87)[C@H](C)C6)nc5)CC4)c(S(=O)(=O)C(C)(C)C)cc23)c1C] | 42% | Method B | 1.12 min | 1113 |

-continued

| Compound Name | Structure | Yield | LCMS RT | ES +ve |
|---|---|---|---|---|
| Example 38 1-(1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-3,3-dimethyl-2,3-dihydro-1H-pyrrolo[3,2-b]pyridin-6-yl)butan-1-one, 3 trifluoroacetic acid | 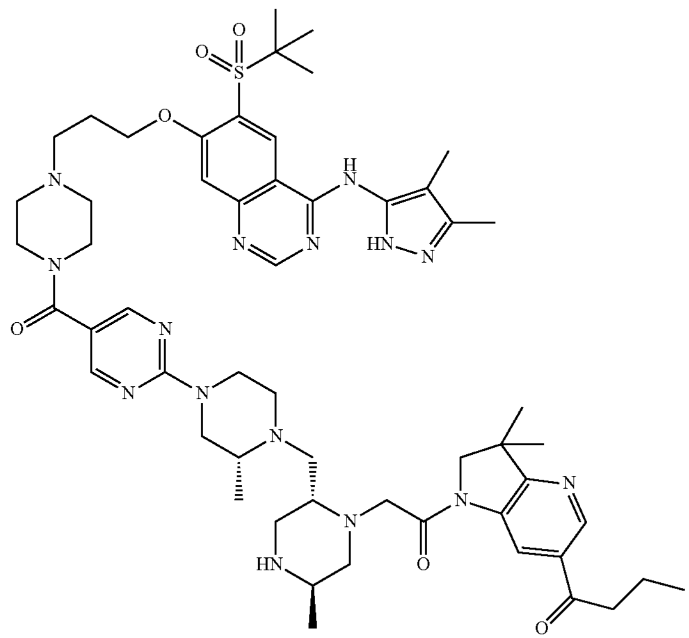 [SMILES: CCCC(=O)c1cnc2c(c1)N(C(=O)CN1C[C@@H](C)NC[C@@H]1CN1CCN(c3ncc(C(=O)N4CCN(CCCOc5cc6ncnc(Nc7[nH]nc(C)c7C)c6cc5S(=O)(=O)C(C)(C)C)CC4)cn3)C[C@H]1C)CC2(C)C] | 35% | Method B 1.08 min | 1076 |

(compound name continued from previous page: fluorobenzyl)-3,3-dimethyl-2,3-dihydro-1H-pyrrolo[3,2-b]pyridin-1-yl)ethanone, 3 trifluoroacetic acid)

-continued

| Compound Name | Structure | Yield | LCMS Method | RT | ES +ve |
|---|---|---|---|---|---|
| Example 39 2-((2R,5R)-2-(((R)-4-(3-((6-tert-butylsulfonyl)-4-(((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-((4-fluorophenyl)(hydroxy)methyl)-3,3-dimethyl-2,3-dihydro-1H-pyrrolo[3,2-b]pyridin-1-yl)ethanone, 3 trifluoroacetic acid | | 36% | B | 1.02 min | 1130 |

-continued

| Compound Name | Structure | Yield | LCMS RT Method | ES +ve |
|---|---|---|---|---|
| Example 40 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1-hydroxybutyl)-3,3-dimethyl-2,3-dihydro-1H-pyrrolo[3,2-b]pyridin-1-yl)ethanone, 3 trifluoroacetic acid | 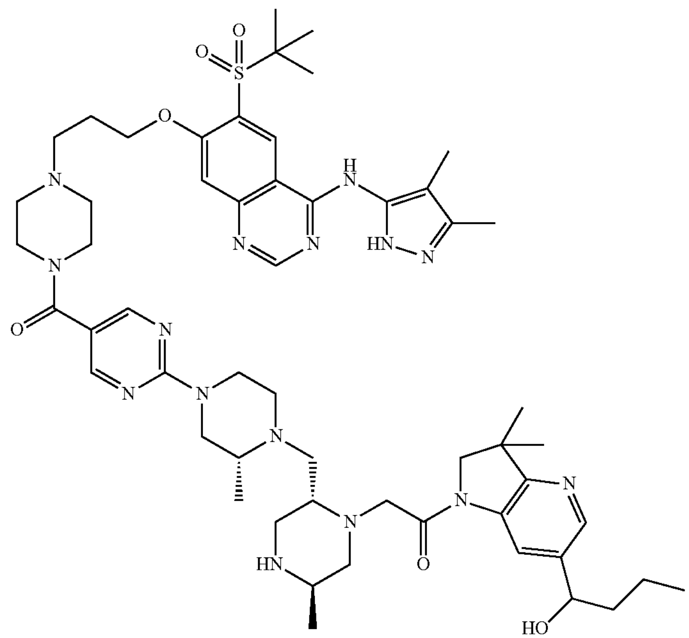 [SMILES: CCCC(O)c1cnc2c(c1)N(C(=O)CN1C[C@@H](C)NC[C@@H]1CN1CCN(c3ncc(C(=O)N4CCN(CCCOc5cc6ncnc(Nc7[nH]nc(C)c7C)c6cc5S(=O)(=O)C(C)(C)C)CC4)cn3)C[C@H]1C)CC2(C)C] | 12% | Method B 0.98 min | 1078 |
| Example 41 1-(2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-6- | 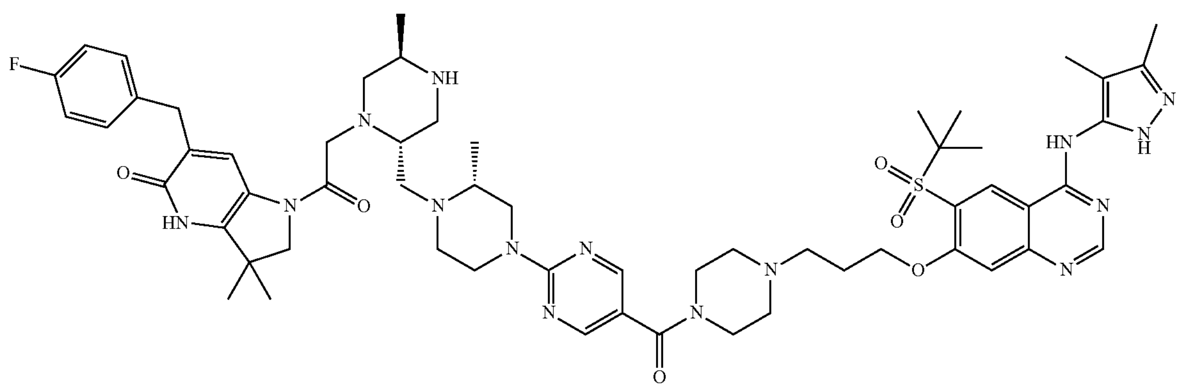 [SMILES: Cc1n[nH]c(Nc2ncnc3cc(OCCCN4CCN(C(=O)c5cnc(N6CCN(C[C@H]7CN[C@H](C)CN7CC(=O)N7CC(C)(C)c8[nH]c(=O)c(Cc9ccc(F)cc9)cc87)[C@H](C)C6)nc5)CC4)c(S(=O)(=O)C(C)(C)C)cc23)c1C] | 67% | Method B 1.01 min | 1130 |

-continued

| Compound Name | Structure | Yield | LCMS RT | ES +ve |
|---|---|---|---|---|
| (4-fluorobenzyl)-3,3-dimethyl-2,3-dihydro-1H-pyrrolo[3,2-b]pyridin-5-(4H)-one, 3 trifluoroacetic acid | | | | |
| Example 42 1-(2-((2R,5R)-2-(((2R,5R)-2-(((2-(4-(3-((6-(Tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methyl-morpholino)methyl)-5-methylpiperazin-1-yl)acetyl)-6-(4-fluorobenzyl)-3,3-dimethyl-2,3-dihydro-1H-pyrrolo[3,2-b]pyridin-5-(4H)-one, 3 Trifluoroacetic acid | | 24% | Method D 1.21 min | 1133 |

-continued

| Compound Name | Structure | Yield | LCMS Method | RT | ES +ve |
|---|---|---|---|---|---|
| Example 43 1-(2-((2R,5R)-2-(((2R,5R)-2-(((2-(4-(3-((6-(tert-butylsulfonyl)-4-(((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one. 3 Trifluoroacetic acid | | 12% | Method D | 1.26 min | 1147 |
| Example 44 2-((2R,5R)-2-(((2R,5R)-2-(((2-(4-(3-((6-(tert-butylsulfonyl)-4-(((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)-1-(6-(4-fluorobenzyl)-3,3-dimethyl-2,3-dihydro-1H- | | 22% | Method D | 1.25 min | 1116.9 |

| Compound Name | Structure | Yield | LCMS RT | ES +ve |
|---|---|---|---|---|
| Example 45 1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3-dimethyl-2,3-dihydro-1H-pyrrolo[3,2-b]pyridin-5(4H)-one. 3 Trifluoroacetic acid | 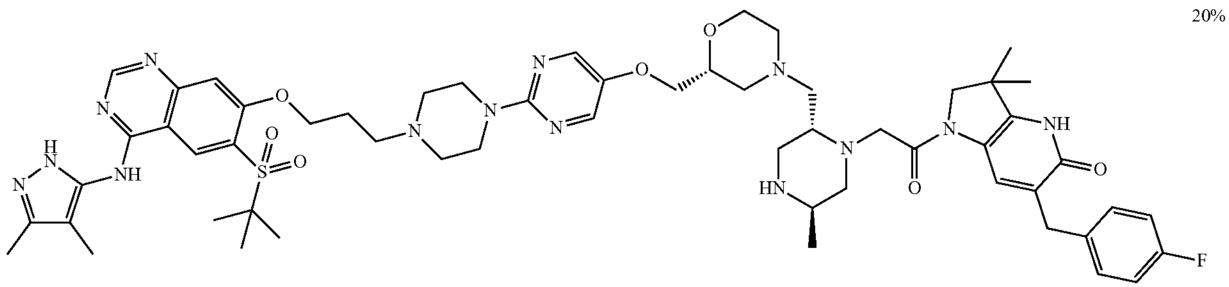 | 20% | Method D 1.25 min | 1119 |
| Example 46 1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin- | 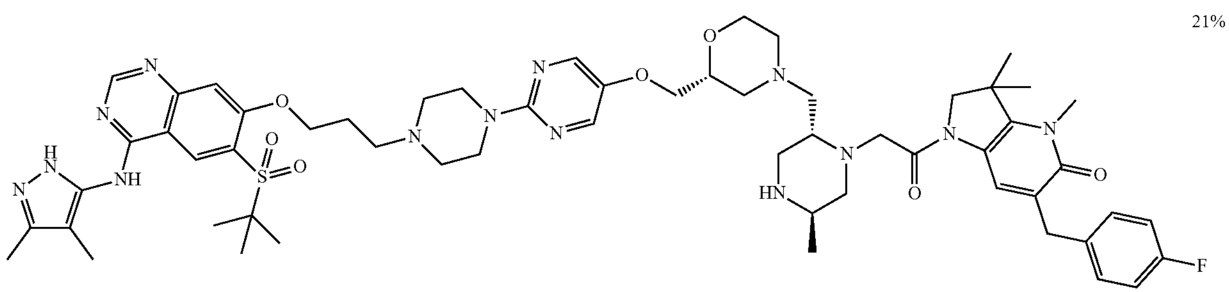 | 21% | Method D 1.33 min | 1133 |

-continued

| Compound Name | Structure | Yield | LCMS RT | Method | ES +ve |
|---|---|---|---|---|---|
| 1-yl)acetyl)-6-(4-fluorobenzyl)-3,3,4-trimethyl-2,3-dihydro-1H-pyrrolo[3,2-b]pyridin-5(4H)-one. 3 Trifluoroacetic acid | | | | | |
| Example 47 1-(2-((2R,5R)-2-(((R)-2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one. 3 Trifluoroacetic acid | | 9% | 1.18 min | D | 1144 |

-continued

| Compound Name | Structure | Yield | LCMS RT Method | ES +ve |
|---|---|---|---|---|
| Example 48 1-(2-((2R,5R)-2-(((R)-4-(5-(4-(3-(((6-(tert-butylsulfonyl)-4-((3,4-dimethyl-1H-pyrazol-5-yl)amino)quinazolin-7-yl)oxy)propyl)piperaizne-1-carbonyl)pyrazin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one. 3 Trifluoroacetic acid | | 10% | D 1.18 min | 1144 |

Example 49

2-(4-(3-((6-(Tert-butylsulfonyl)-4-((3,4-dimethyl-1H-pyrazol-5-yl)amino)quinazolin-7-yl)oxy)propyl)piperazin-1-yl)-1-((R)-4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)ethanone

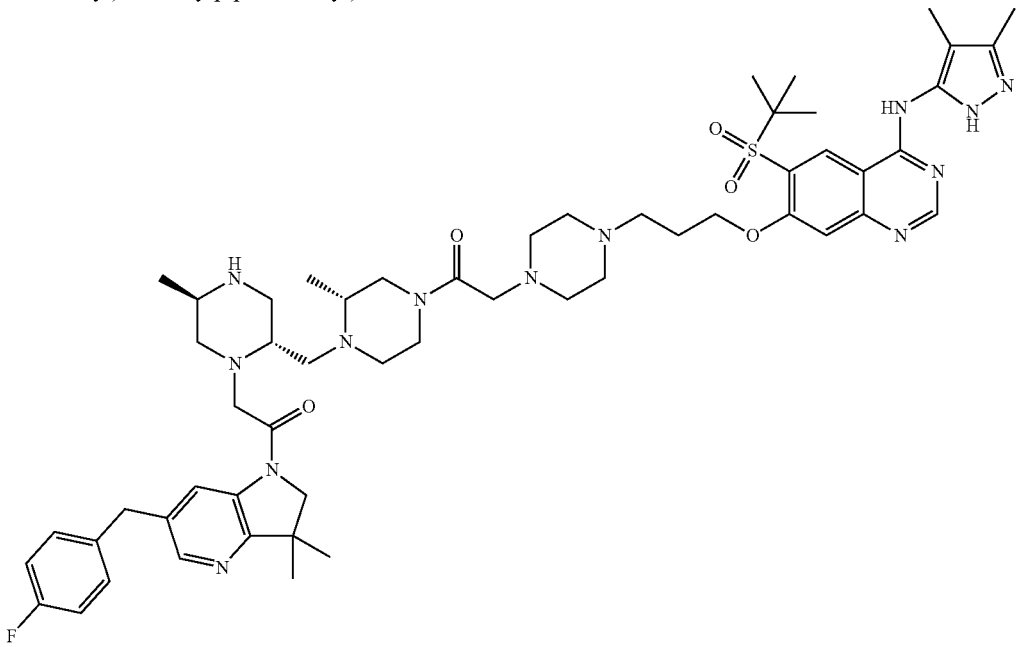

To a solution of (2R,5S)-tert-butyl 5-(((R)-4-(2-(4-(3-((6-(tert-butylsulfonyl)-4-((3,4-dimethyl-1H-pyrazol-5-yl)amino)quinazolin-7-yl)oxy)propyl)piperazin-1-yl)acetyl)-2-methylpiperazin-1-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (117 mg, 0.10 mmol) in methanol (0.5 mL) was added HCl (0.508 mL, 2.03 mmol, 4.0M in dioxane) and the reaction was stirred at room temperature for 1 hour. The volatiles were removed under vacuum, and the product was redissolved in methanol (2 mL) and passed through a 10 g aminopropyl column to elute free base. The column was washed with 50 mL methanol, and the volatiles were removed under vacuum to afford the title compound (52 mg, 0.05 mmol, 49% yield). LCMS Method B RT=1.09 min, ES+ve 1050.

Using a method analogous to that above, the following compounds were prepared:

| Compound Name | Structure | Yield | LCMS RT | ES+ve |
|---|---|---|---|---|
| Example 50<br>1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one | | 87% | Method B 1.06 min | 1144 |

| Compound Name | Structure | Yield | LCMS RT | ES +ve |
|---|---|---|---|---|
| Example 51 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-((S)-2-(4-(4-fluorobenzoyl)thiazol-2-yl)pyrrolidin-1-yl)ethanone | 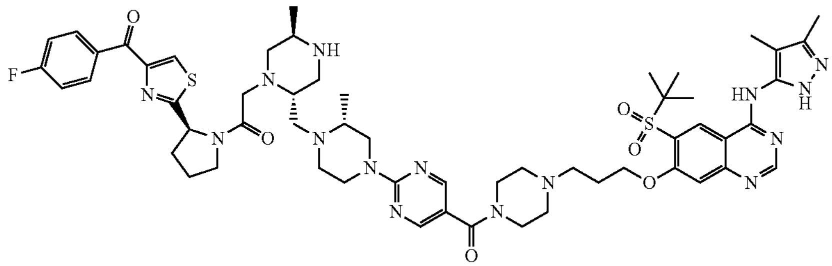 [SMILES: Cc1n[nH]c(Nc2ncnc3cc(OCCCN4CCN(C(=O)c5cnc(N6CCN(C[C@H]7CN[C@H](C)CN7CC(=O)N7CCC[C@H]7c7nc(C(=O)c8ccc(F)cc8)cs7)[C@H](C)C6)nc5)CC4)c(S(=O)(=O)C(C)(C)C)cc23)c1C] | 34% | Method B 1.09 min | 1134 |
| Example 52 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1,1-difluorobutyl)-3,3-dimethyl-2,3-dihydro-1H-pyrrolo[3,2-b]pyridin-1-yl)ethanone | 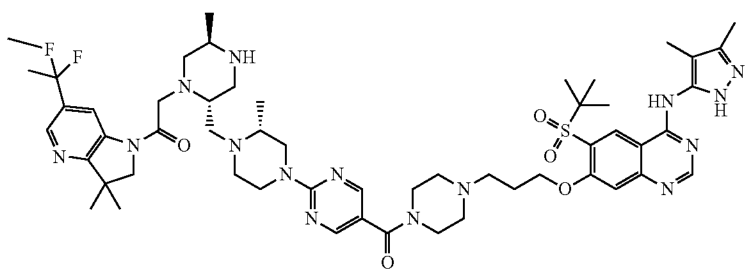 | 38% | Method B 1.18 min | 1098 |

Example 53

6-(4-(3-((6-(tert-butylsulfonyl)-4-((3,4-dimethyl-1H-pyrazol-5-yl)amino)quinazolin-7-yl)oxy)propyl)piperazine-1-carbonyl)-2-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)ethyl)isoindolin-1-one, 2 Hydrochloride

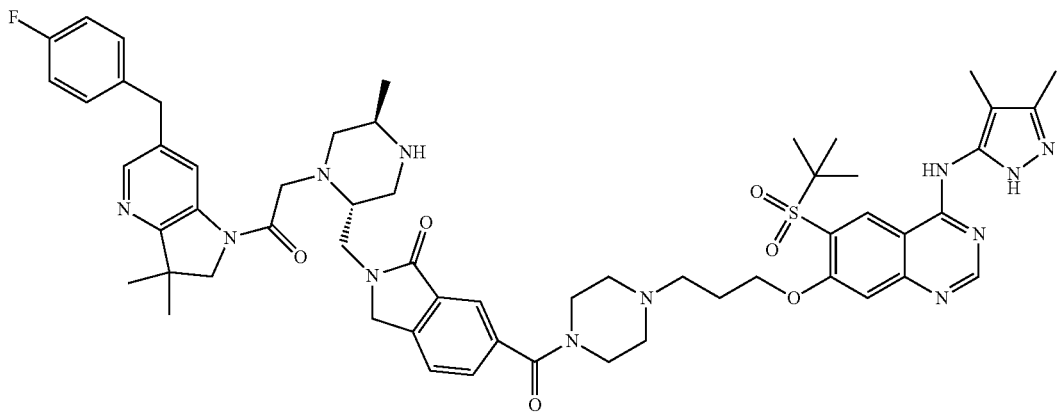 [SMILES: Cc1n[nH]c(Nc2ncnc3cc(OCCCN4CCN(C(=O)c5ccc6c(c5)C(=O)N(C[C@H]5CN[C@H](C)CN5CC(=O)N5CC(C)(C)c7ncc(Cc8ccc(F)cc8)cc75)C6)CC4)c(S(=O)(=O)C(C)(C)C)cc23)c1C]

To a solution of (2R,5S)-tert-butyl 5-((6-(4-(3-((6-(tert-butylsulfonyl)-4-((3,4-dimethyl-1H-pyrazol-5-yl)amino)quinazolin-7-yl)oxy)propyl)piperazine-1-carbonyl)-1-oxoisoindolin-2-yl)methyl)-4-(2-(6-(4-fluorobenzyl)-3,3-dimethyl-2,3-dihydro-1H-pyrrolo[3,2-b]pyridin-1-yl)-2-oxoethyl)-2-methylpiperazine-1-carboxylate (10 mg, 0.01 μmol) in Methanol (0.5 mL) was added hydrochloric acid (0.043 mL, 0.17 mmol) 4M in dioxane and the reaction was stirred at room temperature for 1 hour. The volatiles were removed under vacuum to afford the title compound (9 mg, 0.01 mmol, 87% yield). LCMS Method B RT=1.02 min, ES+ve 1069.

Using a method analogous to that above, the following compounds were prepared:

| Compound Name | Structure | Yield | LCMS Method | RT | ES + ve |
|---|---|---|---|---|---|
| Example 54 1-(2-((2R,5R)-2-(((R)-4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-2-methyl-3-oxo-piperazin-1-yl)methyl)-5-methyl-piperazin-1-yl)acetyl)-6-(4-fluorobenzyl)-3,3,4-trimethyl-2,3-dihydro-1H-pyrrolo[3,2-b]pyridin-5(4H)-one, 2 hydrochloride | | 61% | Method D | 1.12 min | 1174 |
| Example 55 (R)-1-(2-((2R,5R)-2-(((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-2-one, 2 hydrochloride | | 70% | Method D | 1.20 min | 1144 |

Example 56

1-(2-((2R, 5R)-2-(((R)-4-(2-(2-(4-(3-(6-(tert-butyl-sulfonyl)-4-(4, 5-dimethyl-1H-pyrazol-3-ylamino)quinazolin-7-yloxy)propyl)piperazin-1-yl)pyrimidin-5-yloxy)ethyl)-2-methyl-3-oxopiperazin-1-yl)methyl)-5-methyl piperazin-1-yl)acetyl)-6-(4-fluorobenzyl)-3,3-dimethyl-2,3-dihydro-1H-pyrrolo[3,2-b] pyridin-5(4H)-one, 3 Trifluoroacetatic Acid

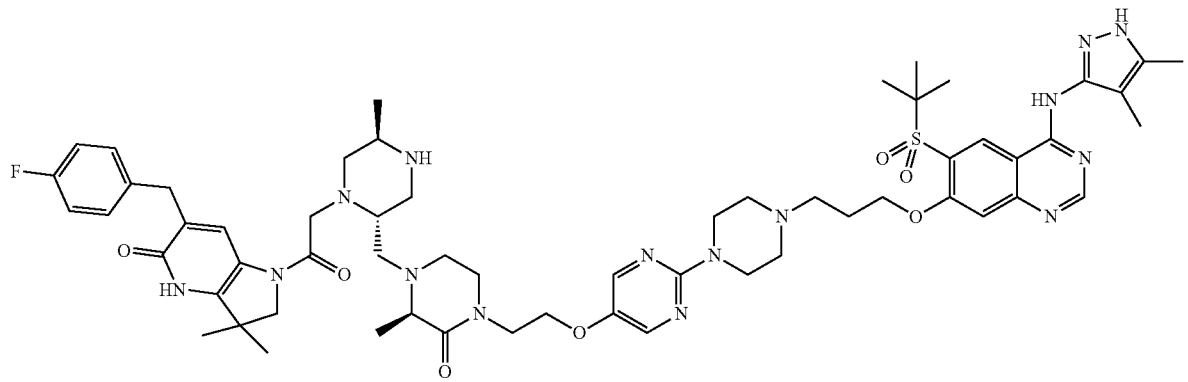 [SMILES: Cc1[nH]nc(Nc2ncnc3cc(OCCCN4CCN(c5ncc(OCCN6CCN(C[C@H]7CN[C@H](C)CN7CC(=O)N7CC(C)(C)c8[nH]c(=O)c(Cc9ccc(F)cc9)cc87)[C@H](C)C6=O)cn5)CC4)c(S(=O)(=O)C(C)(C)C)cc23)c1C]

To a stirred solution of (2R, 5S)-tert-butyl 4-(2-(5-(ben-zyloxy)-6-(4-fluorobenzyl)-3, 3-dimethyl-2, 3-dihydropyrrolo [3,2-b] pyridin-1-yl)-2-oxoethyl)-5-(((R)-4-(2-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yloxy)ethyl)-2-methyl-3-oxopiperazin-1-yl)methyl)-2-methylpiperazine-1-carboxylate (35 mg, 0.026 mmol) in Dichloromethane (DCM) (4 mL) at 0° C. was added trifluoroacetic acid (2 mL) slowly. The reaction mixture was warmed to room temperature, and was stirred for 3 hours. The solvent was removed under vacuum, and the residue was purified by prep-HPLC (Method B, Gradient: 20-25%) to give the title compound (23 mg, 0.015 mmol, 77% yield) as yellow solid. LCMS Method E RT: 1.19 min, ES+ve=1160.8.

Using a method analogous to that above, the following compounds were prepared:

| Compound Name | Structure | Yield | LCMS RT | ES+ve |
|---|---|---|---|---|
| Example 57 1-(2-((2R,5R)-2-(((R)-4-(5-(4-(3-(6-(tert-butylsulfonyl)-4-(4,5-dimethyl-1H-pyrazol-3-ylamino)quinazolin-7-yloxy)propyl)piperazine-1-carbonyl)pyrazin-2-yl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b]pyridin-5(4H)-one, 3 trifluoroacetic acid | 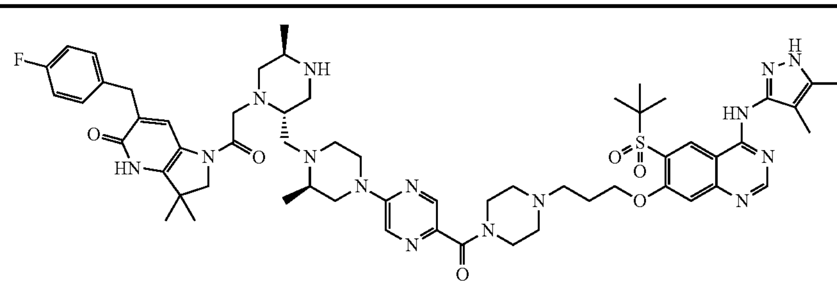 | 22% | Method D 1.20 min | 1130 |

| Compound Name | Structure | Yield | LCMS RT | ES +ve |
|---|---|---|---|---|
| Example 58 1-(2-((2R,5R)-2-(((R)-4-(5-(4-(3-(6-(tert-butylsulfonyl)-4-(4,5-dimethyl-1H-pyrazol-3-ylamino)quinazolin-7-yloxy)propyl)piperazin-1-yl)pyrazine-2-carbonyl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b]pyridin-5(4H)-one, 3 trifluoroacetic acid | 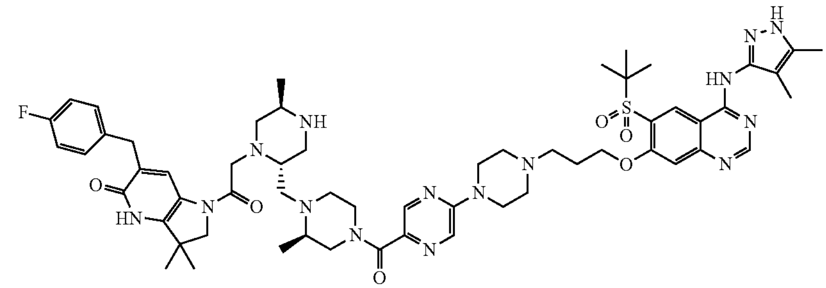 [SMILES: Cc1[nH]nc(Nc2ncnc3cc(OCCCN4CCN(c5cnc(C(=O)N6CCN(C[C@H]7CN[C@H](C)CN7CC(=O)N7CC(C)(C)c8[nH]c(=O)c(Cc9ccc(F)cc9)cc87)[C@H](C)C6)cn5)CC4)c(S(=O)(=O)C(C)(C)C)cc23)c1C] | 13% | Method D 1.17 min | 1130 |
| Example 59 1-(2-((2R,5R)-2-(((R)-4-(2-(4-(3-(6-(tert-butylsulfonyl)-4-(4,5-dimethyl-1H-pyraozl-3-ylamino)quinazolin-7-yloxy)propyl)piperazin-1-yl)pyrimidine-5-carbonyl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 3 trifluoroacetic acid | 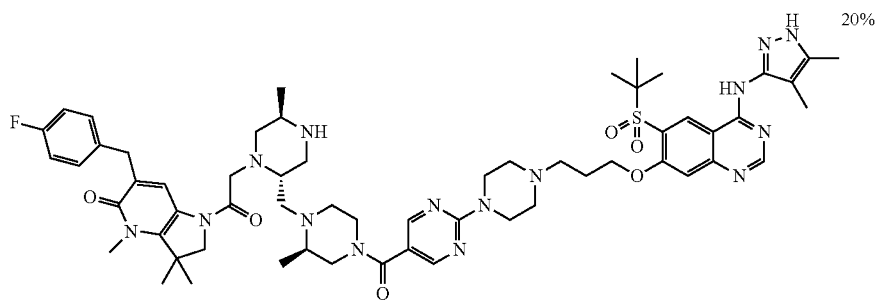 | 20% | Method D 1.20 min | 1144 |

Western Blot Quantification of RIP2 Levels in THP1 Cells

Compounds were tested in THP1 cells (acute myeloid leukaemia—BioCat 106491) and the effect on RIP2 protein levels were assessed by Western blotting. For each sample $7.5 \times 10^6$ cells were resuspended in media containing the indicated concentrations of PROTAC and incubated 37° C. and 5% $CO_2$ overnight. The following day, cells were harvested, and the total amount of protein was quantified using the Pierce™ BCA Protein Assay kit (Thermo Scientific, 23227). 25 μg of total protein were separated on a polyacrylamide Bis-Tris gel at constant voltage and further transferred onto PVDF membranes (Millipore, IPFL00010). Membranes were blocked against non-specific binding with Odyssey blocking buffer (Licor, 927-40000) for 1 hour at room temperature, then incubated with the primary antibodies rabbit anti-RIPK2 (Cell Signaling, 4142) overnight at 4° C. Next day the mouse anti-actin (Sigma, A2228) at a 1:20 000 dilution was added and the membranes were further incubated for 2 hours at room temperature. Membranes were washed 3 times with PBS +0.1% Tween 20 then incubated with donkey anti-mouse 800CW (Licor, 926-32212) and donkey anti-mouse IRdye 680RD (Licor, 926-68072) diluted 1:5 000 in Odyssey blocking buffer+0.1% Tween 20+0.01% SDS, 1 hour at room temperature, followed by washing in PBS +0.1% Tween 20. The infrared signal was detected using an Odyssey scanner (Licor Biosciences) and densitometry was performed using the Odyssey 2.1 Analyser software (Licor Biosciences).

RIPK2 degradation was expressed relative to the DMSO only treated sample. Compounds displayed >80% degradation of RIP2 at concentrations<1 uM.

What is claimed is:

1. A compound of formula (I):

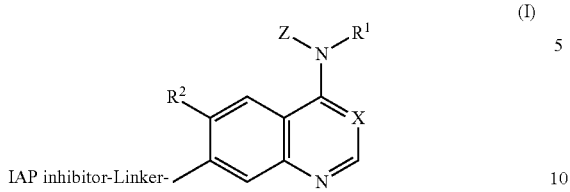

wherein

X represents N or CH;

L is a straight chain alkylene group of 4-20 carbon atoms wherein one or more carbon atoms are replaced by a group each independently selected from —O—, —NH—, —N(CH$_3$)—, —CO—, piperidine, piperazine, pyrimidine, pyridine and phenyl;

$R^1$ is H, —SO$_2$(C$_1$-C$_4$)alkyl, —CO(C$_1$-C$_4$)alkyl, or (C$_1$-C$_4$)alkyl;

$R^2$ is —SR$^a$, —SOR$^a$, —SO$_2$R$^a$, —SO$_2$NH$_2$, or —SO$_2$NR$^b$R$^c$, wherein R$^a$ is (C$_1$-C$_6$)alkyl, halo(C$_1$-C$_6$)alkyl, (C$_3$-C$_7$)cycloalkyl, 4-7 membered heterocycloalkyl, aryl, or heteroaryl, wherein:

said (C$_1$-C$_6$)alkyl is optionally substituted by one or two groups each independently selected from the group consisting of cyano, hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, —SO$_2$(C$_1$-C$_4$)alkyl, (C$_3$-C$_7$)cycloalkyl, phenyl, 5-6 membered heteroaryl, 9-10 membered heteroaryl, 4-7 membered heterocycloalkyl and (phenyl)(C$_1$-C$_4$ alkyl)amino-, wherein said (C$_3$-C$_7$)cycloalkyl, phenyl, (phenyl)(C$_1$-C$_4$ alkyl)amino-, 5-6 membered heteroaryl, 9-10 membered heteroaryl or 4-7 membered heterocycloalkyl is optionally substituted by 1-3 groups each independently selected from the group consisting of halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl (C$_1$-C$_4$)alkyl-, hydroxy(C$_1$-C$_4$)alkyl and (C$_1$-C$_4$)alkoxy, said (C$_3$-C$_7$)cycloalkyl or 4-7 membered heterocycloalkyl is optionally substituted by 1-3 groups each independently selected from the group consisting of halogen, —CF$_3$, hydroxyl, amino, ((C$_1$-C$_4$)alkyl) amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl-, oxo and (C$_1$-C$_4$)alkoxy, and said aryl or heteroaryl is optionally substituted by 1-3 groups each independently selected from the group consisting of halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl- and (C$_1$-C$_4$)alkoxy;

R$^b$ is (C$_1$-C$_6$)alkyl or 4-7 membered heterocycloalkyl, wherein:

said (C$_1$-C$_6$)alkyl is optionally substituted by one or two groups each independently selected from the group consisting of hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, (C$_1$-C$_4$ alkyl)amino-, (C$_1$-C$_4$ alkyl)(C$_1$-C$_4$ alkyl)amino-, 5-6 membered heteroaryl, and 4-7 membered heterocycloalkyl, wherein said 5-6 membered heteroaryl or 4-7 membered heterocycloalkyl is optionally substituted by 1-3 groups each independently selected from the group consisting of halogen, (C$_1$-C$_4$)alkyl, hydroxy(C$_1$-C$_4$)alkyl and (C$_1$-C$_4$)alkoxy, said 4-7 membered heterocycloalkyl is optionally substituted by 1-3 groups each independently selected from the group consisting of hydroxyl, amino, (C$_1$-C$_4$)alkyl, (C$_1$-C$_4$)alkoxycarbonyl-, hydroxy(C$_1$-C$_4$)alkyl-, oxo and (C$_1$-C$_4$)alkoxy, and R$^c$ is H, (C$_1$-C$_4$)alkoxy or (C$_1$-C$_6$)alkyl;

or R$^b$ and R$^c$ taken together with the nitrogen atom to which they are attached form a 3-7 membered heterocycloalkyl group, optionally containing one or two additional ring heteroatoms each independently selected from nitrogen and oxygen, wherein said 3-7 membered heterocycloalkyl is optionally substituted by 1-3 groups each independently selected from the group consisting of (C$_1$-C$_4$)alkyl, hydroxy, —CO$_2$H and —CO(C$_1$-C$_4$)alkyl;

Z is phenyl or aryl(C$_1$-C$_4$)alkyl-, wherein in the phenyl group or the aryl moiety of the aryl(C$_1$-C$_4$)alkyl- group is substituted by R$^4$, R$^5$, R$^6$ and R$^7$, wherein:

R$^4$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, wherein the phenyl moiety of said phenoxy or phenyl(C$_1$-C$_4$)alkoxy- is optionally substituted by 1-3 substituents each independently selected from the group consisting of halogen, —CF$_3$, (C$_1$-C$_4$)alkyl and (C$_1$-C$_4$)alkoxy; and each of R$^5$, R$^6$ and R$^7$ is independently selected from the group consisting of H, hydroxyl, halogen, —CF$_3$, hydroxy(C$_1$-C$_4$)alkyl, (C$_1$-C$_4$)alkyl and (C$_1$-C$_4$) alkoxy; or Z is phenyl or pyridyl, substituted by R$^8$, R$^9$ and R$^{10}$, wherein:

R$^8$ and R$^9$ are located on adjacent atoms and taken together with the atoms to which they are attached form a 5-membered ring containing 1, 2 or 3 heteroatoms each independently selected from N, O and S, which 5-membered ring is substituted by R$^{11}$;

wherein one of R$^{10}$ or R$^{11}$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, where the phenyl moiety of said phenoxy or phenyl(C$_1$-C$_4$)alkoxy is optionally substituted by 1-3 substituents each independently selected from the group consisting of halogen, —CF$_3$, (C$_1$-C$_4$)alkyl and (C$_1$-C$_4$)alkoxy; and the other of R$^{10}$ or R$^{11}$ is H, hydroxyl, halogen, —CF$_3$, hydroxy(C$_1$-C$_4$)alkyl, (C$_1$-C$_4$)alkyl or (C$_1$-C$_4$)alkoxy; or

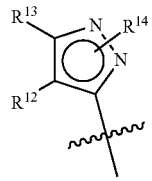

Z is pyrazolyl, having the formula: wherein:

R$^{12}$ is H, methyl or hydroxymethyl;

R$^{13}$ is methyl, trifluoromethyl or hydroxymethyl;

R$^{14}$ is H, OH, or (C$_1$-C$_3$)alkyl; or

R$^{12}$ and R$^{13}$, taken together with the atoms to which they are attached, form a 6-membered ring substituted by R$^{15}$ and R$^{16}$, wherein the 6-membered ring optionally contains 1 nitrogen atom;

wherein R$^{15}$ and R$^{16}$ are each independently selected from the group consisting of H, halogen, cyano, ($C_1$-$C_4$)alkyl, halo($C_1$-$C_4$)alkyl, ($C_1$-$C_4$)alkoxy, phenoxy, phenyl($C_1$-$C_4$)alkoxy, hydroxyl, hydroxy($C_1$-$C_4$)alkyl-, and aminocarbonyl, wherein the phenyl moiety of said phenoxy or phenyl($C_1$-$C_4$)alkoxy is optionally substituted by 1-3 substituents each independently selected from the group consisting of halogen, —$CF_3$, ($C_1$-$C_4$)alkyl and ($C_1$-$C_4$)alkoxy;

and the IAP moiety is of formula II, IIA, III, IV V or VA (L in the formulae below denotes the linker)

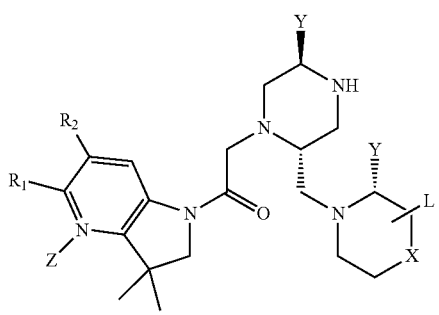

(II)

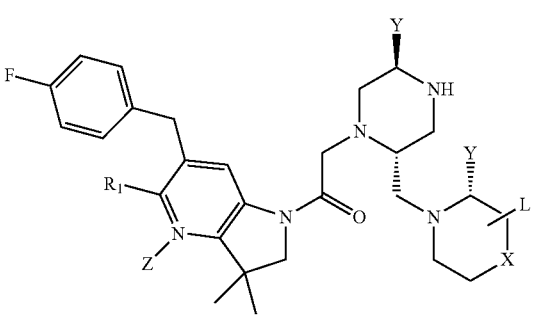

(II)A

Where each Y in Formula (II) and (IIA) is independently H or $C_{1-3}$ alkyl and X is CH, O or N (but cannot be O when attached to the linker), Z represents $C_1$-3 alkyl or is absent, $R^1$ is oxo or is absent, $R_2$ in Formula (II) is $CH(F_2)CH_2CH_2CH_3$, $COCH_2CH_2CH_3$, $CH(OH)CH_2CH_2CH_3$,

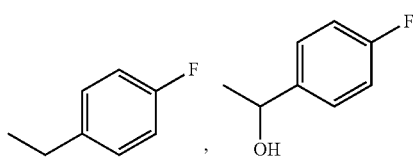

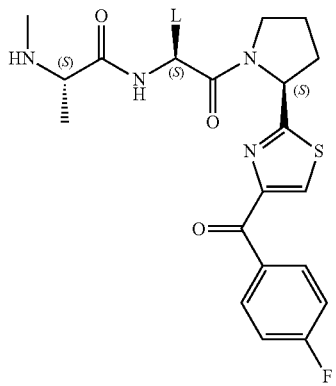

(III)

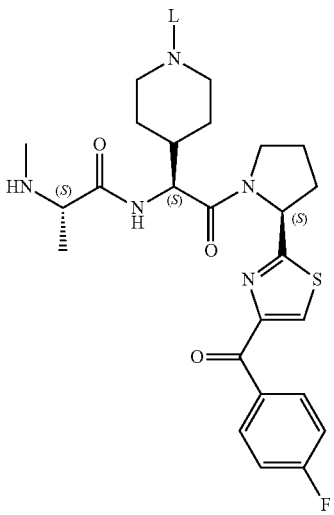

(IV)

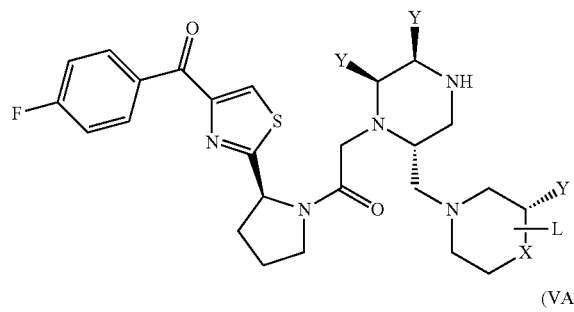

(V)

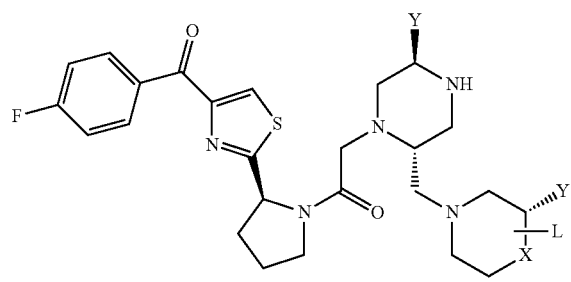

(VA)

Where each Y is independently H or $C_1$-3 alkyl and X is CH, O or N (but cannot be O when attached to the linker), or a pharmaceutically acceptable salt thereof.

2. A compound or a pharmaceutically acceptable salt thereof according to claim 1 wherein the RIP2 kinase inhibitor is

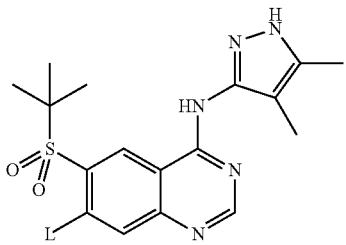

or

-continued

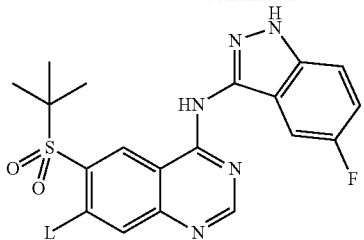

where L denotes the linker.

3. A compound or salt according to claim 1 wherein the linker is 4-20 atoms in shortest length.

4. A compound or salt according to claim 1 wherein the linker is (in the direction RIP2 Kinase inhibitor-IAP inhibitor) selected from the group consisting of:

(OCH$_2$CH$_2$)$_{1-4}$,
(OCH$_2$CH$_2$)$_{1-4}$OCH$_2$CO,

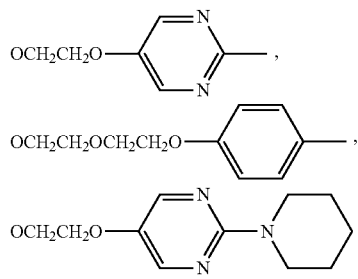

Directly bonded, thus forming a spiro group,

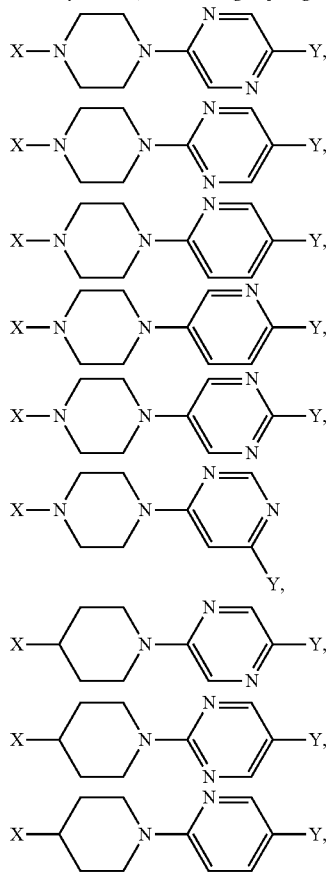

-continued

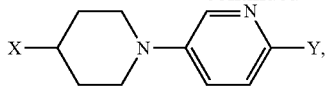

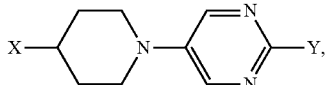

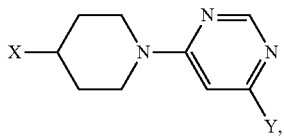

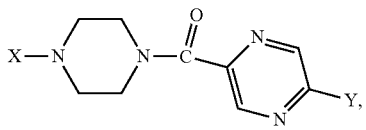

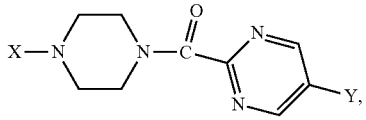

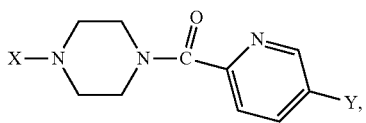

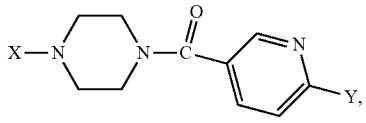

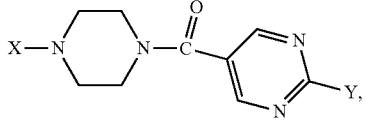

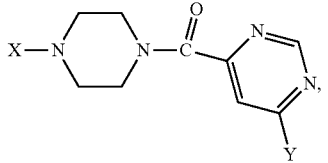

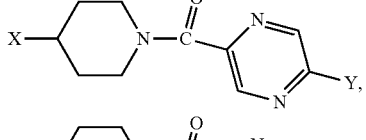

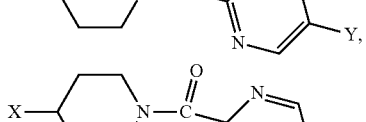

wherein X is —O(CH$_2$CH$_2$)$_{0-4}$, -,
and Y is a bond, -, —O—, O(CH$_2$)$_{1-3}$ or —CO—.
5. A compound or pharmaceutically acceptable salt thereof according to claim 1 wherein the IAP binding moiety is (L denotes the linker) selected from the group consisting of
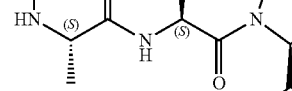

-continued

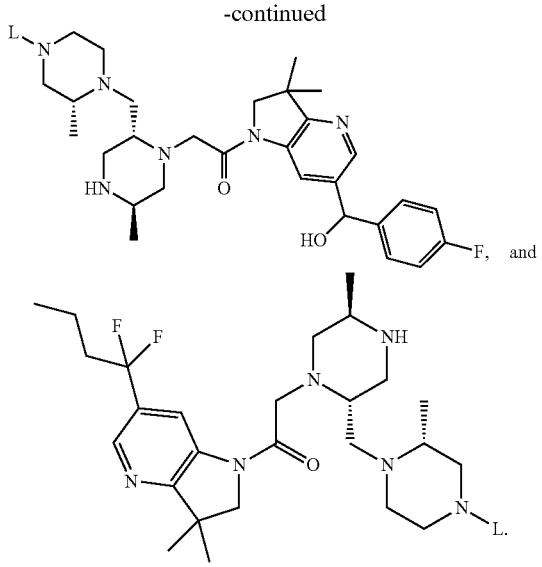

6. A compound according to claim 1 which is selected from the group consisting of
14-((6-(Tert-butylsulfonyl)-4-((3,4-dimethyl-1H-pyrazol-5-yl)amino)quinazolin-7-yl)oxy)-1-(4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)-3,6,9,12-tetraoxatetradecan-1-one,
2-((2R,5R)-2-(((R)-4-(5-(2-((6-(Tert-butylsulfonyl)-4-((3,4-dimethyl-1H-pyrazol-5-yl)amino)quinazolin-7-yl)oxy)ethoxy)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(((6-(Tert-butylsulfonyl)-4-((3,4-dimethyl-1H-pyrazol-5-yl)amino)quinazolin-7-yl)oxy)methyl)piperidin-1-yl)pyrimidin-4-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((9-(5-(2-((6-(Tert-butylsulfonyl)-4-((3,4-dimethyl-1H-pyrazol-5-yl)amino)quinazolin-7-yl)oxy)ethoxy)pyrimidin-2-yl)-3,9-diazaspiro[5.5]undecan-3-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((4-((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidin-1-yl)methyl)-5-methylpiperazin-1-yl)-1-((S)-2-(4-(4-fluorobenzoyl)thiazol-2-yl)pyrrolidin-1-yl)ethanone,
2-((2R,5R)-2-(((R)-4-(2-(2-(2-(2-((6-(tert-butylsulfonyl)-4-((5-fluoro-1H-indazol-3-yl)amino)quinolin-7-yl)oxy)ethoxy)ethoxy)ethoxy)ethyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(3-((6-(tert-butylsulfonyl)-4-((3,4-dimethyl-1H-pyrazol-5-yl)amino)quinazolin-7-yl)oxy)propyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(3-((6-(Tert-butylsulfonyl)-4-((3,4-dimethyl-1H-pyrazol-5-yl)amino)quinazolin-7-yl)oxy)propyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(6-(4-(2-((6-(Tert-butylsulfonyl)-4-((3,4-dimethyl-1H-pyrazol-5-yl)amino)quinazolin-7-yl)oxy)ethyl)piperazin-1-yl)nicotinoyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethenone,
2-((2R,5R)-2-(((R)-2-(((2-(4-(2-((6-(tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-((S)-2-(4-(4-fluorobenzoyl)thiazol-2-yl)pyrrolidin-1-yl)ethanone,
2-((2R,5R)-2-(((R)-2-(((2-(4-(((6-(Tert-butylsulfonyl)-4-((3,4-dimethyl-1H-pyrazol-5-yl)amino)quinazolin-7-yl)oxy)methyl)piperidin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-2-(((2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-((9-(5-(2-((6-(tert-butylsulfonyl)-4-((4,5-dimethyl-1H-pyrazol-3-yl)amino)quinazolin-7-yl)oxy)ethoxy)pyrimidin-2-yl)-3,9-diazaspiro[5.5]undecan-3-yl)methyl)-5-methylpiperazin-1-yl)-1-((S)-2-(4-(4-fluorobenzoyl)thiazol-2-yl)pyrrolidin-1-yl)ethanone,
2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrazine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazin-1-yl)pyrimidine-2-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone,
2-((2R,5R)-2-(((R)-2-(((2-(4-(3-((6-(tert-butylsulfonyl)-4-((3,4-dimethyl-1H-pyrazol-5-yl)amino)quinazolin- 7-yl)oxy)propyl)piperazin-1-yl)pyrimidin-5-yl)oxy)methyl)morpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(2-(4-(2-((6-(Tert-butylsulfonyl)-4-((3,4-dimethyl-1H-pyrazol-5-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(2-(4-(3-((6-(Tert-butylsulfonyl)-4-((3,4-dimethyl-1H-pyrazol-5-yl)amino)quinazolin-7-yl)oxy)propyl)piperidin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, (S)—N—((S)-3-(4-(2-(2-((6-(Tert-butylsulfonyl)-4-((4,5-dimethyl-1H-pyrazol-3-yl)amino)quinazolin-7-yl)oxy)ethoxy)ethoxy)phenyl)-1-((S)-2-(4-(4-fluorobenzoyl)thiazol-2-yl)pyrrolidin-1-yl)-1-oxopropan-2-yl)-2-(methylamino)propanamide, (S)—N—((S)-1-(1-(2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(6-(4-(2-((6-(tert-butylsulfonyl)-4-((4,5-dimethyl-1H-pyrazol-3-yl)amino)quinazolin-7-yl)oxy)ethyl)piperazin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, (S)—N—((S)-1-(1-(6-(4-(2-((6-(tert-butylsulfonyl)-4-((4,5-dimethyl-1H-pyrazol-3-yl)amino)quinazolin-7-yl)oxy)ethyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, (S)—N—((S)-1-(1-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(2-(4-(((6-(tert-butylsulfonyl)-4-((4,5-dimethyl-1H-pyrazol-3-yl)amino)quinazolin-7-yl)oxy)methyl)piperidin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(5-(4-(3-((6-(Tert-butylsulfonyl)-4-((4,5-dimethyl-1H-pyrazol-3-yl)amino)quinazolin-7-yl)oxy)propyl)piperazin-1-yl)pyrazine-2-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(2-(4-(3-((6-(Tert-butylsulfonyl)-4-((4,5-dimethyl-1H-pyrazol-3-yl)amino)quinazolin-7-yl)oxy)propyl)piperazin-1-yl)pyrimidine-5-carbonyl)piperidin-4-yl)-2-((S)-2-(4-(4-fluorobenzoyl)thiazol-2-yl)pyrrolidin-1-yl)-2-oxoethyl)-2-(methylamino)propenamide, (S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperidin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, (S)—N—((S)-1-(1-(6-(4-(3-((6-(tert-butylsulfonyl)-4-((4,5-dimethyl-1H-pyrazol-3-yl)amino)quinazolin-7-yl)oxy)propyl)piperazin-1-yl)nicotinoyl)piperidin-4-yl)-2-((S)-2-(4-(4-fluorobenzoyl)thiazol-2-yl)pyrrolidin-1-yl)-2-oxoethyl)-2-(methylamino)propanamide, 2-((2R,5R)-2-(((R)-4-(2-(4-(2-((6-(tert-butylsulfonyl)-4-((5-fluoro-1H-indazol-3-yl)amino)quinazolin-7-yl)oxy)ethyl)piperazin-1-yl)pyrimidine-5-carbonyl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyridin-2-yl)-2-methylpiperazin-1-yl)methyl)-5-methylpiperazin-1-yl)-1-(6-(4-fluorobenzyl)-3,3-dimethyl-2,3-dihydro-1H-pyrrolo[3,2-b]pyridin-1-yl)ethanone, 1-(1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-3,3-dimethyl-2,3-dihydro-1H-pyrrolo[3,2-b]pyridin-6-yl)butan-1-one, 2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-((4-fluorophenyl)(hydroxy)methyl)-3,3-dimethyl-2,3-dihydro-1H-pyrrolo[3,2-b]pyridin-1-yl)ethanone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1-hydroxybutyl)-3,3-dimethyl-2,3-dihydro-1H-pyrrolo[3,2-b]pyridin-1-yl)ethanone, 1-(2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5- methylpiperazin-1-yl)acetyl)-6-(4-fluorobenzyl)-3,3-dimethyl-2,3-dihydro-1H-pyrrolo[3,2-b]pyridin-5(4H)-one, 1-(2-((2R,5R)-2-(((2R,5R)-2-(((2-(4-(3-((6-(Tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)acetyl)-6-(4-fluorobenzyl)-3,3-dimethyl-2,3-dihydro-1H-pyrrolo[3,2-b]pyridin-5(4H)-one, 1-(2-((2R,5R)-2-(((2R,5R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 2-((2R,5R)-2-(((2R,5R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)-5-methylmorpholino)methyl)-5-methylpiperazin-1-yl)-1-(6-(4-fluorobenzyl)-3,3-dimethyl-2,3-dihydro-1H-pyrrolo[3,2-b]pyridin-1-yl)ethenone, 1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3-dimethyl-2,3-dihydro-1H-pyrrolo[3,2-b]pyridin-5(4H)-one, 1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 1-(2-((2R,5R)-2-(((R)-2-(((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)methyl)morpholino)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrazin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 2-(4-(3-((6-(Tert-butylsulfonyl)-4-((3,4-dimethyl-1H-pyrazol-5-yl)amino)quinazolin-7-yl)oxy)propyl)piperazin-1-yl)-1-((R)-4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-1-yl)ethenone, 1-(2-((2R,5R)-2-(((R)-4-(5-(4-(3-((6-(tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-((S)-2-(4-(4-fluorobenzoyl)thiazol-2-yl)pyrrolidin-1-yl)ethenone, 2-((2R,5R)-2-(((R)-4-(5-(4-(3-((6-(Tert-butylsulfonyl)-4-((3,4-dimethyl-1H-pyrazol-5-yl)amino)quinazolin-7-yl)oxy)propyl)piperazine-1-carbonyl)pyrimidin-2-yl)-2-methylpiperazin-1-yl)methyl)-5-methylpiperazin-1-yl)-1-(6-(1,1-difluorobutyl)-3,3-dimethyl-2,3-dihydro-1H-pyrrolo[3,2-b]pyridin-1-yl)ethenone, 6-(4-(3-((6-(tert-butylsulfonyl)-4-((3,4-dimethyl-1H-pyrazol-5-yl)amino)quinazolin-7-yl)oxy)propyl)piperazine-1-carbonyl)-2-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)isoindolin-1-one, 1-(2-((2R,5R)-2-(((R)-4-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-2-methyl-3-oxopiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, (R)-1-(2-((2-(4-(3-((6-(tert-butylsulfonyl)-4-((3,4-dimethyl-1H-pyrazol-5-yl)amino)quinazolin-7-yl)oxy)propyl)piperazin-1-yl)pyrimidin-5-yl)oxy)ethyl)-4-(((2R,5R)-1-(2-(6-(4-fluorobenzyl)-3,3-dimethyl-2,3-dihydro-1H-pyrrolo[3,2-b]pyridin-1-yl)-2-oxoethyl)-5-methylpiperazin-2-yl)methyl)-3-methylpiperazin-2-one, 1-(2-((2R,5R)-2-(((R)-4-(2-(2-(4-(3-(6-(tert-butylsulfonyl)-4-(4,5-dimethyl-1H-pyrazol-3-ylamino)quinazolin-7-yloxy)propyl)piperazin-1-yl)pyrimidin-5-yloxy)ethyl)-2-methyl-3-oxopiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R,5R)-2-(((R)-4-(5-(4-(3-(6-(tert-butylsulfonyl)-4-(4, 5-dimethyl-1H-pyrazol-3-ylamino)quinazolin-7-yloxy)propyl)piperazine-1-carbonyl)pyrazin-2-yl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R, 5R)-2-(((R)-4-(5-(4-(3-(6-(tert-butylsulfonyl)-4-(4,5-dimethyl-1H-pyrazol-3-ylamino)quinazolin-7-yloxy)propyl)piperazin-1-yl)pyrazine-2-carbonyl)-2-methylpiperazin-1-yl)methyl)-5-methylpiperazin-1-yl)acetyl)-6-(4-fluorobenzyl)-3,3-dimethyl-2,3-dihydro-1H-pyrrolo[3,2-b] pyridin-5(4H)-one, 1-(2-((2R,5R)-2-(((R)-4-(2-(4-(3-(6-(tert-butylsulfonyl)-4-(4,5-dimethyl-1H-pyrazol-3-ylamino)quinazolin-7-yloxy)propyl)piperazin-1-yl)pyrimidine-5-carbonyl)-2-methylpiperazin-1-yl)methyl)-5-methylpiperazin-1-yl)acetyl)-6-(4-fluorobenzyl)-3,3,4-trimethyl-2,3-dihydro-1H-pyrrolo[3,2-b]pyridin-5(4H)-one, and pharmaceutically acceptable salts thereof.

7. A pharmaceutical composition comprising a compound of formula (I) or a pharmaceutically acceptable salt thereof according to claim 1 and one or more of pharmaceutically acceptable carriers, diluents and excipients.

8. A combination comprising a compound of formula (I), or a pharmaceutically acceptable salt thereof according to claim 1 and at least one further therapeutic agent.

9. A method of degrading RIP2 kinase comprising administering to a human in need thereof according to claim 1 a therapeutically effective amount of a compound of Formula (I) or a pharmaceutically acceptable salt thereof.

* * * * *